United States Patent
Lal et al.

(10) Patent No.: US 7,834,001 B2
(45) Date of Patent: Nov. 16, 2010

(54) TRICYCLIC GUANIDINE DERIVATIVES AS SODIUM-PROTON EXCHANGE INHIBITORS

(75) Inventors: Bansi Lal, Mumbai (IN); Swati Bal-Tembe, Mumbai (IN); Usha Ghosh, Mumbai (IN); Arun Kumar Jain, Mumbai (IN); Tulsidas More, Mumbai (IN)

(73) Assignee: Piramal Life Sciences Limited, Mumbai (IN)

( * ) Notice: Subject to any disclaimer, the term of this patent is extended or adjusted under 35 U.S.C. 154(b) by 642 days.

(21) Appl. No.: 11/667,583

(22) PCT Filed: Nov. 8, 2005

(86) PCT No.: PCT/IB2005/053653

§ 371 (c)(1),
(2), (4) Date: May 10, 2007

(87) PCT Pub. No.: WO2006/051476

PCT Pub. Date: May 18, 2006

(65) Prior Publication Data

US 2007/0299051 A1    Dec. 27, 2007

Related U.S. Application Data

(60) Provisional application No. 60/637,208, filed on Dec. 17, 2004.

(30) Foreign Application Priority Data

Nov. 10, 2004 (IN) ................... 1225/MUM/2004

(51) Int. Cl.
  *C07D 327/08* (2006.01)
  *A61K 31/382* (2006.01)

(52) U.S. Cl. ............... 514/211.11; 514/232.8; 514/252.11; 514/253.11; 514/254.11; 514/338; 514/397; 514/422; 514/431; 540/549; 540/550; 544/145; 544/357; 544/364; 544/378; 546/279.7; 548/311.7; 548/526; 549/10

(58) Field of Classification Search ............ 514/211.11, 514/232.8, 252.11, 253.11, 254.11, 338, 514/397, 422, 431; 540/549, 550; 544/145, 544/357, 364, 378; 546/279.7; 548/311.7, 548/526; 549/10
See application file for complete search history.

(56) References Cited

U.S. PATENT DOCUMENTS

| | | | |
|---|---|---|---|
| 4,431,808 A | 2/1984 | Protiva et al. | |
| 5,036,067 A | 7/1991 | Girard et al. | |
| 5,591,754 A | 1/1997 | Lang et al. | |
| 5,700,839 A | 12/1997 | Gericke et al. | |
| 6,028,069 A | 2/2000 | Baumgarth et al. | |

FOREIGN PATENT DOCUMENTS

| | | |
|---|---|---|
| WO | WO 99/01435 | 1/1999 |
| WO | WO 00/64445 | 11/2000 |
| WO | WO 03/066620 A1 | 8/2003 |

OTHER PUBLICATIONS

Putney et al., "The Changing Face of the Na+/H+ Exchanger, NHE1: Structure, Regulation and Cellular Actions." *Annual Review of Pharmacology and Toxicology* 42(2002): 527-552.
Sheldon et al., "Na+/H+ exchange: molecular regulation to therapeutic development." *Clinical and Investigative Medicine* 25;6(2002): 229-232.
Goyal et al., "Renal expression of novel Na+/H+ exchanger isoform NHE8." *American Journal of Physiology- Renal Physiology* 284(2003): F467-F473.
Allen et al., "Activity of the Na+/H+ exchanger contributes to cardiac damage following Ischaemia and Reperfusion." *Clinical and Experimental Pharmacology* 27(2000): 727-733.
Duff, Henry J., "Clinical and in vivo antiarrhythmic potential of sodium-hydrogen exchange inhibitors." *Cardiovascular Research* 29(1995): 189-193.
Scholz et al., "Potential of selective sodium-hydrogen exchange inhibitors in cardiovascular therapy." *Cardiovascular Research* 29(1995): 184-188.
Fukuhiro et al., "Cardioplegic Strategies for Calcium Control ." *Circulation* 102(2000): III319-III325.

(Continued)

*Primary Examiner*—Bruck Kifle
(74) *Attorney, Agent, or Firm*—Merchant & Gould P.C.

(57) ABSTRACT

Guanidine derivatives having a condensed tricyclic ring of formula 1:

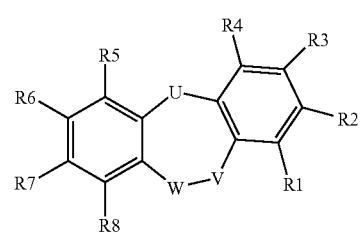

are disclosed, wherein U is C(O), $CR^aR^b$, O, $NR^a$ or $S(O)_m$; V is $CR^aR^b$ or $NR^a$; W is $S(O)_m$; wherein $R^a$ is H, alkyl, cycloalkyl, alkenyl or aralkyl; $R^b$ is H, alkyl, OH, $OR^a$ or $OCOR^a$, and m is the integer 0, 1 or 2; R1, R2, R3, R4, R5, R6, R7 and R8 are as defined herein with the proviso that at least one of R1, R2, R3, R4, R5, R6, R7 or R8 is guanidino or guanidino carbonyl. These derivatives are sodium-proton exchange inhibitors and are useful as medicaments for the treatment of, for example, organ disorders associated with ischemia and reperfusion, cardiac arrhythmia, cardiac hypertrophy, hypertension, cell proliferative disorders and diabetes.

16 Claims, No Drawings

OTHER PUBLICATIONS

Dennis et al., "Effects of Proton Buffering and of Amiloride Derivatives on Reperfusion Arrhythmias in Isolated Rat Hearts." *Circulation Res.* 66(1990): 1156-1159.

Duff et al., "Antiarrhythmic Activity of Amiloride: Mechanisms." *Journal of Cardiovascular Pharmacology* 17(1991): 879-888.

Ohara et al., "Protective Effect of FR168888, a New Na+/H+ Exchange Inhibitor, on Ischemia and Reperfusion-Induced Arrhythmia and Myocardial Infarction in Rats: in Comparison With Other Cardioprotective Compounds." *Japanese Journal of Pharmacology* 80(1999): 295-302.

Aihara et al., "TY-12533, a novel Na+/H+ exchange inhibitor, prevents myocardial stunning in dogs." *European Journal of Pharmacology* 419(2001): 93-97.

Ritter et al., "Na+/H+ Exchangers: Linking Osmotic Dysequilibrium to Modified Cell Function." *Cellular Physiology and Biochemistry* 11(2001): 1-18.

Siffert et al., "Sodium-Proton Exchange and Primary Hypertension." *Hypertension* 26(1995): 649-655.

Gumina et al., "Na+/H+ exchange inhibition-induced cardioprotection in dogs: effects on neutrophils versus cardiomyocytes." *American Journal of Physiology Heart and Circulatory Physiology* 279(2000): H1563-H1570.

Matteucci et al., "Sodium/hydrogen exchange activity in Type 1 diabetes mellitus: the never-ending story." *Diab. Nutr. Metab.* 14(2001): 225-233.

Karmazyn, Morris, "Role of sodium-hydrogen exchange in cardiac hypertrophy and heart failure: a novel and promising therapeutic target." *Basic Research in Cardiology* 96(2001): 325-328.

Oda et al., "Cleavage of vinyl carbon-silicon bond with tetrabutylammonium flouride." *Tetrahedron* 41(1985): 3257-3267.

Baruah, Robindra N., "An efficient system: Cobalt (II) chloride hexahydrate-zinc-dimethylformamide-water for reduction of nitroarenes." *Indian Journal of Chemistry* 33B(1994): 758.

Overman et al., "The Reduction of Arul Disulfides with Triphenylphosphine and Water." *Synthesis* (1974): 59-60.

Baumgarth et al., "(2-Methyl-5-(methylsulfonyl)benzoyl) guanidine Na+/H+ Antiporter Inhibitors." *Journal of Medicinal Chemistry* 40(1997): 2017-2034.

Jephcote et al., "Synthesis and Absolute Configuration of Optically Active E-1-Alkoxymethoxy-but-2-enyl(tri-n-butyl)stannanes: Stereoselective Reactions with Aldehydes." *J. Chem. Soc., Chem. Commun.* (1982): 800-802.

Bu et al., "Synthesis and Cytotoxic Activity of 7-Oxo-7H-dibenz[f, ij]isoquinoline and 7-Oxo-7H-benzo[e]perimidine Derivatives." *Journal of Medicinal Chemistry* 44(2001): 2004-2014.

Fukuyama et al., "2,4-Dinitrobenzensulfonamides: a Simple and Practical Method for the Preparation of a Variety of Secondary amines and Diamines." *Tetrahedron Letters* 38:33(1997): 5831-5834.

Mattson et al., "An Improved Method for Reductive Alkylation of Amines Using Titanium (IV) Isopropoxide and Sodium Cyanoborohydride[1]." *Journal of Organic Chemistry* 55(1990): 2552-2554.

Ghosh et al., "A Chemoenzymatic Approach to (R)-Tetrahydro-5-Oxo-2-(2-Hydroxyethyl)Furan, a Useful Chiral Synthon: Application to the Synthesis of (S)-4-Hexanolide, Pheromone Antipode of Trogoderma Glabrum." *Tetrahedron* 47(1991): 3089-3094.

Yong et al., "Facile and Efficient Guanylation of Amines Using Thioureas and Mukaiyama's Reagent." *Journal of Organic Chemistry* 62(1997): 1540-1542.

Larden et al., "Synthesis of α-Aminoacyl [1] Derivatives of Melphalan for use in Antibody Directed Enzyme Pro-drug Therapy." *Tetrahedron* 55(1999): 3265-3276.

Grunewald et al., "3,7-Disubstituted-1,2,3,4-tetrahydroisoquinolines Display Remarkable Potency and Selectivity as Inhibitors of Phenylethanolamine N-Methyltransferase versus the $\alpha_2$-adrenoceptor [1a]." *Journal of Medicinal Chemistry* 42(1999): 1982-1990.

Scheule et al., "Hearts from Non-Heart-Beating Donors: Sodium-Hydrogen-Inhibitor Cariporide Improves Functional Recovery." *Transplantation Proceedings* 33(2001): 841-842.

Heaney et al., "Triphenylene." *Organic Syntheses* 40(1973): 1120-1123.

Barluenga et al., "A New and Specific Method for the Monomethylation of Primary Amines." *J. Chem. Soc. Chem. Commun.* (1984): 1334-1335.

Barco et al., "The Use of Phase-Transfer Catalysis for the N-Alkylation of Indole." *Synthesis* (1976): 124-125.

Ackrell et al., "Synthesis of Antiinflammatory Activity of 6,11-Dihydro-11-oxodibenzo[b,e] thiepinalkanoic Acids and Related Compounds[1]." *Journal of Medicinal Chemistry* 21:10(1978): 1035-1044.

Scholz et al., "Protective effects of HOE642, a selective sodium-hydrogen exchange subtype 1 inhibitor, on cardiac ischaemia and reperfusion." *Cardiovascular Research* 29(1995): 260-268.

Baumgarth et al., "Bicyclic Acylguanidine Na+/H+ Antiporter Inhibitors." *Journal of Medicinal Chemistry* 41(1998): 3736-3747.

Walker et al., "The Lambeth Conventions: guidelines for the study of arrhythmias in ischaemia, infarction, and reperfusion." *Cardiovascular Research* 22(1988): 447-455.

Knight et al., "A Novel Sodium-Hydrogen Exchanger Isoform-1 Inhibitor, Zoniporide, Reduces Ischemic Myocardial Injury in Vitro and in Vivo." *The Journal of Pharmacology and Experimental Therapeutics* 297:1(2001): 254-259.

PCT International Search Report (Form PCT/ISA/210) for PCT/IB2005/053653, (2005).

TRICYCLIC GUANIDINE DERIVATIVES AS SODIUM-PROTON EXCHANGE INHIBITORS

CROSS-REFERENCE TO RELATED APPLICATIONS

'This application is related to our copending PCT patent application entitled: 'Fused tricyclic compounds as inhibitors of tumor necrosis factor-alpha', filed on the same date as the present application.'

FIELD OF THE INVENTION

The present invention relates to novel tricyclic guanidine derivatives which are sodium/proton (Na+/H+) exchange (NHE) inhibitors, to processes for their preparation, pharmaceutical compositions containing them and their use in medicines for the treatment and prevention of diseases caused by increased sodium-proton exchange activity.

BACKGROUND OF THE INVENTION

A sodium-proton exchange mechanism is present in the plasma membrane of most cells and is involved in the regulation of intracellular pH, cell volume and cell growth. In the NHE family of ion exchangers there are at least eight isoforms of NHE (NHE-1, NHE-2, NHE-3, NHE-4, NHE-5, NHE-6, NHE-7, NHE-8) known to date. NHE-1 is the ubiquitously expressed isoform and is called the housekeeping isoform, regulating intracellular pH, cell volume, cell proliferation, besides serving as the membrane anchor for the actin based cytoskeleton (Annu. Rev. Pharmacol. Toxicol. 42, 527-552, (2002)). It is a 110-kDa glycoprotein and constitutes the major isoform found in the mammalian myocardium. The other isoforms have a more restricted tissue distribution. NHE-2 and NHE-3 are confined to membranes of the renal and gastrointestinal tracts while NHE-4 is expressed in the gastrointestinal tract, and kidney. NHE-5 is expressed in the brain and kidney and may be involved in the regulation of cell pH and volume, while NHE-6 is a mitochondrial isoform regulating intra mitochondrial $Na^+$, $H^+$ and $Ca^{++}$ levels (Annu. Rev. Pharmacol. Toxicol. 42, 527-552, (2002)). NHE-6 and NHE-7, which share only about 20% amino acid homology with other isoforms, are expressed in membranes of intracellular organelles (Clin. Invest. Med., vol. 25, no. 6, 229-232, (2002)). The most recently identified and cloned isoform NHE-8 is expressed in the kidney and is a candidate to mediate apical membrane ion transport in the proximal tubule (Am. J. Physiol. Renal Physiol. 284, F467-F473, (2003)). The NHE-1 isoform plays a major role in the regulation of cell volume and intracellular pH (Annu. Rev. Pharmacol., 42, 527-552, (2002)) and any changes in these cell parameters activate the NHE which cause transmembrane $Na^+$ and $H^+$ fluxes along the ionic gradients to regain homeostatic conditions. During ischemia, intracellular pH falls due to accumulation of protons, and subsequent NHE activation mediated proton efflux is associated with intracellular $Na^+$ accumulation. Excess $Na^+$ within the cell cannot be extruded because of depressed $Na^+/K^+$ adenosine triphosphate (ATP) ase activity and reduction in the transmembrane $Na^+$ gradient will result in increased intracellular $Ca^{++}$ levels via the $Na^+/Ca^+$ exchange mechanism acting in reverse mode. Intracellular $Ca^{++}$ overload ultimately kills the cell. The loss of intracellular ATP during ischemia also results in phospholipase and protease activation causing cell membrane injury leading to necrosis (Clin. Exp. Pharmacol. Physiol, 27, 727-733, (2000)).

Currently, an unmet medical need exists for an agent that can minimize cardiac injury occurring both due to ischemia before thrombolytic therapy or coronary intervention and reperfusion thereafter. NHE activation leading to an intracellular $Ca^{++}$ overload has been pathophysiologically linked to ischemic injury subsequently leading to arrhythmias, myocardial infarction and sudden death. In the light of the limitations of class I and class III anti-arrhythmic agents in treating such arrhythmias, this alternative approach via NHE inhibition is very promising. A chronic treatment using NHE inhibitors, given to patients suffering from acute myocardial infarction, may be helpful in minimizing injury due to subsequent ischemic episodes. Those with predisposing factors like obesity, diabetes and raised blood pressure are more likely to suffer from acute myocardial infarction and a prophylactic treatment using NHE inhibitors may expand the myocardial survival time till reperfusion can be restored. NHE inhibition can also retard gradual progression of angina pectoris into congestive heart failure (resulting from formation of microinfarcts) and improve post reperfusion cardiac performance (Cardiovasc. Res. 29, 189-193, (1995)).

In pre-clinical experiments, inhibition of cardiac NHE has been shown to significantly minimize the associated damage and arrhythmias. (Clin. Expt. Pharmacol. Physiol, 27, 727-733, (2000)). NHE inhibitors have been shown to offer cardioprotection in many animal models of ischemia and reperfusion injury and hence have good clinical potential in applications such as cardiac surgeries-Coronary Artery Bypass Grafting (CABG), Percutaneous Transluminal Coronary Angioplasty (PTCA), valve surgery, cardiac transplantation AMI and angina pectoris. (Cardiovascular Res., 29, 184-188, (1995)). They improve post ischemia/reperfusion cardiac performance and reduce myocardial infarction in animals (Clin. Expt. Pharmacol. Physiol., 27, 727-733, (2000)) and also in man (Circulation, 102 (suppl. III):III-319-III-325, (2000)). These compounds, when added into cardioplegic and organ preserving solutions, have been found to reduce ischemia/reperfusion-induced $Ca^{++}$ overload and improve post surgical (e.g. CABG) or post transplant cardiac performance (Circulation, 102 (suppl. III):III-319-III-325, (2000)). The protective effect of NHE inhibitors against ischemia and reperfusion injury is evident for many other organs such as the brain, lungs and the skeletal muscle. Preoperative administration of NHE inhibitors is expected to reduce the incidence, extent and progression of cardiac injury and improve postoperative and post ischemia/reperfusion myocardial performance. This treatment is also expected to decrease morbidity and mortality and improve the quality of life in the 'high risk' group of patients prone to cardiac dysfunction.

Amiloride, a potassium sparing diuretic, was the first NHE inhibitor to be studied in ischemic isolated rat hearts (Circulation Res. 66:1156-1159, (1990)). Due to its low potency and specificity, the anti-arrhythmic activity of amiloride was found to be associated with undesirable side effects (Journal of Cardiovasc. Pharmacology, 17, 879-888, (1991)). Better potency, specificity and NHE-1 selectivity of the N-5 substituted derivatives of amiloride developed later, was not enough for eventual therapeutic development.

Like Amiloride, most of the known NHE inhibitors belong to the acylguanidine class of compounds, although in recent times non-acylguanidine NHE inhibitors have also been reported (WO 99/01435). Monocyclic acylguanidine NHE inhibitors are described in U.S. Pat. No. 5,591,754 (benzoylguanidines) and U.S. Pat. No. 5,700,839 (alkyl-5-methylsulfonylbenzoylguanidines). Bicyclic acylguanidine NHE inhibitors are described in U.S. Pat. No. 6,028,069 (heterocyclyl-condensed benzoylguanidines) and WO 00/64445.

Tricyclic acylguanidine NHE inhibitors are described in WO 03/066620 (dihydrothiaphenanthrenecarbonylguanidines).

Acylguanidine derivatives as NHE inhibitors have also been described in the literature, see for example; Jpn. J. Pharmacol., 80:295-302, (1999); Eur. J. Pharm., 419, 93-97, (2001).

A variety of diseases are characterized by intracellular changes leading to harmful/undesirable effects following NHE activation caused by a variety of stimuli, such as ischemia, hypoxia, hypertonicity, hormones, mitogens and growth promoters (Cell Physiol. and Biochem., 11, 1-18, (2001)). Hypoxia/ischemia induced NHE activation ultimately leads to intracellular loading of $Ca^{++}$ and cell death (Circulation, 102 (suppl III): III-319-III-325, (2000)). NHE expression has been linked to the development of malignant transformation. Neuronal $pH_i$ and osmoregulation, both closely regulated by NHE, have been shown to be disturbed during abnormal neuronal activity in depression and epileptic seizures. NHE-1 activation induced cellular swelling has been shown to be a prerequisite for directed migration of polymorphonuclear neutrophils in immune defense. NHE-1 may play an important homeostatic role in Airway Surface Liquid (ASL) osmolarity indispensable for normal lung function (Cell Physiol Biochem., 11, 1-8, (2001)). Metabolic acidosis, high sodium intake and raised levels of circulating insulin have been shown to be associated with NHE activation (Hypertension, 26, 649-655, (1995)). Cardioprotection against ischemial/reperfusion induced injury has been shown to be associated with inhibition of neutrophil activity (Am. J. Physiol.—Heart Circ. Physiol. 279: 4, H1563-H1570, (2000)). NHE-1 activity is increased in various cell types in hypertension and Type 1 diabetes (Diab. Nutr. Metab., 14, 225-233, (2001)). NHE-1 inhibition can prevent multifactorial hypertrophy of cardiomyocytes and reduce heart failure in vivo, independent of reduction in infarct size (Basic Res. Cardiol., 96, 325-328, (2001)).

There is a need for improved and alternative medicaments for the prevention and treatment of diseases associated with Na+/H+ exchange activity.

SUMMARY OF THE INVENTION

The present invention relates to novel tricyclic guanidine derivatives of formula 1 (as provided herein below), as well as prodrugs, tautomeric forms, stereoisomers, pharmaceutically acceptable salts or solvates or polymorphs thereof, which inhibit the sodium-proton exchange mechanism. The compounds of formula 1 can be used as medicaments for the treatment of all diseases caused primarily or secondarily by abnormal sodium-proton exchange activity, for example, hypertension, arrhythmia, angina pectoris, cardiac hypertrophy, and organ disorders associated with ischemic reperfusion.

The invention further relates to pharmaceutical compositions comprising the subject tricyclic guanidine derivatives as active ingredient for the medical uses indicated herein.

The invention still further relates to processes for producing the subject tricyclic guanidine derivatives of formula 1.

DETAILED DESCRIPTION OF THE INVENTION

The present invention relates to inhibitors of the sodium-proton exchange mechanism (NHE inhibitors) that are structurally clearly different from the NHE inhibitors described in the prior art. The present compounds are represented by the following formula 1:

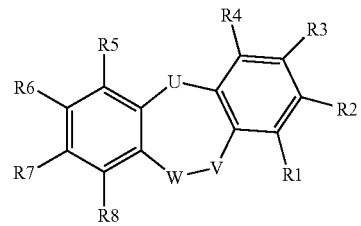

wherein:
R1, R2, R3, R4, R5, R6, R7 and R8 are Independently from Each Other Selected from: hydrogen, halogen, hydroxy, hydroxyalkyl, formyl, alkoxy, cycloalkoxy, aryloxy, alkylthio, alkylcarbonyl, carboxy, alkyl carboxylate, alkyl, alkenyl, cycloalkyl, aryl, aryloxycarbonyl, alkylaminoalkylaminocarbonyl, cyano, nitro, amidino, sulfonyl chloride, sulfonyl hydrazide, alkyl sulfonyl, heterocyclylsulfonyl, heteroarylsulfonyl, sulfonamide, alkyl-NH—$SO_2$—, cycloalkyl-NH—$SO_2$—, heterocyclyl-NH—$SO_2$—, heteroaryl-NH—$SO_2$—, heteroaryl-alkyl-NH—$SO_2$—, aralkyl, heterocyclyl, heteroaryl, guanidino carbonyl, guanidino, —NR'R" and N=R''';

R' and R" are independently from each other selected from: hydrogen, alkyl, cycloalkyl, aryl, aralkyl, haloalkyl, thioalkyl, hydroxyalkyl, alkoxyalkyl, aryloxyalkyl, carboxyalkyl, aminoalkyl, mono- or di-alkyl-substituted aminoalkyl, cycloalkylamino alkyl, aralkylaminoalkyl, alkoxyaralkylaminoalkyl, heterocyclylalkyl, heterocyclylamino alkyl, heterocyclylalkylaminoalkyl, heterocyclylalkyl-N(alkyl)-)alkyl, heteroarylalkyl, heteroaralkylaminoalkyl, alkoxyaralkyl-N(alkyl)-alkyl, aralkyl-N(alkyl)-alkyl, alkoxycarbonyl, cycloalkylcarbonyl, cycloalkylaminocarbonyl, aryl carbonyl, aryloxycarbonyl, aralkoxycarbonyl, heterocyclylcarbonyl, CHO, alkylcarbonyl (where the alkyl is unsubstituted or substituted by one, two or three of the same or different groups selected from: halo, hydroxy, alkoxy, alkylamino, cycloalkyl amino, aryl and heterocyclyl);

R''' is selected from: heterocyclyl, cycloalkyl and alkyl;

where aryl is unsubstituted or substituted by one or two of the same or different groups selected from: nitro, alkyl, alkoxy, halogen, haloalkyl, amino, mono- or di-alkylamino and heterocyclyl alkylamino alkyl; heteroaryl is unsubstituted or substituted by one or two of the same or different groups selected from: halogen, nitro, amino, alkylamino, alkyl, alkoxy and alkylcarbonyl; heterocyclyl is unsubstituted or substituted by one or two of the same or different groups selected from: alkyl, cycloalkyl, hydroxy alkyl, alkylaminoalkyl, cycloalkylalkyl, cycloalkylcarbonyl, heterocyclylalkyl, heteroaralkyl, heteroarylcarbonyl, aralkyl and oxo; guanidino and guanidinocarbonyl are unsubstituted or substituted by one, two or three of the same or different groups selected from: alkyl and alkylcarbonyl;

with the proviso that at least one of R1, R2, R3, R4, R5, R6, R7 or R8 is guanidino or guanidino carbonyl;

U is C(O), $CR^aR^b$, O, $NR^a$, or $S(O)_m$;
V is $CR^aR^b$ or $NR^a$; and
W is $S(O)_m$;

wherein $R^a$ is H, alkyl, cycloalkyl, alkenyl or aralkyl;
$R^b$ is H, alkyl, OH, $OR^a$ or $OCOR^a$, and
M is the Integer 0, 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

A feature of the compounds of the present invention is the ring C which represents a 7-membered heterocyclic ring that is fused to each of ring A and ring B on either side of it such that ring A and ring B each have two carbon atoms in common with ring C, in a tricyclic formation.

Listed below are definitions which apply to the terms as they are used throughout the specification and the appended claims (unless they are otherwise limited in specific instances), either individually or as part of a larger group. These broad or preferred definitions apply both to the end products of the formula 1 (above) and formulae 1a-1c (as provided herein below) and, correspondingly, to the starting materials and intermediates required in each case for the preparation. These definitions should not be interpreted in the literal sense as they are not general definitions and are relevant only for this application.

As used herein, the term "alkyl" whether used alone or as part of a substituent group, refers to the radical of saturated aliphatic groups, including straight or branched-chain alkyl groups and cycloalkyl substituted alkyl groups. Furthermore, unless stated otherwise, the term "alkyl" includes unsubstituted alkyl groups as well as alkyl groups, which are substituted by one or more different substituents. In preferred embodiments, a straight chain or branched chain alkyl has 20 or fewer carbon atoms in its backbone (e.g., $C_1$-$C_{20}$ for straight chain, $C_3$-$C_{20}$ for branched chain), and more preferably 15, 10 or fewer carbon atoms. Examples of alkyl residues containing from 1 to 20 carbon atoms are: methyl, ethyl, propyl, butyl, pentyl, hexyl, heptyl, octyl, nonyl, decyl, undecyl, dodecyl, tetradecyl, hexadecyl, octadecyl and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl or tert-butyl. Preferred examples of alkyl residue contain from 1 to 4 carbon atoms and are 5 methyl, ethyl, propyl, isopropyl, n-propyl, t-butyl, n-butyl, sec-butyl and iso-butyl.

The term "cycloalkyl" refers to a saturated mono, bi or poly-cyclic ring system containing a specified number of carbon atoms; Preferred cycloalkyls have from 3-10 carbon atoms in their ring structure, and more preferably have 3, 4, 5, 6, 7 or 8 carbon atoms in the ring structure. Examples of cycloalkyl residues containing 3, 4, 5, 6 or 7 ring carbon atoms are cyclopropyl, cyclobutyl, cyclopentyl, cyclohexyl or cycloheptyl. The term 'cycloalkyl' includes unsubstituted cycloalkyl and cycloalkyl which is substituted by one or more identical or different groups selected from: alkyl and any substitution mentioned below for alkyl.

Unless stated otherwise, and irrespective of any specific substituents bonded to alkyl groups that are indicated in the definition of the compounds of the formula 1 (above) and formulae 1a-1c (below), alkyl groups can in general be unsubstituted or substituted by one or more (for example 1, 2, 3, 4 or 5) identical or different substituents. Any kind of substituent present in substituted alkyl residues can be present in any desired position provided that the substitution does not lead to an unstable molecule. A substituted alkyl refers to an alkyl residue in which one or more, for example, 1, 2, 3, 4 or 5 hydrogen atoms are replaced with substituents, for example, halogen, hydroxyl, carbonyl, alkoxyl, ester, ether, cyano, amino, amido, imino, guanidino carbonyl, guanidino, sulfhydryl, alkylthio, thioester, sulfonyl, nitro, azido, acyloxy, heterocyclo, aralkyl, or an aryl or heteroaryl group. The carbon backbone of the alkyl group may contain heteroatoms such as oxygen, sulfur or nitrogen. Examples of substituted acyclic alkyls are hydroxymethyl, hydroxyethyl, 2-hydroxyethyl, aminoethyl or morpholinoethyl. Examples of substituted cyclic alkyls are guanidinocarbonylcyclopropyl and the like.

It will be understood by those skilled in the art that the moieties substituted on the hydrocarbon chain can themselves be substituted, if appropriate. For example, the substituents of a substituted alkyl may include substituted and unsubstituted forms of amino, imino, amido, guanidino, sulfonyl (including sulfonate and sulfonamide), as well as ether, alkylthio, carbonyl (including ketones, aldehydes, carboxylates and esters), fluoroalkyls such as —$CF_3$, cyano and the like. Cycloalkyls can be further substituted with alkyl, alkenyl, alkoxyl, alkylthio, aminoalkyls, carbonyl-substituted alkyl, fluoroalkyls such as —$CF_3$, cyano, amino, and the like.

The terms "alkenyl" and "alkynyl" refer to unsaturated aliphatic groups analogous in length and possible substitution to the alkyls described above, but that contain at least one double or triple bond, respectively, for example 1, 2 or 3 double bonds and/or triple bonds, provided that the double bonds are not located within a cyclic alkyl group in such a manner that an aromatic system results. Examples of alkenyl groups include vinyl, 1-propenyl, 2-propenyl, 2-butenyl, 2-methyl-1-propenyl and 3-methyl-2-butenyl. Examples of alkynyl groups include ethynyl, 2-propynyl, 2-butynyl, and 3-butynyl.

Furthermore, unless otherwise stated, the terms "alkenyl" and "alkynyl" include unsubstituted alkenyl and alkynyl groups as well as alkenyl and alkynyl groups which are substituted by one or more (for example 1, 2, 3, 4 or 5), identical or different groups mentioned above for alkyl, for example, aminoalkenyl, aminoalkynyl, amidoalkenyl, amidoalkynyl, iminoalkenyl, iminoalkynyl, thioalkenyl, thioalkynyl, carbonyl-substituted alkenyl or alkynyl, alkenoxyl or alkynoxyl.

As used herein the terms "alkoxyl" or "alkoxy" refers to an alkyl group having an oxygen radical attached thereto, wherein alkyl is as defined above. Representative alkoxyl groups include methoxy, ethoxy, propoxy, tert-butoxy and the like.

As used herein the term "acyl" refers to any group or organic radical (G), such as alkyl (which can be further substituted with an alkyl, alkoxy, cycloalkylamino, hydroxy or halo), cycloalkyl, aryl, heteroaryl or guanidine, attached to a carbonyl group, to form —C(O)-G, wherein alkyl, cycloalkyl, aryl and heteroaryl are as defined herein. For example, unsubstituted guanidinoacyl is guanidinocarbonyl or the group —C(O)—N=C($NH_2$)$NH_2$. An example of a substituted alkylacyl is —C(O)—$CH_2$Cl.

As used herein the term "aryl" refers to monocyclic or polycyclic hydrocarbon groups having up to 14 ring carbon atoms, preferably up to 10 ring carbon atoms, in which at least one carbocyclic ring is present that has a conjugated π electron system. Suitable examples of ($C_6$-$C_{14}$)-aryl residues include phenyl, naphthyl, biphenyl, fluorenyl or anthracenyl, especially phenyl and naphthyl. Unless stated otherwise, and irrespective of any specific substituents bonded to aryl groups which are indicated in the definition of the compounds of formula 1 (above) and formulae 1a-1c (below), aryl residues, for example phenyl, naphthyl or fluorenyl, can in general be optionally substituted by one or more substituents, preferably up to five identical or different substituents selected from: halogen, alkyl, alkenyl, alkynyl, fluoroalkyls such as $CF_3$, hydroxyl, aryloxy, amino, substituted amino, cyano, nitro, thiol, imine, amide or carbonyl (such as carboxyl, formate, carbamide, ester, ketone or aldehyde), sulfhydryl, alkylthio, silyl ether, thiocarbonyl (such as thioester, thioacetate or thioformate), sulfonyl, aminoacid ester, or a heterocyclo group which is saturated, partially unsaturated or aromatic. Aryl residues can be bonded via any desired position, and in substituted aryl residues the substituents can be located in any desired position. For example, in monosubstituted phenyl residues the substituent can be located in the 2-position, the 3-position, the 4-position or the 5-position. If the phenyl group carries two substituents, they can be located in 2,3-position, 2,4-position, 2,5-position, 2,6-position, 3,4-position or 3,5-position.

The term "heteroatom" as used herein means an atom of any element other than carbon or hydrogen. Preferred heteroatoms are nitrogen, oxygen and sulfur. It should be noted that any heteroatom with unsatisfied valences is assumed to have a hydrogen atom to satisfy the valences.

The terms "heterocyclyl", "heterocycle" and "heterocyclo" refer to a saturated, partially unsaturated or aromatic monocyclic or polycyclic heterocyclic ring system containing 3, 4, 5, 6, 7, 8, 9, 10, 11, 12, 13 or 14 ring atoms of which 1, 2, 3 or 4 are identical or different heteroatoms selected from nitrogen, oxygen and sulfur. The heterocyclyl group may, for example, have 1 or 2 oxygen atoms and/or 1 or 2 sulfur atoms and/or 1 to 4 nitrogen atoms in the ring. In monocyclic groups, heterocyclyl preferably is a 3-membered, 4-membered, 5-membered, 6-membered or 7-membered ring, more preferably a 5- or 6-membered ring. Suitable examples of such heterocyclyl groups are piperazinyl, piperidinyl, imidazolyl, pyrrolidinyl and morpholinyl. In polycyclic groups, heterocyclyl may comprise either fused rings in which two or more carbons are common to two adjoining rings, or bridged rings in which rings are joined through non-adjacent atoms. In polycyclic groups, heterocyclyl preferably comprises two fused rings (bicyclic) one of which is a 5- or 6-membered heterocyclic ring and the other of which is a 5- or 6-membered heterocyclic ring. Exemplary bicyclic and tricyclic heterocyclic groups include benzoxazolyl, quinolyl, isoquinolyl, carbazolyl, indolyl, isoindolyl, phenoxazinyl, benzothiazolyl, benzimidazolyl, benzoxadiazolyl and benzofurazanyl.

The ring heteroatoms can be present in any desired number and in any position with respect to each other provided that the resulting heterocyclic system is known in the art and is stable and suitable as a subgroup in a drug substance. Preferred are heterocyclyl groups having 1 or 2 identical or different heteroatoms selected from: nitrogen, oxygen and sulfur. Examples of such heterocyclyl groups are: pyrrolyl, furyl, thiophenyl, imidazolyl, oxazolyl, isoxazolyl, thiazolyl, isothiazolyl, triazolyl, pyrazolyl, pyridinyl, pyrazinyl, pyridazinyl, pyrimidinyl, azepinyl, tetrahydrothiophenyl, tetrahydrofuranyl, morpholinyl, thiomorpholinyl, tetrahydropyranyl, lactams, pyrrolidinyl, azetidinyl, piperidinyl, piperazinyl and the like.

The heterocyclyl group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be 1-pyrrolidinyl (=pyrrolidino), 2-pyrrolidinyl or 3-pyrrolidinyl, and imidazolyl can be 1-imidazolyl, 2-imidazolyl, 4-imidazolyl or 5-imidazolyl.

Heterocyclyl comprises saturated heterocyclic ring systems which do not contain any double bonds within the rings, as well as unsaturated heterocyclic ring systems which contain one or more, preferably up to 5 double bonds within the rings provided that the resulting system is stable. Unsaturated rings may be non-aromatic or aromatic. Aromatic heterocyclyl groups may also be referred to by the customary term "heteroaryl" for which all the definitions and explanations above and below relating to heterocyclyl apply.

Unless stated otherwise, and irrespective of any substituents bonded to heterocyclyl groups which are indicated in the definition of the compounds of formula 1 (above) and formulae 1a-1c (below), the heterocyclyl group can be unsubstituted or substituted on ring carbon atoms with one or more substituents, preferably up to five identical or different substituents. Each suitable ring nitrogen atom in a heterocyclyl group can independently of the other be unsubstituted, i.e. carry a hydrogen atom, or can be substituted. Suitable examples of substituents for the ring carbon and ring nitrogen atoms are: $(C_1-C_8)$-alkyl, in particular $(C_1-C_4)$-alkyl, alkoxy, halogen, hydroxyl, hydroxy-$(C_1-C_4)$-alkyl such as, for example, hydroxymethyl, 1-hydroxyethyl or 2-hydroxyethyl, alkenyl, alkynyl, fluoroalkyl such as $CF_3$, aryloxy, amino, cyano, nitro, thiol, imine, amide or carbonyl (such as carboxyl, formate, carbamide, an ester, ketone or aldehyde), silyl ether, thiocarbonyl (such as thioesters, a thioacetate or a thioformate), sulfonyl, aminoacid ester, heterocyclo, aryl or the like. The substituents can be present at one or more positions provided that a stable molecule results.

As used herein the term "aralkyl" refers to an alkyl group substituted with an aryl or heteroaryl group, wherein the terms alkyl, aryl and heteroaryl are as defined above. Exemplary aralkyl groups include —$(CH_2)_p$-phenyl, —$(CH_2)_p$-pyridyl, —$(CH_2)_p$-imidazolyl, —$(CH_2)_p$-thiophenyl and —$(CH_2)_p$-furyl, wherein p is an integer from 1 to 3.

Furthermore, unless stated otherwise, the term "guanidine" or "guanidino" includes guanidine that is substituted by one or more, preferably one, two or three, substituents independently selected from: alkyl and alkylcarbonyl, as well as unsubstituted guanidine.

The term "halogen" refers to fluorine, chlorine, bromine or iodine, preferably fluorine, chlorine or bromine.

The term "$S(O)_m$", wherein m is 0, 1 or 2, refers to S, SO, $SO_2$.

As used herein the term, "mono- or di-substituted amino" refers to an amino group substituted by one or two groups which may be the same or different. For instance, monosubstituted amino means an amino group in which only one hydrogen atom is replaced with a substituent. Di-substituted amino means an amino group in which both the hydrogen atoms are replaced with the same or different substituents. The substituents on the amino group may be independently selected from alkyl, haloalkyl, hydroxyalkyl, alkoxyalkyl, acyl, haloacyl, heterocyclylalkyl, heteroaryalkyl, aminoalkyl and alkoxyaralkyl. It will be understood by those skilled in the art that the moieties on the amino group can themselves be substituted, if appropriate.

It will be understood that "substitution" or "substituted with" includes the implicit proviso that such substitution is in accordance with permitted valence of the substituted atom and the substituent, as well as represents a stable compound, which does not readily undergo transformation such as by rearrangement, cyclization or elimination.

In preferred embodiments of the present invention of the formula 1, the substituents R1, R2, R3, R4, R5, R6, R7, R8, U, V, W, independently from each other have the following meanings:

R1, R2, R3, R4, R5, R6, R7 and R8 are independently from each other selected from: hydrogen, halogen, hydroxy, cyano, nitro, formyl, carboxy, guanidino, guanidinocarbonyl, $(C_1-C_4)$alkyl, $(C_3-C_6)$cycloalkyl, $(C_1-C_4)$alkoxy, $(C_3-C_6)$cycloalkoxy, $(C_1-C_4)$alkylthio, $(C_1-C_4)$alkoxycarbonyl, $(C_6-C_{10})$aryloxycarbonyl, $(C_6-C_{10})$aryl, $(C_6-C_{10})$aryloxy, pyrrolyl, pyrrolidinyl, piperidinyl, piperazinyl, morpholinyl, amino, $(C_1-C_{10})$alkylamino, thio-$(C_1-C_4)$alkylamino, $(C_1-C_4)$alkoxy-substituted$(C_1-C_4)$alkylamino, di-$(C_1-C_4$-alkyl) amino, chloro-$(C_1-C_4)$alkylamino, di-[chloro-$(C_1-C_4)$alkyl]amino, hydroxy-$(C_1-C_4)$alkylamino, di-[hydroxy-$(C_1-C_4)$alkyl]amino, mono- or di-$(C_1-C_4$-alkyl) substituted-amino ($C_1$-$C_4$)alkylamino, ($C_6$-$C_{10}$)aryloxy-($C_1$-$C_4$)alkylamino, ($C_6$-$C_{10}$)aryl-($C_1$-$C_4$)alkoxy-($C_1$-$C_4$)alkylamino, benzylamino, morpholinyl-($C_1$-$C_4$)alkylamino, ($C_1$-$C_4$)alkyl substituted-thiophenyl-($C_1$-$C_4$)alkylamino, pyrrolidinyl($C_1$-$C_4$) alkylamino, pyridyl($C_1$-$C_4$)alkylamino, piperidinyl-($C_1$-$C_4$) alkylamino, 3H-imidazolyl($C_1$-$C_4$)alkylamino, piperazinyl ($C_1$-$C_4$)alkylamino, morpholinyl($C_1$-$C_4$)alkylamino($C_1$-$C_4$) alkyl, pyrrolidinyl($C_1$-$C_4$)alkylamino($C_1$-$C_4$)alkyl, piperidinyl($C_1$-$C_4$)alkylamino($C_1$-$C_4$)alkyl, furanyl($C_1$-$C_4$) alkylamino, benzylamino-($C_1$-$C_4$)alkylamino, morpholinylamino($C_1$-$C_4$)alkylamino, ($C_3$-$C_6$)cycloalkylamino-($C_1$-$C_4$) alkylamino, furanyl($C_1$-$C_4$)alkyl-N[($C_1$-$C_4$)alkyl]-$CH_2CH_2$—N[($C_1$-$C_4$)alkyl]-, thiophenyl($C_1$-$C_4$)alkylN[($C_1$-$C_4$)alkyl]-$CH_2CH_2$—N[($C_1$-$C_4$)alkyl]-, benzyl-N[($C_1$-$C_4$-)alkyl]-$CH_2CH_2$—N[($C_1$-$C_4$)alkyl]-, ($C_1$-$C_4$) alkylcarbonylamino, ($C_1$-$C_4$)alkoxycarbonylamino, ($C_6$-$C_{10}$)aryloxycarbonylamino, ($C_6$-$C_{10}$)aryl($C_1$-$C_4$) alkoxycarbonylamino, morpholinylacetamido, morpholinyl ($C_1$-$C_4$)alkyl-N[C(O)$CH_3$]—, morpholinyl($C_1$-$C_4$)alkyl—N [C(O)$CH_2CH_3$]—, morpholinyl($C_1$-$C_4$)alkyl-N[C(O) $CH_2OCH_3$]—, morpholinyl-($C_1$-$C_4$)alkyl-N[C(O)-isobutoxy]-, morpholinyl($C_1$-$C_4$)alkyl-N[C(O) cyclopropyl]-, pyrrolidinyl($C_1$-$C_4$)alkyl-N[C(O)$CH_3$]—, pyrrolidinyl($C_1$-$C_4$)alkyl-N[C(O)$CH_2CH_3$]—, pyrrolidinyl ($C_1$-$C_4$)alkyl-N[C(O)isobutoxy]-, pyrrolidinyl($C_1$-$C_4$)alkyl-N[C(O)cyclopropyl]-, pyrrolidinyl($C_1$-$C_4$)alkyl-N[C(O) $CH_2Cl$]—, piperidinyl($C_1$-$C_4$)alkyl-N[C(O)—$CH_3$]-, piperidinyl($C_1$-$C_4$)alkyl-N[C(O)—$CH_2OCH_3$]—, piperidinyl($C_1$-$C_4$)alkyl-N[C(O)—$CH_2OH$]—, piperidinyl($C_1$-$C_4$) alkyl-N[C(O)C($CH_3$)$_3$]—, piperidinyl($C_1$-$C_4$)alkyl-N[C(O)-isobutoxy]-, piperidinyl-($C_1$-$C_4$)alkyl-N[C(O)-cyclopropyl]-, ($C_1$-$C_4$)alkylamino($C_1$-$C_4$)alkyl-N[C(O)—$CH_3$]—, ($C_1$-$C_4$)alkylamino($C_1$-$C_4$)alkyl-N[C(O) C($CH_3$)$_3$]—, halo-($C_1$-$C_4$)alkyl-N[C(O)—$CH_2Cl$]—, ($C_3$-$C_6$)cycloalkyl-NH-acetamido, ($C_1$-$C_4$)alkyl-NH-acetamido, ($C_1$-$C_4$)alkylamino($C_1$-$C_4$)alkylacetamido, pyrrolidinylacetamido, piperidinylacetamido, piperazinylacetamido, phenylpiperazinylacetamido, imidazolylacetamido, 1-carboxyalkylpyrrolidinium-($C_1$-$C_4$)alkylamino, 1-carboxy,4-($C_1$-$C_4$-alkyl)piperazinium($C_1$-$C_4$)alkylamino, sulfonylchloride, ($C_1$-$C_4$)alkylsulfonyl, heterocyclylsulfonyl, heteroarylsulfonyl, sulfonylhydrazide, sulfonamide, ($C_1$-$C_4$)alkyl-NH—$SO_2$—, ($C_3$-$C_6$)cycloalkyl-NH—$SO_2$—, heterocyclyl-NH—$SO_2$—, heteroaryl-NH—$SO_2$— and heterocyclyl=N—;

where pyrrolyl, pyrrolidinyl, piperidinyl, piperazinyl, morpholinyl, furanyl, benzyl and imidazolyl are each unsubstituted or substituted by one or two of the same or different groups selected from: ($C_1$-$C_4$)alkyl, hydroxy($C_1$-$C_4$)alkyl, ($C_1$-$C_4$)alkoxy, oxo, ($C_1$-$C_4$)alkylamino ($C_1$-$C_4$)alkyl, ($C_3$-$C_6$)cycloalkyl, ($C_3$-$C_6$)cycloalkyl($C_1$-$C_4$)alkyl, ($C_1$-$C_4$)alkylcarbonyl, ($C_3$-$C_6$)cycloalkylcarbonyl, heterocyclylcarbonyl, heterocyclyl($C_1$-$C_4$)alkyl, benzyl (where the benzyl is unsubstituted or substituted by one or two of the same or different groups selected from: ($C_1$-$C_4$)alkyl, ($C_1$-$C_4$)alkoxy, amino, mono or di-substituted amino [where the substituents on the amino group may be independently selected from ($C_1$-$C_4$) alkyl, halo($C_1$-$C_4$)alkyl, hydroxy($C_1$-$C_4$)alkyl, ($C_1$-$C_4$) alkoxyalkyl, acyl, haloacyl, heterocyclyl($C_1$-$C_4$)alkyl, hetero ($C_1$-$C_4$)arylalkyl, amino($C_1$-$C_4$)alkyl and ($C_1$-$C_4$) alkoxyaralkyl], nitro, halo, halo ($C_1$-$C_4$)alkyl and heterocyclyl($C_1$-$C_4$)alkylamino($C_1$-$C_4$)alkyl); alkyl is unsubstituted or substituted by one or two of the same or different groups selected from: halo, hydroxy, mono- or di-substituted amino [where the substituents on the amino group may be independently selected from ($C_1$-$C_4$)alkyl, halo($C_1$-$C_4$)alkyl, hydroxy($C_1$-$C_4$)alkyl, ($C_1$-$C_4$)alkoxyalkyl, acyl, haloacyl, heterocyclyl($C_1$-$C_4$)alkyl, hetero($C_6$-$C_{10}$)aryl($C_1$-$C_4$)alkyl, amino($C_1$-$C_4$)alkyl and ($C_1$-$C_4$)alkoxy($C_6$-$C_{10}$)aryl ($C_1$-$C_4$)alkyl], benzyl amino, pyridyl, piperidinyl, pyrrole, furanyl, morpholinyl, thiophenyl, phenyl, ($C_3$-$C_6$)cycloalkyl, heterocyclyl and heteroaryl; and aryl, heteroaryl and heterocyclyl are independently from each other unsubstituted or substituted by one or two of the same or different groups selected from: ($C_1$-$C_4$)alkyl, ($C_1$-$C_4$)alkoxy and halo($C_1$-$C_4$) alkyl.

V is selected from: $CH_2$, $CHCH_3$, $C(CH_3)_2$, NH and $NCH_3$.

U is selected from: O, C(O), CHOH, $CH_2$, NH and $NCH_3$.

W is $S(O)_2$.

In one embodiment, the present invention provides novel tricyclic guanidine derivatives of the following formula 1a:

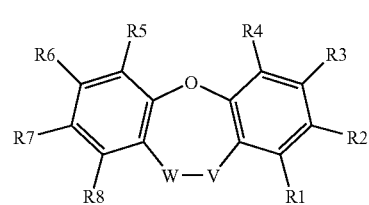

1a wherein:

R1, R2, R3, R4, R5, R6, R7, R8, V and W are as defined above in respect of formula 1, with the proviso that at least one of R1, R2, R3, R4, R5, R6, R7 or R8 is guanidino or guanidinocarbonyl;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In another embodiment, the present invention provides novel tricyclic guanidine derivatives of the following formula 1b:

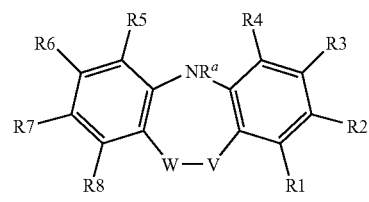

1b wherein:

R1, R2, R3, R4, R5, R6, R7, R8, V and W are as defined above with respect to formula 1, with the proviso that at least one of R1, R2, R3, R4, R5, R6, R7 or R8 is guanidino or guanidino carbonyl;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In one embodiment of formula 1b, $R^a$ is H, ($C_1$-$C_4$)alkyl, ($C_3$-$C_6$)cycloalkyl or ($C_2$-$C_4$)alkenyl; and V is $CH_2$, $CHCH_3$, $C(CH_3)_2$, NH or $NCH_3$.

In a further embodiment, the present invention provides novel tricyclic guanidine derivatives of the formula 1c:

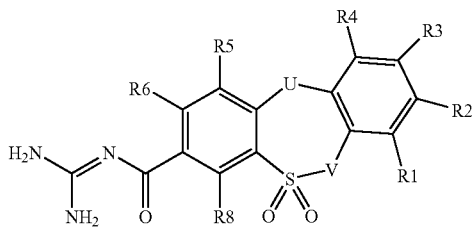

wherein:

R1, R2, R3, R4, R5, R6 and R8 are independently from each other selected from: hydrogen, halogen, hydroxy, hydroxy-($C_1$-$C_4$)alkyl, formyl, ($C_1$-$C_4$)alkoxy, ($C_3$-$C_6$)cycloalkoxy, ($C_6$-C10)aryloxy, ($C_1$-$C_4$)alkylthio, ($C_1$-$C_4$)alkylcarbonyl, carboxy, ($C_1$-$C_4$)alkyl carboxylate, ($C_1$-$C_{12}$)alkyl, ($C_2$-$C_6$)alkenyl, ($C_3$-$C_6$)cycloalkyl, ($C_6$-$C_{10}$)aryl, ($C_6$-$C_{10}$)aryloxycarbonyl, ($C_1$-$C_4$)alkylamino($C_1$-$C_4$)alkylaminocarbonyl, cyano, nitro, amidino, sulfonyl chloride, sulfonyl hydrazide, ($C_1$-$C_4$)alkyl sulfonyl, heterocyclylsulfonyl, heteroarylsulfonyl, sulfonamide, ($C_1$-$C_4$)alkyl-NH—$SO_2$—, ($C_3$-$C_6$)cycloalkyl-NH—$SO_2$—, heterocyclyl-NH—$SO_2$—, heteroaryl-NH—$SO_2$—, heteroaryl-($C_1$-$C_4$)alkyl-NH—$SO_2$—, ($C_6$-$C_{10}$)aryl-($C_1$-$C_4$)alkyl, heterocyclyl, heteroaryl, guanidino, —NR'R" and N=R'";

R' and R" are independently from each other selected from: hydrogen, ($C_1$-$C_4$)alkyl, ($C_3$-$C_6$)cycloalkyl, ($C_6$-$C_{10}$)aryl, ($C_6$-$C_{10}$)aryl($C_1$-$C_4$)alkyl, halo($C_1$-$C_4$)alkyl, thio($C_1$-$C_4$)alkyl, hydroxy($C_1$-$C_4$)alkyl, ($C_1$-$C_4$)alkoxy($C_1$-$C_4$)alkyl, ($C_6$-$C_{10}$) aryloxy($C_1$-$C_4$)alkyl, carboxy($C_1$-$C_4$)alkyl, amino($C_1$-$C_4$)alkyl, mono- or di-($C_1$-$C_4$)alkyl-substituted amino($C_1$-$C_4$)alkyl, ($C_3$-$C_6$)cycloalkylamino($C_1$-$C_4$)alkyl, ($C_6$-$C_{10}$)aryl($C_1$-$C_4$)alkylamino($C_1$-$C_4$)alkyl, ($C_1$-$C_4$)alkoxy($C_6$-$C_{10}$)aryl($C_1$-$C_4$)alkylamino($C_1$-$C_4$)alkyl, heterocyclyl($C_1$-$C_4$)alkyl, heterocyclylamino($C_1$-$C_4$)alkyl, heterocyclyl($C_1$-$C_4$)alkylamino($C_1$-$C_4$)alkyl, heterocyclyl($C_1$-$C_4$)alkyl-N[($C_1$-$C_4$)alkyl]-($C_1$-$C_4$)alkyl, heteroaryl($C_1$-$C_4$)alkyl, heteroaryl($C_1$-$C_4$)alkylamino($C_1$-$C_4$)alkyl, ($C_1$-$C_4$)alkoxy($C_6$-$C_{10}$)aryl($C_1$-$C_4$)alkyl-N[($C_1$-$C_4$)alkyl]-($C_1$-$C_4$)alkyl, ($C_6$-$C_{10}$)aryl($C_1$-$C_4$)alkyl-N[($C_1$-$C_4$-)alkyl]-($C_1$-$C_4$)alkyl, ($C_1$-$C_4$)alkoxycarbonyl, ($C_3$-$C_6$)cycloalkylcarbonyl, ($C_3$-$C_6$)cycloalkylaminocarbonyl, ($C_6$-$C_{10}$)arylcarbonyl, ($C_6$-$C_{10}$)aryloxycarbonyl, ($C_6$-$C_{10}$)aralkoxycarbonyl, heterocyclylcarbonyl, CHO, ($C_1$-$C_4$)alkylcarbonyl (where the alkyl is unsubstituted or substituted by one, two or three of the same or different groups selected from: halo, hydroxy, ($C_1$-$C_4$)alkoxy, ($C_1$-$C_4$)alkylamino, ($C_3$-$C_6$)cycloalkyl amino, ($C_6$-$C_{10}$)aryl and heterocyclyl);

R'" is selected from: heterocyclyl, ($C_3$-$C_6$)cycloalkyl and ($C_1$-$C_4$)alkyl;

where aryl is unsubstituted or substituted by one or two of the same or different groups selected from: nitro, ($C_1$-$C_4$)alkyl, ($C_1$-$C_4$)alkoxy, halogen, halo($C_1$-$C_4$)alkyl, amino, mono- or di-($C_1$-$C_4$)alkylamino and heterocyclyl($C_1$-$C_4$)alkylaminoalkyl; heteroaryl is unsubstituted or substituted by one or two of the same or different groups selected from: halogen, nitro, amino, ($C_1$-$C_4$)alkylamino, ($C_1$-$C_4$)alkyl, ($C_1$-$C_4$)alkoxy and ($C_1$-$C_4$)alkylcarbonyl; heterocyclyl is unsubstituted or substituted by one or two of the same or different groups selected from: ($C_1$-$C_4$)alkyl, ($C_3$-$C_6$)cycloalkyl, hydroxy($C_1$-$C_4$)alkyl, ($C_1$-$C_4$)alkylamino($C_1$-$C_4$)alkyl, ($C_3$-$C_6$)cycloalkyl ($C_1$-$C_4$)alkyl, ($C_3$-$C_6$)cycloalkylcarbonyl, heterocyclyl($C_1$-$C_4$)alkyl, heteroaryl($C_1$-$C_4$)alkyl, heteroarylcarbonyl, ($C_6$-$C_{10}$)aryl($C_1$-$C_4$)alkyl and oxo; guanidino is unsubstituted or substituted by one, two or three of the same or different groups selected from: ($C_1$-$C_4$)alkyl and ($C_1$-$C_4$)alkyl-carbonyl;

U is C(O), $CR^aR^b$, O, $NR^a$, or $S(O)_m$; and

V is $CR^aR^b$ or $NR^a$;

wherein $R^a$ is H, ($C_1$-$C_4$)alkyl, ($C_3$-$C_6$)cycloalkyl, ($C_2$-$C_6$)alkenyl or ($C_6$-$C_{10}$)aryl($C_1$-$C_4$)alkyl;

$R^b$ is H, ($C_1$-$C_4$)alkyl, OH, $OR^a$ or $OCOR^a$, and m is the integer 0, 1 or 2;

in all its stereoisomeric and tautomeric forms and mixtures thereof in all ratios, and its pharmaceutically acceptable salts, pharmaceutically acceptable solvates, pharmaceutically acceptable polymorphs and prodrugs.

In the compound of formula 1c, V may be selected from: $CH_2$, $CHCH_3$, $C(CH_3)_2$, NH and $NCH_3$, especially $CH_2$.

In the compound of formula 1c, U may be selected from: O, C(O), CHOH, $CH_2$, NH and N—$CH_3$, especially O, NH and N—$CH_3$.

In other embodiments of formula 1c, any one or more of R1, R2, R3, R4, R5, R6, R8, U and V is selected from the preferred substituents defined in respect of the above preferred embodiments of formula 1, 1a or 1b of the present invention.

In another embodiment, the present invention provides a compound of the formula 1, 1a, 1b or 1c, wherein R1, R3, R4, R5, R6 and R8 are independently from each other selected from: hydrogen, hydroxyl, halogen, nitro, cyano, amino, ($C_1$-$C_4$)alkyl, ($C_3$-$C_6$)cycloalkyl, ($C_1$-$C_4$)alkoxy, ($C_1$-$C_4$)alkylcarbonyl, ($C_1$-$C_4$)carboxy, phenyl, 5- or 6-membered heterocyclyl, 5- or 6-membered heteroaryl, 5- or 6-membered heterocyclyl ($C_1$-$C_4$)alkyleneamino, 5- or 6-membered heteroarylamino, and phenyl ($C_1$-$C_4$)alkylene amino.

From the tested compounds of the present invention, it is clear that R2 can vary widely in structure. Therefore, compounds that have any one or more of the pharmacological activities described herein but that differ from the present compounds in that the structure of R2 group falls outside the literal wording of the claims below is to be considered as within the scope of the present invention. In general, R2 can be any group defined above for R1 to R8 in respect of formula 1 or formula 1a-1c. In one embodiment of the present invention is a compound of the formula 1, 1a, 1b or 1c, wherein R1, R3-R8, U, V and W are as defined and R2 is hydrogen, amino or a nitrogen-containing group with fewer than 20 carbon atoms, preferably fewer that 14 carbon atoms. The nitrogen-containing group may be selected from —NR'R", —N=R'", and —N=C(NH$_2$)$_2$ where R', R" and R'" are as defined above. Some examples of nitrogen-containing groups are: amino($C_1$-$C_4$)alkylene, 2-imidazol-1-yl-ethylene-amino, 4-benzyl-piperazinyl-1-yl, 2-pyrrolidin-1-yl-ethylene-N (ethyl)-, pyridinyl-3-yl-methylene-NH—S(O)$_2$— and 4-cyclopropyl-2-oxo-piperazin-1-yl. Examples of the R1, R2, R3, R4, R5, R6, R7 or R8 groups, in particular the R2 group, including further examples of nitrogen-containing groups with fewer than 14 carbon atoms, are provided in Table 1 below. The right hand column of Table 1 shows the structure of one possible group falling within the group definition given in the left hand column.

TABLE 1

| Group | Structure |
|---|---|
| pyridinyl-(C₁-C₄)alkylene-NH-(C₁-C₄)alkylene-NH— | |
| morpholinyl(C₁-C₄)alkylene-NH— | |
| (C₁-C₄)alkyl substituted-thiophenyl-(C₁-C₄)alkylene-NH— | |
| pyrrolidinyl(C₁-C₄)alkylene-NH— | |
| piperidinyl(C₁-C₄)alkylene-NH— | |
| 3H-imidazolyl(C₁-C₄)alkylene-NH— | |
| methyl substituted piperazinyl-(C₁-C₄)alkylene-NH— | |
| morpholinyl(C₁-C₄)alkylene-N[(C₁-C₄)alkyl]- | |
| pyrrolidinyl(C₁-C₄)alkylene-N[(C₁-C₄)alkyl]- | |
| piperidinyl(C₁-C₄)alkylene-N[(C₁-C₄)alkyl]- | |

TABLE 1-continued

| Group | Structure |
|---|---|
| furanyl(C₁-C₄)alkylene-NH— | |
| benzyl-NH(C₁-C₄)alkylene-NH— | |
| morpholinyl-NH-(C₁-C₄)alkylene-NH— | |
| cycloalkyl-NH-(C₁-C₄)alkylene-NH— | |
| furanyl(C₁-C₄)alkylene-N[(C₁-C₄)alkyl]CH₂CH₂—N[(C₁-C₄)alkyl]- | |
| thiophenyl(C₁-C₄)alkylene-N[(C₁-C₄)alkyl]-CH₂CH₂—N[(C₁-C₄)alkyl]- | |
| benzyl-N[(C₁-C₄)alkyl]-CH₂CH₂—N[(C₁-C₄)alkyl]- | |
| morpholinylacetamido | |
| morpholinyl(C₁-C₄)alkylene-N[C(=O)-methyl]- | |

TABLE 1-continued

| Group | Structure |
|---|---|
| morpholinyl(C$_1$-C$_4$)alkylene-N[C(=O)-ethyl]- | |
| morpholinyl(C$_1$-C$_4$)alkylene-N[C(=O)-isobutoxy]- | |
| morpholinyl(C$_1$-C$_4$)alkylene-N[C(=O)-cyclopropyl]- | |
| pyrrolidinyl(C$_1$-C$_4$)alkylene-N[C(=O)-methyl]- | |
| pyrrolidinyl(C$_1$-C$_4$)alkylene-N[C(=O)-ethyl]- | |
| pyrrolidinyl(C$_1$-C$_4$)alkylene-N[C(=O)-isobutoxy]- | |
| pyrrolidinyl(C$_1$-C$_4$)alkylene-N[C(=O)-cyclopropyl]- | |
| piperidinyl(C$_1$-C$_4$)alkylene-N[C(=O)-methyl]- | |
| piperidinyl(C$_1$-C$_4$)alkylene-N[C(=O)-C(CH$_3$)$_3$]- | |
| piperidinyl(C$_1$-C$_4$)alkylene-N[C(=O)-isobutoxy]- | |
| piperidinyl(C$_1$-C$_4$)alkylene-N[C(=O)-cyclopropyl]- | |
| cycloalkyl-NH-acetamido | |
| (C$_1$-C$_4$)alkyl-NH-acetamido | |
| pyrrolidinyl acetamido | |
| imidazolyl acetamido | |
| aryloxy(C$_1$-C$_4$)alkylene-NH | |
| aralkoxy(C$_1$-C$_4$)alkylene-NH | |
| (C$_1$-C$_4$)alkylthio-NH | |
| (C$_1$-C$_4$)alkylthio(C$_1$-C$_4$)alkylene-NH | |

TABLE 1-continued

| Group | Structure |
|---|---|
| aryloxy-C(=O)-NH— | (phenyl-O-C(=O)-NH-CH3) |
| aralkoxy-C(=O)-NH— | (benzyl-O-C(=O)-NH-CH3) |
| methyl substituted heterocyclylsulfonyl | (H3C-N-piperazinyl-SO2-) |
| sulfonylhydrazide | (H2N-NH-SO2-CH3) |
| Sulfonamide | (H2N-SO2-CH3) |
| (C1-C4)alkyl-NH—SO2— | (H3C-CH2-NH-SO2-CH3) |
| cyclopropyl-substituted heterocyclyl-NH—SO2— | (cyclopropyl-thiadiazolyl-NH-SO2-CH3) |
| R'''=N—, where R''' is methyl substituted heterocyclyl | (N-methyl-pyrrolidinylidene=N-) |

In an even further preferred embodiment, the present invention provides a tricyclic guanidine derivative selected from the following:

N-(10,10-Dioxo-10,11-dihydro-5-oxa-10lambda*6*-thia-dibenzo[a,d]cycloheptene-8-carbonyl)-guanidine;

N-(2,4-Dichloro-10,10-dioxo-10,11-dihydro-5-oxa-10lambda*6*-thia-dibenzo[a,d]cycloheptene-8-carbonyl)-guanidine;

N-(2-Chloro-10,10-dioxo-10,11-dihydro-5-oxa-10lambda*6*-thia-dibenzo[a,d]cycloheptene-8-carbonyl)-guanidine;

N-(4-Chloro-10,10-dioxo-10,11-dihydro-5-oxa-10lambda*6*-thia-dibenzo[a,d]cycloheptene-8-carbonyl)-guanidine;

N-(3-Fluoro-10,10-dioxo-10,11-dihydro-5-oxa-10lambda*6*-thia-dibenzo[a,d]cycloheptene-8-carbonyl)-guanidine;

N-(1-Fluoro-10,10-dioxo-10,11-dihydro-5-oxa-10lambda*6*-thia-dibenzo[a,d]cycloheptene-8-carbonyl)-guanidine;

N-(2-Fluoro-10,10-dioxo-10,11-dihydro-5-oxa-10lambda*6*-thia-dibenzo[a,d]cycloheptene-8-carbonyl)-guanidine;

N-(4-Isopropyl-10,10-dioxo-10,11-dihydro-5-oxa-10lambda*6*-thia-dibenzo[a,d]cycloheptene-8-carbonyl)-guanidine;

N-(4-Methyl-10,10-dioxo-10,11-dihydro-5-oxa-10lambda*6*-thia-dibenzo[a,d]cycloheptene-8-carbonyl)-guanidine;

N-(4-Amino-10,10-dioxo-10,11-dihydro-5-oxa-10lambda*6*-thia-dibenzo[a,d]cycloheptene-8-carbonyl)-guanidine;

N-(10,10-dioxo-4-pyrrol-1-yl-10,11-dihydro-5-oxa-10lambda*6*-thia-dibenzo[a,d]cycloheptene-8-carbonyl)-guanidine;

N-(2-Methanesulfonyl-10,10-dioxo-10,11-dihydro-5-oxa-10lambda*6*-thia-dibenzo[a,d]cycloheptene-8-carbonyl)-guanidine;

N-(7-Chloro-10,10-dioxo-10,11-dihydro-5-oxa-10lambda*6*-thia-dibenzo[a,d]cycloheptene-8-carbonyl)-guanidine;

N-(10,10-dioxo-7-piperidin-1-yl-10,11-dihydro-5-oxa-10lambda*6*-thia-dibenzo[a,d]cycloheptene-8-carbonyl)-guanidine;

N-(10,10-dioxo-7-pyrrolidin-1-yl-10,11-dihydro-5-oxa-10lambda*6*-thia-dibenzo[a,d]cycloheptene-8-carbonyl)-guanidine;

N-(7-Chloro-1-fluoro-10,10-dioxo-10,11-dihydro-5-oxa-10lambda*6*-thia-dibenzo[a,d]cycloheptene-8-carbonyl)-guanidine;

N-(7-Chloro-2-fluoro-10,10-dioxo-10,11-dihydro-5-oxa-10lambda*6*-thia-dibenzo[a,d]cycloheptene-8-carbonyl)-guanidine;

N-(10,10-Dioxo-7-pyrrol-1-yl-10,11-dihydro-5-oxa-10lambda*6*-thia-dibenzo[a,d]cycloheptene-8-carbonyl)-guanidine;

N-(7-Chloro-4-methyl-10,10-dioxo-10,11-dihydro-5-oxa-10lambda*6*-thia-dibenzo[a,d]cycloheptene-8-carbonyl)-guanidine;

N-(4-Methyl-10,10-dioxo-7-pyrrol-1-yl-10,11-dihydro-5-oxa-10lambda*6*-thia-dibenzo[a,d]cycloheptene-8-carbonyl)-guanidine;

N-(7-Chloro-2-methanesulfonyl-4-methyl-10,10-dioxo-10,11-dihydro-5-oxa-10lambda*6*-thia-dibenzo[a,d]cycloheptene-8-carbonyl)-guanidine;

N-(7-Chloro-4-isopropyl-10,10-dioxo-10,11-dihydro-5-oxa-10lambda*6*-thia-dibenzo[a,d]cycloheptene-8-carbonyl)-guanidine;

N-(2,7-Dichloro-10,10-dioxo-10,11-dihydro-5-oxa-10lambda*6*-thia-dibenzo[a,d]cycloheptene-8-carbonyl)-guanidine;

N-(7-Benzylamino-4-methyl-10,10-dioxo-10,11-dihydro-5-oxa-10lambda*6*-thia-dibenzo[a,d]cycloheptene-8-carbonyl)-guanidine;

N-(4-Chloro-7-methyl-10,10-dioxo-10,11-dihydro-5-oxa-10lambda*6*-thia-dibenzo[a,d]cycloheptene-8-carbonyl)-guanidine;

N-(4,7-Dimethyl-10,10-dioxo-10,11-dihydro-5-oxa-10lambda*6*-thia-dibenzo[a,d]cycloheptene-8-carbonyl)-guanidine;

N-(7-Methyl-10,10-dioxo-10,11-dihydro-5-oxa-10lambda*6*-thia-dibenzo[a,d]cycloheptene-8-carbonyl)-guanidine;

N-(4-Chloro-6-methyl-10,10-dioxo-10,11-dihydro-5-oxa-10lambda*6*-thia-dibenzo[a,d]cycloheptene-8-carbonyl)-guanidine;
N-(2-Chloro-6-methyl-10,10-dioxo-10,11-dihydro-5-oxa-10lambda*6*-thia-dibenzo[a,d]cycloheptene-8-carbonyl)-guanidine;
N-(4-Chloro-2-methanesulfonyl-6-methyl-10,10-dioxo-10,11-dihydro-5-oxa-10lambda*6*-thia-dibenzo[a,d]cycloheptene-8-carbonyl)-guanidine;
N-(4-Isopropyl-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-2-nitro-10,10-dioxo-10,11-dihydro-5-oxa-10lambda*6*-thia-dibenzo[a,d]cycloheptene-8-carbonyl)-guanidine;
N-(4,6-Dimethyl-10,10-dioxo-10,11-dihydro-5-oxa-10lambda*6*-thia-dibenzo[a,d]cycloheptene-8-carbonyl)-guanidine;
N-(4-Isopropyl-6-methyl-2-nitro-10,10-dioxo-10,11-dihydro-5-oxa-10lambda*6*-thia-dibenzo[a,d]cycloheptene-8-carbonyl)-guanidine;
N-(2-Amino-4-chloro-6-methyl-10,10-dioxo-10,11-dihydro-5-oxa-10lambda*6*-thia-dibenzo[a,d]cycloheptene-8-carbonyl)-guanidine;
N-(2-Amino-4,6-dimethyl-10,10-dioxo-10,11-dihydro-5-oxa-10lambda*6*-thia-dibenzo[a,d]cycloheptene-8-carbonyl)-guanidine;
N-(4-Chloro-2-iodo-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-10,10-dioxo-2-pyrrol-1-yl-10,11-dihydro-5-oxa-10lambda*6*-thia-dibenzo[a,d]cycloheptene-8-carbonyl)-guanidine;
N-(2-(2,5-Dimethyl-pyrrol-1-yl)-4,6-dimethyl-10,10-dioxo-10,11-dihydro-5-oxa-10lambda*6*-thia-dibenzo[a,d]cycloheptene-8-carbonyl)-guanidine;
N-(2-Dimethylamino-4,6-dimethyl-10,10-dioxo-10,11-dihydro-5-oxa-10lambda*6*-thia-dibenzo[a,d]cycloheptene-8-carbonyl)-guanidine;
N-(4-Chloro-2-dimethylamino-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-2-methylamino-10,10-dioxo-10,11-dihydro-5-oxa-10lambda*6*-thia-dibenzo[a,d]cycloheptene-8-carbonyl)-guanidine;
N-(2-[N-Benzyloxycarbonyl-guanidino]-4-chloro-6-methyl-10,10-dioxo-10,11-dihydro-5-oxa-10lambda*6*-thia-dibenzo[a,d]cycloheptene-8-carbonyl)-guanidine;
N-(4-Chloro-2-isobutylamino-6-methyl-10,10-dioxo-10,11-dihydro-5-oxa-10lambda*6*-thia-dibenzo[a,d]cycloheptene-8-carbonyl)-guanidine;
N-(4,6-Dichloro-10,10-dioxo-10,11-dihydro-5-oxa-10lambda*6*-thia-dibenzo[a,d]cycloheptene-8-carbonyl)-guanidine,
N-(2-Amino-4,6-dichloro-10,10-dioxo-10,11-dihydro-5-oxa-10lambda*6*-thia-dibenzo[a,d]cycloheptene-8-carbonyl)-guanidine;
N-(6-Chloro-4-methyl-10,10-dioxo-10,11-dihydro-5-oxa-10lambda*6*-thia-dibenzo[a,d]cycloheptene-8-carbonyl)-guanidine;
N-(2-Amino-6-chloro-4-methyl-10,10-dioxo-10,11-dihydro-5-oxa-10lambda*6*-thia-dibenzo[a,d]cycloheptene-8-carbonyl)-guanidine;
4-Chloro-8-guanidinocarbonyl-6-methyl-10,10-dioxo-10,11-dihydro-5-oxa-10lambda*6*-thia-dibenzo[a,d]cycloheptene-2-sulfonic acid amide;
N-(6-Chloro-4-methyl-10,10-dioxo-10,11-dihydro-5-oxa-10lambda*6*-thia-dibenzo[a,d]cyclopentene-2-carbonyl)-guanidine;
4-Chloro-8-guanidinocarbonyl-6-methyl-10,10-dioxo-10,11-dihydro-5-oxa-10lambda*6*-thia-dibenzo[a,d]cycloheptene-2-sulfonic acid (5-cyclopropyl-[1,3,4]thiadiazol-2-yl)-amide;
4-Chloro-8-guanidinocarbonyl-6-methyl-10,10-dioxo-10,11-dihydro-5-oxa-10lambda*6*-thia-dibenzo[a,d]cycloheptene-2-sulfonic acid (pyridin-3-ylmethyl)-amide;
N-[4-Chloro-6-methyl-10,10-dioxo-2-(piperazine-1-sulfonyl)-10,11-dihydro-5-oxa-10lambda*6*-thia-dibenzo[a,d]cycloheptene-8-carbonyl]-guanidine;
N-[4-Chloro-6-methyl-2-(4-methyl-piperazine-1-sulfonyl)-10,10-dioxo-10,11-dihydro-5-oxa-10lambda*6*-thia-dibenzo[a,d]cyclohepten-8-carbonyl]-guanidine;
N-[4-Chloro-6-methyl-2-(morpholine-4-sulfonyl)-10,10-dioxo-10,11-dihydro-5-oxa-10lambda*6*-thia-dibenzo[a,d]cycloheptene-8-carbonyl]-guanidine;
N-[4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[4-Chloro-2-(4-cyclopentyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[4-Chloro-2-(4-isopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[2-(4-Benzyl-2-oxo-piperazin-1-yl)-4-chloro-6-methyl-10,10-dioxo-10,11-dihydro-5-oxa-10lambda*6*-thia-dibenzo[a,d]cycloheptene-8-carbonyl]-guanidine;
N-{4-Chloro-6-methyl-2-[2-(4-methylpiperazin-1-yl)-ethylamino]-10,10-dioxo-10,11-dihydro-5-oxa-10lambda*6*-thia-dibenzo[a,d]cycloheptene-8-carbonyl}-guanidine;
1-Carboxymethyl-1-[2-(4-chloro-8-guanidinocarbonyl-6-methyl-10,10-dioxo-10,11-dihydro-5-oxa-10lambda*6*-thia-dibenzo[a,d]cyclohepten-2-ylamino)-ethyl]-4-methylpiperazin-1-ium;
N-[4-Chloro-2-(2-imidazol-1-yl-ethylamino)-6-methyl-10,10-dioxo-10,11-dihydro-5-oxa-10lambda*6*-thia-dibenzo[a,d]cycloheptene-8-carbonyl]-guanidine;
N-[2-(2-Amino-ethylamino)-4-chloro-6-methyl-10,10-dioxo-10,11-dihydro-5-oxa-10lambda*6*-thia-dibenzo[a,d]cycloheptene-8-carbonyl]-guanidine;
N-[4-Chloro-6-methyl-2-(2-morpholin-4-yl-ethylamino)-10,10-dioxo-10,11-dihydro-5-oxa-10lambda*6*-thia-dibenzo[a,d]cycloheptene-8-carbonyl]-guanidine;
N-{4-Chloro-2-[ethyl-(2-morpholin-4-yl-ethyl)-amino]-6-methyl-10,10-dioxo-10,11-dihydro-5-oxa-10lambda*6*-thia-dibenzo[a,d]cycloheptene-8-carbonyl}-guanidine;
N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-morpholin-4-yl-ethyl)-acetamide;
N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-morpholin-4-yl-ethyl)-acetamide;
N-(4-Chloro-2-{2-[4-(2-hydroxy-ethyl)-piperazin-1-yl]-ethylamino}-6-methyl-10,10-dioxo-10,11-dihydro-5-oxa-10lambda*6*-thia-dibenzo[a,d]cycloheptene-8-carbonyl)-guanidine;
N-[4-Chloro-6-methyl-2-(2-methylamino-ethylamino)-10,10-dioxo-10,11-dihydro-5-oxa-10lambda*6*-thia-dibenzo[a,d]cycloheptene-8-carbonyl]-guanidine;

N-[4-Chloro-6-methyl-10,10-dioxo-2-(2-pyrrolidin-1-yl-ethylamino)-10,10-dioxo-10,11-dihydro-5-oxa-10lambda*6*-thia-dibenzo[a,d]cycloheptene-8-carbonyl]-guanidine;

N-{4-Chloro-2-[ethyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carbonyl}-guanidine;

(4-Chloro-8-guanidinocarbonyl-6-methyl-10,10-dioxo-10,11-dihydro-5-oxa-10lambda*-6*-thia-dibenzo[a,d]cyclohepten-2-yl)-(2-pyrrolidin-1-yl-ethyl)-carbamic acid isobutylester;

1-Carboxymethyl-1-[2-(4-chloro-8-guanidinocarbonyl-6-methyl-10,10-dioxo-10,11-dihydro-5-oxa-10-lambda*6*-thia-dibenzo[a,d]cyclohepten-2-ylamino)-ethyl]-pyrrolidinium;

Cyclopropanecarboxylic acid (4-chloro-8-guanidinocarbonyl-6-methyl-10,10-dioxo-10,11-dihydro-5-oxa-10lambda*6*-thia-dibenzo[a,d]cyclohepten-2-yl)-(2-pyrrolidin-1-yl-ethyl)-amide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-pyrrolidin-1-yl-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-pyrrolidin-1-yl-ethyl)-acetamide;

N-{4-Chloro-6-methyl-2-[2-(2-morpholin-4-yl-ethylamino)-ethylamino]-10,10-dioxo-10,11-dihydro-5-oxa-10lambda*6*-thia-dibenzo[a,d]cycloheptene-8-carbonyl}-guanidine;

N-{4-Chloro-6-methyl-2-[2-(2-morpholin-4-ylamino)-ethylamino]-10,10-dioxo-10,11-dihydro-5-oxa-10lambda*6*-thia-dibenzo[a,d]cycloheptene-8-carbonyl}-guanidine;

N-[4-Chloro-2-(2-cyclopropylamino-ethylamino)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-2-(3-morpholin-4-yl-propylamino)-10,10-dioxo-10,11-dihydro-5-oxa-10lambda*6*-thia-dibenzo[a,d]cycloheptene-8-carbonyl]-guanidine;

N-{4-Chloro-6-methyl-10,10-dioxo-2-[2-(2-pyridin-2-yl-ethylamino)-ethylamino]-10,11-dihydro-5-oxa-10lambda*6*-thia-dibenzo[a,d]cycloheptene-8-carbonyl}-guanidine;

N-(4-Chloro-2-{2-[(furan-2-ylmethyl)-amino]-ethylamino-}-6-methyl-10,10-dioxo-10,11-dihydro-5-oxa-10lambda*6*-thia-dibenzo[a,d]cycloheptene-8-carbonyl)-guanidine;

N-(4-Chloro-2-{ethyl-[2-(ethyl-furan-2-ylmethyl-amino)-ethyl]-amino-}-6-methyl-10,10-dioxo-10,11-dihydro-5-oxa-10lambda*6*-thia-dibenzo[a,d]cycloheptene-8-carbonyl)-guanidine;

N-(4-Chloro-6-methyl-10,10-dioxo-2-{2-[(thiophen-2-ylmethyl)-amino]-ethylamino}-10,11-dihydro-5-oxa-10lambda*6*thia-dibenzo[a,d]cycloheptene-8-carbonyl)-guanidine;

N-(4-Chloro-2-{ethyl-[2-(ethyl-thiophen-2-ylmethyl-amino)-ethyl]-amino}-6-methyl-10,10-dioxo-10,11-dihydro-5-oxa-10lambda*6*-thia-dibenzo[a,d]cycloheptene-8-carbonyl)-guanidine;

N-[2-(2-Benzylamino-ethylamino)-4-chloro-6-methyl-10,10-dioxo-10,11-dihydro-5-oxa-10lambda*6*-thia-dibenzo[a,d]cycloheptene-8-carbonyl]-guanidine;

N-(2-{[2-(Benzyl-ethyl-amino)-ethyl]-ethyl-amino}-4-chloro-6-methyl-10,10dioxo-10,11-dihydro-5-oxa-10lambda*6*-thia-dibenzo[a,d]cycloheptene-8-carbonyl)-guanidine;

N-{4-Chloro-2-[2-(2-methoxy-benzylamino)-ethylamino]-6-methyl-10,10-dioxo-10,11-dihydro-5-oxa-10lambda*6*-thia-dibenzo[a,d]cycloheptene-8-carbonyl}-guanidine;

N-(4-Chloro-2-{2-[ethyl-(2-methoxy-benzyl)-amino]-ethylamino}-6-methyl-10,10-dioxo-10,11-dihydro-5-oxa-10lambda*6*-thia-dibenzo[a,d]cycloheptene-8-carbonyl)-guanidine;

N-[4-Chloro-6-methyl-10,10-dioxo-2-(2-piperidin-1-yl-ethylamino]-10,11-dihydro-5-oxa-10lambda*6*-thia-dibenzo[a,d]cycloheptene-8-carbonyl)-guanidine;

N-{4-Chloro-2-[ethyl-(2-piperidin-1-yl-ethyl)-amino]-6-methyl-10,10-dioxo-10,11-dihydro-5-oxa-10lambda*6*-thia-dibenzo[a,d]cycloheptene-8-carbonyl}-guanidine;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-hydroxy-N-(2-piperidin-1-yl-ethyl)-acetamide;

Cyclopropanecarboxylic acid (4-chloro-8-guanidinocarbonyl-6-methyl-10,10-dioxo-10,11-dihydro-5-oxa-10lambda*6*-thia-dibenzo[a,d]cyclohepten-2-yl)-(2-piperidin-1-yl-ethyl)-amide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2,2-dimethyl-N-(2-piperidin-1-yl-ethyl)-propionamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-piperidin-1-yl-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-piperidin-1-yl-ethyl)-acetamide;

N-(4-Chloro-2-(2-dimethylamino-ethylamino)-6-methyl-10,10-dioxo-10,11-dihydro-5-oxa-10lambda*6*-thia-dibenzo[a,d]cyclohepten-8-carbonyl-guanidine;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-2,2-dimethyl-propionamide;

N-[4-Chloro-6-methyl-2-(4-methylpiperazin-1-yl)-10,10-dioxo-10,11-dihydro-5-oxa-10lambda*6*-thia-dibenzo[a,d]cycloheptene-8-carbonyl]-guanidine;

N-(4-Chloro-6-methyl-10,10-dioxo-2-piperazin-1-yl-10,11-dihydro-5-oxa-10lambda*6*-thia-dibenzo[a,d]cycloheptene-8-carbonyl)-guanidine;

N-[4-Chloro-2-(4-decyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-10,10-dioxo-2-(4-pentyl-piperazin-1-yl)-10,11-dihydro-5-oxa-10-lambda*6*-thia-dibenzo[a,d]cycloheptene-8-carbonyl]-guanidine;

N-[4-Chloro-2-(4-cyclopropanecarbonyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{4-Chloro-2-[4-(4-dimethylamino-benzyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-{4-Chloro-2-[4-(2,4-dichloro-benzyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-{4-Chloro-6-methyl-10,10-dioxo-2-[4-(1H-pyrrole-2-carbonyl)-piperazin-1-yl]-10,11-dihydro-5-oxa-10lambda*6*-thia-dibenzo[a,d]cycloheptene-8-carbonyl}-guanidine;

N-{4-Chloro-6-methyl-2-[4-(5-methyl-furan-2-ylmethyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-2-[4-(2-methyl-benzyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-2-[4-(5-methyl-thiophen-2-ylmethyl)-piperazin-1-yl]-10,10-dioxo-10,11-dihydro-5-oxa-10lambda*6*-1-thia-dibenzo[a,d]cycloheptene-8-carbonyl}-guanidine;

N-{4-Chloro-2-[4-(3,4-dimethoxy-benzyl)-piperazin-1-yl]-6-methyl-10,10-dioxo-10,11-dihydro-5-oxa-10lambda*6*-thia-dibenzo[a,d]cycloheptene-8-carboxy}-guanidine;

N-{4-Chloro-6-methyl-10,10-dioxo-2-[4-(4-trifluoromethyl-benzyl)-piperazin-1-yl]-10,11-dihydro-5-oxa-10lambda*6*-thia-dibenzo[a,d]cycloheptene-8-carbonyl}-guanidine;

N-[4-Chloro-2-(4-ethyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-2-morpholin-4-yl-10,10-dioxo-10,11-dihydro-5-oxa-10lambda*6*-thia-dibenzo[a,d]cycloheptene-8-carbonyl]-guanidine;

N-[2-(4-Benzyl-piperazin-1-yl)-4-chloro-6-methyl-10,10-dioxo-10,11-dihydro-5-oxa-10lambda*6*-thia-dibenzo[a,d]cycloheptene-8-carbonyl]-guanidine;

N-{4-Chloro-2-[4-(2-dimethylamino-ethyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-[4-Chloro-2-(4-isopropyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{4-Chloro-6-methyl-2-[4-(2-morpholin-4-yl-ethyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-10,10-dioxo-2-[4-(2-pyrrolidin-1-yl-ethyl)-piperazin-1-yl]-10,11-dihydro-5-oxa-10lambda*6*-thia-dibenzo[a,d]cycloheptene-8-carbonyl}-guanidine;

N-[4-Chloro-2-(4-cyclopropylmethyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{4-Chloro-6-methyl-10,10-dioxo-2-[4-(2-piperazin-1-yl-ethyl)-piperazin-1-yl]-10,11-dihydro-5-oxa-10lambda*6*-thia-dibenzo[a,d]cycloheptene-8-carbonyl}-guanidine;

N-[4-Chloro-2-(4-cyclopropyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{2-[4-(3-Amino-benzyl)-piperazin-1-yl]-4-chloro-6-methyl-10,10-dioxo-10,11-dihydro-5-oxa-10lambda*6*-thia-dibenzo[a,d]cycloheptene-8-carbonyl}-guanidine;

N-[4-Chloro-6-methyl-10,10-dioxo-2-(4-pyridin-3-ylmethyl-piperazin-1-yl)-10,11-dihydro-5-oxa-10lambda*6*-thia-dibenzo[a,d]cycloheptene-8-carbonyl]-guanidine;

N-[4-Chloro-2-(4-cyclobutyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-2-(4-cyclohexyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-10,10-dioxo-2-(4-thiophen-2-ylmethyl-piperazin-1-yl)-10,11-dihydro-5-oxa-10lambda*6*-thia-dibenzo[a,d]cycloheptene-8-carbonyl]-guanidine;

N-{4-Chloro-2-[4-(2-methoxy-benzyl)-piperazin-1-yl]-6-methyl-10,10-dioxo-10,11-dihydro-5-oxa-10lambda*6*-1-thia-dibenzo[a,d]cycloheptene-8-carbonyl}-guanidine;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-piperidin-1-yl-acetamide;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-(2,2,2-trifluoro-ethylamino)-acetamide;

N-(4-Chloro-8-guanidinocarbonyl-6-methyl-10,10-dioxo-10,11-dihydro-5-oxa-10lambda*-6*-thia-dibenzo[a,d]cycloheptene-2-yl)-2-hydroxy-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-imidazol-1-yl-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclopropylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclohexylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclopentylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-isopropylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-dimethylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cycylobutylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-morpholin-4-yl-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-[4-(3-trifluoromethyl-phenyl)-piperazin-1-yl]-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methylamino-acetamide dimesylate;

N-(4-Chloro-8-guanidinocarbonyl-6-methyl-10,10-dioxo-10,11-dihydro-5-oxa-10lambda*6*-thia-dibenzo[a,d]-cyclohepten-2-yl)-2-pyrrolidine-1-yl-acetamide;

N-{2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carbonyl}-guanidine;

N-(2-Amino-4-chloro-6,11,11-trimethyl-10,10-dioxo-10,11-dihydro-5-oxa-10lambda*6*-thia-dibenzo[a,d]cycloheptene-8-carbonyl)-guanidine;

N-(4-Chloro-8-guanidinocarbonyl-6-methyl-10,10-dioxo-10,11-dihydro-5-oxa-10-lambda*6*-thia-dibenzo[a,d]cycloheptene-2-yl)-2-cyclopropylamino-N-(2-pyrrolidin-1-yl-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclopenten-2-yl)-2-(4-methyl-piperazin-1-yl)-acetamide;

N-{4-Chloro-6-methyl-10,10-dioxo-2-[4-(tetrahydro-furan-2-ylmethyl)-piperazin-1-yl]-10,11-dihydro-5-oxa-10lambda*6*-thia-dibenzo[a,d]cycloheptene-8-carbonyl}-guanidine;

N-(2-Amino-4-chloro-6-methyl-10-oxo-10,11-dihydro-5-oxa-10lambda*4*-thia-dibenzo[a,d]cycloheptene-8-carbonyl)-guanidine;

N-(6-Methyl-10,10-dioxo-10,11-dihydro-5-oxa-10lambda*6*-thia-11-aza-dibenzo[a,d]cycloheptene-8-carbonyl)-guanidine;

N-[4-Chloro-6-methyl-2-(1-methyl-pyrrolidin-2ylidineamino)-10,10-dioxo-10,11-dihydro-5-oxa-10lambda*6*-thia-dibenzo[a,d]cycloheptene-8-carbonyl]-guanidine;

2-(4-Benzyl-piperazin-1-yl)-4-chloro-6-methyl-10,10-dioxo-10,11-dihydro-5-oxa-10lambda*6*-thia-dibenzo[a,d]cycloheptene-8-yl-methylene amino guanidine;

N-[4-Amino-6-methyl-10,10-dioxo-10,11-dihydro-5-oxa-10lambda*6*-thia-dibenzo[a,d]cycloheptene-8-carbonyl]-guanidine;

N-[6-Methyl-4-(2-morpholin-4-yl-ethylamino)-10,10-dioxo-10,11-dihydro-5-oxa-10lambda*6*-thia-dibenzo[a,d]cycloheptene-8-carbonyl]-guanidine;

N-{4-Chloro-2-[(3H-imidazol-4-ylmethyl)-amino]-6-methyl-10,10-dioxo-10,11-dihydro-5-oxa-10lambda*6*-thia-dibenzo[a,d]cycloheptene-8-carbonyl}-guanidine;

N-{4-Chloro-6-methyl-2-[(5-methyl-thiophen-2-ylmethyl)-amino]-10,10-dioxo-10,11-dihydro-5-oxa-10lambda*6*-thia-dibenzo[a,d]cycloheptene-8-carbonyl}-guanidine;

N-{4-Chloro-6-methyl-10,10-dioxo-2-[(pyridin-3-ylmethyl)-amino]-10,11-dihydro-5-oxa-10lambda*6*-thia-dibenzo[a,d]cycloheptene-8-carbonyl}-guanidine;

N-(10,10-Dioxo-10,11-dihydro-5H-10lambda*6*-thia-5-aza-dibenzo[a.d]cycloheptene-8-carbonyl)-guanidine;

N-(2-Chloro-10,10-dioxo-10,11-dihydro-5H-10lambda*6*-thia-5-aza-dibenzo[a.d]cycloheptene-8-carbonyl)-guanidine;

N-(4-Chloro-10,10-dioxo-10,11-dihydro-5H-10lambda*6*-thia-5-aza-dibenzo[a.d]cycloheptene-8-carbonyl)-guanidine;

N-(3-Chloro-10,10-dioxo-10,11-dihydro-5H-10lambda*6*-thia-5-aza-dibenzo[a.d]cycloheptene-8-carbonyl)-guanidine;

N-(1-Chloro-10,10-dioxo-10,11-dihydro-5H-10lambda*6*-thia-5-aza-dibenzo[a.d]cycloheptene-8-carbonyl)-guanidine;

N-(3-Fluoro-10,10-dioxo-10,11-dihydro-5H-10lambda*6*-thia-5-aza-dibenzo[a.d]cycloheptene-8-carbonyl)-guanidine;

N-(2-Fluoro-10,10-dioxo-10,11-dihydro-5H-10lambda*6*-thia-5-aza-dibenzo[a.d]cycloheptene-8-carbonyl)-guanidine;

N-(2-Ethanesulfonyl-4-methyl-10,10-dioxo-10,11-dihydro-5H-10lambda*6*-thia-5-aza-dibenzo[a.d]cycloheptene-8-carbonyl)-guanidine;

N-(7-Chloro-10,10-dioxo-10,11-dihydro-5H-10lambda*6*-thia-5-aza-dibenzo[a.d]cycloheptene-8-carbonyl)-guanidine;

N-(4,7-Dichloro-10,10-dioxo-10,11-dihydro-5H-10lambda*6*-thia-5-aza-dibenzo[a.d]cycloheptene-8-carbonyl)-guanidine;

N-(4-tert-Butyl-7-chloro-10,10-dioxo-10,11-dihydro-5H-10lambda*6*-thia-5-aza-dibenzo[a.d]cycloheptene-8-carbonyl)-guanidine;

N-(7-Chloro-4-methyl-10,10-dioxo-10,11-dihydro-5H-10lambda*6*-thia-5-aza-dibenzo[a.d]cycloheptene-8-carbonyl)-guanidine;

N-(7-Chloro-1-fluoro-10,10-dioxo-10,11-dihydro-5H-10lambda*6*-thia-5-aza-dibenzo[a.d]cycloheptene-8-carbonyl)-guanidine;

N-(2,7-Dichloro-10,10-dioxo-10,11-dihydro-5H-10lambda*6*-thia-5-aza-dibenzo[a.d]cycloheptene-8-carbonyl)-guanidine;

N-(7-Chloro-2-fluoro-10,10-dioxo-10,11-dihydro-5H-10lambda*6*-thia-5-aza-dibenzo[a.d]cycloheptene-8-carbonyl)-guanidine;

N-(7-Chloro-2-ethanesulfonyl-4-methyl-10,10-dioxo-10,11-dihydro-5H-10lambda*6*-thia-5-aza-dibenzo[a.d]cycloheptene-8-carbonyl)-guanidine;

N-(1,7-Dichloro-10,10-dioxo-10,11-dihydro-5H-10lambda*6*-thia-5-aza-dibenzo[a.d]cycloheptene-8-carbonyl)-guanidine;

N-(7-Methyl-10,10-dioxo-10,11-dihydro-5H-10lambda*6*-thia-5-aza-dibenzo[a.d]cycloheptene-8-carbonyl)-guanidine;

N-(4,7-Dimethyl-10,10-dioxo-10,11-dihydro-5H-10lambda*6*-thia-5-aza-dibenzo[a.d]cycloheptene-8-carbonyl)-guanidine;

N-(4-Chloro-7-methyl-10,10-dioxo-10,11-dihydro-5H-10lambda*6*-thia-5-aza-dibenzo[a.d]cycloheptene-8-carbonyl)-guanidine;

N-(4,6-Dimethyl-10,10-dioxo-10,11-dihydro-5H-10lambda*6*-thia-5-aza-dibenzo[a.d]cycloheptene-8-carbonyl)-guanidine;

N-(1-Fluoro-6-methyl-10,10-dioxo-10,11-dihydro-5H-10lambda*6*-thia-5-aza-dibenzo[a.d]cycloheptene-8-carbonyl)-guanidine;

N-(4-Chloro-6-methyl-10,10-dioxo-10,11-dihydro-5H-10lambda*6*-thia-5-aza-dibenzo[a.d]cycloheptene-8-carbonyl)-guanidine;

N-(6-Methyl-10,10-dioxo-10,11-dihydro-5H-10lambda*6*-thia-5-aza-dibenzo[a.d]cycloheptene-8-carbonyl)-guanidine;

N-(10,10-Dioxo-7-pyrrol-1-yl-10,11-dihydro-5H-10lambda*6*-thia-5-aza-dibenzo[a.d]cycloheptene-8-carbonyl)-guanidine;

N-(7-Benzylamino-10,10-dioxo-10,11-dihydro-5H-10lambda*6*-thia-5-aza-dibenzo[a.d]cycloheptene-8-carbonyl)-guanidine;

N-(5-Methyl-10,10-dioxo-10,11-dihydro-5H-10lambda*6*-thia-5-aza-dibenzo[a.d]cycloheptene-8-carbonyl)-guanidine;

N-(5-Allyl-10,10-dioxo-10,11-dihydro-5H-10lambda*6*-thia-5-aza-dibenzo[a.d]cycloheptene-8-carbonyl)-guanidine;

N-(4-Chloro-5,6,11-trimethyl-10,10-dioxo-10,11-dihydro-5H-10lambda*6*-thia-5-aza-dibenzo[a.d]cycloheptene-8-carbonyl)-guanidine;

N-(10,10-Dioxo-10,11-dihydro-5H-10lambda*6*-thia-5-aza-dibenzo[a.d]cycloheptene-2-carbonyl)-guanidine;

N-(10,10-Dioxo-10,11-dihydro-5H-10lambda*6*-thia-5-aza-dibenzo[a.d]cycloheptene-1-carbonyl)-guanidine;

N-{4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-(2-Aminomethyl-4-chloro-6-methyl-10,10-dioxo-10,11-dihydro-5-oxa-10lambda*6*-thia-dibenzo[a.d]cycloheptene-8-carbonyl)-guanidine;

N-(4-chloro-2-diethylaminomethyl-6-methyl-10,10-dioxo-10,11-dihydro-5-oxa-10lambda*6*-thia-dibenzo[a,d]cycloheptene-8-carbonyl)-guanidine;

N-(4-Chloro-6-methyl-10,10-dioxo-2-pyrrol-1-ylmethyl-10,11-dihydro-5-oxa-10lambda*6*-thia-dibenzo[a,d]cycloheptene-8-carbonyl)-guanidine; and N-[2-(Benzylamino-methyl)-4-chloro-6-methyl-10,10-dioxo-10,11-dihydro-5-oxa-10lambda*6*-thia-dibenzo[a,d]cycloheptene-8-carbonyl]-guanidine.

All the compounds of the present invention also include all stereoisomeric forms and mixtures thereof in all ratios and their pharmaceutically acceptable salts, solvates and polymorphs. Furthermore, all the compounds of the present invention are a subject of the present invention in the form of their prodrugs and other derivatives, for example in the form of their esters and amides.

The present invention further relates to intermediates of the formula 2 and salts thereof:

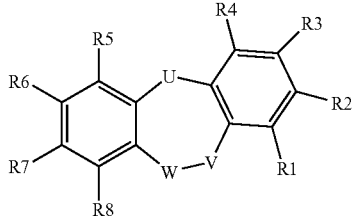

2 wherein:
R7 is C(=O)Y, wherein Y is hydrogen, hydroxyl, ($C_1$-$C_{10}$) alkoxy, cyclo($C_3$-$C_{10}$)alkyl-O—, halogen, ($C_6$-$C_{10}$)aryloxy or a nitrogen heterocyclyl, and U, V, W, R1, R2, R3, R4, R5, R6 and R8 are as defined in any one of formula 1, 1a, 1b or 1c above.

In alternative embodiments of the intermediates of the formula 2, the substituents R1 to R8, U, V and W independently from each other have the following meanings:
R7 is C(=O)Y, wherein Y is hydrogen, halogen, or a 5- or 6-membered nitrogen heterocyclyl, such as imidazolyl;
U is C(O), $CR^aR^b$ or $NR^a$;
wherein $R^a$ is H, alkyl, cycloalkyl or alkenyl; $R^b$ is H, OH, $OR^a$ or $OCOR^a$ A process for the preparation of a compound of formula 1:

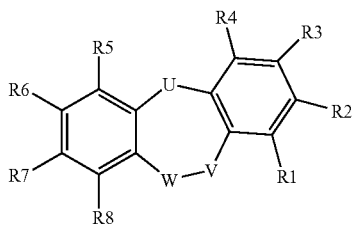

1 wherein:
U, V and W are as defined above and at least one of R1, R2, R3, R4, R5, R6, R7 and R8 is —C(O)N=C(NH$_2$)$_2$, and the remaining groups R1 to R8 are as defined above, comprises reacting a compound of the formula 3 below:

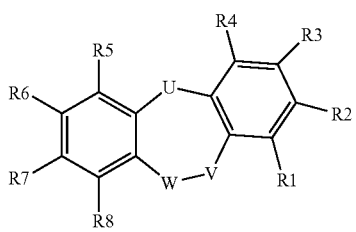

3 wherein:
U, V and W are as defined above and at least one of R1, R2, R3, R4, R5, R6, R7 and R8 is —C(O)Y, wherein Y is a leaving group, and the remaining groups R1 to R8 are as defined above, with guanidine to form the title compound of formula 1, and, optionally, treating with an acid or base as appropriate to convert the compound of formula 1 into a pharmaceutically acceptable salt.

Suitable leaving groups (Y) are known to the skilled person and may be a halide, ($C_1$-$C_{10}$)alkoxy, ($C_3$-$C_{10}$)cycloalkyloxy, ($C_6$-$C_{10}$)aryloxy, a nitrogen heterocyclyl, such as imidazolyl, or the like.

In a preferred process, the groups U, V and W in formula 1 and 3 are as follows: U is O or NH; V is $CH_2$; W is $SO_2$.

In one embodiment, the process for the preparation of a compound of formula 1

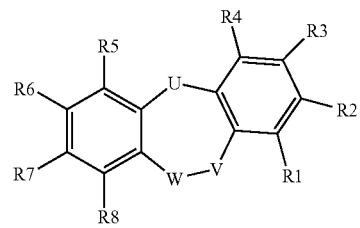

1 wherein:
U is O or NH; V is $CH_2$; W is $SO_2$, at least one of R1, R2, R3, R4, R5, R6, R7 and R8 is —CON=C(NH$_2$)$_2$, and the remaining groups are as defined above, comprises alkylating an appropriately substituted o-halo mercaptobenzoic acid of formula A below;

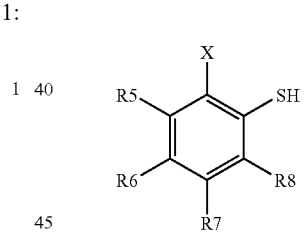

A wherein X is a halogen, at least one of R5, R6, R7 and R8 is an alkyl carboxylate and the remaining groups are as defined above, with an appropriately substituted 1-halomethyl-2-(protected)hydroxybenzene or 1-halomethyl-2-nitrobenzene of formula B below:

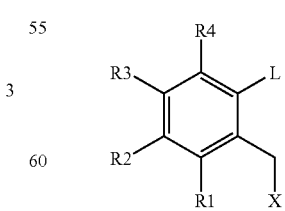

B wherein X is a halogen, L is either protected hydroxy or nitro and at least one of R1, R2, R3 and R4 is an alkyl carboxylate group and the remaining groups are as defined above, to obtain a sulfanyl compound of formula C below:

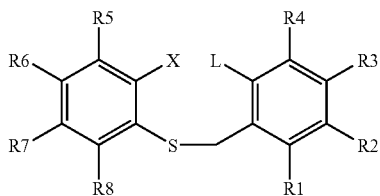

C wherein X and L are as defined above; at least one of R1, R2, R3, R4, R5, R6, R7 and R8 is an alkyl carboxylate group and the remaining groups are as defined above; oxidizing the compound of formula C to its sulfonyl derivative of formula D;

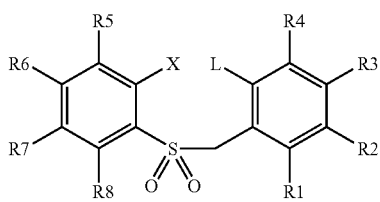

D wherein X and L are as defined above; and at least one of R1, R2, R3, R4, R5, R6, R7 and R8 is an alkyl carboxylate group and the remaining groups are as defined above; and a) where L is nitro, subjecting the resulting sulfonyl derivative of formula D to reduction; or b) where L is a protected hydroxy group, subjecting the resulting sulfonyl derivative of formula D to deprotection of the hydroxy group, to obtain the compound of formula D wherein L is amino or hydroxy; cyclising the resulting compound D (wherein L is amino or hydroxy; and X and R1, R2, R3, R4, R5, R6, R7 and R8 are as defined above) to obtain the cyclised intermediate of formula E below:

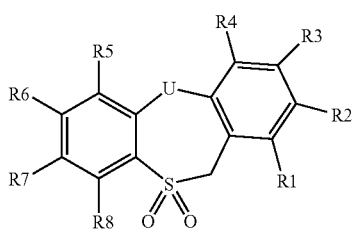

E wherein U is O or NH and at least one of R1, R2, R3, R4, R5, R6, R7 and R8 is an alkyl carboxylate group, and the remaining groups are as defined above; and either c) treating the compound of formula E with guanidine under suitable reaction conditions, to obtain the title compound of formula 1, or d) subjecting the compound of formula E to hydrolysis under acidic or alkaline conditions followed by converting the resulting compound of formula E (wherein U is O or NH and at least one of R1, R2, R3, R4, R5, R6, R7 and R8 is —COOH, and the remaining groups are as defined above) to its acid chloride or an active ester under suitable reaction conditions, and treating the resulting compound with guanidine under suitable reaction conditions, to obtain the title compound of formula 1.

According to a further feature of the present invention there are provided processes for the synthesis of compounds of the present invention of formula 1, including compounds of the formulae 1a, 1b and 1c.

The compounds of the present invention can be prepared in a number of ways using methods well known to the skilled person. Examples of methods to prepare the present compounds are described below and illustrated in Schemes I and II. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention are referred to with general symbols namely A, A-i, A-ii, A-iii, A-iv, B, B-i, B-ii, C, D, E, E1, G-i, P, Q, Q1, Q2, S, T, Y and Z, of which the compounds designated as A, B, C, D, E, E1, P, Q, Q1, Q2, S, T, Y and Z are key intermediates. The key intermediates B, C, D, E and E1 may represent more than one type of compound depending on the definition of the groups U, V and L. For instance:

1. In the intermediates of general formula B, C and D, the substituent L may represent a group selected from amino, nitro or a protected hydroxy group, wherein the protective group may be selected from t-butyl-dimethylsilyl(TBDMS) or acetyl, and the like;

2. In the intermediate of general formula E, the group U may be selected from O, NH, CH(OH), C(O) or $CH_2$;

3. In the intermediate of general formula E1, the group U may be selected from O or NH; and V may be selected from $CH_2$ or NH.

Throughout the process description, the corresponding substituent groups in the various formulae representing starting compounds and intermediates have the same meanings as that for the compounds of formula 1, 1a, 1b or 1c unless stated otherwise.

A general route for the synthesis of compounds of the present invention involves: alkylation of an appropriately substituted o-bromo mercaptobenzoic acid (A) with an appropriately substituted (2-halomethylphenoxy) tert-butyldimethylsilane (B), followed by oxidation of the resulting sulfanyl derivative (C) to its sulfonyl derivative (D). The sulfonyl derivative (D), thus obtained may then be subjected to deprotection of the silyl ether group followed by in situ cyclisation and a series of reaction steps (understood by those skilled in the art) for suitable modification of the functional groups, to obtain a desired compound of the invention, more particularly a compound of the formula 1. Alternatively, the sulfanyl derivative (C) may be subjected to a series of reactions involving desilylation and cyclisation, followed by nitration which may result into partial oxidation of the ring sulfur atom into its sulfoxide (Q1), which may be converted to a desired compound of the invention, more particularly to a compound of the formula 1 by standard procedures known to those skilled in the art.

Alternatively, alkylation of an appropriately substituted o-bromo mercaptobenzoic acid (A) may be carried out with an appropriately substituted 1-halomethyl-2-nitrobenzene (B) to obtain a sulfanyl derivative (C) which may then be oxidized to its sulfonyl derivative (D). The resulting sulfonyl derivative (D) wherein L is NO₂ may be subjected to reduction with an appropriate reducing agent for the conversion of nitro to amino group, followed by cyclisation and a series of reaction steps (understood by those skilled in the art) for suitable modification of the functional groups, to obtain a desired compound of the invention, more particularly a compound of the formula 1.

Another general route for the synthesis of compounds of the present invention may involve condensation of an appropriately substituted o-bromo-chlorosulfonyl-benzoic acid (S) with an appropriately substituted o-aminophenol (T) and subsequent cyclisation of the resulting intermediate. The resulting cyclised intermediate may be converted to a desired compound of the present invention, more particularly to a compound of formula 1, by subjecting it to a series of reaction steps (understood by those skilled in the art) for suitable modification of the functional groups.

Suitable processes for the preparation of compounds of the present invention are described below and illustrated in Scheme I:

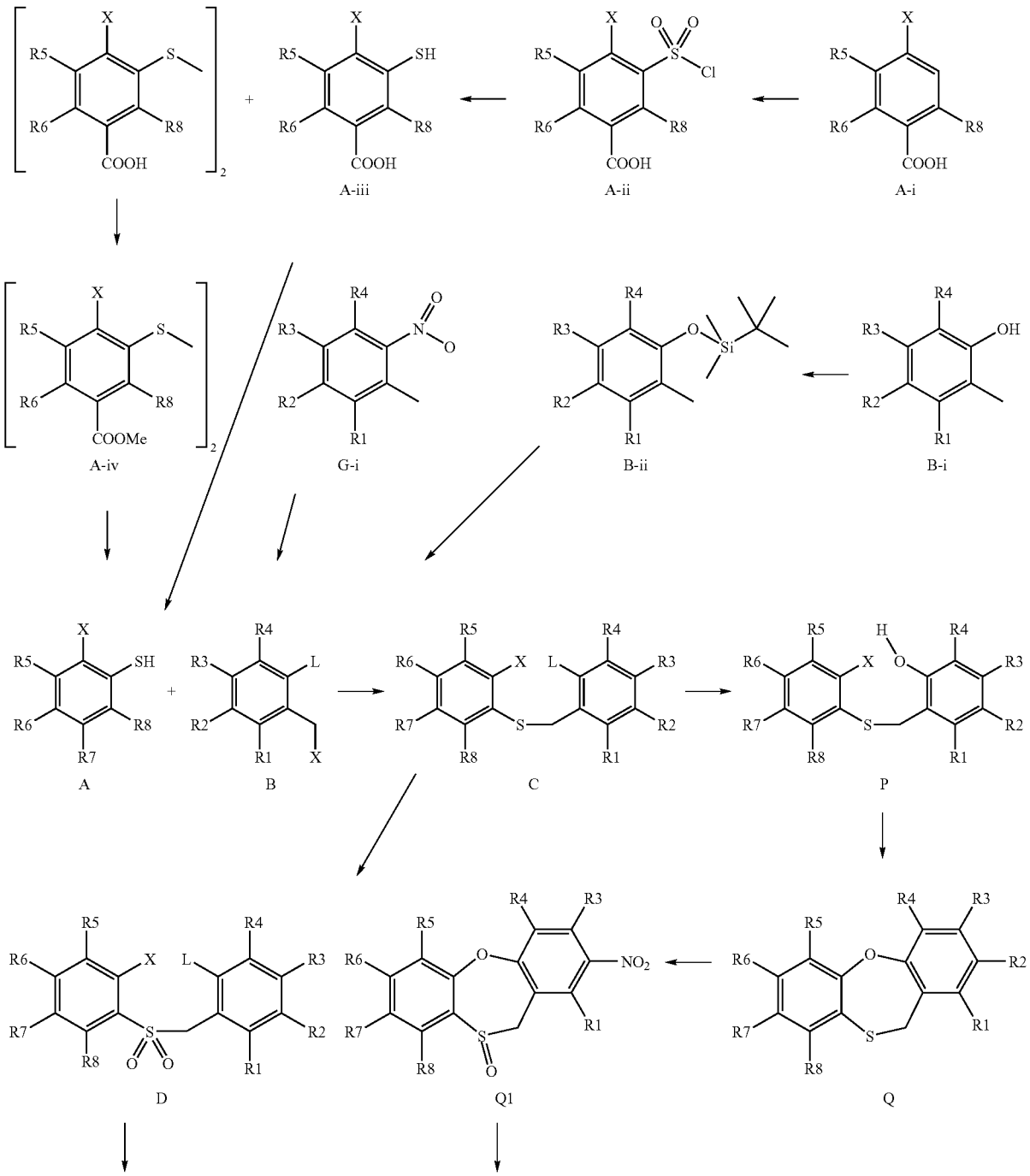

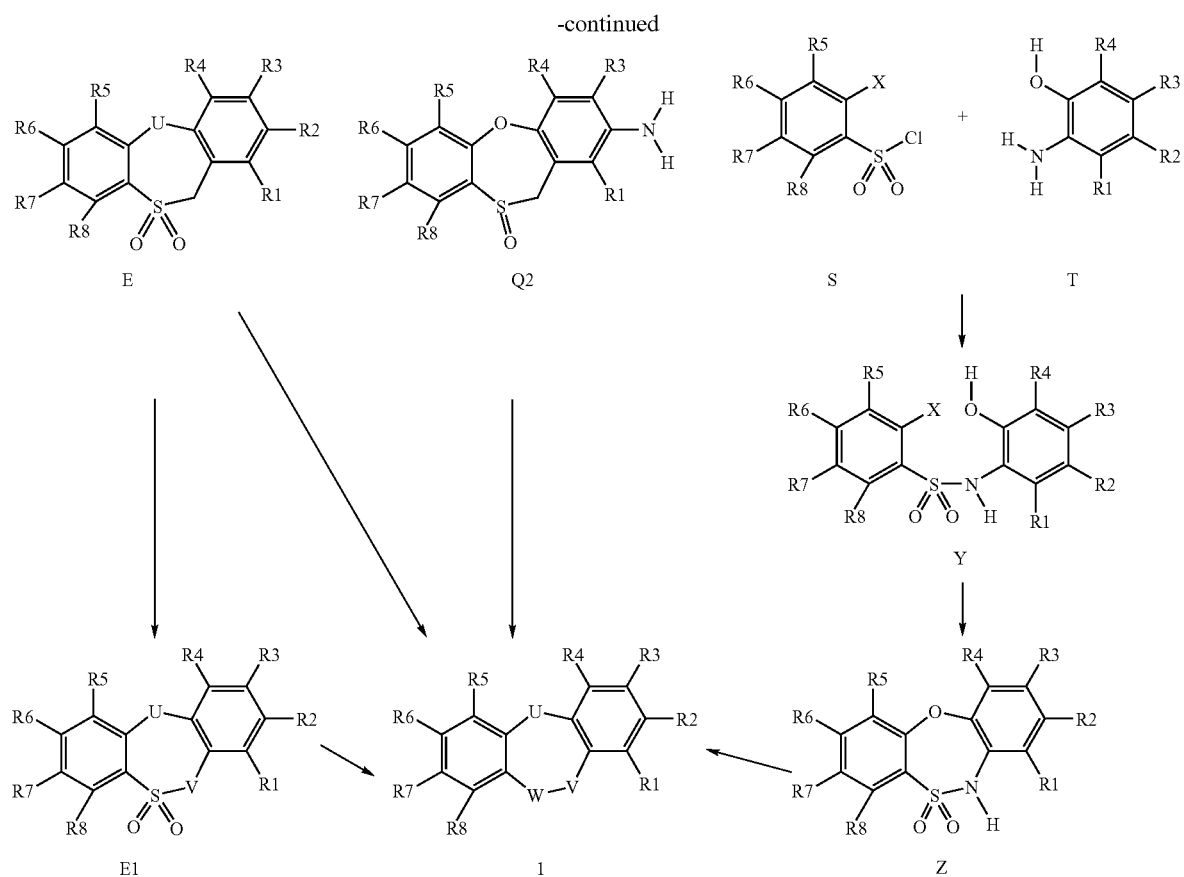

Process 1: Preparation of Key Intermediates of General Formulae E and E1:

Step (i): Preparation of the Compounds of General Formula C:

A thiol compound of the general formula A (wherein R5, R6 & R8 are as defined herein above; R7 represents alkyl carboxylate; X represents halogen, preferably Br) may be subjected to a nucleophilic substitution, more particularly to an S alkylation, with a compound of the general formula B (wherein R1, R2, R3 & R4 are as defined herein above; X represents halogen, preferably Br; and L represents a protected hydroxy group, such as t-butyl-dimethylsilyloxy), in the presence of a base in an aprotic solvent, over a time period of 0.5 h to 10 h, at a temperature range of 0° C. to ambient, in the presence or absence of an inert atmosphere using gases, such as $N_2$, Ar, He, and processed in a manner known to one skilled in the art to obtain the sulfanyl derivative, a compound of the general formula C (wherein R1, R2, R3, R4, R5, R6 & R8 are as defined herein above; R7 represents alkyl carboxylate; X represents halogen, preferably Br; and L represents a protected hydroxy group, such as a t-butyl-dimethylsilyloxy group).

When the thiol compound of the general formula A is alkylated with the compound of general formula B (wherein L represents $NO_2$), the key intermediate of formula C (wherein R1, R2, R3, R4, R5, R6 & R8 are as defined herein above; R7 represents alkyl carboxylate; X represents halogen, preferably Br; and L represents $NO_2$) is obtained.

The base used in the above substitution reaction may be an organic or an inorganic base. The organic base may be selected from: triethylamine, pyridine, lutidine, collidine and the like or a mixture thereof. The inorganic base may be selected from: sodium hydroxide, potassium hydroxide, sodium carbonate, potassium carbonate, sodium hydride, potassium hydride, sodamide, n-butyllithium, and the like. The amount of base used may range from 1 to 5 equivalents, preferably 1 to 3 equivalents of the starting compound of general formula A.

The aprotic solvent, in which the above substitution reaction is carried out, may be selected from: a hydrocarbon, such as hexane, benzene, toluene or xylene; a halogenated hydrocarbon, such as dichloroethane or chloroform; or an ether, such as tetrahydrofuran (THF), dioxane, diethyl ether or t-butyl methyl ether; or any other solvent, such as DMF or DMSO, suitable for carrying out the substitution reaction.

Step (ii): Conversion of the Compounds of Formula C to the Compounds of Formula D:

The compounds of the general formula C, as obtained in the above step (i) (wherein R1, R2, R3, R4, R5, R6 and R8 are as defined herein above, R7 represents alkyl carboxylate; L represents t-butyl-dimethylsilyloxy or $NO_2$; and X represents halogen, preferably Br), may be oxidized using an oxidizing agent selected from hydrogen peroxide, m-chloroperbenzoic acid (m-CPBA), potassium perchlorate or OXONE™, preferably m-CPBA, in the presence of an organic solvent selected from: a halogenated hydrocarbon, such as dichloromethane, or a protic solvent, such as methanol, ethanol and the like, at a temperature range of 0° C. to reflux, over a time period of 1 h to 8 h, and further processed in a manner known to one skilled in the art to obtain the corresponding sulfonyl derivative, a compound of the general formula D (wherein R1, R2, R3, R4, R5, R6 & R8 are as defined herein above; R7 represents alkyl carboxylate; L represents t-butyl-dimethylsilyloxy, or $NO_2$; and X represents halogen, preferably Br).

The compound of formula D (wherein L represents $NO_2$) may be subjected to reduction with an appropriate reducing agent to obtain its corresponding amine derivative, a compound of formula D (wherein R1, R2, R3, R4, R5, R6 & R8 are as defined herein above; R7 represents alkyl carboxylate; L represents $NH_2$; and X represents halogen, preferably Br).

The reduction reaction may be carried out using various reduction methods known to one skilled in the art, for example, by catalytic hydrogenation in the presence of a catalyst, such as Raney nickel, palladium-carbon, platinum-carbon, rhodium-carbon and the like. Other reduction methods, such as those involving use of sodium borohydride, sodium cyanoborohydride, tin-hydrochloric acid or iron-hydrochloric acid, may also be used for carrying out the reduction reaction. However, the reduction method, involving catalytic hydrogenation using Raney nickel as the catalyst, is the preferred method.

The organic solvent used for carrying out the reduction reaction may be selected from: N,N-dimethylformamide (DMF), tetrahydrofuran (THF), ethyl acetate, ethanol, methanol, toluene, benzene, diethyl ether and dioxane; with DMF being the preferred solvent.

Step (iii): Conversion of the Compounds of Formula D to the Compounds of Formula E.

The compound of the general formula D as obtained in the above step (ii) (wherein R1, R2, R3, R4, R5, R6 & R8 are as defined herein above; R7 represents alkyl carboxylate; L represents $NO_2$ or $NH_2$; and X represents halogen, preferably Br) may undergo cyclisation in the presence of an inorganic base, such as sodium hydride. The cyclisation reaction may be carried out in an aprotic solvent, such as DMF, in the presence or absence of an inert atmosphere, at a temperature range of 0° C. to 100° C., over a time period of 2 h to 24 h to obtain the cyclic intermediate, a compound of the general formula E (wherein R1, R2, R3, R4, R5, R6 & R8 are as defined herein above; R7 represents alkyl carboxylate; and U represents NH).

Alternatively, the compound of the general formula D (wherein R1, R2, R3, R4, R5, R6 & R8 are as defined herein above; R7 represents alkyl carboxylate; L represents t-butyl-dimethylsilyloxy; and X represents halogen, preferably Br) may be subjected to deprotection of the silyl ether group using a suitable deprotecting reagent, such as tetraalkylammonium fluoride, to obtain the corresponding hydroxy compound which may also undergo in situ cyclisation to obtain the cyclic intermediate, a compound of the general formula E (wherein R1, R2, R3, R4, R5, R6 & R8 are as defined herein above; R7 represents alkyl carboxylate; and U represents O).

Step (iv): Conversion of the Compound of Formula E to the Compound of Formula E1:

The compound of the general formula E as obtained in the above step (iii) (wherein R1, R2, R3, R4, R5, R6 & R8 are as defined herein above; R7 represents alkyl carboxylate, U represents O or NH; and V represents $CH_2$) may be subjected to alkylation with an alkyl halide, such as methyl iodide, in the presence of a base [selected from a group mentioned in Process 1—step (i)] in an aprotic solvent, such as N,N-dimethylformamide (DMF), dimethysulfoxide (DMSO), hexamethylphosphoramide (HMPA) or N-methylpyrrolidine (NMP), or in a solvent mixture of a protic and/or an aprotic solvent, in the presence or absence of a phase transfer catalyst, such as a quaternary ammonium salt selected from: tetrabutylammonium hydrogen sulfate and tetrabutylammonium chloride, at ambient temperature over a time period of 2 h to 10 h and processed in a manner known to one skilled in the art to obtain a dimethylated compound of the general formula E1 (wherein R1, R2, R3, R4, R5, R6 & R8 are as defined herein above; R7 represents alkyl carboxylate; U represents O or NH; and V represents $C(CH_3)_2$).

The compounds of the general formula E (wherein R1, R2, R3, R4, R5, R6 & R8 are as defined herein above; R7 represents alkyl carboxylate; and both U and V independently represent $CH_2$ or NH) when subjected to alkylation using an alkylating agent, such as methyl iodide or allyl bromide, in presence of a base, such as sodium hydroxide, in a solvent mixture of water and benzene and in the presence of a phase transfer catalyst, such as tetrabutylammonium hydrogen sulphate, at ambient temperature over a time period of 2 h to 24 h to obtain the monomethyl derivative, a compound of the general formula E1 (wherein R1, R2, R3, R4, R5, R6 & R8 are as defined herein above; R7 represents alkyl carboxylate; and both U and V independently represent $CHCH_3$, N—$CH_3$ or N-allyl).

Process 2: Preparation of the Key Intermediates of General Formulae P, Q, Q1 and Q2:

Step (i): Preparation of the Key Intermediate of General Formula P:

A compound of the general formula C as obtained in Process 1—step (i) (wherein R1, R2, R3, R4, R5, R6 and R8 are as defined herein above, R7 represents alkyl carboxylate; L represents t-butyl-dimethylsilyloxy; and X represents halogen, preferably Br) may be subjected to deprotection of the silyl ether group by treating the compound with a suitable deprotecting reagent in an appropriate organic solvent in the presence or absence of an inert atmosphere using a gas, such as nitrogen, at a temperature range of 0° C. to reflux over a time period of 0.5 h to 3 h (as reported in Tetrahedron, 41, 3257, (1985) ) to obtain the hydroxy intermediate, a compound of the general formula P (wherein R1, R2, R3, R4, R5, R6 and R8 are as defined herein above, R7 represents alkyl carboxylate; and X represents halogen, preferably Br).

The deprotecting agent used in the above step may be selected from: a chemoselective reagent, such as tetraalkylammonium halide, preferably tetrabutylammonium fluoride and any other suitable deprotecting agent, such as hydrogen fluoride (HF), HF-pyridine, acetic acid, trifluoroacetic acid (TFA) or hydrochloric acid.

The organic solvent in which the deprotection (desilylation) reaction is carried out may be selected from: tetrahydrofuran (THF), methanol, methylene dichloride, chloroform, benzene, toluene and any other known suitable organic solvent.

Step (ii): Conversion of the Compound of Formula P to the Compound of Formula Q:

The compound of the general formula P as obtained in the above step (i) (wherein R1, R2, R3, R4, R5, R6 & R8 are as defined herein above; R7 represents alkyl carboxylate; and X represents halogen, preferably Br) may undergo cyclisation in the presence of a base, such as potassium carbonate. The cyclisation may be carried out in an aprotic solvent, such as DMF, in the presence or absence of an inert atmosphere, at a temperature range of 0° C. to 100° C., over a time period of 2 h to 24 h to obtain the cyclic intermediate, a compound of the general formula Q (wherein R1, R2, R3, R4, R5, R6 & R8 are as defined herein above; R7 represents alkyl carboxylate).

Step (iii): Conversion of the Compound of Formula Q to the Compound of Formula Q1:

The compound of general formula Q as obtained in the above step (ii) (wherein R1, R2, R3, R4, R5, R6 & R8 are as defined herein above; R7 represents alkyl carboxylate) may be subjected to nitration using nitric acid-sulfuric acid as per any standard nitration procedure known in the art. For instance, the nitration reaction may be carried out at a temperature range of 0° C. to 40° C., over a time period of 1 h to 20 h to obtain the corresponding nitro derivative, a compound of the general formula Q1 (wherein R1, R3, R4, R5, R6 & R8 are as defined herein above; R2 represents $NO_2$; and R7 represents alkyl carboxylate). This reaction may also result in the partial oxidation of the ring sulfur atom into its sulfoxide.

Step (iv): Conversion of the Compound of Formula Q1 to the Compound of Formula Q2:

The nitro group in the compound of formula Q1 as obtained in the above step (iii) (wherein R1, R3, R4, R5, R6 & R8 are as defined herein above; R2 represents $NO_2$ and R7 represents alkyl carboxylate) may be subjected to reduction by using a suitable reducing agent in an organic solvent at ambient temperature and worked up in a manner known to one skilled in the art, to obtain the corresponding amino derivative, a compound of the general formula Q2 (wherein R1, R3, R4, R5, R6 & R8 are as defined herein above; R2 represents $NH_2$; and R7 represents alkyl carboxylate).

The reduction reaction may be carried out using various reduction methods known to one skilled in the art, for example, by catalytic hydrogenation in presence of a catalyst, such as Raney nickel, palladium-carbon, platinum-carbon, Rhodium-carbon and the like. Other reduction methods, such as those involving use of sodium borohydride, sodium cyanoborohydride, tin-hydrochloric acid (Sn—HCl) or iron-hydrochloric acid (Fe—HCl), may also be used for carrying out the reduction reaction. However, the reduction method involving catalytic hydrogenation using Raney nickel as the catalyst is the preferred method.

The organic solvent used for carrying out the reduction reaction may be selected from: dimethylformamide (DMF), tetrahydrofuran (THF), ethyl acetate, ethanol, methanol, toluene, benzene, diethyl ether, dioxane and any other known suitable organic solvent; with DMF being the preferred solvent.

Process 3: Preparation of the Key Intermediates of General Formulae Y and Z:

Step (i): Preparation of the Compounds of General Formula Y:

A compound of the general formula S (wherein R5, R6, R7 and R8 are as defined herein above; and X represents halogen, preferably Br), may be condensed with an o-hydroxy aniline derivative, a compound of the general formula T (wherein R1, R2, R3 and R4 are as defined herein above) in the presence of a base at a temperature range of 0° C. to 80° C. over a time period of 2 h to 24 h, using an organic solvent to obtain the sulfamoyl derivative, a compound of the general formula Y (wherein R1, R2, R3, R4, R5, R6, R7 and R8 are as defined herein above; X is a halogen, preferably Br).

Step (ii): Conversion of Compounds of Formula Y to Compounds of Formula Z:

The compound of general formula Y as obtained in the above step (i) (wherein R1, R2, R3, R4, R5, R6, R7 and R8 are as defined herein above; X is a halogen, preferably Br) may be converted to the corresponding cyclised intermediate, a compound of general formula Z (wherein R1, R2, R3, R4, R5, R6, R7 and R8 are as defined herein above) by following a procedure similar to that utilized for the cyclisation of compounds of general formulae D and P to the respective cyclised intermediates, the compounds of formulae E (Process 1—Step (iii)) and Q (Process 2—Step (ii)).

The thiol compound of general formula A and the compound of general formula B used in the above process 1—step (i) may be prepared in accordance with the following processes 4 and 5.

Process 4: Preparation of the Thiol Compound of General Formula A:

Step (i): Preparation of compounds of the general formulae A-i and A-ii:

An appropriately substituted aryl halide, preferably an appropriately substituted 4-halo-benzoic acid of general formula A-i (wherein R5, R6, R8 are as defined herein above; R7 represents COOH; and X represents halogen, preferably Br) may be treated with chlorosulfonic acid at a temperature range of 40° C. to 140° C., for a time period of 4 h to 24 h by following a standard procedure to obtain the corresponding chlorosulfonyl derivative, a compound of general formula A-ii (wherein R5, R6, R8 are as defined herein above; R7 represents COOH; and X represents halogen, preferably Br).

The compound of formula A-i may be either commercially available or obtained by subjecting an appropriately substituted 4-nitro-benzoic acid to a sequence of reactions namely reduction, diazotisation and a Sandmeyer reaction. For example, the nitro group in the 4-nitrobenzoic acid may be reduced to the corresponding amine by catalytic hydrogenation or transfer hydrogenation, with ammonium formate in the presence of a catalyst, such as Pd, Pt, Pd—C or Raney-Ni, in an organic solvent, such as ethyl acetate, methanol, ethanol, isopropanol, DMF, or a mixture thereof. This reduction may also be carried out by any conventional method known in the art, such as that involving use of Zn and HCl or $CoCl_2$ (Ind. J. Chem., 33B, 758, (1994)) or $NaBH_4$. The resulting amino compound may then be subjected to diazotisation followed by a Sandmeyer reaction to obtain the desired compound of general formula A-i (wherein R5, R6, R8 are as defined herein above; R7 represents COOH; and X represents halogen, preferably Br).

Step (ii): Conversion of the Compounds of Formula A-ii to the Compounds of Formula A-iii:

A compound of the general formula A-ii as obtained in the above step (i) (wherein R5, R6, R8 are as defined herein above; R7 represents COOH; and X represents halogen, preferably Br) may be subjected to reduction under acidic condition, more specifically the reduction reaction may be carried out using glacial acetic acid-stannous chloride in HCl—$H_2O$ (4:1v/v) with stirring, at a temperature of 80° C. for a time period of 1 h to obtain a thiol compound of general formula A-iii (wherein R5, R6, R8 are as defined herein above; R7 represents COOH; and X represents halogen, preferably Br). In the process of this reaction a disulfide is also obtained as a major by-product, which may be converted to its thiol compound of formula A-iii by subjecting it to reductive cleavage using triphenylphosphine in aqueous methanol as reported in (Synthesis, 59,(1974)) or by procedures known to one skilled in the art.

Step (iii): Conversion of the Compound of Formula A-iii (and its Disulfide) to the Compound of Formula A (and the Compound of Formula A-iv):

The thiol compound of formula A-iii as obtained in the above step (ii), (wherein R5, R6, R8 are as defined herein above; R7 represents COOH; and X represents halogen, preferably Br) and its disulfide may be esterified by refluxing with an appropriate alcohol, such as methanol, in the presence of a mineral acid, such as sulphuric acid or hydrochloric acid, or by any other standard method known in the art, for example, treating the compound of formula A-iii with thionyl chloride and an appropriate alcohol, such as methanol, to obtain the corresponding ester of general formula A (wherein R5, R6, R8 are as defined herein above; R7 represents alkyl carboxylate; and X represents halogen, preferably Br) along with its dimer ester of the general formula A-iv. The most preferred method may involve treating the mixture of the compound of formula A-iii and its dimer in a solvent such as methanol with a mixture of 15% MeOH-conc. $H_2SO_4$ added dropwise under reflux and with stirring for a time period of 6 h to 24 h.

The aryl disulfide ester of the general formula A-iv may be converted to the compound of general formula A using a reported procedure (Synthesis, 59, (1974)). More specifically, the procedure involves reduction of the compound of formula A-iv using triphenylphosphine, sodium borohydride, sodium cyanoborohydride or the like, at an ambient temperature with stirring for a time period of 15 h in a protic solvent mixture, such as methanol:water (4:1v/v), and the compound may be further processed in a manner known to one skilled in the art.

Process 5-1: Preparation of Compounds of the General Formula B:

Step (i): Preparation of Compound of Formula B-i:

The hydroxy group in an appropriately substituted o-cresol of general formula B-i (wherein R1, R2, R3 and R4 are as defined herein above) may be protected using any standard procedure known in the art. Thus, the compound of general formula B-i may be treated with a suitable hydroxy protecting reagent, to obtain the corresponding hydroxy protected derivative of general formula B-ii (wherein R1, R2, R3 and R4 are as defined herein above).

Suitable examples of hydroxy protecting reagents are: acetyl chloride, acetic anhydride, benzoyl chloride, benzoic anhydride, benzyl chloroformate, hexamethyldisilazane, trimethyllsilyl chloride and t-butyldimethylsilyl chloride.

According to the present invention, preferred protecting groups are an acetyl or a t-butyldimethyl silyl group, more preferably, a t-butyldimethyl silyl group. Accordingly, the compound of formula B-i may be treated with t-butyldimethylsilyl chloride, to obtain the t-butyldimethylsilyloxy derivative of general formula B-ii (wherein R1, R2, R3 and R4 are as defined herein above) in accordance with methods known in the art.

Step (ii): Conversion of the Compound of Formula B-ii to the Compound of Formula B:

The compound of formula B-ii, as obtained in the above step-(i) (wherein R1, R2, R3 and R4 are as defined herein above), may be treated with a conventional halogenating reagent known in the art so that the methyl group in the compound of formula B-ii is converted to a methyl halide group. Thus, the compound of formula B-ii may be subjected to a halogenation reaction in accordance with methods known in the art. One such method involves treating the compound with a suitable halogenating agent, such as N-bromosuccinimide (NBS), in the presence of an oxidising agent, such as benzoyl peroxide or 2,2'-azobisisobutyronitrile (AIBN), in a solvent, such as $CCl_4$, over a time period of 2 h to 24 h, to obtain the compound of general formula B (wherein R1, R2, R3 and R4 are as defined herein above; X represents halogen, preferably Br; and L represents a t-butyldimethyl silyloxy group).

Process 5-2: Preparation of the Compound of Formula B from the Compound of Formula G-i:

The compound of general formula B (wherein R1, R2, R3 and R4 are as defined herein above; X represents halogen, preferably Br; and L represents $NO_2$) may also be synthesized by subjecting an appropriately substituted compound of general formula G-i (wherein R1, R2, R3 and R4 are as defined herein above) to halogenation in a manner similar to that described in Process 5-1—Step (ii).

Process 6: Conversion of the Key Intermediates of Formulae E, E1, Q2 and Z to the Tricyclic Acylguanidine Compounds of Formula 1:

The key intermediates, the compounds of the general formulae E, E1, Q2 and Z as obtained according to the above described processes (wherein R1, R2, R3, R4, R5, R6, R8, U, V and W are as defined herein above; R7 represents a carboxylate ester group, such as an alkylcarboxylate, a cycloalkylcarboxylate or a substituted cycloalkyl carboxylate group, preferably a methyl carboxylate group) may be subjected to hydrolysis using acidic or alkaline conditions, more preferably using an alkali, such as sodium hydroxide, in a solvent or a solvent mixture, such as THF-water, at a temperature range of 0° C. to 60° C., over a time period of 0.5 h to 10 h, and worked up in a manner known to one skilled in the art to obtain the corresponding carboxylic acids represented by the general formulae E, E1, Q2 and Z (wherein R1, R2, R3, R4, R5, R6, R8, U, V and W are as defined herein above; R7 represents —COOH). The carboxylic acids may then be converted into activated carboxylic acid derivatives (—C(=O)Y, where Y is a leaving group), such as acid chlorides or active esters, using activating agents, such as 1,1-carbonyldiimidazole, thionyl chloride, oxalyl chloride, tosyl chloride or the like, and subjected to treatment with guanidine. The leaving group Y may be imidazolyl, halide, alkoxy or aryloxy. The reaction of the activated carboxylic acid derivative with guanidine may be carried out in an inert atmosphere or otherwise. The reaction may take place in an organic solvent, such as methanol, isopropanol, THF, DMF, dioxane, dimethoxyethane, or water in combination with a base, e.g. NaOH, or otherwise, at a temperature range of 0° C. to 80° C., over a time period of 2 h to 18 h using any standard procedure known to one skilled in the art to obtain acylguanidines of the formula 1 (wherein R1, R2, R3, R4, R5, R6, R8, U, V and W are as defined herein above; R7 represents —CON=C(NH$_2$)$_2$).

Alternatively, the methyl carboxylate ester group may be subjected to treatment with guanidine in the presence or absence of an inert atmosphere like nitrogen, at an ambient temperature using any standard procedure known to one skilled in the art to obtain the acylguanidines, compounds of formula 1 (wherein R1, R2, R3, R4, R5, R6, R8, U, V and W are as defined herein above; R7 represents —CON=C(NH$_2$)$_2$)

These acylguanidino derivatives may subsequently be converted into their organic or inorganic salts. The methane sulfonic acid salt, for example, may be prepared by treatment of the acylguanidino derivative with methane sulfonic acid in a dry solvent, like ethyl acetate, dioxane, diethyl ether, methanol, ethanol or the like, and processed in a manner known to one skilled in the art.

Scheme-II

Scheme-II illustrates further functionalisation of tricyclic compounds of the formula 1, including compounds of the formulae 1a, 1b and 1c, and the process steps are described below.

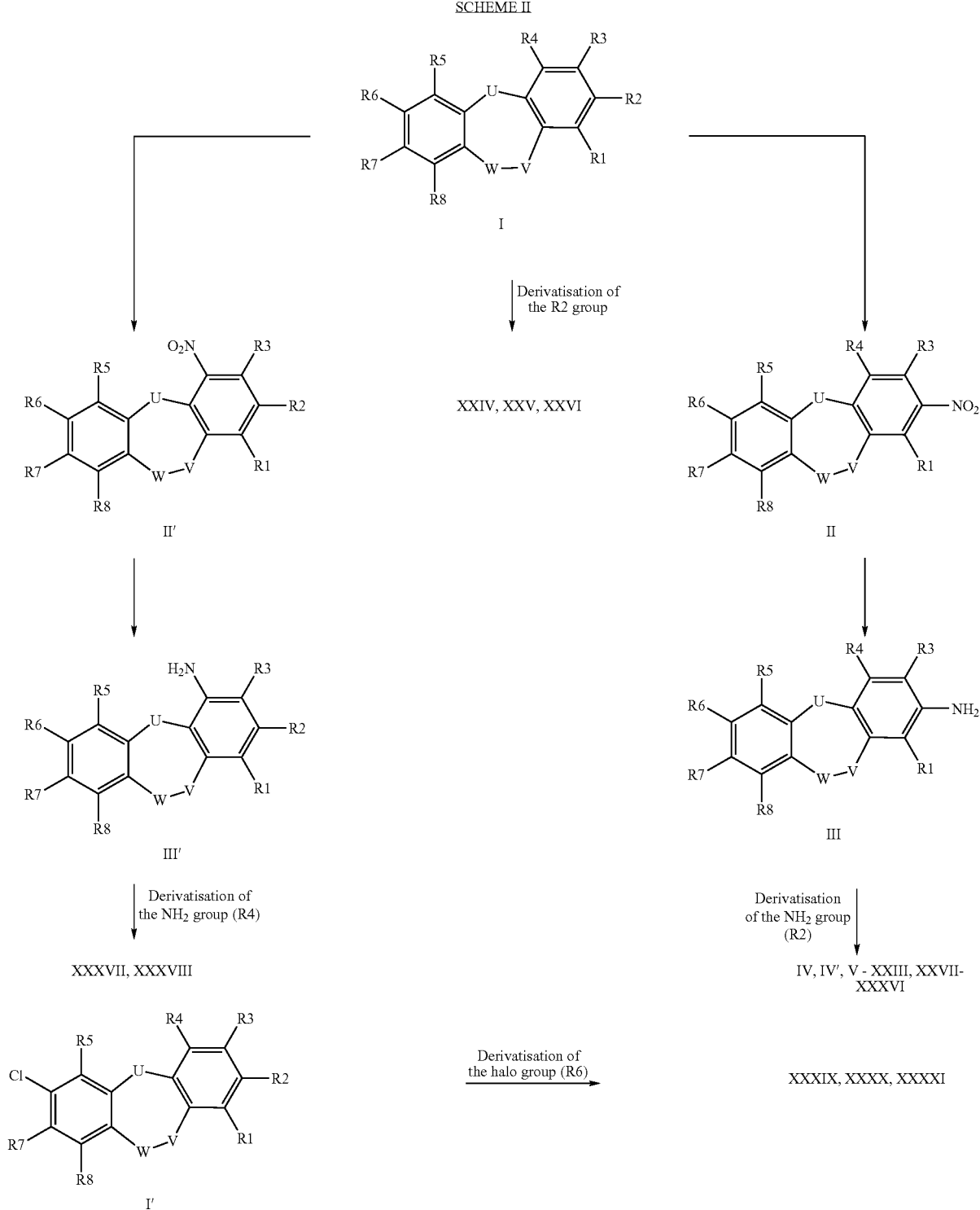

The compounds represented by the formula 1 in Scheme-II (corresponding to the compounds of the formula 1, including formulae 1a, 1b and 1c; wherein R1, R3, R4, R5, R6 and R8 are as defined herein above; R7 represents carboxylic acid or alkyl carboxylate ; R2 represents hydrogen), may be subjected to nitration using any standard procedure known in the art such as that described in the above Process 2-step (iii) to obtain the nitro derivative of general formula II (corresponding to the compounds of the present invention of the formula 1; wherein R1, R3, R4, R5, R6 and R8 are as defined herein above; R2 represents $NO_2$; and R7 represents carboxylic acid or alkyl carboxylate).

The resulting nitro derivative of the general formula II may be subjected to reduction by using any conventional reduction method known to one skilled in the art, such as that described in Process 2—Step (iv), to obtain the amino derivative of the general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate).

The amino derivative of the general formula III may further be functionalised/derivatised at the primary amino group (R2), and/or an amino group located at any other position of the compound, by subjecting it to a series of reactions to obtain various derivatives, which are also incorporated in the formula 1.

For instance the primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate) may be reacted with 2,5-dimethoxy tetrahydrofuran in the presence of 2-chloropyridine hydrochloride or 4-chloropyridine hydrochloride, in an organic solvent, such as dioxane, at reflux temperature as reported in the literature (J. Med. Chem, 2017, (1997)) to obtain the pyrrol-1-yl derivative, a compound represented by the general formula XIX (wherein R1, R3, R4, R5, R6 & R8 are as defined herein above; R2 represents pyrrol-1-yl; and R7 represents carboxylic acid or alkyl carboxylate) as illustrated in Scheme II.

The primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate ) may also be converted to the 2,5-dimethyl-pyrrol-1-yl derivative, a compound represented by the general formula XVIII (wherein R1, R3, R4, R5, R6 & R8 are as defined herein above; R2 represents 2,5-dimethyl-pyrrolyl ; and R7 represents carboxylic acid or alkyl carboxylate), by subjecting it to a treatment with acetonylacetone/acetic acid at reflux temperature using a hydrocarbon solvent, such as toluene, over a period of 6 h, following a procedure similar to that reported in the literature (J. Chem. Soc., Chem. Commun., 800-801, (1982)).

The primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate may also be subjected to a reaction with an acyclic or a cyclic carbonyl compound, for example, N-methyl-pyrrolidone in the presence of $POCl_3$, in a solvent, such as acetonitrile, at ambient temperature over a time period of 1 h as reported in the literature (J. Med. Chem. 44, 2004-2014, (2001)). The resulting compound is a 1-methyl-pyrrolidin-2-ylidine amino derivative, an amidine represented by the general formula XXIX (wherein R1, R3, R4, R5, R6 & R8 are as defined herein above; R2 represents 1-methyl-pyrrolidin-2-ylidine amino; and R7 represents carboxylic acid or alkyl carboxylate group).

The primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate) may also be subjected to a reductive monoalkylation, such as a mono methylation reaction, using paraformaldehyde in the presence of a strong base, such as sodium methoxide, (generated in situ) using a protic solvent, such as methanol. The intermediate so formed may in turn be subjected to an in situ reduction, with a reducing agent, such as sodium borohydride, as known in the art to obtain the monomethyl amino derivative, a compound represented by the general formula XVII (wherein R1, R3, R4, R5, R6 & R8 are as defined herein above; R2 represents NHR" in which R" is $CH_3$; and R7 represents carboxylic acid or alkyl carboxylate group).

The primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate) may also be reacted with an aldehyde, such as formaldehyde, acetaldehyde, isopropaldehyde, butyraldehyde or isobutyraldehyde, more specifically isobutyraldehyde, in a solvent, such as methanol, in the presence of TFA, and subsequently reduced using sodium cyanoborohydride following a procedure similar to that reported in the literature (Tet. Letters, 38, 5831, (1997)). The resulting compound is an alkylamino derivative, more specifically an isobutylamino derivative represented by the general formula XVII (wherein R1, R3, R4, R5, R6 & R8 are as defined herein above; R2 represents NHR" in which R" is $CH_2CH(CH_3)_2$; and R7 represents carboxylic acid or alkyl carboxylate).

A dialkylation of the amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate) may be effected using the Eschweiler-Clarke procedure wherein aqueous HCHO—HCOOH is used to obtain a N,N-dimethylamino derivative, a compound represented by the general formula XVI (wherein R1, R3, R4, R5, R6 & R8 are as defined herein above; R2 represents $N(CH_3)_2$; and R7 represents carboxylic acid or alkyl carboxylate). The reaction may be carried out at a temperature range of ambient to 110° C. over a time period of 3 h to 20 h and processed in a manner known to one skilled in the art.

Likewise, the primary amino group in the compound of general formula III (corresponding to the compounds of the present invention of the formula 1; wherein R1, R3, R4, R5, R6 & R8 are as defined herein above; R2 represents $NH_2$; and R7 represents carboxylic acid or alkyl carboxylate) may also be subjected to a reductive N-alkylation as well known in the art using a halocarbonyl compound, such as chloroacetic acid or chloropropionic acid, and a reducing agent, such as sodium borohydride or sodium cyanoborohydride, in a solvent mixture, such as THF/benzene, or any equivalent mixture of solvents or a solvent selected from: a hydrocarbon (for example, benzene, toluene), an ether (for example, THF, diethyl ether) and a protic solvent (for example methanol), at a temperature range of 0° C. to reflux, over a time period of 0.5 h to 18 h. The resulting compound is a mono-chloroalkylamino derivative, more specifically a chloroethyl amino derivative represented by the general formula IV (wherein R1, R3, R4, R5, R6 & R8 are as defined herein above; R2 represents $NH(CH_2CH_2Cl)$ or a chloropropionyl amino derivative represented by the general formula IV'. (wherein R1, R3, R4, R5, R6 & R8 are as defined herein above; R2 represents $NH(CH_2CH_2CH_2Cl)$) However, if the proportion of halocarbonyl compound is raised, a bis-chloroalkylamino derivative, more specifically a tertiary bis chloroethylamino derivative represented by the general formula V (wherein R1, R3, R4, R5, R6 & R8 are as defined herein above; R2 represents $N(CH_2CH_2Cl)_2$ and R7 represents carboxylic acid or alkyl carboxylate ) may be obtained.

Likewise, the primary amino group in the compound of general formula III (corresponding to the compounds of the formula 1; wherein R1, R3, R4, R5, R6 & R8 are as defined herein above; R2 represents $NH_2$; and R7 represents a carboxylic acid or an alkyl carboxylate group) may also be subjected to a reductive N-alkylation using heterocyclyl carbonyl compounds and any of the conventional reductive N-alkylation conditions described herein to obtain the corresponding N-alkylheterocyclylamino derivatives, compounds represented by the general formula XV (wherein R1, R3, R4, R5, R6 & R8 are as defined herein above; R2 represents $NHCH_2$-heterocyclyl; and R7 represents carboxylic acid or alkyl carboxylate).

Suitable examples of heterocyclyl carbonyl compounds used in the above reaction include: 2-imidazole carboxaldehyde, 5-methyl-2-thiophene carboxaldehyde, pyridine-3-carboxaldehye, tetrahydrofurfuraldehyde, substituted furfural, pyrimidine aldehyde, substituted pyrazine aldehyde and substituted pyrrole-3-aldehyde.

The secondary haloalkylamino derivatives, more specifically the chloroethylamino derivatives of the general formula IV may be subjected to a nucleophilic substitution reaction using different amines, with or without the use of a phase transfer catalyst, such as tetraalkylammonium halide, more specifically tetra-n-butylammonium iodide, in the presence of a solvent selected from: methanol and DMF, at a temperature range of 50° C.-110° C. over a time period of 1 h to 7 h, with or without the use of a pressure reactor vessel and in the presence or absence of an inert atmosphere which may be maintained using gases, such as $N_2$, Ar and He. The resulting compounds are secondary amino derivatives, which may be aminoalkylamino, heterocyclylalkylaminoalkylamino, cycloalkylaminoalkylamino, arylalkylaminoalkyl-amino or the like derivatives represented by the general formula VI (wherein R1, R3, R4, R5; R6 & R8 are as defined herein above; R7 represents carboxylic acid or alkyl carboxylate and R2 represents $NHCH_2CH_2R'$ in which R' represents an amine. Suitable examples of amines (R') as used herein include: 1-methylpiperazine, imidazole, 2-methylamino-N-methylimidazole, trifluoromethylbenzylamine, aqueous ammonia, morpholine, 2-piperazin-1-yl-ethanol, methylamine, pyrrolidine, 2-morpholin-4-yl-ethylamine, morpholin-4-ylamine, cyclopropylamine, 2-(2-aminoethyl)pyridine, furfurylamine, 2-aminomethyl thiophene, benzylamine, o-methoxybenzylamine, piperidine and dimethylamine.

Similarly, the chloropropionyl amino derivative of the general formula IV' may be subjected to a nucleophilic substitution reaction using morpholine to obtain a morpholinoethylamino derivative represented by the general formula VI (wherein R1, R3, R4, R5, R6 & R8 are as defined herein above; R2 represents $NHCH_2CH_2$—R' in which R' represents morpholinyl; and R7 represents carboxylic acid or alkyl carboxylate).

Some of these secondary amino derivatives of general formula VI (wherein R1, R3, R4, R5, R6 & R8 are as defined herein above; R7 represents carboxylic acid or alkyl carboxylate and R2 represents $NHCH_2CH_2R'$ in which R' represents an amine, preferably morpholino-ethylamino, pyrrolidinylethylamino or piperidinlylethylamino) may be further subjected to an N-acylation with an appropriate acid chloride in the presence or absence of an organic or inorganic base, such as triethylamine or pyridine, at a temperature range of 55° C.-80° C., over a time period of 0.5 h to 48 h, in the presence or absence of a solvent, such as $CH_2Cl_2$, and processed in a manner known to one skilled in the art to obtain the tertiary acylamino derivatives, namely the N-haloacyl N-heterocyclylalkylamino derivatives represented by the general formula IX (wherein R1, R3, R4, R5, R6 & R8 are as defined herein above; R7 represents carboxylic acid or alkyl carboxylate and R2 represents $N(COR")CH_2CH_2$-heterocyclyl, in which R" represents haloalkyl, preferably chloromethyl).

Suitable examples of acid chlorides are acetyl chloride, methoxy-acetyl chloride, chloro-acetyl chloride, cyclopropanecarbonyl chloride, pivolyl chloride and isobutylchloroformate.

The N-chloro-acyl N-heterocyclylalkylamino derivative of general formula IX obtained from chloro-acetyl chloride may be subjected to an in situ hydrolysis to obtain the N-hydroxyacyl N-heterocyclylalkylamino derivative of general formula IX (wherein R1, R3, R4, R5, R6 & R8 are as defined herein above; R2 represents $N(COR")CH_2CH_2$-heterocyclyl in which R" represents hydroxyalkyl, preferably hydroxymethyl; and R7 represents carboxylic acid or alkyl carboxylate).

The N-chloroacyl N-heterocyclylalkylamino derivative of general formula IX, more particularly the N-chloroacetyl, N-pyrrolidin-1-yl-ethylamino derivative (wherein R" represents chloromethyl and heterocyclyl represents pyrrolidinyl) obtained from chloro-acetyl chloride may also be subjected to a nucleophilic substitution reaction with an amine, such as cyclopropyl amine, and processed in a manner known to one skilled in the art to obtain the N-cyclopropyl aminoacetyl, N-pyrrolidin-1-yl-ethylamino derivative represented by the general formula X (wherein R1, R3, R4, R5, R6 & R8 are as defined, herein above; R2 represents $N(COR")CH_2CH_2$-heterocyclyl in which R" represents cyclopropylaminomethyl; and R7 represents carboxylic acid or alkyl carboxylate).

Some of these secondary amino derivatives mentioned above, such as the 2-(2-morpholino-4-yl-ethylamino derivative of the general formula VI, may be subjected to a reductive alkylation with an aldehyde, such as acetaldehyde, in the presence of TFA, in a solvent, such as THF, methanol or ethanol, at a temperature range of 0° C. to reflux, over a time period of 2 h-24 h, and in the presence of a reducing agent, such as $NaBH_3CN$, following a methodology similar to that reported in the literature (Tet. Letters, 38, 5831, (1997)) to obtain a 2-[N-ethyl-(2-morpholino-4-yl-]ethyl amino derivative of the general formula VII (wherein R1, R3, R4, R5, R6 & R8 are as defined herein above; R2 represents —$N(CH_2CH_3)CH_2CH_2$-heterocyclyl in which the heterocycle is morpholine; and R7 represents carboxylic acid or alkyl carboxylate).

Similarly, a compound of general formula VIII (wherein R1, R3, R4, R5, R6 & R8 are as defined herein above; R2 represents —$N(CH_2CH_3)CH_2CH_2N(CH_2CH_3)CH_2$-heterocyclyl and R7 represents carboxylic acid or alkyl carboxylate ) was obtained by di-reductive alkylation of general formula VI.

The secondary monohaloalkyl amino derivative, more particularly the chloroethylamino derivative of the general formula IV may be subjected to an N-acylation with an appropriate acid chloride, such as chloro-acetyl chloride, in the presence or absence of an inert atmosphere, at a temperature ranging from 0° C.-100° C., over a time period of 1 h to 7 h, and processed in a manner known to one skilled in the art to obtain the N-chloro-acetyl derivative, more specifically the N-chloro-acetyl, N-chloroethyl amino derivative of general formula XI (wherein R1, R3, R4, R5, R6 & R8 are as defined herein above; R2 represents —$N(COCH_2Cl)CH_2CH_2Cl$; and R7 represents carboxylic acid or alkyl carboxylate). This derivative may be subjected to a cyclisation reaction with different amines, like cyclopropylamine, cyclopentylamine, isopropylamine, benzylamine and substituted benzylamine, in an organic solvent, such as DMF, $CH_2Cl_2$, THF and any other suitable known solvent, at a temperature range of 50° C. to 80° C. over a time period of 1.5 h to 6 h, and processed in a manner known to one skilled in the art to obtain the 2-oxo-heterocyclyl derivatives represented by the general formula XXIII (wherein R1, R3, R4, R5, R6 & R8 are as defined herein above; R2 represents N-substituted 2-oxo-heterocyclyl group, preferably N-substituted-2-oxo-piperazinyl; and R7 represents carboxylic acid or alkyl carboxylate group).

The tertiary bis-(chloroethyl)amino derivative of the general formula V, may also be subjected to a cyclisation reaction with an amine in the presence or absence of an inert atmosphere of gases, such as $N_2$, Ar or He, at a temperature range of 60° C. to 80° C., over a time period of 1.5 h to 8 h, with or without the use of a phase transfer catalyst, such as tetraalkylammonium halide, ammonium sulfate or KI, preferably tetrabutylammonium iodide. The reaction may optionally be carried out in a pressure reactor vessel to obtain substituted or unsubstituted heterocyclyl derivatives represented by the general formula XII (wherein R1, R3, R4, R5, R6 & R8 are as defined herein above; R2 represents a substituted or unsubstituted heterocyclyl group, preferably a substituted or unsubstituted piperazinyl; and R7 represents carboxylic acid or alkyl carboxylate ).

Suitable examples of amines used in the above reaction are aqueous $NH_3$, ethylamine, benzylamine, N,N-dimethylamino ethanol, isopropylamine, 1-(2-aminoethyl)-morpholine, 1-(2-aminoethyl)pyrrolidine, cyclopropylmethylamine, N-aminoethyl-piperazine, cyclopropylamine, 3-aminomethyl-pyridine, cyclobutylamine, cyclohexyl-amine, thiophenemethylamine, 2-methoxybenzylamine, tetrahydrofurfurylamine and ethanolamine.

Furthermore the unsubstituted heterocyclyl derivative, such as the piperazinyl derivative of the general formula XII, may be subjected to an N-acylation reaction using different acid chlorides, for example cyclopropyl carbonylchloride and pyrrole-2-carbonylchloride, in the presence of a base, such as pyridine, TEA, lutidine and diisopropylamine, preferably pyridine, at a temperature range of 10° C.-25° C. for 0.5 h-48 h in an organic solvent, such as methylene chloride, N,N-dimethylformamide or tetrahydrofuran. The resulting piperazinyl carbonyl derivatives are represented by the general formula XIII (wherein R1, R3, R4, R5, R6 & R8 are as defined herein above; R2' represents a substituted heterocyclyl group, preferably the 4-COR'''-piperazin-1-yl group in which R''' represents an alkyl, cycloalkyl, aryl or heteroaryl group; and R7 represents carboxylic acid or alkyl carboxylate).

The unsubstituted heterocyclyl derivative, such as the piperazinyl derivative of the general formula XII, may also be subjected to a reductive N-alkylation in the presence of a mild effective Lewis acid catalyst, such as titanium (IV) isopropoxide, with an aldehyde or a ketone and a reducing agent, such as sodium cyanoborohydride (as reported in J. Org. Chem., 55, 2552-2554, (1990)), in an organic solvent, such as methanol, at a temperature range of 10° C.-25° C. (before the addition of sodium cyanoborohydride), which may then be raised over a range of ambient to reflux. The resulting N-alkyl piperazinyl derivatives are represented by the general formula XIV (wherein R1, R3, R4, R5, R6 & R8 are as defined herein above; R2 represents a substituted heterocyclyl group, preferably the 4-$CH_2$R'''-piperazin-1-yl group in which R''' represents an alkyl, aryl or heteroaryl group; and R7 represents carboxylic acid or alkyl carboxylate).

Examples of the aldehydes used in the above reaction include: decanaldehyde, pentanaldehyde, dimethylamino benzaldehyde, 2,4-dichlorobenzaldehyde, furfuraldehyde, tolualdehyde, 5-methyl-thiophene-2-carboxaldehyde, veratraldehyde, p-(trifluoromethyl) benzaldehyde and m-nitrobenzaldehyde.

Furthermore the unsubstituted heterocyclyl derivative, such as the piperazinyl derivative of the general formula XII (wherein R1, R3, R4, R5, R6 & R8 are as defined herein above; R2 represents unsubstituted heterocyclyl group, preferably unsubstituted piperazinyl; and R7 represents carboxylic acid or alkyl carboxylate ) may be subjected to a reaction with a $BF_3$-THF complex in a manner reported in (Tetrahedron, Vol. 47, 3089-3094, (1991)), whereby the carboxylic acid group at R7 gets converted to the corresponding hydroxy functionality. The resulting hydroxy compound may be further oxidized to a carbonyl group, more specifically the aldehyde group, using a combination of dimethylsulfoxide (DMSO) and oxalyl chloride by following a method known in the art to obtain an aldehyde derivative represented by the general formula XXII (wherein R1, R3, R4, R5, R6 & R8 are as defined herein above; R2 represents unsubstituted heterocyclyl group, preferably unsubstituted piperazinyl; and R7 represents CHO).

The primary amino group in the compound of general formula III (corresponding to compounds of the formula 1; wherein R1, R3, R4, R5, R6, R7, R8 are as defined above; R2 represents $NH_2$) may be subjected to a diazotisation reaction, followed by a Sandmeyer reaction using a potassium halide by following a method known in the art to obtain a nuclear halo derivative, more particularly an iodo derivative represented by the general formula XX (wherein R1, R3, R4, R5, R6, R7, R8 are as defined above; R2 represents halogen, preferably I).

The primary amino group in the compound of general formula III (corresponding to compounds of the formula 1; wherein R1, R3, R4, R5, R6, R7, R8 are as defined above; R2 represents $NH_2$) may be subjected to a treatment with diprotected S-methyl isothiourea in a solvent, such as DMF, at a temperature of ambient to 120° C. over a time period of 2 h to 24 h and processed in a manner as reported in (J. Org. Chem., 62, 1540-1542, (1997)) to obtain an N-benzoyl-guanidino derivative represented by the general formula XXI (wherein R1, R3, R4, R5, R6, R7, R8 are as defined above; R2 represents NHC(=NH)NHCO$_2$CH$_2$Ph).

The primary amino group in the compound of general formula III (corresponding to compounds of the formula 1; wherein R1, R3, R4, R5, R6, R7, R8 are as defined above; R2 represents $NH_2$), may be reacted with ethylene oxide in dilute acetic acid at a temperature range of 0° C. to 5° C. over a time period of 12 h to 18 h using a procedure reported in (Tetrahedron, 55, 3265-3276, (1999)), to obtain the bis-(2-hydroxyethyl)amino derivative represented by the general formula XXVII (wherein R1, R3, R4, R5, R6, R7, R8 are as defined above; R2 represents N(CH$_2$CH$_2$OH)$_2$). This derivative may be subjected to cyclisation in the presence of a catalyst, such as p-toluenesulfonic acid (PTSA), in an organic solvent, such as toluene, over a time period of 6 h to 18 h, at reflux temperature and processed in a manner known to one skilled in the art to obtain a morpholino derivative represented by the general formula XXVIII (wherein R1, R3, R4, R5, R6, R7, R8 are as defined above; R2 represents morpholinyl). Cyclisation of the compound of formula XXVII may also be effected using dehydrating agents, such as PPA, $P_2O_5$ or $H_2SO_4$.

The primary amino group in the compound of general formula III (corresponding to compounds of the formula 1; wherein R1, R3, R4, R5, R6, R7, R8 are as defined above; R2 represents $NH_2$), may be subjected to an acylation, a Schotten-Baumann type of reaction with chloro-acetyl chloride in the presence of an organic base such as pyridine, using a halogenated solvent, like methylene chloride, at a temperature range of 0° C. to 80° C., over a time period of 1 h to 10 h, to obtain a 2-chloro-acetylamino derivative represented by the general formula XXX (wherein R1, R3, R4, R5, R6, R7, R8 are as defined above; R2 represents NHCOCH$_2$Cl). This derivative may be subjected to a nucleophilic substitution reaction with an amine or amine hydrochloride, in an organic solvent, such as DMF, and in the presence of an inorganic base, such as potassium carbonate (if an amine hydrochloride is used), at a temperature range of 50° C. to 120° C., over a time range of 1 h to 24 h, to obtain the corresponding substituted or unsubstituted amino-acetylamino derivatives represented by the general formula XXXI (wherein R1, R3, R4, R5, R6, R7, R8 are as defined above; R2 represents NHCOCH$_2$NR''' in which R''' represents alkyl, cycloalkyl, aryl or heteroaryl).

Examples of amines used in the above nucleophilic substitution reaction include: piperidine, 2,2,2-trifluoroethyl amine hydrochloride, imidazole, cyclopropyl amine, cyclohexylamine, cyclopentylamine, isopropylamine, dimethylamine hydrochloride, cyclobutyl amine, morpholine, 1-(3-trifluoromethyl-phenyl)-piperazine, methylamine hydrochloride, pyrrolidine and N-methylpiperazine.

When 2,2,2-trifluoroethylamine hydrochloride is used in the above nucleophilic substitution reaction, a by-product, namely the 2-hydroxy-acetylamino derivative, may also be obtained along with the corresponding (2,2,2-trifluoroethylamino)-acetylamino derivative of the general formula XXXI (wherein R1, R3, R4, R5, R6, R7, R8 are as defined above; R2 represents NHCOCH$_2$NR''' in which R''' represents 2,2,2-trifluoroethyl).

The primary amino group in the compound of general formula III (corresponding to compounds of the formula 1; wherein R1, R3, R4, R5, R6, R7, R8 are as defined above; R2 represents NH$_2$), may be subjected to a diazotisation reaction, followed by a Sandmeyer reaction using potassium cyanide and cuprous cyanide under standard reaction conditions known in the art to obtain the nuclear cyano derivative represented by the general formula XXXII (wherein R1, R3, R4, R5, R6, R7, R8 are as defined above; R2 represents CN). This derivative may be subjected to a reduction as described in the Process 4—Step (i) or using platinum oxide in an organic solvent, such as glacial acetic acid, DMF, or ethanol, to obtain an aminomethyl derivative represented by the general formula XXXIII (wherein R1, R3, R4, R5, R6, R7, R8 are as defined above; R2 represents —CH$_2$NH$_2$).

The aminomethyl derivative represented by the general formula XXXIII may be subjected to a reductive alkylation reaction using an arylaldehyde, such as benzaldehyde, in the presence of a salt, like NaOAc, and using a reducing agent, like sodium borohydride, to obtain an aralkyl aminoalkyl derivative represented by the general formula XXXIV (wherein R1, R3, R4, R5, R6, R7, R8 are as defined above; R2 represents —CH$_2$NHCH$_2$phenyl).

The aminomethyl derivative represented by the general formula XXXIII may also be converted into its 2-pyrrolylmethyl derivative represented by the general formula XXXV (wherein R1, R3, R4, R5, R6, R7, R8 are as defined above; R2 represents —CH$_2$-pyrrolyl) by following a procedure as described herein above using 2,5-dimethoxytetrahydrofuran.

The aminomethyl derivative represented by the general formula XXXIII (wherein R1, R3, R4, R5, R6, R7, R8 are as defined above; R2 represents —CH$_2$NH$_2$) may also be subjected to a bis-alkylation using an aldehyde, such as acetaldehyde, in a reductive alkylation process mentioned herein above, in an organic solvent, such as methanol, in the presence of TFA, and a reducing agent, such as sodium cyano borohydride, following a procedure known in the art to obtain a diethylaminomethyl derivative represented by the general formula XXXVI (wherein R1, R3, R4, R5, R6, R7, R8 are as defined above; R2 represents —CH$_2$N(CH$_2$CH$_3$)$_2$).

The compounds of general formula I (corresponding to the compounds of the formula 1; wherein at least one of R1, R2, R3, R4, R5, R6, R7 or R8 represent hydrogen, preferably R2 represents hydrogen; and the remaining substituents are as defined herein above) may be subjected to a chlorosulfonation reaction, by following a procedure known in the art using chilled chlorosulfonic acid at 0° C. The reaction temperature may be later raised to ambient over time period of 12 h. The reaction mixture may be processed in a manner known to one skilled in the art to obtain the sulfonyl chloride (chlorosulfonyl) derivative represented by the general formula XXIV (wherein R1, R3, R4, R5, R6, R7 and R8 are as defined hereinabove; and R2 represents SO$_2$Cl).

The chlorosulfonyl derivative represented by the general formula XXIV as obtained above, may be reacted with hydrazine hydrate and processed in a manner known to one skilled in the art to obtain a sulfonyl hydrazide derivative which in turn may be reacted with methyl iodide under anhydrous conditions using an organic solvent, like dry ethanol, in the presence of sodium acetate under reflux conditions as reported in (J. Med. Chemistry, 42, 1982-1990, (1999)) to obtain the methanesulfonyl derivative represented by general formula XXV (wherein R1, R3, R4, R5, R6, R7 and R8 are as defined herein above; and R2 represents SO$_2$CH$_3$).

The chlorosulfonyl derivative represented by the general formula XXIV as obtained above, may be treated with an amine in the presence or absence of a base, more specifically using an organic base, such as pyridine, in an organic solvent, such as ethyl acetate at ambient temperature over time period of 1 h to 15 h and processed in a manner known to one skilled in the art to obtain the sulfonamido derivatives represented by the general formula XXVI (wherein R1, R3, R4, R5, R6, R7 and R8 are as defined herein above; and R2 represents SO$_2$R' in which R' represents an amino moiety).

Examples of amines as used in the above reaction include: aqueous ammonia, 2-amino-5-cyclopropyl-1,3,4-thiadiazole, 3-(aminomethyl)pyridine, N-methyl-piperazine and morpholine.

A compound of the formula I (corresponding to the compounds of the formula 1; wherein R1, R2, R3, R5, R6 and R8 are as defined herein above; R4 represents NO$_2$; and R7 represents carboxylic acid or alkyl carboxylate), may be reduced to obtain its corresponding amino derivative of the general formula III' (wherein R1, R2, R3, R5, R6 and R8 are as defined herein above; R4 represents NH$_2$; and R7 represents carboxylic acid or alkyl carboxylate) by following a procedure similar to that used in Process 2—Step (iv) or by any other conventional reduction method known in the art. The resulting amino derivative of general formula III' may further be subjected to a reductive N-alkylation using a halocarbonyl compound, such as chloro-acetic acid, and a reducing agent, such as sodium borohydride, in a suitable organic solvent or mixture of solvents, such as THF-benzene, as described herein above to obtain the chloroethylamino derivative of general formula XXXVII (wherein R1, R2, R3, R5, R6 and R8 are as defined herein above; R4 represents NHCH$_2$CH$_2$Cl; and R7 represents carboxylic acid or alkyl carboxylate). This derivative may be subjected to a nucleophilic substitution using a secondary amine, such as morpholine, and processed in a manner known to one skilled in the art to obtain the morpholine-1-ylethylamino derivative of general formula XXXVIII (wherein R1, R2, R3, R5, R6 and R8 are as defined herein above; R4 represents NHCH$_2$CH$_2$-morpholin-1-yl; and R7 represents carboxylic acid or alkyl carboxylate).

The compounds of the formula 1; wherein R1, R2, R3, R4, R5 and R8 are as defined herein above; R6 represents halogen, preferably Cl; and R7 represents carboxylic acid or alkyl carboxylate) may be subjected to a facile nucleophilic displacement of the chloro group using an aralkyl amine, such as benzylamine or a heterocyclylamine, such as piperidine or pyrrolidine, without the use of solvents to obtain the corresponding amine derivative represented by the general formula XXXIX (wherein R1, R2, R3, R4, R5 and R8 are as defined herein above; R6 represents NHCH$_2$phenyl; and R7 represents carboxylic acid or alkyl carboxylate) or the heterocyclylamine derivative represented by the general formula XXXX (wherein R1, R2, R3, R4, R5 and R8 are as defined herein above; R6 represents NH-heterocyclyl in which the heterocyclyl may be pyrrolidinyl or piperidinyl; and R7 represents carboxylic acid or alkyl carboxylate ).

The benzylamino derivative of the general formula XXXIX (wherein R1, R2, R3, R4, R5 and R8 are as defined herein above; R6 represents NHCH$_2$phenyl; and R7 represents carboxylic acid or alkyl carboxylate) as obtained above may be subjected to a hydrogenolysis reaction using 10% Pd/C and a protic solvent, such as methanol, and processed in a manner known to one in the art, to obtain the primary amino derivative represented by the general formula XXXXI (wherein R1, R2, R3, R4, R5 and R8 are as defined herein above; R6 represents NH$_2$; and R7 represents carboxylic acid or alkyl carboxylate).

It will also be appreciated by those skilled in the art that the compounds of the present invention may also be utilized in the form of their pharmaceutically acceptable salts or solvates thereof. The pharmaceutically acceptable salts of the compounds of the present invention are in particular salts which are non-toxic, or which can be used physiologically.

Thus, when the compounds of the present invention represented by the formula 1, more particularly by the formulae 1a, 1b and 1c, contain one or more basic groups, i.e. groups which can be protonated, they can form an addition salt with a non-toxic inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art. Preferred salts of the compounds of formula 1 include methane sulphonic acid, hydrochloric acid and p-toluenesulphonic acid salts.

Thus, when the compounds of the present invention represented by the formula 1, more particularly by the formulae 1a, 1b and 1c, contain an acidic group they can form an addition salt with a suitable base. For example, such salts of the compounds of the present invention may include their alkali metal salts, such as Li, Na and K salts, or alkaline earth metal salts, like Ca and Mg salts, or aluminium salts, or salts with ammonia or salts of organic bases, such as lysine, arginine, guanidine, diethanolamine, choline and tromethamine.

The pharmaceutically acceptable salts of the present invention can be synthesized from the subject compound, which contains a basic or an acidic moiety, by conventional chemical methods. Generally, the salts are prepared by contacting the free base or acid with stoichiometric amounts or with an excess of the desired salt-forming inorganic or organic acid or base in a suitable solvent or dispersant or from another salt by cation or anion exchange. Suitable solvents are, for example, ethyl acetate, ether, alcohols, acetone, THF, dioxane, or mixtures of these solvents.

The present invention furthermore includes all solvates of the compounds of the formula 1, more particularly of the formulae 1a, 1b and 1c, for example hydrates, and the solvates formed with other solvents of crystallization, such as alcohols, ethers, ethyl acetate, dioxane, DMF, or a lower alkyl ketone, such as acetone, or mixtures thereof.

The present invention also includes prodrug forms of the compounds of the formula 1, more particularly of the formulae 1a, 1b and 1c, for example the alkyl esters of acids or any of the prodrugs for guanidines known to one skilled in the art. Thus, the present invention includes those compounds produced in vivo after administration of a different compound (or prodrug of the compound). The in vivo effects of compounds described herein, may not be exerted by those compounds as such, but by one or more degradation products.

Various polymorphs of compounds forming part of the present invention may be prepared by crystallization of compounds of the formula 1, more particularly of the formulae 1a, 1b and 1c, under different conditions. Examples of different conditions are: using different commonly used solvents or their mixtures for crystallization; crystallization at different temperatures; and various modes of cooling, ranging from very fast to very slow cooling during crystallizations. Polymorphs may also be obtained by heating or melting the compound followed by gradual or fast cooling. The presence of polymorphs may be determined by IR spectroscopy, solid probe NMR spectroscopy, differential scanning calorimetry, powder X-ray diffraction or such other techniques.

The compounds of the present invention can have asymmetric centres at any of the carbon atoms, including any one of the R substituents. Consequently, compounds of the formula 1, more particularly of the formulae 1a, 1b and 1c, can exist in enantiomeric or diastereomeric forms either in pure or substantially pure form or in mixtures thereof in all ratios. When diastereomeric or enantiomeric products are prepared, they can be separated by conventional methods for example, chromatographic or fractional crystallization. If mobile hydrogen atoms are present, the present invention also encompasses all tautomeric forms of the compounds of the general formula 1, more particularly of the general formulae 1a, 1b and 1c.

The present compounds are inhibitors of the sodium proton exchange mechanism, more particularly NHE-1, and find use in prophylactic/protective/reducing therapies for diseases characterized by tissue ischemia or/and reperfusion, (e.g. cardiac and cerebral infarctions), excessive cell growth, such as cancers, hypertrophies, proliferative disorders, cardiovascular abnormalities, pulmonary and nephrological disorders, fibrotic diseases, immunological disorders and restenosis.

The term "reduction" is intended to include partial prevention or prevention which, although greater than that which would result from taking no compound or from taking a placebo, is less than 100%, in addition to substantially total prevention.

The term "ischemia" as employed herein refers to conditions directly associated with reduced blood flow to tissue, for example due to an obstruction in blood vessels supplying blood to the subject tissue and resulting, inter alia, in lowered oxygen transport to such tissue, leading to impaired tissue performances, tissue dysfunction and/or necrosis. Alternatively, where perfusion of an organ may be quantitatively adequate, the oxygen carrying capacity of the perfusion medium or blood may be reduced, e.g., in hypoxic environment, such that oxygen supply to the tissue is lowered, and impaired tissue performance, tissue dysfunction, and/or tissue necrosis ensues.

The term "reperfusion" refers to reflow/resupply of blood after removal of an ischemic condition to the various tissues.

The term "treating", "treat" or "treatment" as used herein includes preventive (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to compounds that are drug precursors which, following administration, release the drug in vivo via some chemical or physiological process, e.g., a prodrug on being brought to the physiological pH or through an enzyme action is converted to the desired drug form.

The compounds of the present invention can be used to inhibit the activity of the sodium proton exchange mechanism (preferably NHE-1) and are helpful pharmaceutical compounds for the treatment of various diseases, which are due to an excessive or abnormal NHE activation. In the context of the present invention, treatment includes the therapy as well as the prophylaxis of the respective diseases.

There are a wide variety of pathological conditions with excessive or abnormal NHE activation, against which the compounds of the present invention can act to provide therapeutic benefits. Examples of such pathological conditions include:

a. Ischemia and/or reperfusion induced tissue damage as occurring in (but not limited to) the following:
  i. Cardiovascular diseases, like angina pectoris, acute coronary syndrome, myocardial infarction, myocardial stunning, arrhythmias, cardiac dysfunction, post-infarct remodeling, hypertension, shock, arteriosclerosis, vascular restenosis;
  ii Cardiovascular surgical procedures, like Coronary Artery Bypass Grafting (CABG), Percutaneous Transluminal Coronary Angioplasty (PTCA) or any Percutaneous Transluminal Coronary Intervention (PTCI), organ transplantation, or other non-cardiac/vascular surgeries;
  iii Cerebrovascular disorders, like cerebral ischemic stroke and edema; cerebrovascular surgeries;
b. Pulmonary disorders, like pulmonary fibrosis;
c. Renal disorders, like glomerulonephrosclerosis;
d. Metabolic disorders, like diabetes and its complications;
e. Fibrotic diseases;
f. Tissue/organ hypertrophy and hyperplasia;
g. Cell proliferative disorders, like cancer; and
h. Thrombosis.

In addition to the above disorders, the present compounds can be used in the treatment of physiological dysfunction involving changes in intracellular pH, cell shape, cell volume, cell adhesion and migration (e.g. disorders involving cell proliferation, thrombosis and immunological responses.)

In addition to the above therapeutic applications (e.g., for both human and veterinary uses) the compounds of the present invention can used as an additive to tissue preserving media, e.g., cardioplegic solutions (Circulation 102 [suppl III]:III-319-325, (2000)) and solutions used for preservation of organs before transplantation (Transplant proc. 33:841-842, (2001)). These compounds are also useful to protect cardiac allografts from ischemia/reperfusion injury and prolong their survival.

Differential screening assays known in the art can be used to select those compounds of the present invention with specificity for non-human NHE inhibition. Thus, compounds that act specifically on eukaryotic pathogens (e.g. anti-parasitic agents), can be selected from the subject compounds of the formula 1.

When used for living beings other than humans, the formulations of the inhibitors can be provided with those inhibitors which inhibit NHE of the non human pathogen with an $IC_{50}$ at least an order of magnitude less than an $IC_{50}$ for inhibition of a human NHE, though more preferably at least two or three orders of magnitude less.

In a similar manner, a selection of the compounds of the present invention can be made on the basis of inhibitory specificity for insect or plant NHEs relative to the mammalian exchange mechanism in a differential screen. Such insect or plant NHE inhibitors of the present invention may find use in insecticides and agricultural applications, respectively.

The primary aspect of the present invention is a method for treating a mammal (e.g., human) having a disease or condition with underlying NHE-1 involvement by administering a therapeutically effective amount of a compound of the formula 1, 1a, 1b or 1c, or a prodrug thereof, or a pharmaceutically acceptable salt of the compound or of the prodrug, to the mammal.

The present invention is accordingly directed to a compound of the formula 1, 1a, 1b or 1c, or a prodrug thereof, or a pharmaceutically acceptable salt of the compound, for the manufacture of a medicament for the treatment of a mammal (e.g., human) having a disease or condition with underlying NHE-1 involvement.

Another aspect of the present invention is directed to a method for preventing and/or minimizing tissue damage resulting from ischemia by administering to an affected mammal, (e.g., a female or male human), a therapeutically effective amount of a compound of the formula 1, 1a, 1b or 1c, or a prodrug thereof, or a pharmaceutically, acceptable salt thereof.

Preferred ischemic tissues are considered individually or as a group and include tissues like cardiac, brain, liver, kidney, lung, gut, skeletal muscle, spleen, pancreas, nerve, spinal cord, retina, vascular or intestinal tissue. The preferred ischemic tissue is a cardiac tissue, especially when compounds are administered prophylactically to prevent perioperative myocardial ischemic injury. The ischemic damage may occur during organ transplantation or preservation of the donated organ. Preferably, the compounds of this invention are administered prior to, during or shortly after, cardiac surgery or non-cardiac surgery.

Another aspect of the present invention is directed to a method of treatment for reducing myocardial tissue damage and/or protecting cardiac tissue from damage during surgery (e.g., Coronary Artery Bypass Grafting (CABG), vascular surgeries, Percutaneous Transluminal Coronary Angioplasty (PTCA) or any Percutaneous Transluminal Coronary Intervention (PTCI), organ transplantation, or other non-cardiac surgeries), comprising administering to a mammal (e.g., a female or male human), a therapeutically effective amount of the compound of the present invention, a prodrug thereof, or a pharmaceutically acceptable salt of the compound or of the prodrug.

Another aspect of the present invention is directed to a method of treatment offering protection by reducing/preventing myocardial tissue damage in patients presented with progressive cardiac (acute coronary syndromes, e.g. myocardial infarction or unstable angina) or cerebral ischemic events (e.g. stroke), comprising administering to a mammal (e.g., a female or male human) a therapeutically effective amount of a compound of the formula 1, 1a, 1b or 1c, a prodrug thereof, or a pharmaceutically acceptable salt of the compound or of the prodrug.

Another aspect of the present invention is directed to a chronic method of minimizing or retarding cardiac injury by preventing or protecting the tissue against damage in a patient diagnosed with coronary heart disease (e.g. pre-existing myocardial infarction or unstable angina) or in a high risk patient susceptible to myocardial infarction (above 65 years and having two or more risk factors for coronary heart disease), comprising administering to a mammal (e.g., a female or male human) a therapeutically effective amount of a compound of the formula 1, 1a, 1b or 1c, a prodrug thereof, or a pharmaceutically acceptable salt of the compound or of the prodrug.

Another aspect of the present invention is directed to a method of prophylactic chronic oral administration of a therapeutically effective amount of a compound of the formula 1, 1a, 1b or 1c, a prodrug of the compound or a pharmaceutically acceptable salt of the compound or of the prodrug, to a mammal in need of such treatment to prevent or reduce ischemic damage.

Another aspect of the present invention is directed to a method of treatment for any one or combination of the diseases: cardiovascular diseases, arteriosclerosis, hypertension, cardiac arrhythmia, angina pectoris, cardiac hypertrophy, renal diseases, diabetic complications, vascular restenosis, diseases of cell proliferation, cancerous diseases, fibrotic diseases, glomerular nephrosclerosis, organ hypertrophies or hyperplasias, pulmonary fibrosis, cerebro ischemic disorders, myocardial stunning, myocardial dysfunction and cerebrovascular diseases, comprising administering to a mammal (e.g., a female or male human) a therapeutically effective amount of a compound of the formula 1, 1a, 1b or 1c, a prodrug thereof, or a pharmaceutically acceptable salt of the compound or of the prodrug.

The present invention also relates to the use of the compound of the formula 1, 1a, 1b or 1c, and/or their pharmaceutically acceptable salts and/or their prodrugs for the preparation of pharmaceuticals (or medicaments) intended for the prevention or the treatment of the diseases mentioned above or below.

The compounds and pharmaceuticals of the present invention can be used for the inhibition of cell proliferation, for example for the therapy and prophylaxis of cancer, for the prevention and treatment inflammation and arthritis, psoriasis, bone diseases, mycotic or viral infections, cardiovascular disorders and Alzheimers's disease.

The present invention also envisages the use of a compound of the formula 1, 1a, 1b, or 1c, a prodrug thereof, or a pharmaceutically acceptable salt of the compound or of the prodrug in combination with one or more other pharmaceutically active compounds. For instance, a pharmaceutical composition comprising a compound of the formula 1, 1a, 1b or 1c, or a pharmaceutically acceptable salt or prodrug thereof, and a cardiovascular agent, may be used for the reduction of tissue damage resulting from tissue ischemia in mammals (e.g., humans, male or female).

The combination product as described is a compound of the present invention, or prodrug thereof, or pharmaceutically acceptable salt of the compound or prodrug, and at least one other pharmaceutically active compound presented for either sequential or simultaneous administration.

Accordingly, another aspect of this invention is a method of reducing tissue damage (e.g., substantially preventing tissue damage, inducing tissue protection) which may result from ischemia, comprising administering to a mammal (e.g., a female or male human):
a. a first compound, said first compound being a compound of the formula 1, 1a, 1b or 1c, a prodrug thereof, or a pharmaceutically acceptable salt of the compound or of the prodrug; and
b. a second compound, said second compound being a cardiovascular agent, wherein the amounts of the first and second compounds result in a therapeutic effect.

In above combination products and combination methods, preferably the cardiovascular agents are, for example, β-blockers (e.g., acebutolol, atenolol, bopindolol, labetolol, mepindolol, nadolol, oxprenolol, pindolol, propranolol, sotalol), calcium channel blockers (e.g., amlodipine, nifedipine, nisoldipine, nitrendipine, verapamil), potassium channel openers, adenosine agonists, ACE inhibitors (e.g., captopril, enalapril), nitrates (e.g., isosorbide dinitrate, isosorbide 5-mononitrate, glyceryl trinitrate), diuretics (e.g., hydrochlorothiazide, indapamide, piretanide, xipamide), glycosides (e.g., digoxin, metildigoxin), thrombolytics (e.g. tPA), platelet inhibitors (e.g., Reopro®), aspirin, dipyridamol, potassium chloride, clonidine, prazosin or adenosine $A_3$ receptor agonists, aldose reductase inhibitors (e.g., zopolrestat) and glycogen phosphorylase inhibitors.

The compounds of the present invention may also be used in combination with an anti-cancer agent, a diuretic, an anti-diabetic agent or an anti-hyperlipidemic agent.

In the above combination products and combination methods, preferred formula 1, 1a, 1b or 1c compounds include the preferred groups of compounds as described in the preferred embodiments of the invention.

In general, the combination products according to the present invention, if formulated as a fixed dose, use the compounds of the present invention within the dose range described below and the other pharmaceutically active agent within its approved dose range.

In the methods of treatment as applied to the compounds, compositions and combinations according to the present invention, the following aspects are preferred:
the ischemic tissue, taken individually or as a group, is cardiac, brain, liver, kidney, lung, gut, skeletal muscle, spleen, pancreas, nerve, spinal cord, retina, the vasculature, or from the intestine. An especially preferred ischemic tissue is cardiac tissue;
the compounds, compositions and combinations are administered: (a) to prevent perioperative myocardial ischemic injury, (b) prophylactically when the ischemic damage may occur during organ transplantation, (c) prior to, during or shortly after, cardiac surgery or non-cardiac surgery, (d) locally, (e) to reduce myocardial tissue damage during surgery, and (f) to reduce myocardial tissue damage in patients presented with ongoing cardiac or cerebral ischemic events.

The present invention furthermore relates to a pharmaceutical composition that contains an therapeutically effective amount of at least one compound of the formula 1, 1a, 1b or 1c, and/or its physiologically tolerable salt and/or its prodrug in addition to a customary pharmaceutically acceptable carrier, and to a process for the production of a pharmaceutical, which comprises bringing at least one compound of the formula 1, 1a, 1b or 1c, into a suitable administration form using a pharmaceutically suitable and physiologically tolerable excipient and, if appropriate, one or more further suitable active compounds, additives or auxiliaries.

The pharmaceutical preparation comprises the compound of the formula 1, 1a, 1b, or 1c, in an amount adequate to inhibit proliferation of a eukaryotic cell, which may be a mammalian cell, a human pathogen, a non human pathogen, an insect cell or a plant cell.

The present invention also relates to a method for the preparation of a medicament for the treatment or prevention of disorders associated with excessive cell proliferation, characterized in that at least one compound of the formula 1, 1a, 1b or 1c, is used as the pharmaceutically active substance.

The pharmaceuticals can be administered orally, for example in the form of pills, tablets, coated tablets, capsules, granules or elixirs. Administration, however, can also be carried out rectally, for example in the form of suppositories, or parentally, for example intravenously, intramuscularly or subcutaneously, in the form of injectable sterile solutions or suspensions, or topically, for example in the form of solutions or transdermal patches, or in other ways, for example in the form of aerosols or nasal sprays.

The pharmaceutical preparations according to the invention are prepared in a manner known per se and familiar to one skilled in the art. Pharmaceutically acceptable inert inorganic and/or organic carriers and/or additives can be used in addition to the compound(s) of the formula 1, 1a, 1b or 1c and/or its (their) physiologically tolerable salts and/or its (their) prodrugs. For the production of pills, tablets, coated tablets and hard gelatin capsules it is possible to use, for example, lactose, corn starch or derivatives thereof, gum arabica, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

The pharmaceutical preparations normally contain about 1 to 99%, preferably about 5 to 70%, most preferably from about 10 to about 30% by weight of the compounds of the formula 1, 1a, 1b or 1c and/or their physiologically tolerable salts and/or their prodrugs. The amount of the active ingredient of the formula 1, 1a, 1b or 1c, and/or its physiologically tolerable salts and/or its prodrugs in the pharmaceutical preparations normally is from about 5 to 500 mg. The dose of the compounds of the present invention, which is to be administered, can cover a wide range. The dose to be administered daily is to be selected to suit the desired effect. About 20 to 1,000 mg are preferably administered daily per patient. If required, higher or lower daily doses can also be administered. A preferred dosage is about 0.001 to 100 mg/kg/day of the compound of general formula 1, 1a, 1b or 1c or a prodrug thereof. An especially preferred dosage is about 0.01 to 50 mg/kg/day of a compound of formula 1, 1a, 1b or 1c, a prodrug thereof, or a pharmaceutically acceptable salt of the compound or of the prodrug. Actual dosage levels of the active ingredients in the pharmaceutical compositions of the present invention may be varied so as to obtain an amount of the active ingredient which is effective to achieve the desired therapeutic response for a particular patient, composition, and mode of administration without being toxic to the patient.

The selected dosage level will depend upon a variety of factors, including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts.

In addition to the active ingredients of the formula 1, 1a, 1b or 1c and/or their physiologically acceptable salts and/or prodrugs and to carrier substances, the pharmaceutical preparations can contain additives such as, for example, fillers, antioxidants, dispersants, emulsifiers, defoamers, flavors, preservatives, solubilizers or colorants. They can also contain two or more compounds of the formula 1, 1a, 1b or 1c and/or their physiologically tolerable salts and/or their prodrugs. Furthermore, in addition to at least one compound of the formula 1, 1a, 1b or 1c, and/or its physiologically tolerable salts and/or its prodrugs, the pharmaceutical preparations can also contain one or more other therapeutically or prophylactically active ingredients.

It is understood that modifications that do not substantially affect the activity of the various embodiments of this invention are included within the invention disclosed herein. Accordingly, the following examples are intended to illustrate but not to limit the present invention.

The invention is explained in detail in the examples given below and should not be construed to limit the scope of the invention:

The following abbreviations are used herein:

RT: room temperature

AcOH: acetic acid $Ac_2O$: acetic anhydride

AIBN: 2,2'-azobis-(2-methylpropionitrile)/2,2'-azobisisobutyronitrile

DMF: N,N-dimethylformamide

DMSO: dimethylsulfoxide

EtOAc: ethyl acetate

EtOH: ethyl alcohol m-CPBA: meta-chloroperbenzoic acid

MeOH: methanol

NBS: N-bromosuccinimide

NMP: N-methylpyrrolidine $PPh_3$: triphenylphosphine

PTSA: 4-toluenesulfonic acid

TEA: triethylamine

TFA: trifluoroacetic acid

THF: tetrahydrofuran

Z: benzyloxycarbonyl $NaBH_4$: sodium borohydride $NaBH_3CN$: sodium cyano borohydride $POCl_3$: phosphorous oxychloride NaH: sodium hydride HOBT: 1-hydroxybenzotriazole DCC: 1,3-dicyclohexylcarbodiimide HMPA: hexamethylphosphoramide PE: petroleum ether

EXAMPLE 1

N-(10,10-Dioxo-10,11-dihydro-5-oxa-10lambda*6*-thia-dibenzo[a.d]cycloheptene-8-carbonyl)-guanidine, methanesulfonic acid salt 1,1-Carbonyldiimidazole (0.2 g, 1.2 mmol) was added in an atmosphere of $N_2$ to a solution of Example 1i (0.25 g, 0.86 mmol) in dry DMF (5 mL). The reaction mixture was stirred for 1 h and subsequently added dropwise with stirring to guanidine (generated as given below from its hydrochloride) in methanol (10 mL). The reaction mixture was stirred for 1 h, concentrated, treated with water, extracted with ethyl acetate, washed with brine, dried and purified using flash chromatography (silica gel, $CHCl_3$/MeOH) to obtain the acyl guanidine (0.28 g, 98%). It was treated with methane sulfonic acid (1.1 eq) in dry ethyl acetate to obtain the title compound. Yield: 0.150 g, (58%); mp: 202-203° C.; $^1H$ NMR (DMSO-$d_6$): δ 2.35 (s, 3H, $CH_3SO_3H$), 5.30 (s, 2H, $CH_2$), 7.35-7.50 (m, 3H, Ar—H), 7.65 (d, 1H, Ar—H), 7.80 (d, 1H, Ar—H), 8.20 (d, 1H, Ar—H), 8.40 (s, 1H, Ar—H) 8.30-8.50 (NH exchangeable with $D_2O$); MS: m/e (EI+) 331 (M+1, free base); IR $cm^{-1}$: 3400-3200, 1725, 1610, 1395, 1150, 1050, 750.

Guanidine (free base) preparation: Guanidine hydrochloride (0.411 g, 4.3 mmol) was treated with sodium (0.094 g, 4.3 mmol) in dry methanol (10 mL). The guanidine obtained was filtered free of NaCl in an atmosphere of $N_2$ and concentrated to be used as mentioned above.

EXAMPLE 1a

4-Bromo-3-chlorosulfonyl-benzoic acid

Chlorosulfonic acid (70 mL, 1.05 mol) cooled to 0° C. was added dropwise with stirring to 4-bromo-benzoic acid (50 g, 0.29 mol). The reaction mixture was heated at 110° C. for 10 h, cooled to room temperature and poured onto crushed ice slowly with stirring. The title compound obtained was filtered, washed with water and dried. Yield: 51 g, (84%); mp: 198-199° C.; MS: m/e (EI+) 299 (M+).

EXAMPLE 1b

4-Bromo-3-mercapto-benzoic acid

A suspension of stannous chloride dihydrate (21 g, 93.1 mmol) in hydrochloric acid and water (25 mL, 4:1, v/v) was added dropwise with stirring to a solution of Example 1a (5.0 g, 16.7 mmol) in glacial acetic acid (57 mL) at 80° C. The reaction mixture was heated for 1 h at 80° C. and treated with ice-water to obtain a mixture of the title compound and its dimer as a white solid, which was washed with water and dried. Yield: 3.2 g, (82%); mp: 315-317° C.; MS: m/e (EI+) 233 (M+).

EXAMPLE 1c

4-Bromo-3-mercapto-benzoic acid methyl ester

Conc. $H_2SO_4$ (6.25 mL) was added dropwise to a refluxing solution of Example 1b and its dimer (3 g) in dry MeOH (60 mL). The reaction mixture was refluxed for 15 h, concentrated and treated with ice to obtain a mixture of the desired ester and that of its dimer, which was filtered, washed with water and dried. Purification was effected using flash chromatography (silica gel, EtOAc/PE60-80° C.) to obtain the title compound and its dimer ester (2.8 g) which was in turn converted into the title compound as given below: Triphenylphosphine (1.5 g, 5.71 mmol) was added to a solution of the dimer ester in MeOH/$H_2O$ (15 mL 4:1, v/v) and allowed to stir overnight at room temperature. The reaction mixture was concentrated, treated with water and extracted with ethyl acetate. The ethyl acetate layer was concentrated and the crude obtained was purified using flash chromatography as above to obtain more of the title compound. Yield: 2.0 g, (72%); mp: 81° C.; $^1H$ NMR (CDCl$_3$): δ 3.90 (s, 3H, OCH$_3$), 4.0 (s, 1H, SH), 7.05-7.25 (m, 3H, Ar); MS: m/e (EI+) 247 (M+).

EXAMPLE 1d tert-Butyl-dimethyl-o-tolyloxy-silane tert-Butyldimethylsilyl chloride (83.6 g, 0.55 mol) and imidazole (78.69 g, 1.15 mol) were added to a solution of o-cresol (50 g, 0.46 mol) in dry DMF (200 mL). The reaction mixture was stirred for 3 h, treated with a 5% aqueous $NaHCO_3$ solution, extracted with petroleum ether and concentrated to obtain the title compound as an oil. Yield: 102 g, (100%); $^1H$ NMR (CDCl$_3$): δ 0.20 (s, 6H, 2CH$_3$), 1.0 (s, 9H, 3CH$_3$), 2.2 (s, 3H, CH$_3$), 6.75 (d, 1H, Ar), 6.85 (q, 1H, Ar), 7.18 (q, 1H, Ar), 7.25 (d, 1H, Ar).

EXAMPLE 1e (2-Bromomethyl-phenoxy)-tert-butyl-dimethyl-silane

A catalytic amount of benzoylperoxide (0.5 g) was added to a refluxing solution of an equimolar mixture of Example 1d (30 g, 0.134 mol) and N-bromosuccinamide (24 g, 0.134 mol) in dry $CCl_4$ (175 mL) for 1.5 h. The reaction mixture was filtered, concentrated and purified using flash chromatography (silica gel, PE60-80° C.) to obtain the title compound as an oil. Yield: 36 g, (90%); $^1H$ NMR (CDCl$_3$): δ 0.30 (s, 6H, 2CH$_3$), 1.10 (s, 9H, 3CH$_3$), 4.5 (s, 2H, CH$_2$), 6.8-7.5 (m, 4H, Ar).

EXAMPLE 1f

4-Bromo-3-[2-(tert-butyl-dimethyl-silanyloxy)-benzylsulfanyl]-benzoic acid methyl ester Triethylamine (0.727 mL, 7.2 mmol) was added dropwise with stirring to a solution of Example 1c (1 g, 4.04 mmol) and Example 1e (1.46 g, 4.8 mmol) in dichloromethane (10 mL) at 0° C. The reaction mixture was stirred for 1 h at 0° C., treated with water and extracted with dichloromethane. The organic layer was washed with water, dried and purified using flash chromatography (silica gel, EtOAc/PE60-80° C.) to obtain the title compound. Yield: 1.2 g, (66%); $^1H$ NMR (CDCl$_3$): δ 0.30 (s, 6H, 2CH$_3$), 1.05 (s, 9H, 3CH$_3$), 3.90 (s, 3H, OCH$_3$), 4.20 (s, 2H, CH$_2$), 6.80 (m, 2H, Ar), 7.20 (t, 1H, Ar), 7.30 (d, 1H, Ar), 7.60 (m, 2H, Ar), 7.90 (s, 1H, Ar); MS: m/e (EI+) 411(M—tert-Butyl).

EXAMPLE 1g

4-Bromo-3-[2-(tert-butyl-dimethyl-silanyloxy)-phenylmethanesulfonyl]-benzoic acid methyl ester m-Chloroperbenzoic acid (0.7 g, 4.05 mmol) was added in small portions to a solution of Example 1f (0.5 g, 1.07 mmol) in dichloromethane (35 mL). The reaction mixture was stirred for 2 h, concentrated, treated with an aqueous 5% $NaHCO_3$ solution, stirred for 20 min. and extracted with ethyl acetate. The organic layer was washed with water, dried and concentrated to obtain the title compound. Yield: 0.55 g, (95%); $^1$H NMR (CDCl$_3$): δ 0.25 (s, 6H, 2CH$_3$), 1.0 (s, 9H, 3CH$_3$), 3.90 (s, 3H, OCH$_3$), 4.70 (s, 2H, CH$_2$), 6.80 (t, 2H, Ar), 7.10 (d, 1H, Ar), 7.15 (t, 1H, Ar), 7.90 (d, 1H, Ar), 8.10 (d, 1H, Ar), 8.50 (s, 1H, Ar); MS: m/e (EI+) 443(M—tert-Butyl).

EXAMPLE 1h 10,10-Dioxo-10,11-dihydro-5-oxa-10lambda*6*-thia-dibenzo[a,d]cycloheptene-8-carboxylic acid methyl ester Tetra-n-butylammonium fluoride (0.693 g, 2.2 mol) in THF (15 mL) was added dropwise to a solution of Example 1g (0.55 g, 1.1 mmol) in dry THF (5 mL) at 0° C. The reaction mixture was stirred for 1 h and treated with crushed ice to obtain the title compound as a solid. It was filtered, washed with water and dried. Yield: 0.25 g, (75%); $^1$H NMR (CDCl$_3$): δ 3.90 (s, 3H, OCH$_3$), 4.60 (s, 2H, CH$_2$), 7.30-7.40 (m, 5H, Ar), 8.20 (d, 1H, Ar), 8.60 (d, 1H, Ar); MS: m/e (EI+) 304 (M+).

EXAMPLE 1i 10,10-Dioxo-10,11-dihydro-5-oxa-10lambda*6*-thia-dibenzo[a,d]cycloheptene-8-carboxylic acid Example 1h (0.450 g, 1.48 mmol) in methanol (10 mL) was treated with aqueous NaOH (0.118 g, 2.95 mmol in 5 mL) and stirred at 45° C. for 2 h. The reaction mixture was concentrated and acidified with 10% HCl to obtain the title compound as a solid. It was filtered, washed with water and dried. Yield: 0.28 g, (65%); $^1$H NMR (CDCl$_3$+DMSO-d$_6$): δ 4.70 (s, 2H, CH$_2$), 7.10-7.30 (m, 5H, Ar), 8.00 (dd, 1H, Ar), 8.45 (d, 1H, Ar).

EXAMPLE 2

N-(2,4-Dichloro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 2i as described in the synthesis of Example 1. Yield: 58%; mp: 270-271° C.; $^1$H NMR (DMSO-d$_6$): δ 2.35 (s, 3H, CH$_3$SO$_3$H), 5.40 (s, 2H, CH$_2$), 7.80 (s, 1H, Ar), 7.85-9.0 (m, 1H, Ar), 8.20-8.30 (m, 2H, Ar), 8.40 (s, 1H, Ar), 8.45-8.55 (NH exchangeable with D$_2$O); IR cm$^{-1}$: 3350, 3100, 1700, 1600, 1450, 1300, 1250, 1175, 1050; analysis: C$_{16}$H$_{15}$Cl$_2$N$_3$O$_3$S$_2$ calcd.: C, 38.06; H, 3.03; N, 7.76; Cl, 14.15; S, 12.14; found: C, 38.72; H, 3.05; N, 8.47 Cl, 14.29; S, 12.92%.

EXAMPLE 2i 2,4-Dichloro-10,10-dioxo-10,11-dihydro-5-oxa-10lambda*6*-thia-dibenzo[a,d]cycloheptene-8-carboxylic acid The title compound was synthesised from methyl 4-bromo-3-mercapto-benzoic acid methyl ester and (2-bromomethyl-4,6-dichloro-phenoxy)-tert-butyl-dimethyl-silane as described in the synthesis of Examples 1f-1i. Yield: 5%; $^1$H NMR (CDCl$_3$+DMSO-d$_6$): δ 4.50 (s, 2H, CH$_2$), 6.90-7.20 (m, 3H, Ar), 7.30 (d, 1H, Ar), 8 (d, 1H, Ar); MS: m/e (EI+) 359 (M+).

(2-Bromomethyl-4,6-dichloro-phenoxy)-tert-butyl-dimethyl-silane) was synthesised from 2,4-dichloro-6-methylphenol as described in the synthesis of Example 1e

EXAMPLE 3

N-(2-Chloro-10,10-dioxo-10,11-dihydro-5-oxa-10lambda*6*-thia-dibenzo[a,d]cycloheptene-8-carbonyl)-guanidine, methanesulfonic acid salt The title compound was synthesised from Example 3i as described in the synthesis of Example 1. Yield: 31%; mp: 280-282° C.; $^1$H NMR (DMSO-d$_6$): δ 2.40 (s, 3H, CH$_3$SO$_3$H), 5.35 (s, 2H, CH$_2$), 7.50 (s, 2H, Ar), 7.65 (s, 1H, Ar), 7.70 (d, 1H, Ar), 8.20 (d, 1H, Ar), 8.40 (s, 1H, Ar), 8.30-8.50 (NH exchangeable with D$_2$O); MS: m/e (ES+) 366 (M+1, free base); IR cm$^{-1}$: 3400-3300, 1700, 1600, 1470, 1300, 1260-1220, 1150, 1050, 790.

EXAMPLE 3i

2-Chloro-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-4-chloro-phenoxy)-tert-butyl-dimethyl-silane as described in the synthesis of Examples 1f-1i. Yield: 31%; mp: 280-282° C.; $^1$H NMR (CDCl$_3$+DMSO-d$_6$): δ 5.40 (s, 2H, CH$_2$), 6.90-7.20 (m, 2H, Ar), 7.50 (d, 1H, Ar), 7.60 (s, 1H, Ar), 7.80 (d, 1H, Ar), 8.10 (s, 1H, Ar); MS: m/e (ES+) 324 (M+, free base).

(2-Bromomethyl-4-chloro-phenoxy)-tert-butyl-dimethylsilane was synthesised from 4-chloro-2-methyl-phenol as described in the synthesis of Example 1e.

EXAMPLE 4

N-(4-Chloro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 4i as described in the synthesis of Example 1. Yield: 31%; mp: 233-235° C.; $^1$H NMR (DMSO-d$_6$): δ 2.40 (s, 3H, CH$_3$SO$_3$H), 5.40 (s, 2H, CH$_2$), 7.45 (t, 1H, Ar), 7.75 (t, 2H, Ar), 7.90 (d, 1H, Ar), 8.30 (d, 1H, Ar), 8.40 (s, 1H, Ar), 8.45-8.50 (NH exchangeable with D$_2$O); MS: m/e (ES+) 365 (M+, free base); IR cm$^{-1}$: 3500-3300, 1710, 1600, 1450, 1310, 1250, 1190, 1050, 930, 860, 790.

EXAMPLE 4i

4-Chloro-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-6-chloro-phenoxy)-tert-butyl-dimethyl-silane as described in the synthesis of Examples 1f-1i. Yield: 8.7%; $^1$H NMR (DMSO-d$_6$): δ 5.40 (s, 2H, CH$_2$), 7.40 (t, 1H, Ar), 7.60 (m, 2H, Ar), 7.70 (d, 1H, Ar), 8.20 (d, 1H, Ar), 8.30 (s, 1H, Ar); MS: m/e (ES+) 324 (M+).

(2-Bromomethyl-6-chloro-phenoxy)-tert-butyl-dimethylsilane was synthesised from 2-chloro-6-methyl-phenol as described in the synthesis of Example 1e.

EXAMPLE 5

N-(3-Fluoro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 5i as described in the synthesis of Example 1. Yield: 34.64%; mp: 214-215° C.; $^1$H NMR (DMSO-$d_6$): δ 2.40 (s, 3H, $CH_3SO_3H$), 5.25 (s, 2H, $CH_2$), 7.20-7.50, (m, 3H, Ar), 7.80 (d, 1H, Ar), 8.20 (d, 1H, Ar), 8.40 (s, 1H, Ar), 8.40-8.50 ($NH_2$ exchangeable with $D_2O$); MS: m/e (ES+) 349 (M+, free base); IR $cm^{-1}$: 3400, 3150, 1725, 1610, 1500, 1250-1150, 1050, 800.

EXAMPLE 5i

3-Fluoro-10,10-dioxo-10,11-dihydro-5-oxa-10lambda*6*-thia-dibenzo[a,d]cycloheptene-8-carboxylic acid The title compound was synthesized from 4-bromo-3-mercapto-benzoic acid methyl ester and (2-Bromomethyl-5-fluoro-phenoxy)-tert-butyl-dimethyl-silane as described in the synthesis of Examples 1f-1i. $^1$H NMR (DMSO-$d_6$): δ 5.30 (s, 2H, $CH_2$), 7.30 (t, 1H, Ar), 7.50-7.60 (m, 4H, Ar), 8.20 (s, 1H, Ar).

(2-Bromomethyl-5-fluoro-phenoxy)-tert-butyl-dimethyl-silane was synthesised from 5-fluoro-2-methylthiophenol as described in the synthesis of Example 1e.

EXAMPLE 6

N-(1-Fluoro-10,10-dioxo-10,11-dihydro-5-oxa-10lambda*6*-thia-dibenzo[a,d]cycloheptene-8-carbonyl)-guanidine, methanesulfonic acid salt The title compound was synthesised from Example 6i as described in the synthesis of Example 1. Yield: 69.44%; mp: 231-232° C.; $^1$H NMR (DMSO-$d_6$): δ 2.40 (s, 3H, $CH_3SO_3H$), 5.30 (s, 2H, $CH_2$), 7.35-7.60 (m, 3H, Ar), 7.80 (d, 1H, Ar), 8.25 (d, 1H, Ar), 8.40 (s, 1H, Ar) 8.50-8.60 ($NH_2$ exchangeable with $D_2O$); MS: m/e (ES+) 349 (M+, free base); IR $cm^{-1}$: 3200, 2950, 2360, 1525, 1390, 1050, 905, 858.

EXAMPLE 6i

1-Fluoro-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-3-fluoro-phenoxy)-tert-butyl-dimethyl-silane as described in the synthesis of Examples 1f-1i. Yield: 40.93%; $^1$H NMR (DMSO-$d_6$): δ 5.20 (s, 2H, $CH_2$), 7.30-7.60 (m, 3H, Ar), 7.80 (d, 1H, Ar), 8.25 (t, 1H, Ar) 8.30 (s, 1H, Ar); MS: m/e (ES+) 308 (M+).

(2-Bromomethyl-3-fluoro-phenoxy)-tert-butyl-dimethyl-silane was synthesised from 3-fluoro-2-methyl-phenol as described in the synthesis of Example 1e.

EXAMPLE 7

N-(2-Fluoro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 7i as described in the synthesis of Example 1. Yield: 56.55%; mp: 264-266° C.; $^1$H NMR (DMSO-$d_6$): δ 2.40 (s, 3H, $CH_3SO_3H$), 5.30 (s, 2H, $CH_2$), 7.30 (t, 1H, Ar), 7.50-7.60 (m, 2H, Ar), 7.80 (d, 1H, Ar), 8.20 (d, 1H, Ar), 8.4 (s, 1H, Ar), 8.45-8.55 ($NH_2$ exchangeable with $D_2O$); MS: m/e (ES+) 349 (M+, free base); IR $cm^{-1}$: 3300, 3100, 1705, 1600, 1500, 1480, 1300, 1050.

EXAMPLE 7i

2-Fluoro-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-4-fluoro-phenoxy)-tert-butyl-dimethyl-silane as described in the synthesis of Examples1f-1i. Yield: 59.27%; $^1$H NMR (DMSO-$d_6$): δ 5.30 (s, 2H, $CH_2$), 7.30 (t, 1H, Ar), 7.55 (m, 2H, Ar), 7.70 (d, 1H, Ar—H), 8.20 (d, 1H, Ar), 8.30 (s, 1H, Ar); MS: m/e (ES+) 308 (M+).

(2-Bromomethyl-4-fluoro-phenoxy)-tert-butyl-dimethyl-silane was synthesised from 4-fluoro-2-methyl-phenol as described in the synthesis of Example 1e.

EXAMPLE 8

N-(4-Isopropyl-10,10-dioxo-10,11-dihydro-5-oxa-10lambda*6*-thia-dibenzo[a,d]cycloheptene-8-carbonyl)-guanidine, methanesulfonic acid salt The title compound was synthesised from Example 8i as described in the synthesis of Example 1. Yield: 52.13%; mp: 220-222° C.; $^1$H NMR (DMSO-$d_6$): δ 1.2 (d, 6H, $2CH_3$), 2.35 (s, 3H, $CH_3SO_3H$), 3.55 (m, 1H, CH), 5.30 (s, 2H, $CH_2$), 7.40 (t, 1H, Ar), 7.45-7.50 (m, 2H, Ar), 7.90 (d, 1H, Ar), 8.20 (d, 1H, Ar), 8.30 ($NH_2$, exchangeable with $D_2O$), 8.45 (s, 1H, Ar); MS: m/e (ES+) 374 (M+1, free base); IR $cm^{-1}$: 3400, 3150, 1750, 1600, 1450, 1350, 1250, 1150, 1050, 700.

EXAMPLE 8i

4-Isopropyl-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-6-isopropyl-phenoxy)-tert-butyl-dimethyl-silane as described in the synthesis of Examples 1f-1i. Yield: 21.64%; $^1$H NMR (DMSO-$d_6$): δ 1.20 (d, 6H, $2CH_3$), 3.60 (m, 1H, CH), 5.20 (s, 2H, $CH_2$), 7.30-7.50 (m, 3H, Ar), 7.70 (d, 1H, Ar), 8.20 (d, 1H, Ar), 8.30 (s, 1H, Ar); MS: m/e (ES+) 333 (M+1).

(2-Bromomethyl-6-isopropyl-phenoxy)-tert-butyl-dimethyl-silane was synthesised from 2-isopropyl-6-methyl-phenol as described in the synthesis of Example 1e.

EXAMPLE 9

N-(4-Methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from example 9i as described in the synthesis of Example 1. Yield: 70%; mp: 260-262° C.; $^1$H NMR (DMSO-d$_6$): δ 2.35 (s, 3H, CH$_3$SO$_3$H), 2.40 (s, 3H, CH$_3$), 5.20 (s, 2H, CH$_2$), 7.30 (m, 2H, Ar), 7.50 (d, 1H, Ar), 7.90 (d, 1H, Ar), 8.20 (d, 1H, Ar), 8.40 (s, 1H, Ar), 8.30-8.50 (NH exchangeable with D$_2$O); MS: m/e (ES+) 345 (M+, free base); IR cm$^{-1}$: 3380, 3300-3200, 1700, 1600, 1580, 1460, 1320, 1230-1180, 1050, 920, 790.

EXAMPLE 9i

4-Methyl-10,10-dioxo-10,11-dihydro-5-oxa-10lambda*6*-thia-dibenzo[a,d]cycloheptene-8-carboxylic acid The title compound was synthesised from 4-bromo-3-mercapto-benzoic acid methyl ester and (2-bromomethyl-6-methyl-phenoxy)-tert-butyl-dimethyl-silane as described in the synthesis of Examples 1f-1i. Yield: 42%; $^1$H NMR (DMSO-d$_6$): δ 2.40 (s, 3H, CH$_3$) 5.70 (s, 2H, CH$_2$), 7.40 (m, 2H, Ar), 7.45 (d, 1H, Ar), 7.80 (d, 1H, Ar), 8.20 (d, 1H, Ar), 8.30 (s, 1H, Ar).

(2-Bromomethyl-6-methyl-phenoxy)-tert-butyl-dimethyl-silane was synthesised from 2,6-dimethyl-phenol as described in the synthesis of Example 1e.

EXAMPLE 10

N-(4-Amino-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 10k as described in the synthesis of Example 1. Yield: 27.64%; mp: 290-292° C.; $^1$H NMR (DMSO-d$_6$): δ 2.40 (s, 3H, CH$_3$SO$_3$H), 5.00 (s, 2H, CH$_2$), 6.70 (d, 1H, Ar), 6.80 (d, 1H, Ar), 7.00 (t, 1H, Ar), 8.05 (d, 1H, Ar), 8.15 (d, 1H, Ar), 8.30 (s, 1H, Ar), 8.50 (NH$_2$ exchangeable with D$_2$O); MS: m/e (ES+) 346 (M+, free base); IR cm$^{-1}$: 3450-3400, 1700, 1600, 1500, 1300, 1280, 1250-1200, 1050, 920, 780.

EXAMPLE 10k

4-Amino-10,10-dioxo-10,11-dihydro-5-oxa-10lambda*6*-thia-dibenzo[a,d]cycloheptene-8-carboxylic acid The title compound was synthesised by catalytic hydrogenation (Raney-Nickel, 20-30 psi, 2 h) of Example 10j (0.99 g, 2.57 mmol) and subsequent hydrolysis of the product obtained, as described in the synthesis of example 1i. Yield: 0.7 g, (85%).

EXAMPLE 10j

4-Nitro-10,10-dioxo-10,11-dihydro-5-oxa-10lambda*6*-thia-dibenzo[a,d]cycloheptene-8-carboxylic acid methyl ester The title compound was synthesised from 4-bromo-3-mercapto-benzoic acid methyl ester and (2-bromomethyl-6-nitro-phenoxy)-tert-butyl-dimethyl-silane as described in the synthesis of Examples 1f-1h. Yield: 23.89%; $^1$H NMR (CDCl$_3$): δ 3.90 (s, 3H, OCH$_3$), 4.80 (s, 2H, CH$_2$), 7.50 (t, 1H, Ar), 7.60 (d, 1H, Ar), 7.75 (d, 1H, Ar), 7.95 (d, 1H, Ar), 8.30 (d, 1H, Ar), 8.60 (s, 1H, Ar); MS: m/e (ES+) 349 (M+, free base).

(2-Bromomethyl-6-nitro-phenoxy)-tert-butyl-dimethyl-silane was synthesised from 2-methyl-6-nitro-phenol as described in the synthesis of Example 1e.

EXAMPLE 11

N-(10,10-dioxo-4-pyrrol-1-yl-10,11-dihydro-5-oxa-10lambda*6*-thia-dibenzo[a,d]cycloheptene-8-carbonyl)-guanidine, methane sulfonic acid salt The title compound was prepared from Example 11j as described in the synthesis of Example 1. Yield: 72.20%; mp: 282-284° C.; $^1$H NMR (DMSO-d$_6$): δ 2.40 (s, 3H; CH$_3$SO$_3$H), 5.40 (s, 2H, CH$_2$), 6.40 (s, 2H, pyrrolyl), 6.90 (d, 1H, Ar), 7.10 (s, 2H, pyrrolyl), 7.50 (m, 2H, Ar), 7.65 (d, 1H, Ar), 8.10 (d, 1H, Ar), 8.30 (s, 1H, Ar), 8.30-8.50 (NH exchangeable with D$_2$O); MS: m/e (EI+) 396 (M+, free base); IR cm$^{-1}$: 400-3370, 3100, 1700, 1600, 1500, 1300, 1280, 1200-1150, 1040, 730.

EXAMPLE 11j 10,10-dioxo-4-pyrrol-1-yl-10,11-dihydro-5-oxa-10lambda*6*-thia-dibenzo[a,d]cycloheptene-8-carboxylic acid 2,5-Dimethoxy tetrahydrofuran (0.053 g, 0.40 mmol) and 4-chloropyridine hydrochloride (0.0047 g, 0.03 mmol) were added to a solution of the methyl ester of Example 10k (0.1 g, 0.31 mmol) in dry dioxan (15 mL). The reaction mixture was refluxed with stirring for 1 h, concentrated and extracted with ethyl acetate. The organic layer was washed with water, brine, dried and concentrated to obtain a product which was subsequently hydrolysed as described in the synthesis of Example 1i to obtain the title compound. Yield: 73.7%; $^1$H NMR (DMSO-d$_6$): δ 5.40 (s, 2H, CH$_2$), 6.40 (s, 2H, pyrrolyl), 6.80 (d, 1H, Ar), 7.10 (s, 2H, pyrrolyl) 7.50-7.70 (m, 3H, Ar), 8.05 (d, 1H, Ar), 8.20 (s, 1H, Ar); MS: m/e (EI+) 355 (M+).

EXAMPLE 12

N-(2-Methanesulfonyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 12j as described in the synthesis of Example 1. Yield: 43%; mp: 248-250° C.; $^1$H NMR (DMSO-d$_6$): δ 2.35 (s, 3H, CH$_3$SO$_3$H), 3.30 (s, 3H, SO$_2$CH$_3$), 5.50 (s, 2H, CH$_2$), 7.80 (d, 1H, Ar), 7.90 (d, 1H, Ar), 8.00 (dd, 1H, Ar), 8.25 (d, 1H, Ar), 8.30 (s, 1H, Ar), 8.45 (s, 1H, Ar); MS: m/e (ES+) 410 (M+1, free base); IR cm$^{-1}$: 3500-3300, 1690, 1610, 1490, 1300, 1250, 1200, 1130, 1050, 930, 780.

EXAMPLE 12j

2-Methanesulfonyl-10,10-dioxo-10,11-dihydro-5-oxa-10lambda*6*-thia-dibenzo[a,d]cycloheptene-8-carboxylic acid Chilled chlorosulphonic acid (0.39 mL, 0.59 mmol) was added with stirring at 0° C. to Example 1i (0.430 g, 1.48 mmol). The reaction mixture was stirred overnight at room temperature, then treated with crushed ice to obtain 2-chlorosulfonyl-10,10-dioxo-10,11-dihydro-5-oxa-10lambda*6*-thia-dibenzo[a,d]cycloheptene-8-carboxylic acid methyl ester as a solid which was filtered, washed with water and dried. Hydrazine hydrate (0.112 mL, 0.231 mmol) was added to this solid in THF (5 mL) at 0° C. and stirred for 0.5 h to obtain the sulphonylhydrazine derivative. Subsequent treatment with anhydrous NaOAC (0.410 g, 0.5 mmol) and methyl iodide (0.260 mL, 0.41 mmol) in absolute EtOH (5 mL) under reflux conditions (J. Med. Chem., 42, 1982-1990, (1999)) gave the 2-methanesulfonyl ester derivative as a solid which was filtered and dried. It was hydrolysed as described in the synthesis of Example 1i to obtain the title compound. Yield: 21.7%; $^1$H NMR (DMSO-$d_6$): δ 3.30 (s, 3H, $SO_2CH_3$), 5.50 (s, 2H, $CH_2$), 7.25 (m, 2H, Ar), 8.10 (d, 1H, Ar), 8.20 (d, 2H, Ar), 8.35 (d, 1H, Ar).

EXAMPLE 13

N-(7-Chloro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 13i as described in the synthesis of Example 1. Yield: 83%; mp: 268-269° C.; $^1$H NMR (DMSO-$d_6$): δ 2.35 (s, 3H, $CH_3SO_3H$), 5.30 (s, 2H, $CH_2$), 7.40 (t, 1H, Ar), 7.45-7.55 (m, 2H, Ar), 7.65 (d, 1H, Ar), 8.00 (s, 1H, Ar), 8.30 (s, 1H, Ar), 8.40-8.50 ($NH_2$ exchangeable with $D_2O$); MS: m/e (ES+) 366 (M+, free base); IR $cm^{-1}$: 3400, 3150, 1750, 1650, 1510, 1350, 1300, 1250-1200, 1050, 800.

EXAMPLE 13i

7-Chloro-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-phenoxy)-tert-butyl-dimethyl-silane as described in the synthesis of Examples 1f-1i. Yield: 27.77%; $^1$H NMR ($CDCl_3$+ DMSO-$d_6$): δ 4.65 (s, 1H, $CH_2$), 7.25-7.35 (m, 5H, Ar), 8.30 (s, 1H, Ar).

2,4-Dichloro-5-mercapto-benzoic acid methyl ester was synthesised from 2-4-dichloro-benzoic acid as described in the synthesis of Examples 1a-1c.

EXAMPLE 14

N-(10,10-dioxo-7-piperidin-1-yl-10,11-dihydro-5-oxa-10lambda*6*-thia-dibenzo[a,d]cycloheptene-8-carbonyl)-guanidine, methane sulfonic acid salt The title compound was synthesised from Example 14j as described in the synthesis of Example 1. Yield: 27.10%; mp: 224-225° C.; $^1$H NMR (DMSO-$d_6$): δ 1.65 (s, 6H, piperidinyl), 2.35 (s, 3H, $CH_3SO_3H$), 3.10 (s, 4H, piperidinyl), 5.15 (s, 2H, $CH_2$), 7.20 (s, 1H, Ar), 7.25-7.60 (m, 4H, Ar), 7.90 (s, 1H, Ar), 8.40-8.30 ($NH_2$ exchangeable with $D_2O$); MS: m/e (ES+) 415 (M+, free base); IR $cm^{-1}$: 3350, 3300, 1700, 1590, 1300, 1200, 1050.

EXAMPLE 14j 10,10-dioxo-7-piperidin-1-yl-10,11-dihydro-5-oxa-10lambda*6*-thia-dibenzo[a,d]cycloheptene-8-carboxylic acid Example 13i (0.250 g, 0.77 mmol) was treated with piperidine (10 mL, 100 mmol), heated at 80° C. for 2 h, diluted with water and extracted with ethyl acetate. The organic layer was washed with water and dried to obtain the title compound. Yield: 69.68%; $^1$H NMR (DMSO-$d_6$): δ 1.60 (s, 6H, piperidinyl), 3.20 (s, 4H, piperidinyl), 5.15 (s, 2H, $CH_2$), 7.25 (m, 5H, Ar), 8 (s, 1H, Ar).

EXAMPLE 15

N-(10,10-dioxo-7-pyrrolidin-1-yl-10,11-dihydro-5-oxa-10lambda*6*-thia-dibenzo[a,d]cycloheptene-8-carbonyl)-guanidine, methane sulfonic acid salt The title compound was synthesised from Example 15i as described in the synthesis of Example 1. Yield: 24.69%; mp: 255-257° C.; $^1$H NMR (DMSO-$d_6$): δ 1.90 (s, 4H, pyrrolidinyl), 2.35 (s, 3H, $CH_3SO_3H$), 3.30 (s, 4H, pyrrolidinyl), 5.10 (s, 2H, $CH_2$), 6.90 (s, 1H, Ar), 7.35 (t, 1H, Ar), 7.40-7.50 (m, 2H, Ar), 7.60 (d, 1H, Ar), 7.90 (s, 1H, Ar), 8.20-8.30 ($NH_2$ exchangeable with $D_2O$); MS: m/e (ES+) 401 (M+, free base); IR $cm^{-1}$: 3400, 3350, 1700, 1600, 1300, 1210, 1050.

EXAMPLE 15i 10,10-dioxo-7-pyrrolidin-1-yl-10,11-dihydro-5-oxa-10lambda*6*-thia-dibenzo[a,d]cycloheptene-8-carboxylic acid Example 13i was treated with pyrrolidine as described in the synthesis of Example 14 to obtain the title compound. Yield: 66.10%; $^1$H NMR (DMSO-$d_6$): δ 2.40 (s, 4H, pyrrolidinyl), 3.30 (s, 4H, pyrrolidinyl), 5.10 (s, 2H, $CH_2$), 6.80 (s, 1H, Ar), 7.30-7.65 (m, 4H, Ar), 7.80 (s, 1H, Ar).

EXAMPLE 16

N-(7-Chloro-1-fluoro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 16i as described in the synthesis of Example 1. Yield: 22%; mp: 240-241° C.; $^1$H NMR (DMSO-$d_6$): δ 2.35 (s, 3H, $CH_3SO_3H$), 5.20 (s, 2H, $CH_2$), 7.30-7.60 (m, 3H, Ar), 8.10 (s, 1H, Ar), 8.35 (s, 1H, Ar), 8.50-8.60 ($NH_2$ exchangeable with $D_2O$); MS: m/e (EI+) 383 (M+, free base); IR $cm^{-1}$: 3400, 3150, 1725, 1625, 1500, 1200-1150, 1050, 825, 750.

EXAMPLE 16i

7-Chloro-1-fluoro-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-3-fluoro-phenoxy)-tert-butyl-dimethyl-silane as described in the synthesis of Examples 1f-1i. Yield: 36.5%; $^1$H NMR (DMSO-$d_6$): δ 5.20 (s, 2H, $CH_2$), 7.30 (t, 1H, Ar), 7.40 (d, 1H, Ar), 7.50 (t, 1H, Ar), 7.70 (s, 1H, Ar), 8.10 (s, 1H, Ar); MS: m/e (EI+) 341 (M+).

EXAMPLE 17

N-(7-Chloro-2-fluoro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 17i as described in the synthesis of Example 1. Yield: 56.55%; mp: 278-279° C.; $^1$H NMR (DMSO-d$_6$): δ 2.35 (s, 3H, CH$_3$SO$_3$H), 5.25 (s, 2H, CH$_2$), 7.30-7.60 (m, 3H, Ar), 7.95 (s, 1H, Ar), 8.25 (s, 1H, Ar), 8.30-8.40 (NH$_2$ exchangeable with D$_2$O); MS: m/e (EI+) 383 (M+, free base); IR cm$^{-1}$: 3350, 3200, 3150, 1725, 1625, 1500, 1200, 1050, 825, 850.

EXAMPLE 17i

7-Chloro-2-fluoro-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-4-fluoro-phenoxy)-tert-butyl-dimethyl-silane as described in the synthesis of Examples 1f-1i. Yield: 59.27%; $^1$H NMR (DMSO-d$_6$): δ 5.30 (s, 2H, CH$_2$), 7.40-7.50 (m, 3H, Ar), 7.90 (s, 1H, Ar), 8.30 (s, 1H, Ar); MS: m/e (EI+) 341 (M+).

EXAMPLE 18

N-(10,10-Dioxo-7-pyrrol-1-yl-10,11-dihydro-5-oxa-10lambda*6*-thia-dibenzo[a,d]cycloheptene-8-carbonyl)-guanidine, methane sulfonic acid salt The title compound was synthesised from Example 18i as described in the synthesis of Example 1. Yield: 54%; mp: 286-288° C.; $^1$H NMR (DMSO-d$_6$): δ 2.35 (s, 3H, CH$_3$SO$_3$H), 5.30 (s, 2H, CH$_2$), 6.35 (s, 2H, pyrrolyl), 7.15 (s, 2H, pyrrolyl), 7.45-7.70 (m, 4H, Ar), 7.80 (s, 1H, Ar), 8.25 (s, 1H, Ar), 8.40-8.50 (NH$_2$ exchangeable with D$_2$O); MS: m/e (ES+) 396 (M+, free base); IR cm$^{-1}$: 3350, 3100, 1700, 1600, 1475, 1300, 1200-1150, 1050, 750.

EXAMPLE 18i 10,10-Dioxo-7-pyrrol-1-yl-10,11-dihydro-5-oxa-10lambda*6*-thia-dibenzo[a,d]cycloheptene-8-carboxylic acid The title compound was synthesized using a known method (J. Med. Chem., 40, 2017-2034, (1997)).

Example 13i (0.887 g, 2.73 mmol) was heated with benzylamine (3.21 mL, 30 mmol) at 110° C. for 5 h, diluted with cold water, adjusted to pH 6 with 10% aqueous HCl and extracted with ethyl acetate. The organic layer was washed with water, dried and concentrated to obtain the 7-amino benzyl derivative (Example 18x), which was subsequently dissolved in MeOH, treated with 10% Pd—C (5 mg) and ammoniumformate (0.279 g, 4.40 mmol) and heated at 70° C. for 5 h. The catalyst was filtered and washed with methanol. The filtrate was then concentrated and purified using flash chromatography (silica gel, MeOH—CHCl$_3$) to obtain the 7-amino-10,10-dioxo-10,11-oxa-10lambda*6*-thia-dibenzo[a,d]cycloheptene-8-carboxylic acid (Example 18y). This carboxylic acid derivative was esterified as described in the synthesis of Example 1c, and was then treated with 2,5-dimethoxy-tetrahydro-furan (0.084 g, 0.622 mmol), 2-chloropyridine hydrochloride (0.0074 g, 0.03 mmol) and dioxane (12 mL) and stirred at 110° C. for 2 h. The reaction mixture was concentrated, extracted with ethyl acetate, purified using flash chromatography (silica gel, ethyl acetate/PE60-80° C.) and subjected to alkaline hydrolysis as described in Example 1i to obtain the title compound. Yield: 34.75%; $^1$H NMR (DMSO-d$_6$): δ 5.30 (s, 2H, CH$_2$), 6.30 (s, 2H, pyrrolyl), 7.10 (s, 2H, pyrrolyl), 7.30-7.55 (m, 4H, Ar), 7.30 (s, 1H, Ar), 8.10 (s, 1H, Ar); MS: m/e (EI+) 354 (M+).

EXAMPLE 19

N-(7-Chloro-4-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 19i as described in the synthesis of Example 1. Yield: 62%; mp: 260-262° C.; $^1$H NMR (DMSO-d$_6$): δ 2.30 (s, 3H, CH$_3$SO$_3$H), 2.40 (s, 3H, CH$_3$), 5.30 (s, 2H, CH$_2$), 7.3 (m, 2H, Ar), 7.45 (d, 1H, Ar), 8.05 (s, 1H, Ar), 8.3 (s, 1H, Ar), 8.25-8.5 (NH exchangeable with D$_2$O); MS: m/e (ES+) 380 (M+, free base); IR cm$^{-1}$: 3300, 3200-3100, 2910, 1720, 1600, 1470, 1310, 1280, 1200-1140, 1040, 890, 790.

EXAMPLE 19i

7-Chloro-4-methyl-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-6-methyl-phenoxy)-tert-butyl-dimethyl-silane as described in the synthesis of Examples 1f-1i. Yield: 29.72%; $^1$H NMR (DMSO-d$_6$): δ 2.50 (s, 3H, CH$_3$), 5.20 (s, 2H, CH$_2$), 7.30-7.45 (s, 3H, Ar), 7.30 (s, 1H, Ar), 8.30 (s, 1H, Ar).

EXAMPLE 20

N-(4-Methyl-10,10-dioxo-7-pyrrol-1-yl-10,11-dihydro-5-oxa-10lambda*6*-thia-dibenzo[a,d]cycloheptene-8-carbonyl)-guanidine, methane sulfonic acid salt The title compound was synthesised from Example 20i as described in the synthesis of Example 1. Yield: 37%; mp: 210-212° C.; $^1$H NMR (DMSO-d$_6$): δ 2.35 (s, 3H; CH$_3$SO$_3$H), 2.45 (s, 3H, CH$_3$), 5.52 (s, 2H, CH$_2$), 6.30 (s, 2H, pyrrolyl), 7.10 (s, 2H, pyrrolyl), 7.30-7.50 (m, 3H, Ar), 7.70 (s, 1H, Ar), 8.25 (s, 1H, Ar), 8.40-8.50 (NH$_2$ exchangeable with D$_2$O); MS: m/e (ES+) 411 (M+1, free base); IR cm$^{-1}$: 3140, 320, 2362, 1700, 1605, 1468, 1058, 988, 840.

EXAMPLE 20i

4-Methyl-10,10-dioxo-7-pyrrol-1-yl-10,11-dihydro-5-oxa-10lambda*6*-thia-dibenzo[a,d]cycloheptene-8-carboxylic acid The title compound was synthesised from Example 19i as described in the synthesis of Example 18i. Yield: 78%; $^1$H NMR (DMSO-d$_6$): δ 2.40 (s, 3H, CH$_3$), 5.20 (s, 2H, CH$_2$), 6.30 (s, 2H, pyrrolyl); 7.10 (s, 2H, pyrrolyl), 7.30-7.50 (m, 3H, Ar), 7.65 (s, 1H, Ar); 8.10 (s, 1H, Ar); MS: m/e (EI+) 369 (M+).

EXAMPLE 21

N-(7-Chloro-2-methanesulfonyl-4-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 21j as described in the synthesis of Example 1. Yield: 68.62%; mp: 190-192° C.; $^1$H NMR (DMSO-$d_6$): δ 2.30 (s, 3H, $CH_3SO_3H$), 2.5 (s, 3H, $CH_3$), 3.25 (s, 3H, $SO_2CH_3$), 5.50 (s, 2H, $CH_2$), 8.00 (s, 1H, Ar), 8.10 (s, 1H, Ar), 8.40 (s, 1H, Ar), 8.40 (s, 1H, Ar), 8.45-8.50 ($NH_2$ exchangeable with $D_2O$); MS: m/e (ES+) 457 (M+, free base); IR $cm^{-1}$: 3400, 3150, 1725, 1610, 1475, 1250, 1050, 800.

EXAMPLE 21j

7-Chloro-2-methanesulfonyl-4-methyl-10,10-dioxo-10,11-dihydro-5-oxa-10lambda*6*-thia-dibenzo[a,d]cycloheptene-8-carboxylic acid The title compound was synthesised from Example 19i as described in the synthesis of Example 12j. Yield: 24.43%; $^1$H NMR (DMSO-$d_6$): δ 2.45 (s, 3H, $CH_3$), 3.25 (s, 3H, $SO_2CH_3$), 5.45 (s, 2H, $CH_2$), 7.60-8.20 (m, 4H, Ar); MS: m/e (EI+) 416 (M+).

EXAMPLE 22

N-(7-Chloro-4-isopropyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 22i as described in the synthesis of Example 1. Yield: 72.81%; mp: 258-260° C.; $^1$H NMR (DMSO-$d_6$): δ 1.20 (d, 6H, $2CH_3$), 2.30 (s, 3H, $CH_3SO_3H$), 3.60 (m, 1H, CH), 5.20 (s, 2H, $CH_2$), 7.40 (t, 1H, Ar), 7.42-7.50 (m, 2H, Ar), 8.10 (s, 1H, Ar), 8.30 (s, 1H, Ar), 8.40-8.50 ($NH_2$ exchangeable with $D_2O$); MS: m/e (ES−) 408 (M+1, free base); IR $cm^{-1}$: 3400, 3350, 3100, 1750, 1600, 1450, 1350, 1150, 1050, 750.

EXAMPLE 22i

7-Chloro-4-isopropyl-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-6-isopropyl-phenoxy)-tert-butyl-dimethyl-silane as described in the synthesis of Examples 1f-1i. Yield: 20.13%; $^1$H NMR (DMSO-$d_6$): δ 1.15 (s, 6H, CH($CH_3$)$_2$), 3.60 (m, 1H, CH), 5.25 (s, 2H, $CH_2$), 7.30-7.45 (m, 3H, Ar), 7.90 (s, 1H, Ar), 8.20 (s, 1H, Ar); MS: m/e (EI+) 366 (M+).

EXAMPLE 23

N-(2,7-Dichloro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 23i as described in the synthesis of Example 1. Yield: 19.32%; mp: 198-199° C.; $^1$H NMR (DMSO-$d_6$): δ 2.38 (s, 3H, $CH_3SO_3H$), 5.35 (s, 2H, $CH_2$), 7.60 (s, 1H, Ar), 7.70 (s, 1H, Ar), 7.78 (s, 1H, Ar), 8 (s, 1H, Ar), 8.30 (s, 1H, Ar), 8.40-8.50 ($NH_2$ exchangeable with $D_2O$); MS: m/e (ES+) 401 (M+1, free base); IR $cm^{-1}$: 350-3400, 1750, 1625, 1475, 1350, 1225, 1050, 800.

EXAMPLE 23i 2,7-Dichloro-10,10-dioxo-10,11-dihydro-5-oxa-10lambda*6*-thia-dibenzo[a,d]cycloheptene-8-carboxylic acid The title compound was synthesised from 2,4-dichloro-5-mercapto-benzoic acid methyl ester and (2-bromomethyl-4-chloro-phenoxy)-tert-butyl-dimethyl-silane as described in the synthesis of Examples 1f-1i. Yield: 57.14%; $^1$H NMR (DMSO-$d_6$): δ 5.30 (s, 2H, $CH_2$), 7.55 (s, 2H, Ar), 7.75 (s, 2H. Ar), 8.05 (s, 1H, Ar); MS: m/e (EI+) 359 (M+).

EXAMPLE 24

N-(7-Benzylamino-4-methyl-10,10-dioxo-10,11-dihydro-5-oxa-10lambda*-6*-thia-dibenzo[a,d]cycloheptene-8-carbonyl)-guanidine, methane sulfonic acid salt The title compound was synthesised from Example 24j as described in the synthesis of Example 1. Yield: 62%; mp: 220-221° C.; $^1$H NMR (DMSO-$d_6$): δ 2.00 (s, 3H, $CH_3$), 2.40 (s, 3H, $CH_3SO_3H$), 4.60 (s, 2H, $CH_2$), 4.95 (s, 2H, $CH_2$), 6.60 (s, 1H, Ar), 7.15-7.40 (m, 8H, Ar), 8.10 (s, 1H, Ar), 8.20-8.40 ($NH_2$ exchangeable with $D_2O$). MS: m/e (EI+) 450 (M+, free base); IR $cm^{-1}$: 3350, 3308, 2360, 1575, 1250-1150, 1050, 750.

EXAMPLE 24j

7-Benzylamino-4-methyl-10,10-dioxo-10,11-dihydro-5-oxa-10lambda*6*-thia-dibenzo[a,d]cycloheptene-8-carboxylic acid The title compound was synthesised from Example 19i as described in the synthesis of Example 18x. Yield: 47%; $^1$H NMR (DMSO-$d_6$): δ 2.00 (s, 3H, $CH_3$), 4.60 (d, 2H, $CH_2$), 5.00 (s, 2H, $CH_2$), 6.50 (s, 1H, Ar), 7.20-7.30 (m, 3H, Ar), 7.35 (s, 5H, Ar), 8.20 (s, 1H, Ar); MS: m/e (EI+) 409 (M+).

EXAMPLE 25

N-(4-Chloro-7-methyl-10,10-dioxo-10,11-dihydro-5-oxa-10lambda*6*-thia-15 dibenzo[a,d]cycloheptene-8-carbonyl)-guanidine, methane sulfonic acid salt The title compound was synthesised from Example 25i as described in the synthesis of Example 1. Yield: 46.42%; mp: 284-286° C.; $^1$H NMR (DMSO-$d_6$): δ 2.40 (s, 3H, $CH_3SO_3H$), 2.50 (s, 3H, $CH_3$), 5.25 (s, 2H, $CH_2$), 7.40 (t, 1H, Ar), 7.60 (t, 2H, Ar), 7.65 (s, 1H, Ar), 8.10 (s, 1H, Ar), 8.30-8.50 (NH exchangeable with D$_2$O); MS: m/e (EI+) 380 (M+, free base); IR cm$^{-1}$: 3380, 3100, 1710, 1600, 1450, 1310, 1210-1150, 1050, 790.

EXAMPLE 25i

4-Chloro-7-methyl-10,10-dioxo-10,11-dihydro-5-oxa-10lambda*6*-thia-dibenzo[a,d]cycloheptene-8-carboxylic acid The title compound was synthesised from 4-bromo-5-mercapto-2-methyl-benzoic acid methyl ester and (2-bromomethyl-6-chloro-phenoxy)-tert-butyl-dimethyl-silane as described in the synthesis of Examples 1f-1i. Yield: 45.51%; $^1$H NMR (DMSO-d$_6$): δ 2.60 (s, 3H, CH$_3$), 5.30 (s, 2H, CH$_2$), 7.40 (t, 1H, Ar), 7.50 (s, 1H, Ar), 7.60 (s, 2H, Ar), 8.20 (s, 1H, Ar); MS: m/e (EI+) 338 (M+).

4-Bromo-5-mercapto-2-methyl benzoic acid methyl ester was synthesised from 4-bromo-2-methyl-benzoic acid as described in the synthesis of Examples 1a-1c.

EXAMPLE 26

N-(4,7-Dimethyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 26i as described in the synthesis of Example 1. Yield: 76.92%; mp: 292-294° C.; $^1$H NMR (DMSO-d$_6$): δ 2.30 (s, 3H, CH$_3$), 2.35 (s, 3H, CH$_3$SO$_3$H), 2.50 (s, 3H, CH$_3$), 5.20 (s, 2H, CH$_2$), 7.30 (m, 2H, Ar), 7.45 (d, 1H, Ar), 7.70 (s, 1H, Ar), 8.10 (s, 1H, Ar), 8.20-8.50 (NH$_2$ exchangeable with D$_2$O); MS: m/e (EI+) 359 (M+, free base); IR cm$^{-1}$: 3450, 1720, 1600, 1510, 1410, 1350-1300, 1250-1200, 1160, 1090, 1010, 830.

EXAMPLE 26i 4,7-Dimethyl-10,10-dioxo-10,11-dihydro-5-oxa-10lambda*6*-thia-dibenzo[a,d]cycloheptene-8-carboxylic acid The title compound was synthesised from 4-bromo-5-mercapto-2-methyl-benzoic acid methyl ester and (2-bromomethyl-6-methyl-phenoxy)-tert-butyl-dimethyl-silane as described in the synthesis of Examples 1f-1i. Yield: 38.40%; $^1$H NMR (DMSO-d$_6$): δ 2.40 (s, 3H, CH$_3$), 2.60 (s, 3H, CH$_3$) 5.20 (s, 2H, CH$_2$), 7.30 (m, 2H, Ar), 7.40 (d, 1H, Ar), 7.60 (s, 1H, Ar), 8.30 (s, 1H, Ar); MS: m/e (EI+) 318 (M+).

EXAMPLE 27

N-(7-Methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 27i as described in the synthesis of Example 1. Yield: 68.96%; mp: 272-274° C.; $^1$H NMR (DMSO-d$_6$): δ 2.40 (s, 3H, CH$_3$SO$_3$H), 2.50 (s, 3H, CH$_3$), 5.20 (s, 2H, CH$_2$), 7.40 (m, 1H, Ar), 7.45 (s, 2H, Ar), 7.60 (m, 2H, Ar), 8.10 (d, 1H, Ar), 8.30-8.50 (NH exchangeable with D$_2$O); MS: m/e (ES−) 344 (M−1, free base); IR cm$^{-1}$: 3350, 3110-3080, 1700, 1600, 1490, 1310, 1290, 1200-1180, 1120, 1050, 780.

EXAMPLE 27i

7-Methyl-10,10-dioxo-10,11-dihydro-5-oxa-10lambda*6*-thia-dibenzo[a,d]cycloheptene-8-carboxylic acid The title compound was synthesised from 4-bromo-5-mercapto-2-methyl-benzoic acid methyl ester and (2-bromomethyl-phenoxy)-tert-butyl-dimethyl-silane as described in the synthesis of Examples 1f-1i. Yield: 65.37%; $^1$H NMR (DMSO-d$_6$): δ 2.60 (s, 3H, CH$_3$), 5.20 (s, 2H, CH$_2$), 7.40 (m, 3H, Ar), 7.50 (s, 1H, Ar), 7.65 (s, 1H, Ar), 8.25 (s, 1H, Ar); MS: m/e (EI+) 304 (M+).

EXAMPLE 28

N-(4-Chloro-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 28i as described in the synthesis of Example 1. Yield: 75%; mp: 280-282° C.; $^1$H NMR (DMSO-d$_6$): δ 2.40 (s, 3H, CH$_3$SO$_3$H), 2.70 (s, 3H, CH$_3$), 5.40 (s, 2H, CH$_2$), 7.45 (t, 1H, Ar), 7.60 (d, 1H, Ar), 7.65 (d, 1H, Ar), 8.20 (d, 1H, Ar), 8.30 (s, 1H, Ar), 8.35-8.50 (NH exchangeable with D$_2$O); MS: m/e (EI+) 379 (M+, free base); IR cm$^{-1}$: 3500, 2970, 1700, 1600, 1450, 1430, 1310, 1210, 1160, 1050, 930, 790.

EXAMPLE 28i

4-Chloro-6-methyl-10,10-dioxo-10,11-dihydro-5-oxa-10lambda*6*-thia-dibenzo[a,d]cycloheptene-8-carboxylic acid The title compound was synthesised from 4-bromo-3-mercapto-5-methyl-benzoic acid methyl ester and (2-bromomethyl-6-chloro-phenoxy)-tert-butyl-dimethyl-silane as described in the synthesis of Examples 1f-1i. Yield: 24.62%; $^1$H NMR (DMSO-d$_6$): δ 2.70 (s, 3H, CH$_3$), 5.35 (s, 2H, CH$_2$) 7.40 (t, 1H, Ar), 7.60 (m, 2H, Ar), 8.10 (s, 1H, Ar), 8.20 (s, H, Ar); MS: m/e (EI+) 338 (M+).

4-Bromo-5-mercapto-2-methyl benzoic acid methyl ester was synthesised from 4-bromo-3-methyl-benzoic acid as described in the synthesis of Examples 1a-1c.

EXAMPLE 29

N-(2-Chloro-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 29i as described in the synthesis of Example 1. Yield: 84%; mp: 260-262° C.; $^1$H NMR (DMSO-d$_6$): δ 2.35 (s, 3H, CH$_3$SO$_3$H), 2.60 (s, 3H, CH$_3$), 5.30 (s, 2H, CH$_2$), 7.60 (m, 2H, Ar), 7.80 (s, 1H, Ar), 8.15 (s, 1H, Ar), 8.25 (s, 1H, Ar), 8.30-8.50 (NH exchangeable with D$_2$O); MS: m/e (EI+) 379 (M+, free base); IR cm$^{-1}$: 3400-3300, 3200-3100, 1720, 1610, 1500, 1470, 1430, 11330, 1240, 1210-1150, 1050, 900, 750.

EXAMPLE 29i

2-Chloro-6-methyl-10,10-dioxo-10,11-dihydro-5-oxa-10lambda*6*-thia-dibenzo[a,d]cycloheptene-8-carboxylic acid The title compound was synthesised from 4-bromo-3-mercapto-5-methyl-benzoic acid methyl ester and (2-bromomethyl-4-chloro-phenoxy)-tert-butyl-dimethyl-silane as described in the synthesis of Examples 1f-1i. Yield: 27.53%; $^1$H NMR (DMSO-d$_6$): δ 2.60 (s, 3H, CH$_3$), 5.70 (s, 2H, CH$_2$) 7.60 (s, 2H, Ar), 7.70 (s, 1H, Ar), 8.20 (d, 2H, Ar); MS: m/e (EI+) 338 (M+).

EXAMPLE 30

N-(4-Chloro-2-methanesulfonyl-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 30j as described in the synthesis of Example 1. Yield: 61.32%; mp: 294-296° C.; $^1$H NMR (DMSO-d$_6$): δ 2.35 (s, 3H, CH$_3$SO$_3$H), 2.70 (s, 3H, CH$_3$), 3.30 (s, 3H, SO$_2$CH$_3$), 5.60 (s, 2H, CH$_2$), 8.20-8.40 (m, 4H, Ar); MS: m/e (ES+) 458 (M+1, free base); IR cm$^{-1}$: 3500-3300, 1720, 1610, 1460, 1320, 1200, 1150, 1050, 980, 810.

EXAMPLE 30j

4-Chloro-2-methanesulfonyl-6-methyl-10,10-dioxo-10,11-dihydro-5-oxa-10lambda*6*-thia-dibenzo[a,d]cycloheptene-8-carboxylic acid The title compound was synthesised from Example 28i as described in the synthesis of Example 12j. Yield: 14.4%; $^1$H NMR (DMSO-d$_6$): δ 2.60 (s, 3H, CH$_3$), 3.30 (s, 3H, SO$_2$CH$_3$), 5.40 (s, 2H, CH$_2$), 8.10-8.20 (m, 4H, Ar); MS: m/e (EI+) 416 (M+).

EXAMPLE 31

N-(4-Isopropyl-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 31i as described in the synthesis of Example 1. Yield: 81.0%; mp: 252-253° C.; $^1$H NMR (DMSO-d$_6$): δ 1.20 (d, 6H, 2CH$_3$), 2.35 (s, 3H, CH$_3$SO$_3$H), 2.6 (s, 3H, CH$_3$), 3.50 (q, 1H, CH), 5.25 (s, 2H, CH$_2$), 7.40 (m, 3H, Ar), 8.15 (s, 1H, Ar), 8.30 (s, 1H, Ar), 8.4 (NH exchangeable with D$_2$O); MS: m/e (EI+) 387 (M+, free base); IR cm$^{-1}$: 3400, 3300-3310, 3000, 1710, 1630, 1500-1430, 13330, 1240, 1200-1150, 1080, 910, 790.

EXAMPLE 31i

4-Isopropyl-6-methyl-10,10-dioxo-10,11-dihydro-5-oxa-10lambda*6*-thia-dibenzo[a,d]cycloheptene-8-carboxylic acid The title compound was synthesised from 4-bromo-3-mercapto-5-methyl-benzoic acid methyl ester and (2-bromomethyl-6-isopropyl-phenoxy)-tert-butyl-dimethyl-silane as described in the synthesis of Examples 1f-1i. Yield: 44.33%; $^1$H NMR (DMSO-d$_6$): δ 1.20 (d, 6H, 2CH$_3$), 2.60 (s, 3H, CH$_3$), 3.45 (m, 1H, CH), 5.20 (s, 2H, CH$_2$), 7.40 (m, 3H, Ar), 8.10 (s, 1H, Ar), 8.20 (s, 1H, Ar); MS: m/e (EI+) 346 (M+).

EXAMPLE 32

N-(4-Chloro-6-methyl-2-nitro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 32j as described in the synthesis of Example 1. Yield: 94.11%; $^1$H NMR (DMSO-d$_6$): δ 2.35 (s, 3H, CH$_3$SO$_3$H), 2.40 (s, 3H, CH$_3$), 4.95 (s, 2H, CH$_2$), 7.05 (NH$_2$ exchangeable with D$_2$O), 8.15 (d, 1H, Ar), 8.16 (d, 1H, Ar), 8.25 (s, 1H, Ar), 8.70 (s, 1H, Ar); MS: m/e (EI+) 425 (M+1, free base).

EXAMPLE 32j

4-Chloro-6-methyl-2-nitro-10,10-dioxo-10,11-dihydro-5-oxa-10lambda*6*-thia-dibenzo[a,d]cycloheptene-8-carboxylic acid Chilled concentrated HNO$_3$ (2 mL) was added to the methylester of Example 28i (0.250 g, 0.7 mmols). The reaction mixture was stirred at 0° C. for 0.5 h. Chilled conc. H$_2$SO$_4$ (0.4 mL) was added and reaction mixture was stirred for 3 h at 0° C. It was then stirred overnight at room temperature, poured onto crushed ice to obtain a solid, which was filtered, washed with water, dried and purified using flash chromatography (silica gel, ethyl acetate-PE60-80° C.). The product obtained was subjected to hydrolysis as described in Example 1i to obtain the title compound. Yield: 73%; $^1$H NMR (DMSO-d$_6$): δ 2.80 (s, 3H, CH$_3$), 4.80 (s, 2H, CH$_2$), 8.10 (s, 1H, Ar), 8.20 (d, 1H, Ar), 8.30 (d, 1H, Ar), 8.40 (s, 1H, Ar).

EXAMPLE 33

N-(4,6-Dimethyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 33i as described in the synthesis of Example 1. Yield: 92%; mp: 280-281° C.; $^1$H NMR (DMSO-d$_6$): δ 2.30 (s, 3H, CH$_3$), 2.35 (s, 3H, CH$_3$SO$_3$H), 2.60 (s, 3H, CH$_3$), 5.20 (s, 2H, CH$_2$), 7.30 (m, 2H, Ar), 7.45 (d, 1H, Ar), 8.10 (s, 1H, Ar), 8.40 (s, 1H, Ar), 8.35-8.50 (NH exchangeable with D$_2$O); MS: m/e (EI+) 359 (M+, free base); IR cm$^{-1}$: 3500-3300, 3100, 3000, 1740, 1630, 1480, 1440, 1330-1300, 1240, 1180, 1080, 920, 800.

EXAMPLE 33i 4,6-Dimethyl-10,10-dioxo-10,11-dihydro-5-oxa-10lambda*6*-thia-dibenzo[a,d]cycloheptene-8-carboxylic acid The title compound was synthesised from 4-bromo-3-mercapto-5-methyl-benzoic acid methyl ester and (2-bromomethyl-6-methyl-phenoxy)-tert-butyl-dimethyl-silane as described in the synthesis of Examples 1f-1i. Yield: 48.34%; $^1$H NMR (DMSO-d$_6$): δ 2.40 (s, 3H, CH$_3$), 2.80 (s, 3H, CH$_3$) 5.10 (s, 2H, CH$_2$), 7.30 (t, 2H, Ar), 7.40 (d, 1H, Ar), 8.10 (d, 1H, Ar), 8.17 (d, 1H, Ar).

EXAMPLE 34

N-(4-Isopropyl-6-methyl-2-nitro-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 34j as described in the synthesis of Example 1. Yield: 81%; mp: 278-279° C.; $^1$H NMR (DMSO-$d_6$): δ 1.25 (d, 6H, CH(C$H_3$)$_2$), 2.35 (s, 3H, CH$_3$SO$_3$H), 2.60 (s, 3H, CH$_3$), 3.50 (m, 1H, CH), 5.40 (s, 2H, CH$_2$), 8.20 (dd, 2H, Ar), 8.35 (d, 1H, Ar), 8.50 (s, 1H, Ar), 8.30-8.40 (NH exchangeable with D$_2$O; MS: m/e (ES−) 431 (M−1, free base).

EXAMPLE 34j

4-Isopropyl-6-methyl-2-nitro-10,10-dioxo-10,11-dihydro-5-oxa-10lambda*6*-thia-dibenzo[a,d]cycloheptene-8-carboxylic acid The title compound was synthesised from the methyl ester of Example 31i as described in the synthesis of Example 32. Yield: 44.33%; $^1$H NMR (DMSO-$d_6$): δ 1.25 (d, 6H, 2CH$_3$), 2.60 (s, 3H, CH$_3$), 3.50 (m, 1H, CH), 5.40 (s, 2H, CH$_2$), 8.10-8.20 (m, 3H, Ar), 8.50 (d, 1H, Ar); MS: m/e (EI+) 391 (M+).

EXAMPLE 35

N-(2-Amino-4-chloro-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 35j as described in the synthesis of Example 1. Yield: 33.97%; mp: 190-192° C.; $^1$H NMR (DMSO-$d_6$): δ 2.35 (s, 3H, CH$_3$SO$_3$H), 2.70 (s, 3H, CH$_3$), 5.20 (s, 2H, CH$_2$), 6.70-6.75 (m, 2H, Ar), 8.10 (d, 1H, Ar), 8.25 (d, 1H, Ar), 8.30-8.60 (NH$_2$ exchangeable with D$_2$O); MS: m/e (ES+) 395 (M+1, free base); IR cm$^{-1}$: 3400, 1700, 1600, 1550-1400, 1300, 1200, 1050, 790.

EXAMPLE 35j

2-Amino-4-chloro-6-methyl-10,10-dioxo-10,11-dihydro-5-oxa-10lambda*6*-thia-dibenzo[a,d]cycloheptene-8-carboxylic acid To a solution of the methyl ester of Example 32j (0.280 g, 0.7 mmols) in DMF (10 mL) was added activated Raney-Nickel (100 mg) and the reaction mixture was subjected to reduction in a Parr hydrogenator (20 psi, 2 h). The reaction mixture was filtered (celite bed), and the filtrate was poured onto crushed ice to obtain a solid which was subjected to hydrolysis as described in the synthesis of Example 1i to obtain the title compound. Yield: 76%; $^1$H NMR (DMSO-$d_6$): δ 2.60 (s, 3H, CH$_3$), 5.10 (s, 2H, CH$_2$), 5.40 (s, 2H, NH$_2$), 6.80 (d, 2H, Ar), 8.10 (s, 1H, Ar), 8.20 (s, 1H, Ar); MS: m/e (EI+) 354 (M+1).

EXAMPLE 36

N-(2-Amino-4,6-dimethyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 36j as described in the synthesis of Example 1. Yield: 25%; mp: 218-219° C.; $^1$H NMR (DMSO-$d_6$): δ 2.25 (s, 3H, CH$_3$SO$_3$H), 2.50 (s, 3H, CH$_3$), 2.65 (s, 3H, CH$_3$), 4.90 (s, 2H, CH$_2$), 6.50 (s, 1H, Ar), 6.60 (s, 1H, Ar), 8.00 (s, 1H, Ar), 8.20 (s, 1H, Ar), 8.40-8.60 (NH$_2$ exchangeable with D$_2$O); MS: m/e (ES+) 375 (M+1, free base); IR cm$^{-1}$: 3450, 3400, 1700, 1600, 1300, 1225, 1175, 1050.

EXAMPLE 36j

2-Amino-4,6-dimethyl-10,10-dioxo-10,11-dihydro-5-oxa-10lambda*6*-thia-dibenzo[a,d]cycloheptene-8-carboxylic acid The methyl ester of Example 33i was subjected to nitration as described in the synthesis of Example 32j. The nitro compound was reduced as described in Example 35j and subsequently hydrolysed as described in the synthesis of Example 1i to obtain the title compound. Yield: 88.35%; $^1$H NMR (DMSO-$d_6$): δ 2.35 (s, 3H, CH$_3$), 2.60 (s, 3H, CH$_3$), 4.90 (s, 2H, CH$_2$), 6.40 (s, 1H, Ar), 6.50 (s, 1H, Ar), 8.05 (s, 1H, Ar), 8.15 (s, 1H, Ar); MS: m/e (EI+) 333 (M+).

EXAMPLE 37

N-(4-Chloro-2-iodo-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 37j as described in the synthesis of Example 1. Yield: 64%; mp: 229-232° C.; $^1$HNMR (DMSO-$d_6$): δ 2.37 (s, 3H, CH$_3$), 2.70 (s, 3H, CH$_3$), 5.34 (s, 2H, CH$_2$), 8.00 (s, 1H, Ar), 8.07 (s, 1H, Ar), 8.13 (s, 1H, Ar), 8.23 (s, 1H, Ar), 8.20-8.50 (m, 4H, guanidinyl); MS: m/e (EI+) 505 (M+, free base).

EXAMPLE 37j

4-Chloro-2-iodo-6-methyl-10,10-dioxo-10,11-dihydro-5-oxa-10lambda*6*-thia-dibenzo[a,d]cycloheptene-8-carboxylic acid The title compound was obtained by subjecting the methyl ester of Example 35j (0.5 g, 1.36 mmol) to a diazotisation reaction, followed by a Sandmeyer reaction using KI (0.246 g, 1.49 mmol), (Organic Syntheses, vol. 5, 1120), and subsequent hydrolysis as described in the synthesis of Example 1i. Yield: 19.03%; $^1$H NMR (DMSO-$d_6$): δ 2.65 (s, 3H, CH$_3$), 5.30 (s, 2H, CH$_2$), 8.10 (s, 1H, Ar), 8.05 (s, 1H, Ar), 8.15 (s, 1H, Ar), 8.20 (s, 1H, Ar); MS: m/e (EI+) 464 (M+).

EXAMPLE 38

N-(4-Chloro-6-methyl-10,10-dioxo-2-pyrrol-1-yl-10,11-dihydro-5-oxa-10lambda*6*-thia-dibenzo[a,d]cycloheptene-8-carbonyl)-guanidine, methane sulfonic acid salt The title compound was synthesised from Example 38j as described in the synthesis of Example 1. Yield: 66.67%; mp: 204-206° C.; $^1$H NMR (DMSO-d$_6$): δ 2.35 (s, 3H, CH$_3$SO$_3$H), 2.80 (s, 3H, CH$_3$), 5.35 (s, 2H, CH$_2$), 6.50 (t, 2H, pyrrolyl), 7.15 (s, 2H, pyrrolyl), 7.50 (t, 2H, Ar), 7.90 (d, 1H, Ar), 8.00 (d, 1H, Ar), 8.20 (d, 1H, Ar), 8.30 (d, 1H, Ar), 8.40 (NH$_2$ exchangeable with D$_2$O); MS: m/e (ES+) 445 (M+, free base); IR cm$^{-1}$: 3500-3300, 1700, 1600, 1500, 1300, 1180, 1050, 730.

EXAMPLE 38j

4-Chloro-6-methyl-10,10-dioxo-2-pyrrol-1-yl-10,11-dihydro-5-oxa-10lambda*6*-thia-dibenzo[a,d]cycloheptene-8-carboxylic acid The title compound was synthesised from Example 35j as described in the synthesis of Example 11j. Yield: 88.23%; $^1$H NMR (DMSO-d$_6$): δ 2.70 (s, 3H, CH$_3$), 5.30 (s, 2H, CH$_2$), 6.35 (s, 2H, pyrrolyl), 7.45 (s, 2H, pyrrolyl), 7.80 (s, 1H, Ar), 8.00 (s, 1H, Ar), 8.15 (s, 1H, Ar), 8.20 (s, 1H, Ar); MS: m/e (EI+) 403 (M+).

EXAMPLE 39

N-[2-(2,5-Dimethyl-pyrrol-1-yl)-4,6-dimethyl-10,10-dioxo-10,11-dihydro-5-oxa-10lambda*6*-thia-dibenzo[a,d]cycloheptene-8-carbonyl]-guanidine, methane sulfonic acid salt The title compound was synthesised from Example 39j as described in the synthesis of Example 1. Yield: 78.7%; mp: 265-266° C.; $^1$H NMR (DMSO-d$_6$): δ 2.0 (s, 6H, 2CH$_3$), 2.40 (s, 3H, CH$_3$SO$_3$H), 2.50 (s, 3H, CH$_3$), 2.70 (s, 3H, CH$_3$), 5.30 (s, 2H, CH$_2$), 5.80 (s, 2H, pyrrolyl), 7.35 (s, 1H, Ar), 7.40 (d, 1H, Ar), 8.20 (s, 1H, Ar), 8.40 (s, 1H, Ar), 8.40 (NH$_2$ exchangeable with D$_2$O); MS: m/e (ES+) 452 (M+, free base).

EXAMPLE 39j 2-(2,5-dimethyl-pyrrol-1-yl)-4,6-dimethyl-10,10-dioxo-10,11-dihydro-5-oxa-10lambda*6*-thia-dibenzo[a,d]cycloheptene-8-carboxylic acid Acetonylacetone (0.040 g, 0.35 mmol)) and acetic acid (0.1 mL, 1.7 mmol) were added to a solution of the methylester of Example 36j in toluene (10 mL). The reaction mixture was refluxed for 6 h, concentrated and triturated with PE60-80° C. The organic extract was concentrated and the crude obtained was purified using flash chromatography (silica gel, EtOAc/PE60-80° C.). It was then subjected to hydrolysis as described in Example 1i to obtain the title compound (J. Chem. Soc., Chem. commun., 800-801, (1982)). Yield: 51%; $^1$H NMR (DMSO-d$_6$): δ 2.0 (s, 6H, 2CH$_3$), 2.40 (s, 3H, CH$_3$), 2.65 (s, 3H, CH$_3$), 5.20 (s, 2H, CH$_2$), 5.70 (s, 2H, pyrrolyl), 7.30 (s, 1H, Ar), 7.35 (s, 1H, Ar), 8.20 (s, 1H, Ar), 8.35 (s, 1H, Ar); MS: m/e (ES+) 411 (M+).

EXAMPLE 40

N-(2-Dimethylamino-4,6-dimethyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 40j as described in the synthesis of Example 1. Yield: 67.70%; mp: 245-247° C. $^1$H NMR (DMSO-d$_6$): δ 2.35 (s, 3H, CH$_3$SO$_3$H), 2.40 (s, 3H, CH$_3$), 2.70 (s, 3H, CH$_3$), 2.90 (s, 6H, N(CH$_3$)$_2$), 5.10 (s, 2H, CH$_2$), 7.70 (s, 1H, Ar), 7.80 (s, 1H, Ar), 8.10 (s, 1H, Ar), 8.30 (s, 1H, Ar), 8.40 (NH$_2$ exchangeable with D$_2$O); MS: m/e (ES+) 402 (M+, free base); IR cm$^{-1}$: 3400-3350, 2600, 1700, 1600, 1550, 1310, 1200, 1050, 750.

EXAMPLE 40j

2-Dimethylamino-4,6-dimethyl-10,10-dioxo-10,11-dihydro-5-oxa-10lambda*6*-thia-dibenzo[a,d]cycloheptene-8-carboxylic acid 37% Aqueous formaldehyde (1.5 mL, 20.43 mmol) solution was added dropwise to a solution of the methylester of Example 36j (0.250 g, 0.68 mmol) in excess anhydrous formic acid (4 mL) at 0° C. The reaction mixture was heated at 70° C. for 10 minutes, then refluxed for 4 h, diluted with water, treated with conc. HCl (0.4 mL) and powdered KOH (600 mg) to reach pH 10. The solid obtained was filtered, dried and purified using flash chromatography (silica gel, EtOAc/PE60-80° C.). It was then subjected to hydrolysis as described in Example 1i to obtain the title compound. Yield: 16.20%; $^1$H NMR (DMSO-d$_6$): δ 2.30 (s, 3H, CH$_3$), 2.60 (s, 3H, CH$_3$), 2.90 (s, 6H, N(CH$_3$)$_2$) 5.10 (s, 2H, CH$_2$), 6.60 (d, 1H, Ar), 6.75 (d, 1H, Ar), 8.10 (s, 1H, Ar) and 8.20 (s, 1H, Ar); MS: m/e (EI+) 361 (M+).

EXAMPLE 41

N-(4-Chloro-2-dimethylamino-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 41j as described in the synthesis of Example 1. Yield: 59.52%; mp: 196-198° C.; $^1$H NMR (DMSO-d$_6$): δ 2.35 (s, 3H, CH$_3$SO$_3$H), 2.70 (s, 3H, CH$_3$), 3.00 (s, 6H, 2CH$_3$), 5.20 (s, 2H, CH$_2$), 6.80 (d, 1H, Ar), 6.90 (d, 1H, Ar), 8.10 (s, 1H, Ar), 8.25 (s, 1H, Ar), 8.30-8.50 (NH$_2$ exchangeable with D$_2$O); MS: m/e (ES+) 423 (M+1, free base); IR cm$^{-1}$: 3320, 1700, 1600, 1500, 1300, 1150, 1050, 910, 780.

EXAMPLE 41j

4-Chloro-2-dimethylamino-6-methyl-10,10-dioxo-10,11-dihydro-5-oxa-10lambda*6*-thia-dibenzo[a,d]cycloheptene-8-carboxylic acid The title compound was synthesised from Example 35j as described in the synthesis of Example 40. Yield: 32.50%; $^1$H NMR (DMSO-d$_6$): δ 2.60 (s, 3H, CH$_3$), 2.95 (s, 6H, N(CH$_3$)$_2$), 5.19 (s, 2H, CH$_2$), 6.75 (d, 1H, Ar), 6.95 (d, 1H, Ar), 8.10 (s, 1H, Ar), 8.20 (s, 1H, Ar); MS: m/e (ES+) 381 (M+).

EXAMPLE 42

N-(4-Chloro-6-methyl-2-methylamino-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 42j as described in the synthesis of Example 1. Yield: 49.66%; mp: 174-175° C.; $^1$H NMR (DMSO-$d_6$): δ 2.40 (s, 3H, $CH_3SO_3H$), 2.70 (s, 6H, 2$CH_3$), 5.20 (s, 2H, $CH_2$), 6.65 (s, 1H, Ar), 6.70 (s, 1H, Ar), 8.10 (s, 1H, Ar), 8.30 (s, 1H, Ar) 8.40-8.50 ($NH_2$ exchangeable with $D_2O$); MS: m/e (ES+) 408 (M+, free base).

EXAMPLE 42j

4-Chloro-6-methyl-2-methylamino-10,10-dioxo-10,11-dihydro-5-oxa-10lambda*6*-thia-dibenzo[a,d]cycloheptene-8-carboxylic acid Methyl ester of Example 35j (0.5 g, 1.36 mmol) was added to solution of sodium methoxide [Na (0.156 g, 6.78 mmol) in methanol (6 mL)], which in turn was added to a solution of paraformaldehyde (0.057 g, 1.90 mmol) in MeOH (5 mL). The reaction mixture was stirred for 5 h at room temperature, treated with sodium borohydride (0.051 g, 1.36 mmol), refluxed for 1 h, cooled, treated with 1M aqueous KOH (1.5 mL) and stirred for 15 mins. It was extracted with ethyl acetate and the aqueous portion was neutralized to pH 5 with 10% aqueous HCl to obtain the title compound (J. Chem. Soc. Chem. Commun., 1334, (1984)). Yield: 38.46%; $^1$H NMR (DMSO-$d_6$): δ 2.60 (s, 3H, N—$CH_3$), 2.70 (s, 3H, $CH_3$), 5.10 (s, 2H, $CH_2$), 6.30 (d, 1H, NH), 6.65 (d, 1H, Ar), 7.50 (d, 1H, Ar), 8.08 (s, 1H, Ar), 8.20 (s, 1H, Ar); MS: m/e (EI+) 367 (M+).

EXAMPLE 43

N-(2-[N-Benzyloxycarbonyl-guanidino]-4-Chloro-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 43j as described in the synthesis of Example 1. Yield: 68%; mp: 236-238° C.; $^1$H NMR (DMSO-$d_6$): δ 2.40 (s, 3H, $CH_3SO_3H$), 2.75 (s, 3H, $CH_3$), 5.20 (s, 2H, $CH_2$), 5.40 (s, 2H, $CH_2$), 7.30-7.80 (m, 7H, Ar), 8.15 (s, 1H, Ar), 8.30 (s, 1H, Ar), 8.40-8.50 ($NH_2$ exchangeable with $D_2O$); MS: m/e (ES−) 569(M−1); IR $cm^{-1}$: 3350, 3150, 1700, 1600, 1550, 1475, 1300, 1225, 1050, 925.

EXAMPLE 43j 2-(N-Benzyloxycarbonyl-guanidino)-4-Chloro-6-methyl-10,10-dioxo-10,11-dihydro-5-oxa-10lambda*6*-thia-dibenzo[a,d]cycloheptene-8-carboxylic acid $Z_2$-S-methyl isothiourea (0.097 g, 0.27 mmol) was added to the methyl ester of Example 35j (0.1 g, 0.27 mmol) in dry DMF (8 mL) and the reaction mixture was heated at 110° C. for 2 h. It was treated with water and extracted with ethyl acetate. The ethyl acetate layer was concentrated and the solid obtained was purified using flash chromatography (silica gel, EtOAc/PE60-80° C.). The product obtained was then subjected to hydrolysis as described in Example 1i to obtain the title compound. Yield: 26.22%; $^1$H NMR (DMSO-$d_6$): δ 2.60 (s, 3H, $CH_3$), 5.20 (s, 2H, $CH_2$), 5.30 (s, 2H, $SO_2$—$CH_2$), 7.35 (m, 5H, Ar), 7.70 (s, 2H, Ar), 8.10 (d, 2H, Ar); MS: m/e (EI+) 529 (M+).

EXAMPLE 44

N-(4-Chloro-2-isobutylamino-6-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 44j as described in the synthesis of Example 1. Yield: 48.12%; mp: 255-256° C.; $^1$H NMR (DMSO-$d_6$): α 0.95 (s, 6H, 2$CH_3$), 1.90 (m, 1H, CH) 2.40 (s, 3H, $CH_3SO_3H$), 2.80 (s, 3H, $CH_3$), 2.90 (d, 2H, $CH_2$), 5.20 (s, 2H, $CH_2$), 6.70 (s, 1H, Ar), 6.75 (s, 1H, Ar), 8.10 (s, 1H, Ar), 8.30 (s, 1H, Ar), 8.40-8.50 ($NH_2$ exchangeable with $D_2O$); MS: m/e (ES+) 451 (M+); IR $cm^{-1}$: 3400, 3250, 2950, 1700, 1600, 1450, 1350, 1050, 925, 750.

EXAMPLE 44j

4-Chloro-2-isobutylamino-6-methyl-10,10-dioxo-10,11-dihydro-5-oxa-10lambda*6*-thia-dibenzo[a,d]cycloheptene-8-carboxylic acid To a mixture of the methyl ester of Example 35j (0.1 g, 0.27 mmol), isobutyraldehyde (0.098 g, 1.35 mmol)), trifluoro acetic acid (0.27 mmol) and sodium cyanoborohydride (0.67 mmol) was added MeOH (15 mL) at 0-5° C. The reaction mixture was stirred overnight at room temperature, treated with chilled water, neutralized with 10% aqueous $NaHCO_3$, extracted with EtOAc, concentrated and subjected to hydrolysis as described in Example 1i to obtain the title compound (Tet. Lett. 38, 5831-5834, (1997)). Yield: 64.74%; $^1$H NMR (DMSO-$d_6$): δ 0.90 (d, 6H, 2$CH_3$), 1.80 (m, 1H, CH), 2.60 (s, 3H, $CH_3$), 2.90 (d, 2H, N—$CH_2$), 5.10 (s, 2H, $CH_2$), 6.70 (s, 2H, Ar), 8.10 (d, 2H, Ar); MS: m/e (EI+) 409 (M+).

EXAMPLE 45

4,6-Dichloro-10,10-dioxo-10,11-dihydro-5-oxa-10lambda*6*-thia-dibenzo[a,d]cycloheptene-8-carbonylguanidine, methane sulfonic acid salt The title compound was synthesised from Example 45i as described in the synthesis of Example 1. Yield: 62.29%; mp: 270-271° C.; $^1$H NMR (DMSO-$d_6$): δ 2.30 (s, 3H, $CH_3SO_3H$), 5.50 (s, 2H, $CH_2$), 7.50 (t, 1H, Ar), 7.70 (dd, 2H, Ar), 8.3 (d, 2H, Ar), 8.35-8.50 (NH exchangeable with $D_2O$); MS: m/e (ES+) 402 (M+); IR $cm^{-1}$: 3500-3300, 1710, 1630, 1470, 1330, 1270, 1250-1150, 1080, 900, 800.

EXAMPLE 45i 4,6-dichloro-10,10-dioxo-10,11-dihydro-5-oxa-10lambda*6*-thia-dibenzo[a,d]cycloheptene-8-carboxylic acid The title compound was synthesised from 3,4-dichloro-5-mercapto-benzoic acid methyl ester and (2-bromomethyl-6-chloro-phenoxy)-tert-butyl-dimethyl-silane as described in the synthesis of Examples 1f-1i. Yield: 33.14%; $^1$H NMR (DMSO-d$_6$): δ 5.50 (s, 2H, CH$_2$), 7.45 (t, 1H, Ar), 7.70 (m, 2H, Ar), 8.30 (d, 2H, Ar); MS: m/e (EI+) 359 (M+).

3,4-dichloro-5-mercapto-benzoic acid methyl ester was synthesised from 3,4-dichloro-benzoic acid as described in the synthesis of Examples 1a-1c.

EXAMPLE 46

N-(2-Amino-4,6-dichloro-10,10-dioxo-10,11-dihydro-5-oxa-10lambda*6*-thia-dibenzo[a,d]cyclohep-tene-8-carbonyl)-guanidine, methane sulfonic acid salt The title compound was synthesised from Example 46j as described in the synthesis of Example 1. Yield: 80%; mp: 210-212° C.; $^1$H NMR (DMSO-d$_6$): δ 2.35 (s, 3H, CH$_3$SO$_3$H), 5.30 (s, 2H, CH$_2$), 6.70 (d, 2H, Ar), 8.30 (s, 2H, Ar), 8.35-8.50 (NH exchangeable with D$_2$O); MS: m/e (ES+) 416 (M+); IR cm$^{-1}$: 3550-3400, 1740, 1500, 1470, 1350, 1230, 1190, 1080, 800, 770.

EXAMPLE 46j

2-Amino-4,6-dichloro-10,10-dioxo-10,11-dihydro-5-oxa-10lambda*6*-thia-dibenzo[a,d]cycloheptene-8-carboxylic acid The title compound was synthesised from Example 45i as described in the synthesis of Example 36. Yield: 18.28%; $^1$H NMR (DMSO-d$_6$): δ 5.30 (s, 2H, CH$_2$), 6.70 (d, 2H, Ar), 8.30 (s, 2H, Ar), 8.40 (s, 2H, NH$_2$); MS: m/e (EI+) 374 (M+).

EXAMPLE 47

6-Chloro-4-methyl-10,10-dioxo-10,11-dihydro-5-oxa-10lambda*6*-thia-dibenzo[a,d]cycloheptene-8-carbonyl)-guanidine, methane sulfonic acid salt The title compound was synthesised from Example 47i as described in the synthesis of Example 1. Yield: 80%; mp: 283-284° C.; $^1$H NMR (DMSO-d$_6$): δ 2.30 (s, 3H, CH$_3$SO$_3$H), 2.45 (s, 3H, CH$_3$), 5.35 (s, 2H, CH$_2$), 7.30 (m, 2H, Ar), 7.40 (d, 1H, Ar), 8.30 (s, 2H, Ar), 8.35-8.50 (NH exchangeable with D$_2$O); MS: m/e (ES+) 379 (M+, free base); IR cm$^{-1}$: 3380, 3300-3000, 1700, 1600, 1450, 1310, 1260, 1230-1150, 1050, 900, 790.

EXAMPLE 47A

N-(6-Chloro-4-methyl-10,10-dioxo-10,11-dihydro-5-oxa-10lambda*6*-thia-dibenzo[a,d]cycloheptene-8-carbonyl)-guanidine, hydrochloric acid The title compound was synthesised from Example 47i using methanolic-HCl as described in the synthesis of Example 1. Yield: 84.21%; mp: 238-239° C.; $^1$H NMR (DMSO-d$_6$): δ 2.40 (s, 3H, CH$_3$), 5.35 (s, 2H, CH$_2$), 7.30 (m, 2H, Ar), 7.40 (d, 1H, Ar), 8.35 (s, 1H, Ar), 8.60 (NH exchangeable with D$_2$O), 8.70 (s, 1H, Ar); MS: m/e (ES+) 380 (M+1, free base); IR cm$^{-1}$: 3500-3300, 1730, 1610, 1480, 1310, 1280, 1190, 980, 750.

EXAMPLE 47B

N-(6-Chloro-4-methyl-10,10-dioxo-10,11-dihydro-5-oxa-10lambda*6*-thia-dibenzo[a,d]cycloheptene-8-carbonyl)-guanidine, p-toluenesulphonic acid salt The title compound was synthesised from Example 47i using p-toluene sulphonic acid as described in the synthesis of Example 1. Yield: 81.39%; mp: 270-271° C.; $^1$H NMR (DMSO-d$_6$): δ 2.30 (s, 3H, CH$_3$), 2.50 (s, 3H, CH$_3$), 5.35 (s, 2H, CH$_2$), 7.15 (d, 2H, Ar), 7.30 (m, 2H, Ar), 7.50 (t, 3H, Ar), 8.30 (s, 2H, Ar), 8.20-8.50 (NH exchangeable with D$_2$O); MS: m/e (ES−) 380 (M+1, free base); IR cm$^{-1}$: 3400, 3300-3000, 1700, 1610, 1460, 1350-1300, 1270, 1220-1180, 1050, 1030, 960, 830, 700.

EXAMPLE 47i

6-Chloro-4-methyl-10,10-dioxo-10,11-dihydro-5-oxa-10lambda*6*-thia-dibenzo[a,d]cycloheptene-8-carboxylic acid The title compound was synthesised from 3,4-dichloro-5-mercapto-benzoic acid methyl ester and (2-bromomethyl-6-methyl-phenoxy)-tert-butyl-dimethyl-silane as described in the synthesis of Examples 1f-1i. Yield: 61.88%; $^1$H NMR (DMSO-d$_6$): δ 2.40 (S, 3H, CH$_3$), 5.30 (s, 2H, CH$_2$), 7.45 (m, 3H, Ar), 8.30 (d, 2H, Ar).

EXAMPLE 48

N-(2-Amino-6-chloro-4-methyl-10,10-dioxo-10,11-dihydro-5-oxa-10lambda*6*-thia-dibenzo[a,d]cyclo-heptene-8-carbonyl)-guanidine, methane sulfonic acid salt The title compound was synthesised from Example 48j as described in the synthesis of Example 1. Yield: 81.08%; mp: 279-280° C.; $^1$H NMR (DMSO-d$_6$): δ 2.30 (s, 6H, 2CH$_3$SO$_3$H), 2.35 (s, 3H, CH$_3$), 5.30 (s, 2H, CH$_2$), 6.80 (d, 2H, Ar), 8.30 (s, 2H, Ar), 8.30-8.50 (NH exchangeable with D$_2$O); MS: m/e (ES+) 375 (M+1); IR cm$^{-1}$: 3520-3400, 2900, 2650, 1740, 1460, 1350, 1280, 1220, 1190, 1080, 780.

EXAMPLE 48j

2-Amino-6-chloro-4-methyl-10,10-dioxo-10,11-dihydro-5-oxa-10lambda*6*-thia-dibenzo[a,d]cyclo-heptene-8-carboxylic acid The title compound was synthesised from Example 47i as described in the synthesis of Example 36. Yield: 46.44%; $^1$H NMR (DMSO-d$_6$): δ 2.30 (s, 3H, CH$_3$), 5.10 (s, 2H, CH$_2$), 6.40 (s, 1H, Ar), 6.55 (s, 1H, Ar), 8.20 (d, 2H, Ar); MS: m/e (EI+) 353 (M+).

EXAMPLE 49

4-Chloro-8-guanidinocarbonyl-6-methyl-10,10-di-oxo-10,11-dihydro-5-oxa-10lambda*6*-thia-dibenzo[a,d]cycloheptene-2-sulfonic acid amide, methane sulfonic acid salt The title compound was synthesised from Example 49k as described in the synthesis of Example 1. Yield: 48.52%; mp: 260-262° C.; $^1$H NMR (DMSO-d$_6$): δ 2.35 (s, 6H, 2CH$_3$SO$_3$H), 2.70 (s, 3H, CH$_3$), 5.50 (s, 2H, CH$_2$), 8.10 (s, 2H, Ar), 8.15 (s, 2H, Ar), 8.30 (s, 1H, Ar), 8.30-8.50 (NH exchangeable with $D_2O$); MS: m/e (ES+) 460 (M+1).

EXAMPLE 49k

4-Chloro-6-methyl-10,10-dioxo-2-sulfamoyl-10,11-dihydro-5-oxa-10lambda*6*-thia-dibenzo[a,d]cycloheptene-8-carboxylic acid Aqueous ammonia solution was added dropwise to Example 49j (0.125 g, 0.28 mmols) in ethyl acetate (15 mL) till pH 9 was obtained. The reaction mixture was stirred for 4 h at room temperature, concentrated and neutralised with 10% HCl to obtain the title compound which was filtered washed with water and dried. Yield: 58.82%; $^1$H NMR (DMSO-$d_6$): δ 2.60 (s, 3H, $CH_3$), 5.40 (s, 2H, $CH_2$), 7.50 (s, 2H, $NH_2$), 8.05 (s, 3H, Ar), 8.15 (s, 1H, Ar).

EXAMPLE 49j

4-Chloro-2-chlorosulfonyl-6-methyl-10,10-dioxo-10,11-dihydro-5-oxa-10lambda*6*-thia-dibenzo[a,d]cycloheptene-8-carboxylic acid The title compound was synthesised from Example 28i (0.5 g, 1.47 mmol) as described in the synthesis of Example 12. Yield: 97%.

EXAMPLE 50

N-(6-Chloro-4-methyl-10,10-dioxo-10,11-dihydro-5-oxa-10lambda*6*-thia-dibenzo[a,d]cycloheptene-2-carbonyl)-guanidine methane sulfonic acid salt The title compound was synthesised from Example 50 h as described below: Guanidine (generated from guanidine HCl 132 mg, 1.4 mmol as described in Example 1) was added to Example 50 h (0.05 g, 0.14 mmol) in DMF (10 mL) at ambient temperature in an inert atmosphere and the reaction mixture was stirred for 0.5 h. It was then concentrated, treated with dil aqueous HCl to neutral pH and the solid that separated was filtered, washed with water and dried. This solid was converted to the methane sulfonic acid salt as described in Example 1. Yield: 0.038 g, (76%); mp: 261° C.; $^1$H NMR (DMSO-$d_6$): δ 2.40 (s, 3H, $CH_3SO_3H$), 2.60 (s, 3H, $CH_3$), 5.10 (s, 2H, $CH_2$), 7.50 (t, 1H, Ar), 7.90-8.10 (m, 4H, Ar), 8.30-8.50 (m, 4H, guanidinyl). MS: m/e (ES+) 381 (M+1).

EXAMPLE 50h

6-Chloro-4-methyl-10,10-dioxo-10,11-dihydro-5-oxa-10lambda*6*-thia-dibenzo[a,d]cycloheptene-2-carboxylic acid methyl ester The title compound was synthesised from 2,3-dichlorobenzenethiol (0.450 g, 3.14 mmol) and 3-bromomethyl-4-(tert-butyl-dimethyl-silanyloxy)-5-methyl-benzoic methyl ester (1 g, 3.14 mmol) as described in the synthesis of Examples 1f-1h. Yield: 10%; $^1$H NMR ($CDCl_3$): δ 2.70 (s, 3H, $CH_3$), 3.91 (s, 3H, $OCH_3$), 5.42 (s, 2H, $CH_2$), 7.43 (s, 1H, Ar), 7.90 (m, 3H, Ar), 8.20 (s, 1H, Ar). MS (EI+): m/e 352 (M+).

EXAMPLE 51

4-Chloro-8-guanidinocarbonyl-6-methyl-10,10-dioxo-10,11-dihydro-5-oxa-10lambda*6*-thia-dibenzo[a,d]cycloheptene-2-sulfonic acid (5-cyclopropyl-[1,3,4]thiadiazol-2-yl)-amide methane sulfonic acid salt The title compound was synthesised from Example 51k as described in the synthesis of Example 1. Yield: 0.017 g, (42%); mp: 221-222° C.; $^1$H NMR (DMSO-$d_6$): δ 0.8 (m, 2H, $CH_2$), 0.95 (m, 2H, $CH_2$), 1.85 (m, 1H, CH), 2.37 (s, 3H, $CH_3$), 2.60 (s, 3H, $CH_3$), 4.7 (s, 2H, $CH_2$), 7.7 (d, 2H, Ar), 8.12 (s, 1H, Ar), 8.2 (s, 1H, Ar), 8.59 (s, 2H, $NH_2$); MS: m/e (ES+) 583 (M+1) (free base); analysis: $C_{22}H_{23}ClN_6O_9S_4$ calcd.: C, 38.91; H, 3.41; N, 12.37; Cl, 5.22; S, 18.88; found: C, 39.45; H, 3.62; N, 12.87; Cl, 5.43; S, 18.79%.

EXAMPLE 51k

4-Chloro-2-(5-cyclopropyl-[1,3,4]thiadiazol-2-ylsulfamoyl)-6-methyl-10,10-dioxo-10,11-dihydro-5-oxa-10lambda*6*-thia-dibenzo[a,d]cycloheptene-8-carboxylic acid 2-Amino-5-cyclopropyl-1,3,4-thiadiazole (0.236 g, 0.126 mmol) was added to a mixture of Example 49j (0.3 g, 0.68 mmol) and pyridine (8 mL) in ethyl acetate (10 mL). The reaction mixture was stirred at room temperature for 15 h, concentrated, treated with water and extracted with n-butanol. The organic extract was washed with water, dried concentrated and purified using flash chromatography (silica gel, 4% methanol/chloroform) to obtain the title compound. Yield: 0.03 g, (8%); $^1$H NMR (DMSO-$d_6$): δ 0.98 (m, 2H, $CH_2$), 1.12 (d, 2H, $CH_2$), 2.3 (m, 1H, CH), 2.7 (s, 3H, $CH_3$), 5.46 (s, 2H, $CH_2$), 7.95 (d, 1H, Ar,), 8.06 (s, 1H, Ar), 8.14 (s, 1H, Ar), 8.16 (s, 1H, Ar).

EXAMPLE 52

4-Chloro-8-guanidinocarbonyl-6-methyl-10,10-dioxo-10,11-dihydro-5-oxa-10lambda*6*-thia-dibenzo[a,d]cycloheptene-2-sulfonic acid (pyridin-3-ylmethyl)-amide dimesylate The title compound was synthesised from Example 52k as described in the synthesis of Example 1. Yield: 0.060 g, (6%); mp: 271-273° C.; $^1$H NMR (DMSO-$d_6$): δ 2.4 (s, 6H, $2CH_3$), 2.8 (s, 3H, $CH_3$), 4.3 (s, 2H, $CH_2$), 5.5 (s, 2H, $CH_2$), 7.9 (t, 1H, Ar), 8.0 (s, 1H, Ar), 8.05 (s, 1H, Ar), 8.2 (s, 1H, Ar), 8.3 (s, 1H, Ar), 8.35 (s, 2H, $NH_2$), 8.6 (s, 2H, $NH_2$), 8.8 (m, 3H, Ar); MS: m/e (ES+) 645 (M+1) (monosalt); analysis: $C_{24}H_{28}ClN_5O_{12}S_4 \cdot H_2O$ calcd.: C, 37.92; H, 3.98; N, 9.21; found: C, 37.58; H, 3.04; N, 8.71%.

EXAMPLE 52k

4-Chloro-6-methyl-10,10-dioxo-2-[(pyridin-3-ylmethyl)-sulfamoyl]-10,11-dihydro-5-oxa-10lambda*6*-thia-dibenzo[a,d]cycloheptene-8-carboxylic acid 3-(Aminomethyl)pyridine (0.22 mL, 2.1 mmol) was added to a suspension of Example 49j (0.8 g, 1.8 mmol) in ethyl acetate (40 mL). The reaction mixture was stirred at room temperature for 15 h, treated with water and extracted with butanol. The organic layer was washed with water, dried, concentrated and purified using flash chromatography (silica gel, methanol/chloroform) to obtain the title compound. Yield: 0.2 g, (20%); $^1$H NMR (DMSO-d$_6$): δ 2.69 (s, 3H, CH$_3$), 4.18 (d, 2H, CH$_2$), 5.45 (s, 2H, CH$_2$), 7.26 (d, 1H, Ar), 7.6 (d, 1H, Ar), 7.9 (s, 1H, Ar), 8.09 (s, 1H, Ar), 8.18 (s, 1H, Ar), 8.24 (s, 1H, Ar), 8.41 (d, 1H, Ar), 8.47 (s, 1H, Ar), 8.6 (s, 1H, OH).

EXAMPLE 53

N-[4-Chloro-6-methyl-10,10-dioxo-2-(piperazine-1-sulfonyl)-10,11-dihydro-5-oxa-10lambda*6*-thia-dibenzo[a,d]cycloheptene-8-carbonyl]-guanidine trimesylate The title compound was synthesised from Example 53k as described in the synthesis of Example 50. Yield: 0.084 g, (12%); mp: 281-282° C.; $^1$H NMR (DMSO-d$_6$) δ 2.3 (s, 9H, 3CH$_3$), 2.6 (s, 3H, CH$_3$), 3.2 (s, 4H, 2CH$_2$); 3.5 (bs, 4H, 2CH$_2$), 5.5 (s, 2H, CH$_2$), 8.2 (d, 2H, Ar), 8.4 (d, 2H, Ar), 8.45 (s, 2H, NH$_2$), 8.5 (s, 2H, NH$_2$); MS: m/e (ES+) 624 (M+1) (monosalt).

EXAMPLE 53k

4-Chloro-6-methyl-10,10-dioxo-2-(piperazine-1-sulfonyl)-10,11-dihydro-5-oxa-10lambda*6*-thia-dibenzo[a,d]cycloheptene-8-carboxylic acid methyl ester A suspension of Example 49j (0.5 g, 1.14 mmol) in ethylacetate (20 mL) was treated with piperazine (0.147 g, 1.7 mmol) at room temperature and allowed to stir overnight. It was concentrated, treated with methanolic-HCl (50 mL) and refluxed overnight. The reaction mixture was concentrated, treated with an aqueous sodium bicarbonate solution and extracted with n-butanol. The organic layer was washed with water, dried, concentrated and purified using flash chromatography (silica gel, methanol/chloroform) to obtain the title compound. Yield: 0.2 g, (35%); $^1$H NMR (DMSO-d$_6$): δ 2.8 (s, 3H, CH$_3$), 2.9 (s, 4H, 2CH$_2$), 3.2 (s, 4H, 2CH$_2$), 3.89 (s, 3H, OCH$_3$), 5.51 (s, 2H, CH$_2$), 8.10 (s, 1H, Ar), 8.21 (s, 1H, Ar), 8.30 (s, 2H, Ar); MS: m/e (ES−) 499(M−1).

EXAMPLE 54

N-[4-Chloro-6-methyl-2-(4-methyl-piperazine-1-sulfonyl)-10,10-dioxo-10,11-dihydro-5-oxa-10lambda*6*-thia-dibenzo[a,d]cyclohepten-8-carbonyl]-guanidine dimesylate The title compound was synthesised from Example 54k as described in the synthesis of Example 1. Yield: 0.055 g, (57.89%); mp: 187-189° C.; $^1$H NMR (DMSO-d$_6$): δ 2.35 (s, 6H, 2CH$_3$), 2.75 (s, 3H, CH$_3$), 2.8 (s, 3H, CH$_3$), 3.15-3.25 (m, 4H, 2CH$_2$), 3.85-3.95 (m, 4H, 2CH$_2$), 5.60 (s, 2H, CH$_2$), 8.10 (s, 1H, Ar), 8.15 (s, 1H, Ar), 8.25 (s, 1H, Ar), 8.30 (s, 1H, Ar), 8.35-8.55 (m, 4H, guanidinyl). MS: m/e (ES+) 542 (M+1); analysis. C$_{22}$H$_{28}$ClN$_5$O$_9$S$_3$.2.H$_2$O. calcd.: C, 35.87; H, 4.70; N, 8.78, Cl, 4.60; found: C, 35.62; H, 4.11; N, 8.78; Cl; 4.99%.

EXAMPLE 54k

4-Chloro-6-methyl-2-(4-methyl-piperazine-1-sulfonyl)-10,10-dioxo-10,11-dihydro-5-oxa-10lambda*6*-thia-dibenzo[a,d]cycloheptene-8-carboxylic acid A mixture of Example 49j (0.2 g, 0.45 mmol) and 1-methyl-piperazine (0.08 mL, 0.9 mmol) in dry ethyl acetate was stirred overnight at 25° C., treated with water and extracted with ethyl acetate. The organic layer was washed with dil aqueous HCl (10%, 50 mL), water, brine, concentrated and purified using flash chromatography (silica gel, methanol/chloroform) to obtain the title compound. Yield: 0.180 g, (80%) $^1$H NMR (DMSO-d$_6$): δ 2.20 (s, 3H, CH$_3$), 2.30 (s, 4H, CH$_2$), 2.80 (s, 3H, CH$_3$), 3.00 (s, 4H, CH$_2$), 5.40 (s, 2H, CH$_2$), 8.00 (s, 1H, Ar), 8.10 (s, 1H, Ar), 8.20 (s, 2H, Ar). MS: m/e (ES+) 501 (M+).

EXAMPLE 55

N-[4-chloro-6-methyl-2-(morpholine-4-sulfonyl)-10,10-dioxo-10,11-dihydro-5-oxa-10lambda*6*-thia-dibenzo[a,d]cycloheptene-8-carbonyl]-guanidine methane sulfonic acid salt The title compound was synthesised from Example 55k as described in the synthesis of Example 1. Yield: 0.06 g, (55%), mp: 292-293° C.; $^1$H NMR (DMSO-d$_6$.): δ 2.4 (s, 3H, CH$_3$), 2.8 (s, 3H, CH$_3$), 3.0 (s, 4H, 2CH$_2$), 3.8 (s, 4H, 2CH$_2$), 5.6 (s, 2H, CH$_2$), 8.0 (s, 1H, Ar), 8.1 (s, 1H, Ar), 8.3 (s, 1H, Ar), 8.4 (s, 1H, Ar), 8.5-8.6 (4H, m, guanidinyl); MS: m/e (ES+) 529 (M+1); analysis: C$_{21}$H$_{25}$ClN$_4$O$_{10}$S$_3$.H$_2$O calcd.: C, 39.22; H, 4.23; N, 8.71; found: C, 39.91; H, 3.66; N, 8.10%

EXAMPLE 55k

4-Chloro-6-methyl-2-(morpholine-4-sulfonyl)-10,10-dioxo-10,11-dihydro-5-oxa-10lambda*6*-thia-dibenzo[a,d]cycloheptene-8-carboxylic acid A mixture of Example 49j (0.2 g, 0.45mm) and morpholine (0.08 mL, 0.9 mmol) in dry ethyl acetate (25 mL) was stirred overnight at room temperature, treated with water and extracted with ethyl acetate. The organic layer was washed with 10% aqueous HCl (50 mL), water, brine, concentrated and purified using flash chromatography (silica gel, methanol/chloroform) to obtain the title compound. Yield: 0.19 g, (86%); $^1$H NMR (DMSO-d$_6$): δ 2.80 (s, 3H, CH$_3$), 3.0 (t, 4H, 2CH$_2$), 3.7 (s, 4H, 2CH$_2$), 5.5 (s, 2H; CH$_2$), 8.0 (s, 1H, Ar), 8.1 (s, 1H, Ar), 8.2 (s, 2H, Ar). MS: m/e (EI+) 487 (M+).

EXAMPLE 56k

4-Chloro-2-(2-chloro-ethylamino)-6-methyl-10,10-dioxo-10,11-dihydro-5-oxa-10lambda*6*-thia-dibenzo[a,d]cycloheptene-8-carboxylic acid methyl ester Sodiumborohydride (1.77 g, 46.78 mmol) was added portionwise to a stirred solution of chloro-acetic acid (7.71 g, 81.59 mmol) in benzene (270 mL) and dry tetrahydrofuran (30 mL) under nitrogen atmosphere at 15° C. The reaction mixture was stirred for 1 h, treated with the methyl ester of Example 35j (5 g, 13.61 mmol) and refluxed for 0.5 h. The reaction mixture was treated with 10% aqueous sodium bicarbonate solution and extracted with ethyl acetate. The organic layer was washed with water, brine, dried, concentrated and purified by crystallization (ethyl acetate/hexane) to obtain the title compound as a white solid. Yield: 5.25 g, (90%); mp: 224-225° C.; $^1$H NMR (DMSO-$d_6$): δ 2.71 (s, 3H, $CH_3$), 3.45 (t, 2H, $CH_2$), 3.75 (t, 2H, $CH_2$), 3.92 (s, 3H, $OCH_3$), 5.15 (s, 2H, $CH_2$), 6.53 (t, 1H, NH), 6.65-6.79 (m, 2H, Ar), 8.10 (s, 1H, Ar), 8.15 (s, 1H, Ar). MS: m/e (ES+) 431 (M+1).

EXAMPLE 57k

4-Chloro-2-[(2-chloro-acetyl)-(2-chloro-ethyl)-amino]-6-methyl-10,10-dioxo-10,11-dihydro-5-oxa-10lambda*6*-thia-dibenzo[a,d]cycloheptene-8-carboxylic acid methyl ester Chloro-acetyl chloride (3 mL, 37.7 mmol) was added to Example 56k (0.95 g, 2.20 mmol) with stirring and heated at 90° C. for 1 h. The reaction mixture was cooled, treated with water and aqueous sodium bicarbonate solution to pH 7.5 to obtain the title compound as a solid. It was filtered, washed with water, dried and crystallized using ethyl acetate/Pet ether Yield: 0.85 g, (76%); $^1$H NMR (DMSO-$d_6$): δ 2.52 (s, 3H, $CH_3$), 3.72 (t, 2H, $CH_2$), 3.91 (s, 3H, $OCH_3$), 4.0 (t, 2H, $CH_2$), 4.15 (s, 2H, $CH_2$), 5.34 (s, 2H, $CH_2$), 7.69 (s, 1H, Ar), 7.85 (s, 1H, Ar), 8.15 (s, 1H, Ar), 8.21 (d, 1H, Ar); MS: m/e (ES+) 506 (M+).

EXAMPLE 58

N-[4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 58k as described in the synthesis of Example 50. Yield: 0.70 g, (40%); mp: 195-196° C.; $^1$H NMR (DMSO-$d_6$): δ 0.85 (complex, 4H, 2$CH_2$), 2.41 (s, 6H, 2$CH_3$), 2.50 (m, 1H, CH), 2.72 (s, 3H, $CH_3$), 3.92 (s, 2H, $CH_2$), 4.02 (s, 2H, $CH_2$), 5.41 (s, 2H, $CH_2$), 7.65 (s, 1H, Ar), 7.76 (s, 1H, Ar), 8.2 (s, 1H, Ar), 8.29 (s, 1H, Ar), 8.56 (d, 4H, 2$NH_2$), 11.48 (s, 1H, OH); MS: m/e (ES+) 518 (M+) (freebase); analysis: $C_{25}H_{32}ClN_5O_{11}S_3$: 3$H_2O$ calcd.: C, 39.2; H, 5.01; N, 9.16; Cl, 4.64; S, 12.59; found: C, 38.31; H, 5.01; N, 8.86; Cl, 4.56; S, 12.33%.

EXAMPLE 58k

4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester Cyclopropylamine (0.082 mL, 1.18 mmol) was added to a solution of Example 57k (0.2 g, 0.39 mmol) in DMF (5 mL) and stirred at 50° C. for 1.5 h. The reaction mixture was concentrated to obtain the title compound which was purified using flash chromatography (silica gel, 1.5% methanol/chloroform). Yield: 0.135 g (71%); $^1$H NMR (CDCl$_3$): δ 0.49 (m, 2H, $CH_2$), 0.56 (m, 2H, $CH_2$), 1.77 (m, 1H, CH), 2.70 (s, 3H, $CH_3$), 3.01 (t, 2H, $CH_2$), 3.82 (s, 2H, $CH_2$), 3.67 (t, 2H, $CH_2$), 3.92 (s, 3H, $OCH_3$), 4.70 (s, 2H, $CH_2$), 7.36 (s, 1H, Ar), 7.44 (d, 1H, Ar), 8.10 (s, 1H, Ar), 8.46 (d, 1H, Ar); MS: m/e (ES+) 491 (M+1).

EXAMPLE 59

N-[4-Chloro-2-(4-cyclopentyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 59k as described in the synthesis of Example 50. Yield (0.101 g, 50%); mp 214-215° C.; $^1$H NMR (DMSO-$d_6$): δ 1.58 (m, 1H, CH), 1.74 (m, 6H, 3$CH_2$), 2.08 (m, 2H, $CH_2$), 2.37 (s, 6H, 2$CH_3$), 2.5 (s, 3H, $CH_3$), 3.86 (s, 2H, $CH_2$), 4.10 (m, 6H, 3$CH_2$), 5.43 (s, 2H, $CH_2$), 7.65 (s, 1H, Ar), 7.75 (s, 1H, Ar), 8.19 (s, 1H, Ar), 8.28 (s, 1H, Ar), 8.35 (s, 2H, $NH_2$), 8.52 (s, 2H, $NH_2$), 10.48 (s, 1H, OH), 11.46 (s, H, $SO_3OH$); MS: m/e (ES−) 736 (M−1); analysis: $C_{27}H_{36}ClN_5O_{11}S_3$.2$H_2O$ calcd.: C, 41.88; H, 5.21; N, 9.05; Cl, 4.58; S, 12.42; found: C, 41.47; H, 5.15; N, 9.01; Cl, 4.62; S, 12.91%.

EXAMPLE 59k

4-Chloro-2-(4-cyclopentyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester The title compound was synthesised from Example 57k (0.2 g, 0.4 mmol) and cyclopentylamine (0.08 mL, 0.8 mmol) as described in the synthesis of Example 95. Yield: 0.165 g, (80%). $^1$H NMR (CDCl$_3$): δ 1.6 (m, 8H, 4$CH_2$), 2.65 (m, 1H, CH), 2.70 (s, 3H, $CH_3$), 2.86 (t, 2H, $CH_2$), 3.28 (s, 2H, $CH_2$), 3.72 (t, 2H, $CH_2$), 3.92 (s, 3H, $OCH_3$), 4.71 (s, 2H, $CH_2$), 7.38 (d, 1H, Ar), 7.46 (d, 1H, Ar), 8.10 (d, 1H, Ar), 8.45 (d, 1H, Ar); MS: m/e (ES+) 519 (M+).

EXAMPLE 60

N-[4-Chloro-2-(4-isopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 60k as described in the synthesis of Example 50. Yield: 0.093 g, (47%); mp: 196-198° C.; $^1$H NMR (DMSO-$d_6$): δ 1.33 (d, 6H, 2$CH_3$), 2.38 (s, 6H, 2$CH_3$), 2.73 (s, 3H, $CH_3$), 3.47 (m, 1H, CH), 3.7-4.0 (m, 6H, 3$CH_2$), 5.45 (s, 2H, $CH_2$), 7.64 (s, 1H, Ar), 7.74 (s, 1H, Ar), 8.2 (s, 1H, Ar), 8.29 (s, 1H, Ar), 8.3-8.5 (bs, 4H, 2$NH_2$), 10.16 (bs, 1H, NH), 11.47 (s, 1H, OH); MS: m/e (ES+) (free base) 520 (M+1); analysis: $C_{25}H_{34}ClN_5O_{11}S_3$, calcd.: C, 42.16; H, 4.81; N, 9.83; Cl, 4.98; S, 13.5; found C, 41.21; H, 5.18; N, 9.62; Cl, 4.63; S, 13.08%.

EXAMPLE 60k

4-Chloro-2-(4-isopropyl-2-oxo-piperazin-1-yl)-6-methyl-10,10-dioxo-10,11-dihydro-5-oxa-10lambda*6*-thia-dibenzo[a,d]cycloheptene-8-carboxylic acid methyl ester Isopropylamine (2 mL, 48.72 mmol) was added to a solution of Example 57k (0.3 g, 0.59 mmol) in DMF (5 mL) and stirred at 80° C. for 3 h. The reaction mixture was concentrated, treated with water, and extracted with chloroform. The organic layer was washed with water, brine and concentrated to obtain the title compound which was purified using flash chromatography (silica gel, 2% methanol/chloroform). Yield: 0.16 g, (55.17%); $^1$H NMR (CDCl$_3$): δ 1.10 (d, 6H, 2CH$_3$), 2.7 (s, 3H, CH$_3$), 2.8 (q, 1H, CH), 2.86 (t, 2H, CH$_2$), 3.41 (s, 2H, CH$_2$), 3.7 (t, 2H, CH$_2$), 3.92 (s, 3H, OCH$_3$), 4.71 (s, 2H, CH$_2$), 7.38 (d, 1H, Ar), 7.46 (d, 1H, Ar), 8.1 (s, 1H, Ar), 8.46 (s, 1H, Ar); MS: m/e (ES+) 493 (M+1).

EXAMPLE 61

N-[2-(4-Benzyl-2-oxo-piperazin-1-yl)-4-chloro-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 61k as described in the synthesis of Example 50. Yield: 0.068 g, (65%); mp: 234-235° C.; $^1$H NMR (DMSO-d$_6$): δ 2.38 (s, 6H, 2CH$_3$), 2.70 (s, 3H, CH$_3$), 3.9 (bs, 4H, 2CH$_2$), 4.41 (bs, 2H, CH$_2$), 5.4 (s, 2H, CH$_2$), 7.5-7.7 (m, 5H, Ar), 7.6 (s, 1H, Ar), 7.63 (s, 1H, Ar), 8.18 (s, 1H, Ar), 8.27 (s, 1H, Ar), 8.27-8.53 (bs, 4H, 2NH$_2$), 11.45 (bs, 1H, OH); MS: m/e (ES+) (free base) 568 (m+1); analysis: C$_{29}$H$_{34}$ClN$_5$O$_{11}$S$_3$, calcd.: C, 45.82; H, 4.51; N, 9.21; Cl, 4.66; S, 12.65; found C, 45.27; H, 4.74; N, 9.01; Cl, 4.38; S, 12.23%.

EXAMPLE 61k 2-(4-Benzyl-2-oxo-piperazin-1-yl)-4-chloro-6-methyl-10,10-dioxo-10,11-dihydro-5-oxa-10lambda*6*-thia-dibenzo[a,d]cycloheptene-8-carboxylic acid methyl ester Benzylamine (0.17 mL, 1.581 mmol) was added to a solution of Example 57k (0.4 g, 0.79 mmol) in DMF (5 mL) and stirred at 80° C. for 5 h. The reaction mixture was concentrated, treated with water and extracted with chloroform. The organic layer was washed with water, brine, dried and concentrated to obtain the crude title compound which was purified using flash chromatography (silica gel, 1% methanol/chloroform). Yield: 125 g, (29.2%); $^1$H NMR (DMSO-d$_6$): δ 2.68 (s, 3H, CH$_3$), 2.8 (t, 2H, CH$_2$), 3.2 (s, 2H, CH$_2$), 3.63 (s, 2H, CH$_2$), 3.7 (t, 2H, CH$_2$), 3.88 (s, 3H, OCH$_3$), 5.31 (s, 2H, CH$_2$), 7.29-7.38 (m, 5H, Ar), 7.66 (s, 1H, Ar), 7.73 (s, 1H, Ar), 8.16 (s, 1H, Ar), 8.19 (s, 1H, Ar); MS: m/e (ES+) 541 (M+1).

EXAMPLE 62

N-{4-Chloro-6-methyl-2-[2-(4-methylpiperazin-1-yl)-ethylamino]-10,10-dioxo-10,11-dihydro-5-oxa-10lambda*6*-thia-dibenzo[a,d]cycloheptene-8-carbonyl}-guanidine trimesylate The title compound was synthesised from Example 62k as described in the synthesis of Example 50. Yield: 0.152 g, (49.03%); mp: 184-186° C.; $^1$H NMR (DMSO-d$_6$): δ 2.4 (s, 9H, 3CH$_3$), 2.60 (m, 4H, 2CH$_2$), 2.7 (s, 3H, CH$_3$), 2.8-2.9 (m, 4H, 2CH$_2$), 3-3.2 (m, 6H, 3CH$_2$), 5.2 (s, 2H, CH$_2$), 6.7 (s, 2H, Ar), 8.15 (s, 1H, Ar), 8.3 (s, 1H, Ar); MS: m/e (ES+) 521 (M+1); analysis: C$_{26}$H$_{41}$ClN$_6$O$_{13}$S$_4$.H$_2$O calcd.: C, 37.75; H, 5.24; N, 10.16; Cl, 4.38; found: C, 37.63; H, 4.77; N, 9.91; Cl, 4.74%.

EXAMPLE 62k

4-Chloro-6-methyl-2-[2-(4-methyl-piperazin-1-yl) ethylamino]-10,10-dioxo-10,11-dihydro-5-oxa-10lambda*6*-thia-dibenzo[a,d]cycloheptene-8-carboxylic acid methyl ester 1-Methyl-piperazine (0.191 g, 1.91 mol) was added to a solution of Example 56k (0.5 g, 1.16 mmol) in dry DMF (10 mL) and stirred at 110° C. for 2 h. The reaction mixture was treated with water and extracted with ethyl acetate. The organic layer was washed with water, brine, dried, concentrated and purified using flash chromatography (silica gel, methanol/chloroform) to obtain the title compound as a white solid. Yield: 0.350 g, (60.97%); $^1$H NMR (DMSO-d$_6$): δ 2.2 (s, 3H, CH$_3$), 2.5-2.60 (m, 10H, 5CH$_2$), 2.70 (s, 3H, CH$_3$), 3.10 (d, 2H, CH$_2$), 3.90 (s, 3H, CH$_3$), 5.10 (s, 2H, CH$_2$), 6.7 (s, 2H, Ar), 8.01 (s, 1H, Ar), 8.20 (s, 1H, Ar); MS: m/e (ES+) 495 (M+1).

EXAMPLE 63

1-Carboxymethyl-1-[2-(4-chloro-8-guanidinocarbonyl-6-methyl-10,10-dioxo-10,11-dihydro-5-oxa-10lambda*6*-thia-dibenzo[a,d]cyclohepten-2-ylamino)-ethyl]-4-methyl piperazin-1-ium trimesylate The title compound was synthesised from Example 63k as described in the synthesis of Example 50. Yield: 0.44 g, (83%); mp: 228-230° C.; $^1$H NMR (DMSO-d$_6$): δ 2.41 (s, 9H, 3CH$_3$), 2.68 (s, 3H, CH$_3$), 2.89 (s, 3H, CH$_3$), 3.65 (m, 8H, 4CH$_2$), 3.70 (s, 3H, OCH$_3$), 4.00 (m, 4H, 2CH$_2$), 5.21 (s, 2H, CH$_2$), 6.5 (s, 1H, NH), 6.81 (s, 2H, Ar), 8.27 (s, 1H, Ar), 8.32 (s, 1H, Ar), 8.52-8.63 (m, 4H, guanidinyl) MS: m/e (ES+) 579 (M+1); analysis: C$_{28}$H$_{44}$ClN$_6$O$_{15}$S$_4$.1.5H$_2$O calcd.: C, 37.94; H, 5.23; N, 9.48; Cl, 4.0; S, 14.47; found: C, 37.38; H, 5.62; N, 10.02; Cl, 4.26; S, 13.68%.

EXAMPLE 63k

1-Carboxymethyl-1-[2-(4-chloro-8-methoxycarbonyl-6-methyl-10,10-dioxo-10,11-dihydro-5-oxa-10lambda*6*-thia-dibenzo[a,d]cyclohepten-2-ylamino)-ethyl]-4-methyl-piperazin-1-ium Chloro-acetyl chloride (2.09 mL, 26.3 mmol) was added in an atmosphere of nitrogen, with stirring to Example 56k (1.3 g, 2.63 mmol). The reaction mixture was heated at 70° C. for 2 h, treated with water, saturated aqueous NaHCO$_3$ solution to neutral pH and extracted with CHCl$_3$. The organic layer was washed with water, brine, concentrated and purified using flash chromatography (silica gel, methanol/chloroform) to obtain the title compound as a white solid. Yield: 0.5 g, (34%); $^1$H NMR (DMSO-d$_6$): δ 2.31 (s, 3H, N—CH$_3$), 2.69 (s, 3H, CH$_3$), 2.77 (s, 2H, CH$_2$N), 3.4 (s, 2H, N—CH$_2$), 3.75 (s, 2H, N—CH$_2$), 3.89 (s, 3H, OCH$_3$), 4.1 (s, 2H, CH$_2$), 4.54 (s, 2H, N—CH$_2$), 7.74 (s, 1H, Ar), 7.91 (s, 1H, Ar), 8.19 (s, 2H, Ar). MS: m/e (ES+) 552 (M+1).

EXAMPLE 64

N-[4-Chloro-2-(2-imidazol-1-yl-ethylamino)-6-methyl-10,10-dioxo-10,11-dihydro-5-oxa-10lambda*6*-thia-dibenzo a,d]cycloheptene-8-carbonyl]-guanidine dimesylate The title compound was synthesised from Example 64k as described in the synthesis of Example 50. Yield: 0.11 g, (68.69%); mp: 243-244° C.; $^1$H NMR (DMSO-d$_6$): δ 2.4 (s, 6H, 2CH$_3$), 2.7 (s, 3H, CH$_3$), 3.50-3.55 (m, 2H, CH$_2$), 4.4 (t, 2H, CH$_2$), 5.2 (s, 2H, CH$_2$), 6.8 (s, 2H, Ar), 7.7 (s, 1H, Ar), 7.8 (s, 1H, Ar), 8.1 (s, 1H, Ar), 8.3 (s, 1H, Ar), 9.1 (s, 1H, Ar); MS: m/e (ES+) 489 (M+1); analysis: C$_{23}$H$_{29}$ClN$_6$O$_{10}$S$_3$ calcd.: C, 40.56; H, 4.29; N, 12.34; Cl, 5.20; S, 14.12; found: C, 39.71; H, 4.33; N, 11.74; Cl, 5.37; S, 14.48%.

EXAMPLE 64k

4-Chloro-2-(2-imidazol-1-yl-ethylamino)-6-methyl-10,10-dioxo-10,11-dihydro-5-oxa-10lambda*6*-thia-dibenzo[a,d]cycloheptene-8-carboxylic acid methyl ester Imidazole (0.118 g, 1.73 mmol) was added in an atmosphere of nitrogen, to a solution of Example 56k (1.3 g, 2.63 mmol) in dry DMF (10 mL) with stirring. The reaction mixture was then maintained at 110° C. for 18 h. It was cooled, concentrated and the solid obtained was filtered washed with water, dried and purified using flash chromatography (silica gel, methanol/chloroform) to obtain the title compound as a white solid. Yield: 0.120 g, (22.38%); $^1$H NMR (DMSO-d$_6$): δ 2.7 (s, 3H, CH$_3$), 3.2 (t, 2H, CH$_2$), 3.9 (s, 3H, OCH$_3$), 4.1 (t, 2H, CH$_2$), 5.2 (s, 2H, CH$_2$), 6.4 (s, 1H, NH), 6.6 (s, 1H, Ar), 6.75 (s, 1H, Ar), 6.9 (s, 1H, Ar), 7.2 (s, 1H, Ar), 7.6 (s, 1H, Ar), 8.1 (s, 1H, Ar), 8.2 (s, 1H, Ar); MS: m/e (ES+) 462 (M+).

EXAMPLE 65

N-[2-(2-Amino-ethylamino)-4-chloro-6-methyl-10,10-dioxo-10,11-dihydro-5-oxa-10lambda*6*-thia-dibenzo[a,d]cycloheptene-8-carbonyl]-guanidine trimesylate The title compound was synthesised from Example 65k as described in the synthesis of Example 50. Yield: 0.110 g, (34.84%); mp: 205-207° C., $^1$H NMR (DMSO-d$_6$): δ 2.40 (s, 9H, 3CH$_3$), 2.70 (s, 3H, CH$_3$), 3.0-3.10 (m, 2H, CH$_2$), 3.25-3.30 (m, 2H, CH$_2$), 5.20 (s, 2H, CH$_2$), 6.70 (s, 2H, Ar), 8.10 (s, 1H, Ar), 8.30 (s, 1H, Ar); MS: m/e (ES−) 436 (M+1); analysis: C$_{21}$H$_{32}$ClN$_5$O$_{13}$S$_4$ calcd.: C, 34.73; H, 4.45; N, 9.64; found: C, 35.50; H, 4.22; N, 10.10%.

EXAMPLE 65k 2-(2-Amino-ethylamino)-4-chloro-6-methyl-10,10-dioxo-10,11-dihydro-5-oxa-10lambda*6*-thia-dibenzo[a,d]cycloheptene-8-carboxylic acid methyl ester Aqueous ammonia solution (2.5 mL, 30%) was added to a solution of Example 56k (0.4 g, 0.93 mmol) in methanol (1 mL). The reaction mixture was sealed under argon in a reactor vessel and kept in an oven at 120° C. for 2 h. It was concentrated and the solid obtained was washed thoroughly with methanol to remove excess ammonia and dried under vacuo. It was treated with a methanolic HCl solution and stirred at 70° C. for 3 h. The reaction mixture was concentrated, treated with 10% aqueous sodium bicarbonate solution and extracted with ethylacetate. The organic layer was washed with water, brine, dried, and purified using flash chromatography (silica gel, 10% methanol/chloroform) to obtain the title compound as a white solid. Yield: 0.340 g, (89.23%); $^1$H NMR (DMSO-d$_6$): δ 2.70 (s, 3H, CH$_3$), 3.00 (t, 2H, CH$_2$), 3.35 (t, 2H, CH$_2$), 3.90 (s, 3H, OCH$_3$), 5.20 (s, 2H, CH$_2$), 6.40 (t, 1H, NH), 6.80 (s, 2H, Ar), 7.80 (t, 2H, NH$_2$), 8.15 (s, 1H, Ar) and 8.30 (s, 1H, Ar). MS: m/e (CI+) 411 (M+).

EXAMPLE 66

N-[4-Chloro-6-methyl-2-(2-morpholin-4-yl-ethylamino)-10,10-dioxo-10,11-dihydro-5-oxa-10lambda*6*-thia-dibenzo[a,d]cycloheptene-8-carbonyl]-guanidine dimesylate The title compound was synthesised from Example 66k as described in the synthesis of Example 50. Yield: 0.158 g, (56%); $^1$H NMR (DMSO-d$_6$): δ 2.40 (s, 6H, 2CH$_3$), 2.80 (s, 3H, CH$_3$), 3.1-3.20 (m, 4H, 2CH$_2$), 3.25-3.30 (m, 4H, 2CH$_2$), 3.80 (t, 2H, CH$_2$), 4.00 (t, 2H, CH$_2$), 5.20 (s, 2H, CH$_2$), 6.40 (t, 1H, NH), 6.80 (s, 2H, Ar), 8.10 (s, 1H, Ar), 8.30 (s, 1H, Ar), 8.30-8.40 (m, 4H, guanidinyl); MS: m/e (ES+) 508M+1); analysis: C$_{24}$H$_{34}$ClN$_5$O$_{11}$S$_3$. calcd.: C, 41.17; H, 4.89; N, 10.00; Cl, 5.06; S, 13.74; found: C, 40.68; H, 4.32; N, 9.56; Cl, 5.40; S, 13.87%.

EXAMPLE 66k

4-Chloro-6-methyl-2-(2-morpholin-4-yl-ethylamino)-10,10-dioxo-10,11-dihydro-5-oxa-10lambda*6*-thia-dibenzo[a,d]cycloheptene-8-carboxylic acid methyl ester Morpholine (1.20 g, 13.77 mmol) was added with stirring in an atmosphere of nitrogen, to Example 56k (4.56 g, 10.59 mmol) in dry DMF (20 mL). The reaction mixture was stirred at 110° C. for 5 h, concentrated and treated with chilled water. The solid obtained was filtered, washed with water, dried and purified using flash chromatography (silica gel, PE 60-80° C./EtOAc) to obtain the title compound as a white solid. Yield: 3.80 g, (74.56%); $^1$H NMR (DMSO-d$_6$): δ 2.40 (t, 2H, CH$_2$), 2.60 (t, 2H, CH$_2$), 2.80 (s, 3H, CH$_3$), 3.20 (t, 4H, CH$_2$—CH$_2$), 3.70 (t, 4H, CH$_2$—CH$_2$), 3.90 (s, 3H, OCH$_3$), 5.20 (s, 2H, CH$_2$), 6.10 (t, 1H, NH), 6.80 (s, 2H, Ar), 8.10 (s, 1H, Ar), 8.30 (s, 1H, Ar); MS: m/e (ES+) 481 (M+).

EXAMPLE 67

N-{4-Chloro-2-[ethyl-(2-morpholin-4-yl-ethyl)-amino]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 67k as described in the synthesis of Example 50. Yield: 0.325 g, (76.47%); mp: 248-250° C.; $^1$H NMR (DMSO-d$_6$): δ 1.10 (t, 3H, CH$_3$), 2.40 (s, 6H, 2CH$_3$), 2.70 (s, 3H, CH$_3$), 3.10-3.50 (m, 8H, 4CH$_2$), 3.65-3.75 (m, 4H, 2CH$_2$), 4.10-4.15 (m, 2H, CH$_2$), 5.25 (s, 2H, CH$_2$), 6.90 (s, 1H, Ar), 7.05 (s, 1H, Ar), 8.10 (s, 1H, Ar), 8.20 (s, 1H, Ar), 8.30-8.45 (m, 3H, guanidinyl); MS: m/e (ES+) 536 (M+1); analysis: C$_{26}$H$_{38}$ClN$_5$O$_{11}$S$_3$H$_2$O calcd.: C, 41.85; H, 5.40; N, 9.38, Cl; 4.75, S; 12.89; found: C, 42.06; H, 5.29; N, 9.34, Cl; 4.68, S; 13.26%.

EXAMPLE 67k

4-Chloro-2-[ethyl-(2-morpholin-4-yl-ethyl)-amino]-6-methyl-10,10-dioxo-10,11-dihydro-5-oxa-10lambda*6*-thia-dibenzo[a,d]cyclohepten-8-carboxylic acid methyl ester Acetaldehyde (0.21 mL, 3.80 mmole) was added to a solution of Example 66k (0.370 gm, 0.76 mmol) in dry methanol (15 mL) followed by the addition of trifluoro-acetic acid (0.06 mL, 0.76 mmol). The reaction mixture was stirred at 0° C. for 2 h, allowed to come to room temperature, treated with sodium cyanoborohydride (0.119 g, 1.9 mmol), and stirred overnight. It was concentrated, treated with 10% aqueous sodium bicarbonate solution, water and extracted with ethyl acetate. The organic layer was washed with water, brine, dried, concentrated and purified using flash chromatography (silica gel, methanol/chloroform) to obtain the title compound as a white solid. Yield: 0.3 g, (76.72%); $^1$H NMR (CDCl$_3$): δ 2.15 (t, 3H, CH$_3$), 2.45-2.55 (m, 6H, 3CH$_2$), 2.70 (s, 3H, CH$_3$), 3.40 (q, 2H, CH$_2$), 3.50 (t, 2H, CH$_2$), 3.70-3.80 (m, 4H, CH$_2$), 3.95 (s, 3H, OCH$_3$), 4.70 (s, 2H, CH$_2$), 6.55 (s, 1H, Ar), 6.70 (s, 1H, Ar), 8.10 (s, 1H, Ar), 8.45 (s, 1H, Ar); MS: m/e (CI+) 511 (M–CH$_3$).

EXAMPLE 68

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-morpholin-4-yl-ethyl)-acetamide dimesylate The title compound was synthesised from Example 68k as described in the synthesis of Example 50. Yield: 0.080 g, (35%); mp: 198-200° C.; $^1$H NMR (DMSO-d$_6$): δ 1.84 (s, 3H, CH$_3$), 2.38 (s, 6H, 2CH$_3$), 2.72 (s, 3H, CH$_3$), 3.16 (bs, 2H, CH$_2$), 3.3 (bs, 2H, CH$_2$), 3.53 (t, 2H, CH$_2$), 3.67 (t, 2H, CH$_2$), 3.98 (bs, 4H, 2CH$_2$), 5.38 (s, 2H, CH$_2$), 7.7 (s, 1H, Ar), 7.87 (s, 1H, Ar), 8.22 (s, 1H, Ar), 8.29 (s, 1H, Ar), 8.3-8.6 (bs, 4H, 2NH$_2$), 9.58 (bs, 1H, NH), 11.5 (s, 1H, OH); MS: m/e (ES+) (free base) 550 (M+1); analysis: C$_{26}$H$_{36}$ClN$_5$O$_{12}$S$_3$, calcd.: C, 42.07; H, 4.89; N, 9.44; Cl, 4.78; S, 12.96; found C, 41.52; H, 4.29; N, 8.61; Cl, 4.36; S, 12.15%.

EXAMPLE 68k

2-[Acetyl-(2-morpholin-4-yl-ethyl)-amino]-4-Chloro-6-methyl-10,10-dioxo-10,11-dihydro-5-oxa-10lambda*6*-thia-dibenzo[a,d]cycloheptene-8-carboxylic acid methyl ester Acetyl chloride (1 mL, 14.1 mmol) was added to Example 66k (0.2 g, 0.4165 mol) with stirring and subsequently refluxed for 2 h. The reaction mixture was cooled, treated with water, aqueous sodium bicarbonate solution to pH 7.5 and extracted with chloroform. The organic layer was washed with water, brine, dried, concentrated and purified using flash chromatography (silica gel, 2.5% methanol/chloroform) to obtain the title compound. Yield: 0.195 g (90%); $^1$H NMR (CDCl$_3$): δ 1.9 (s, 3H, CH$_3$), 2.44 (m, 6H, 3CH$_2$), 2.72 (s, 3H, CH$_3$), 3.66 (t, 4H, 2CH$_2$), 3.81 (t, 2H, CH$_2$), 3.92 (s, 3H, OCH$_3$), 4.72 (s, 2H, CH$_2$), 7.3 (d, 1H, Ar), 7.52 (s, 1H, Ar), 8.12 (s, 1H, Ar), 8.45 (d, 1H, Ar); MS: m/e (ES+) 523 (M+1).

EXAMPLE 69

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-morpholin-4-yl-ethyl)-acetamide dimesylate The title compound was synthesised from Example 69k as described in the synthesis of Example 50. Yield: 0.140 g, (60%); mp: 168-169° C.; $^1$H NMR (DMSO-d$_6$): δ 2.396 (s, 6H, 2CH$_3$), 2.73 (s, 3H, CH$_3$), 3.2 (m, 6H, 2CH$_3$), 3.5-3.62 (m, 8H, 4CH$_2$), 3.72 (s, 2H, CH$_2$), 3.84 (b, 4H, 2CH$_2$), 5.38 (s, 2H, CH$_2$), 7.74 (s, 1H, Ar), 7.89 (s, 1H, Ar), 8.23 (s, 1H, Ar), 8.31 (s, 1H, Ar), 8.37-8.62 (b, 4H, 2NH$_2$), 9.65 (b, 1H, NH), 11.52 (s, 1H, OH); MS: m/e (ES+) (free base) 580 (M+1); analysis: C$_{27}$H$_{38}$ClN$_5$O$_{13}$S$_3$. (Hygroscopic), calcd.; C, 41.99; H, 4.96; N, 9.07; Cl, 4.59; S, 12.45; found C, 41.37; H, 5.17; N, 8.60%.

EXAMPLE 69k

4-Chloro-2-[(2-methoxy-acetyl)-(2-morpholin-4-yl-ethyl)-amino]-6-methyl-10,10-dioxo-10,11-dihydro-5-oxa-10lambda*6*-thia-dibenzo[a,d]cycloheptene-8-carboxylic acid methyl ester Methoxy-acetyl chloride (1 mL, 10.92 mmol) was added to Example 66k (0.2 g, 0.416 mmol) with stirring and then heated at 80° C. for 2 h. The reaction mixture was cooled, treated with methanol (1 mL), water and extracted with chloroform. The organic layer was washed with water, brine, concentrated and purified using flash chromatography (silica gel, 3% methanol/chloroform) to obtain the title compound. Yield: 0.2 g, (87%); $^1$H NMR (CDCl$_3$): δ 2.47 (m, 6H, 3CH$_2$), 2.72 (s, 3H, CH$_3$), 3.34 (s, 3H, OCH$_3$), 3.65 (t, 4H, 2CH$_2$), 3.82 (bs, 2H, CH$_2$), 3.84 (t, 4H, 2CH$_2$), 3.93 (s, 3H, OCH$_3$), 4.72 (s, 2H, CH$_2$), 7.33 (s, H, Ar), 7.54 (s, 1H, Ar), 8.13 (s, 1H, Ar), 8.46 (s, 1H, Ar); MS: m/e (ES+) 553 (M+1).

EXAMPLE 70

N-(4-Chloro-2-{2-[4-(2-hydroxy-ethyl)-piperazin-1-yl]-ethylamino}-6-methyl-10,10-dioxo-10,11-dihydro-5-oxa-10lambda*6*-thia-dibenzo[a,d]cycloheptene-8-carbonyl)-guanidine trimesylate The title compound was synthesised from Example 70k as described in the synthesis of Example 50. Yield: 0.153 g, (71%); mp: 218-220° C.; $^1$H NMR (DMSO-d$_6$): δ 2.40 (s, 9H, 3CH$_3$), 2.70 (s, 3H, CH$_3$), 3.30 (m, 8H, 4CH$_2$), 3.70 (m, 8H, 4CH$_2$), 5.20 (s, 2H, CH$_2$), 6.80 (s, 2H, 2Ar), 8.10 (s, 1H, Ar), 8.30 (s, 1H, Ar), 8.30-8.60 (m, 4H, guanidinyl); MS: m/e (ES+) 551 (M+1); analysis: C$_{27}$H$_{43}$ClN$_6$O$_{14}$S$_4$. calcd.: C, 38.62; H, 5.12; N, 10.01; Cl, 4.22; S, 15.28; found: C, 38.69; H, 5.63; N, 9.71; Cl, 4.71; S, 15.28%.

EXAMPLE 70k

4-Chloro-2-{2-[4-(2-hydroxy-ethyl)-piperazin-1-yl]-ethylamino}-6-methyl-10,10-dioxo-10,11-dihydro-5-oxa-10lambda*6*-thia-dibenzo[a,d]cycloheptene-8-carboxylic acid methyl ester 2-Piperazin-1-yl-ethanol (0.227 g, 1.74 mmol) was added with stirring to a solution of Example 56k (0.5 g, 1.16 mmol) in DMF (10 mL) in an atmosphere of nitrogen. The reaction mixture was stirred at 110° C. for 6 h, concentrated, treated with chilled water and extracted with n-butanol. The organic layer was washed with water, brine, dried, concentrated and purified using flash chromatography (silica gel, methanol/chloroform) to obtain the title compound as an off-white solid. Yield: 0.521 g, (85.69%); $^1$H NMR (DMSO-d$_6$): δ 2.50 (s, 3H, CH$_3$), 3.10 (t, 4H, 2CH$_2$), 3.70 (t, 10H, 5CH$_2$), 3.90 (s, 3H, OCH$_3$), 4.40 (s, 2H, CH$_2$), 5.20 (s, 2H, CH$_2$), 6.10 (s, 1H, Ar), 6.80-6.85 (m, 2H, Ar), 8.10 (m, 2H, Ar); MS: m/e (ES+) 551 (M+).

EXAMPLE 71

N-[4-Chloro-6-methyl-2-(2-methylamino-ethylamino)-10,10-dioxo-10,11-dihydro-5-oxa-10lambda*6*-thia-dibenzo[a,d]cycloheptene-8-carbonyl]-guanidine dimesylate The title compound was synthesised from Example 71k as described in the synthesis of Example 50. Yield: 0.180 g, (63%); mp: 250-251° C.; $^1$H NMR (DMSO-d$_6$): δ 2.40 (s, 6H, 2CH$_3$), 2.60 (d, 3H, CH$_3$), 2.70 (s, 3H, CH$_3$), 3.10 (m, 2H, CH$_2$), 3.40 (m, 2H, CH$_2$), 5.20 (s, 2H, CH$_2$), 6.8 (s, 2H, 2Ar), 8.10 (s, 1H, Ar), 8.20 (s, 1H, Ar), 8.30-8.50 (m, 4H, guanidinyl), 8.60 (bs, 1H, NH); MS: m/e (ES+) 452 (M+1); analysis: C$_{21}$H$_{30}$ClN$_5$O$_{10}$S$_3$.2H$_2$O calcd.: C, 37.08; H, 5.04; N, 10.30; Cl, 5.21; S, 14.14; found: C, 37.08; H, 4.55; N, 10.10; Cl, 5.56; S, 14.66%.

EXAMPLE 71k

4-Chloro-6-methyl-2-(2-methylamino-ethylamino)-10,10-dioxo-10,11-dihydro-5-oxa-10lambda*6*-thia-dibenzo[a,d]cycloheptene-8-carboxylic acid methyl ester A 30% methanolic methylamine solution (4 mL) was added to a solution of the carboxylic acid of Example 56k (0.5 g, 1.16 mmol) in methanol, in a pressure reactor vessel under nitrogen atmosphere and kept at 110° C. for 4 h. The reaction mixture was cooled, concentrated partially and the solid that precipitated was filtered, washed with methanol, dried, treated with methanolic HCl solution (10 mL) and stirred at 70° C. for 1.5 h. The reaction mixture was cooled and the solid that precipitated was filtered and washed with methanol to obtain the title compound as an off white solid. Yield: 0.325 g, (65.92%); $^1$H NMR (DMSO-d$_6$): δ 2.50 (d, 3H, CH$_3$), 2.80 (s, 3H, CH$_3$), 3.10 (t, 2H, CH$_2$), 3.30 (t, 2H, CH$_2$), 3.90 (s, 3H, OCH$_3$), 5.10 (s, 2H, CH$_2$), 6.85-6.90 (m, 2H, Ar), 8.10 (s, 1H, Ar), 8.20 (s, 1H, Ar), 9.0 (t, 1H, NH); MS: m/e (ES+) 425 (M+).

EXAMPLE 72

N-[4-Chloro-6-methyl-10,10-dioxo-2-(2-pyrrolidin-1-yl-ethylamino)-10,11-dihydro-5-oxa-10lambda*6*-thia-dibenzo[a,d]cycloheptene-8-carbonyl]-guanidine dimesylate The title compound was synthesised from Example 72k as described in the synthesis of Example 50. Yield: 0.320 g, (65.84%); mp: 235-236° C.; $^1$H NMR (DMSO-d$_6$): δ 1.85-1.90 (m, 2H, CH$_2$), 1.95-2.0 (m, 2H, CH$_2$), 2.40 (s, 6H, 2CH$_3$), 2.70 (s, 3H, CH$_3$), 3.05-3.10 (m, 4H, 2CH$_2$), 3.30-3.35 (m, 2H, CH$_2$), 3.60-3.65 (m, 2H, CH$_2$), 5.25 (s, 2H, CH$_2$), 6.50 (t, 1H, NH), 6.85 (s, 2H, Ar), 8.10 (s, 1H, Ar), 8.30 (s, 1H, Ar); MS: m/e (ES+) 492 (M+1); analysis: C$_{24}$H$_{34}$ClN$_5$O$_{10}$S$_3$ calcd.: C, 42.04; H, 5.07; N, 10.58; Cl, 5.55, S; 14.25; found: C, 42.13; H, 5.01; N, 10.24, Cl; 5.18, S; 14.06%.

EXAMPLE 72k

4-Chloro-6-methyl-10,10-dioxo-2-(2-pyrrolidin-1-yl-ethylamino)-10,11-dihydro-5-oxa-10lambda*6*-thia-dibenzo[a,d]cycloheptene-8-carboxylic acid methyl ester Pyrrolidine (0.14 mL, 1.74 mmol) was added to a solution of Example 56k (0.5 g, 1.16 mmol) in dry DMF (5 mL) in an atmosphere of nitrogen. It was stirred at 100° C. for 5 h. The reaction mixture was concentrated and treated with chilled water to obtain a solid which was filtered, washed with water, dried and purified using flash chromatography (silica gel, 2% methanol/chloroform) to obtain the title compound. Yield: 0.375 g, (69.44%); $^1$H NMR (DMSO-d$_6$): δ 1.75 (m, 4H, 2CH$_2$), 2.70 (s, 3H, CH$_3$), 2.85 (m, 2H, CH$_2$), 3.20 (m, 2H, CH$_2$), 3.90 (s, 3H, OCH$_3$), 5.20 (s, 2H, CH$_2$), 6.25 (t, 1H, NH), 6.7 (s, 2H, 2Ar), 8.20 (s, 1H, Ar), 8.25 (s, 1H, Ar); MS: m/e (ES−) 463 (M+).

EXAMPLE 73

N-{4-Chloro-2-[ethyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 73k as described in the synthesis of Example 50. Yield: 0.099 g, (42.85%); mp: 258-260° C.; $^1$H NMR (DMSO-d$_6$): δ 1.10 (t, 3H, CH$_3$), 1.90-2.15 (m, 4H, 2CH$_2$), 2.40 (s, 6H, 2CH$_3$), 2.75 (s, 3H, CH$_3$), 3.10-3.15 (m, 2H, CH$_2$), 3.50-3.70 (m, 8H, 4CH$_2$), 5.25 (s, 2H, CH$_2$), 6.90 (s, 1H, Ar), 7.05 (s, 1H, Ar), 8.15 (s, 1H, Ar), 8.25 (s, 1H, Ar), 8.30-8.50 (m, 4H, guanidinyl); MS: m/e (ES+) 520 (M+1); analysis: C$_{26}$H$_{38}$ClN$_5$O$_{10}$S$_3$ calcd.: C, 43.85; H, 5.38; N, 9.83; Cl, 4.98; S, 13.50; found: C, 44.23; H, 5.95; N, 10.28, Cl, 4.65; S, 13.20%.

EXAMPLE 73k

4-Chloro-2-[ethyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Distilled acetaldehyde (0.11 mL, 1.90 mmol) was added to a solution of Example 72k (0.180 g, 0.38 mmol) in dry methanol (15 mL), followed by the addition of trifluoroacetic acid (0.03 mL, 0.38 mmol). The reaction mixture was stirred at 0° C. for 2 h. Sodium cyanoborohydride was added and the reaction mixture was allowed to come to room temperature and then left stirring overnight. It was concentrated, treated with 10% aqueous sodium bicarbonate solution, water and extracted with ethyl acetate. The organic layer was washed with water, brine, dried, concentrated and purified using flash chromatography (silica gel, methanol/chloroform) to obtain the title compound as a white solid. Yield: 0.118 g (62%); $^1$H NMR (DMSO-d$_6$): δ 1.20 (t, 3H, CH$_3$), 1.90-2.00 (m, 4H, 2CH$_2$), 2.60-2.69 (m, 4H, 2CH$_2$), 2.70 (s, 3H, CH$_3$), 3.45 (q, 2H, CH$_2$), 3.55 (t, 2H, CH$_2$), 3.90 (s, 3H, OCH$_3$), 4.70 (s, 2H, CH$_2$), 6.65 (s, 1H, Ar), 6.75 (s, 1H, Ar), 8.10 (s, 1H, Ar), 8.55 (s, 1H, Ar); MS: m/e (ES+) 493 (M+1).

EXAMPLE 74

(4-Chloro-8-guanidinocarbonyl-6-methyl-10,10-dioxo-10,11-dihydro-5-oxa-10lambda*6*-thia-dibenzo[a,d]cycloheptene-2-yl)-(2-pyrrolidin-1-yl-ethyl)-carbamic acid isobutylester dimesylate The title compound was synthesised from Example 74k as described in the synthesis of Example 1. Yield: 0.170 g, (48.85%); mp: 198-200° C.; $^1$H NMR (DMSO-d$_6$): δ 0.80 (m, 6H, 2CH$_3$), 1.1 (t, 1H, CH), 1.90-2.05 (m, 4H, 2CH$_2$), 2.7 (s, 3H, CH$_3$), 3.05-3.15 (m, 2H, CH$_2$), 3.3-3.35 (m, 2H, CH$_2$), 3.55-3.6 (m, 2H, CH$_2$), 3.80-3.85 (m, 2H, CH$_2$), 4.05-4.10 (m, 2H, CH$_2$), 5.35 (s, 2H, CH$_2$), 7.65 (s, 1H, Ar), 7.85 (s, 1H, Ar), 8.25 (s, 1H, Ar), 8.30 (s, 1H, Ar), 8.40-8.50 (m, 3H, guanidinyl); MS: m/e (ES+) 592 (M+1); analysis: C$_{29}$H$_{42}$ClN$_5$O$_{12}$S$_3$.2H$_2$O calcd.: C, 42.46; H, 5.65; N, 8.54; found: C, 42.39; H, 5.78; N, 8.75%.

EXAMPLE 74k

4-Chloro-2-[isobutoxycarbonyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carboxylic acid Isobutylchloroformate (0.17 mL, 1.33 mmol) was added to a solution of Example 72k (0.40 g, 0.88 mmol) in dry CH$_2$Cl$_2$ (15 mL). Triethylamine (0.23 ml, 1.67 mmol) was added and the reaction mixture was stirred at 0° C. for 1 h. It was brought to room temperature, treated with water and extracted with chloroform. The organic layer was washed with water, brine, dried, concentrated and crystallised using ethyl acetate to obtain the title compound as a white solid. Yield: 0.280 g, (58%). $^1$H NMR (DMSO-d$_6$): δ 0.80 (d, 6H, 2CH$_3$), 1.70-1.80 (m, 5H, 2CH$_2$, CH), 2.50-2.89 (m, 1H, 4CH$_2$, CH$_3$), 3.90 (d, 2H, CH$_2$), 5.19 (s, 2H, CH$_2$), 7.55 (s, 1H, Ar), 7.75 (s, 1H, Ar), 8.10 (s, 1H, Ar), 8.20 (s, 1H, Ar). MS: m/e (EI+) 565 (M+).

EXAMPLE 75

1-Carboxymethyl-1-[2-(4-chloro-8-guanidinocarbonyl-6-methyl-10,10-dioxo-10,11-dihydro-5-oxa-10-lambda*6*-thia-dibenzo[a,d]cycloheptene-2-ylamino)-ethyl]-pyrrolidinium dimesylate The title compound was synthesised from Example 75k as described in the synthesis of Example 50. Yield: 0.180 g, (25.38%); mp: 300-301° C.; $^1$H NMR (DMSO-d$_6$): δ 2.15-2.25 (m, 4H, 2CH$_2$), 2.52 (s, 6H, 2CH$_3$), 2.66 (s, 3H, CH$_3$), 3.50-3.55 (m, 4H, 2CH$_2$), 3.65-3.74 (m, 4H, 2CH$_2$), 4.42 (s, 2H, CH$_2$), 5.14 (s, 2H, CH$_2$), 6.78 (s, 2H, Ar), 8.09 (s, 1H, Ar), 8.27 (s, 1H, Ar); MS: m/e (ES+) 550 (M+1). analysis: C$_{26}$H$_{36}$ClN$_5$O$_{12}$S$_3$. calcd.: C, 42.07; H, 4.90; N, 9.44, found: C, 42.34; H, 5.59; N, 9.75%.

EXAMPLE 75k

1-Carboxymethyl-1-[2-(4-chloro-8-methoxycarbonyl-6-methyl-10,10-dioxo-10,11-dihydro-5-oxa-10lambda*6*-thia-dibenzo[a,d]cyclohepten-2-ylamino)-ethyl]-pyrrolidinium Chloro-acetyl chloride (2.30 mL, 29 mmol) was added to a solution of Example 72k (1.35 gm, 2.90 mmol) and the reaction mixture was stirred for 2 h at 90° C. It was cooled and treated with an aqueous sodium bicarbonate solution. The solid that precipitated was filtered, washed with water and purified using flash chromatography (silica gel, methanol/chloroform) to obtain the title compound as a white solid. Yield: 0.960 g, (64.17%); $^1$H NMR (DMSO-d$_6$): δ 2.10-2.19 (m, 4H, 2CH$_2$), 2.70 (s, 3H, CH$_3$), 3.80-3.90 (m, 4H, 2CH$_2$), 3.95 (s, 3H, OCH$_3$), 4-4.20 (m, 4H, 2CH$_2$), 4.40 (s, 2H, CH$_2$), 5.38 (s, 2H, CH$_2$), 7.73 (s, 1H, Ar), 7.78 (s, 1H, Ar), 8.19 (s, 1H, Ar), 8.20 (s, 1H, Ar); MS: m/e (EI+) 506 (M+1).

EXAMPLE 76

Cyclopropanecarboxylic acid (4-chloro-8-guanidinocarbonyl-6-methyl-10,10-dioxo-10,11-dihydro-5-oxa-10lambda*6*-thia-dibenzo[a,d]cyclohepten-2-yl)-(2-pyrrolidin-1-yl-ethyl)-amide dimesylate The title compound was synthesised from Example 76k as described in the synthesis of Example 50. Yield: 0.280 g, (55%), mp: 178-179° C.; $^1$H NMR (DMSO-d$_6$): δ 0.65-0.75 (m, 2H, CH$_2$), 0.85-0.95 (m, 2H, CH$_2$), 1.30-1.35 (m, 1H, CH), 1.90-2.0 (m, 4H, 2CH$_2$), 2.41 (s, 6H, 2CH$_3$), 2.72 (s, 1H, CH$_3$), 3.05-3.15 (m, 2H, CH$_2$), 3.30-3.35 (m, 2H, CH$_2$), 3.60-3.70 (m, 2H, CH$_2$), 4.00-4.10 (m, 2H, CH$_2$), 5.40 (s, 2H, CH$_2$), 7.80 (s, 1H, Ar), 8.0 (s, 1H, Ar), 8.40 (s, 2H, Ar), 8.50-8.70 (m, 4H, guanidinyl); MS: m/e (ES+) 560 (M+1); analysis: C$_{28}$H$_{38}$ClN$_5$O$_{11}$S$_3$.2 mol. H$_2$O. calcd.: C, 42.66; H, 5.37; N, 8.88; found: C, 42.23; H, 5.46; N, 8.46%

EXAMPLE 76k

4-Chloro-2-[cyclopropanecarbonyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Cyclopropanecarbonyl chloride (0.44 mL, 4.8 mmol) was added to a solution of Example 72k (0.3 g, 0.64 mmol) and the reaction mixture was stirred at 55° C. for 2 h. It was treated with methanol (1 mL), water and extracted with chloroform. The organic layer was washed with water, brine, dried and purified using flash chromatography (silica gel, methanol/chloroform) to obtain the title compound as a white solid. Yield: 0.280 g, (81.63%); $^1$H NMR (DMSO-d$_6$): δ 0.71 (bs, 2H, CH$_2$), 0.88 (bs, 2H, CH$_2$), 1.87 (bs, 2H, CH$_2$), 2.01 (bs, 2H, CH$_2$), 2.70 (s, 3H, CH$_3$), 3.00 (bs, 2H, CH$_2$), 3.18 (bs, 2H, CH$_2$), 3.57 (bs, 2H, CH$_2$), 3.70 (s, 3H, CH$_3$), 3.91 (s, 3H, OCH$_3$), 4.04 (bs, 2H, CH$_2$), 5.38 (s, 2H, CH$_2$), 7.78 (s, 1H, Ar), 7.98 (s, 1H, Ar), 8.19 (s, 1H, Ar), 8.22 (s, 1H, Ar); MS: m/e (CI+) 533 (M+1).

EXAMPLE 77

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-pyrrolidin-1-yl-ethyl)-acetamide dimesylate The title compound was synthesised from Example 77k as described in the synthesis of Example 50. Yield: 0.160 g, (45.19%); mp: 204-206° C., $^1$H NMR (DMSO-d$_6$): δ 1.90-2.05 (m, 4H, 2CH$_2$), 2.41 (s, 6H, 2CH$_3$), 2.72 (s, 3H, CH$_3$), 3.08-3.10 (m, 2H, CH$_2$), 3.20-3.30 (m, 2H, CH$_2$), 3.60-3.65 (m, 2H, CH$_2$), 3.80-3.85 (m, 2H, CH$_2$), 3.90-3.99 (m, 2H, CH$_2$), 5.37 (s, 2H, CH$_2$), 7.75 (s, 1H, Ar), 7.89 (s, 1H, Ar), 8.23 (s, 1H, Ar), 8.30 (s, 1H, Ar), 8.39-8.63 (m, 4H, guanidinyl); MS: m/e (ES+) 564 (M+1); analysis: C$_{27}$H$_{38}$ClN$_5$O$_{12}$S$_3$.2H$_2$O. calcd.: C, 41.88; H, 5.21; N, 9.05; found: C, 41.96; H, 5.63; N, 9.35%.

EXAMPLE 77k

4-Chloro-2-[(2-methoxy-acetyl)-(2-pyrrolidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Methoxy-acetyl chloride (0.6 mL, 6.4 mmol) was added to a solution of Example 72k (0.3 g, 0.64 mmol) with stirring. The temperature was raised to 80° C. and stirring continued for 2 h. The reaction mixture was treated with methanol (1 mL), water and extracted with chloroform. The organic layer was washed with water, brine, dried and purified using flash chromatography (silica gel, methanol/chloroform) to obtain the title compound as a white solid. Yield: 0.260 g (75.14%); $^1$H NMR (DMSO-d$_6$): δ 0.71 (bs, 4H, 2CH$_2$), 2.60 (bs, 4H, 2CH$_2$), 2.70 (s, 3H, CH$_3$), 3.20 (s, 3H, OCH$_3$), 3.70 (s, 3H, CH$_3$), 3.80 (bs, 4H, 2CH$_2$), 4.00 (s, 3H, OCH$_3$), 5.40 (s, 2H, CH$_2$), 7.65 (s, 1H, Ar), 7.80 (s, 1H, Ar), 8.19 (s, 1H, Ar). 8.22 (s, 1H, Ar); MS: m/e (CI+) 533 (M+1).

EXAMPLE 78

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-pyrrolidin-1-yl-ethyl)-acetamide trimesylate The title compound was synthesised from Example 78k as described in the synthesis of Example 50. Yield: 0.110 g, (54.45%); mp: 198-199° C.; $^1$H NMR (DMSO-d$_6$): δ 1.84 (s, 3H, CH$_3$), 1.90-2.10 (m, 4H, 2CH$_2$), 2.40 (s, 9H, 3CH$_3$), 2.75 (s, 3H, CH$_3$), 3.05-3.15 (m, 4H, 2CH$_2$), 3.30-3.35 (m, 2H, CH$_2$), 3.60-3.65 (m, 2H, CH$_2$), 4.95-4 (m, 2H, CH$_2$), 5.36 (s, 2H, CH$_2$), 7.05 (s, 1H, OH), 7.75 (s, 1H, Ar), 7.93 (s, 1H, Ar), 8.30 (s, 1H, Ar), 8.39 (s, 1H, Ar), 8.50-8.63 (m, 4H, guanidinyl). MS: m/e (ES+) 535 (M+1); analysis: C$_{28}$H$_{44}$ClN$_5$O$_{17}$S$_4$ calcd.: C, 36.62; H, 4.83; N, 7.63; found: C, 36.56; H, 4.53; N, 7.65%.

EXAMPLE 78k

2-[Acetyl-(2-pyrrolidin-1-yl-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Acetyl chloride (0.46 mL, 6.4 mmol) was added with stirring to Example 72k (0.3 g, 0.64 mmol). The reaction mixture was then stirred at 70° C. for 2 h, treated with methanol (1 mL), water and extracted with chloroform. The organic layer was washed with water, brine, dried and purified using flash chromatography (silica gel, methanol/chloroform) to obtain the title compound as a white solid. Yield: 0.140 g (42.81%); $^1$H NMR (DMSO-d$_6$): δ 1.80-1.95 (m, 4H, 2CH$_2$), 2.60 (s, 3H, CH$_3$), 2.90-3.10 (m, 4H, 2CH$_2$), 3.30-3.35 (m, 2H, CH$_2$), 3.90 (s, 3H, OCH$_3$), 3.95 (t, 2H, CH$_2$), 4.70 (s, 2H, CH$_2$), 7.45 (s, 2H, Ar), 8.05 (s, 1H, Ar), 8.35 (s, 1H, Ar); MS: m/e (EI+) 506 (M+1).

EXAMPLE 79

N-{4-Chloro-6-methyl-2-[2-(2-morpholin-4-yl-ethylamino)-ethylamino]-10,10-dioxo-10,11-dihydro-5-oxa-10lambda*6*-thia-dibenzo[a,d]cycloheptene-8-carbonyl}-guanidine dimesylate The title compound was synthesised from Example 79k as described in the synthesis of Example 50. Yield: 0.120 g, (60.09%); mp: 255-256° C.; $^1$H NMR (DMSO-d$_6$): δ 2.40 (s, 6H, 2CH$_3$), 2.70 (s, 3H, CH$_3$), 2.85-2.90 (m, 4H, 2CH$_2$), 3.20-3.25 (m, 4H, 2CH$_2$), 3.35-3.55 (m, 8H, 4CH$_2$), 5.20 (s, 2H, CH$_2$), 6.85 (s, 2H, Ar), 8.20 (s, 1H, Ar), 8.30 (s, 1H, Ar); MS: m/e (ES+) 551 (M+1); analysis: C$_{26}$H$_{39}$ClN$_6$O$_{11}$S$_3$ 2H$_2$O calcd.: C, 40.07; H, 5.50; N, 10.78; Cl, 4.55, S; 12.34; found: C, 39.49; H, 4.90; N, 10.99, Cl; 4.98, S; 11.98%.

EXAMPLE 79k

4-Chloro-6-methyl-2-[2-(2-morpholin-4-yl-ethylamino)-ethylamino]-10,10-dioxo-10,11-dihydro-5-oxa-10lambda*6*-thia-dibenzo[a,d]cycloheptene-8-carboxylic acid methyl ester 2-Morpholin-4-yl-ethylamine (0.18 mL, 1.44 mmol) and tetrabutylammonium iodide (0.075 g, 0.2 mmol) were sequentially added with stirring to a solution of the carboxylic acid of Example 56k (0.5 g, 1.2 mmol) in dry DMF (1 mL). The reaction mixture was then stirred at 120° C. for 3 h in an atmosphere of nitrogen. It was treated with cold water and the solid that precipitated was filtered, washed with water, and dried. The solid was treated with a methanolic HCl solution (10 mL), and refluxed at 70° C. for 3 h. The reaction mixture was concentrated and treated with an aqueous sodium bicarbonate solution. The solid that precipitated was filtered, washed with water, dried and purified using flash chromatography (silica gel, 2% methanol/chloroform) to obtain the title compound. Yield: 0.150 g, (24.19%); $^1$H NMR (DMSO-d$_6$): δ 2.40 (t, 4H, 2CH$_2$), 2.50-2.60 (m, 4H, 2CH$_2$), 3.10 (m, 4H, 2CH$_2$), 3.15-3.20 (m, 4H, 2CH$_2$), 3.90 (s, 3H, OCH$_3$), 4.50 (t, 1H, NH), 5.15 (s, 2H, CH$_2$), 6.10 (t, 1H, NH), 6.7 (s, 2H, 2Ar), 8.10 (s, 1H, Ar), 8.25 (s, 1H, Ar); MS : m/e (EI+) 524 (M+).

EXAMPLE 80

N-{4-Chloro-6-methyl-2-[2-(2-morpholin-4-ylamino)-ethylamino]-10,10-dioxo-10,11-dihydro-5-oxa-10lambda*6*-thia-dibenzo[a,d]cycloheptene-8-carbonyl}-guanidine trimesylate The title compound was synthesised from Example 80k as described in the synthesis of Example 50. Yield: 0.08 g, (62.5%), mp: 178-180° C., $^1$H NMR (DMSO-d$_6$): δ 2.35 (s, 9H, 3CH$_3$), 2.65 (s, 3H, CH$_3$), 3.00-3.10 (m, 4H, 2CH$_2$), 3.20-3.50 (m, 6H, 3CH$_2$), 3.65-3.75 (m, 2H, CH$_2$), 5.20 (s, 2H, CH$_2$), 6.80 (s, 1H, Ar), 6.85 (s, 1H, Ar), 8.25 (s, 1H, Ar), 8.30 (s, 1H, Ar), MS: m/e (ES+) 523 (M+1); analysis: C$_{25}$H$_{39}$ClN$_6$O$_{14}$S$_4$ 2.H$_2$O calcd.: C, 35.44; H, 5.11; N, 9.92; Cl, 4.18, S; 15.13; found: C, 35.27; H, 4.53; N, 9.39, Cl; 4.45, S; 15.04%.

EXAMPLE 80k

4-Chloro-6-methyl-2-[2-(morpholin-4-ylamino)-ethylamino]-10,10-dioxo-10,11-dihydro-5-oxa-10lambda*6*-thia-dibenzo[a,d]cycloheptene-8-carboxylic acid methyl ester Morpholin-4-ylamine (0.1 mL, 1.16 mmol) and tetrabutylammonium iodide (0.075 g, 0.2 mmol) were sequentially added with stirring to a solution of the carboxylic acid of Example 56k (0.250 g, 0.59 mmol) in dry DMF (4 mL). The reaction mixture was then stirred at 120° C. for 5.5 h in an atmosphere of nitrogen. It was treated with cold water and the solid that precipitated was filtered, washed with water, and dried. The solid was treated with a methanolic HCl solution and refluxed at 70° C. for 3 h. The solution was concentrated and treated with an aqueous sodium bicarbonate solution. The solid that precipitated was filtered, washed with water, dried and purified using flash chromatography (silica gel, 2% methanol/chloroform) to obtain the title compound. Yield: 0.105 g, (36.45%). $^1$H NMR (DMSO-d$_6$): δ 2.50-2.60 (m, 4H, 2CH$_2$), 2.70 (s, 3H, CH$_3$), 2.80 (t, 2H, CH$_2$), 2.80 (t, 2H, CH$_2$), 3.62-3.70 (m, 4H, 2CH$_2$), 3.90 (s, 3H, OCH$_3$), 5.20 (s, 2H, CH$_2$), 6.20 (t, 1H, NH), 6.85 (s, 2H, 2Ar), 8.15 (s, 1H, Ar), 8.25 (s, 1H, Ar); MS: m/e (CI+) 496 (M+).

EXAMPLE 81

N-[4-Chloro-2-(2-cyclopropylamino-ethylamino)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 81k as described in the synthesis of Example 50. Yield: 0.056 g, (55%); $^1$H NMR (DMSO-d$_6$): δ 0.72-0.83 (m, 4H, 2CH$_2$), 2.10 (m, 1H, CH), 2.5 (s, 6H, 2CH$_3$), 2.7 (s, 3H, CH$_3$), 2.92 (m, 2H, CH$_2$), 3.2 (m, 2H, CH$_2$), 5.22 (s, 2H, CH$_2$), 6.4 (bs, 1H, NH), 6.9 (s, 2H, Ar), 8.11 (s, 1H, Ar), 8.22 (s, 1H, Ar); 8.3-8.55 (bs, 4H, 2NH$_2$); MS: m/e (ES+) (Free base) 478 (M+1).

EXAMPLE 81k

4-Chloro-2-(2-cyclopropylamino-ethylamino)-6-methyl-10,10-dioxo-10,11-dihydro-5-oxa-10lambda*6*-thia-dibenzo[a,d]cycloheptene-8-carboxylic acid methyl ester Cyclopropylamine (0.819 g, 1.4 mmol) and tetrabutylammonium iodide (0.010 g, 0.027 mmol) were sequentially added with stirring to a solution of the carboxylic acid of Example 56k (0.59 g, 1.2 mmol) in dry methanol (10 mL). The reaction mixture was stirred at 110° C. for 5 h in an atmosphere of nitrogen. It was concentrated, treated with a methanolic HCl solution (15 mL) and refluxed for 2 h. The reaction mixture was concentrated, treated with an aqueous sodium bicarbonate solution to pH 7, water and extracted with n-butanol. The organic layer was washed with water, brine, dried and purified using flash chromatography (silica gel, methanol/chloroform) to obtain the title compound as a white solid. Yield: 0.120 g, (22%); $^1$H NMR (DMSO-d$_6$): δ 0.20 (d, 2H, CH$_2$), 0.40 (d, 2H, CH$_2$), 2.10 (m, 1H, CH), 2.60 (s, 3H, CH$_3$), 2.80 (t, 2H, CH$_2$), 3.10 (d, 2H, CH$_2$), 3.90 (s, 3H, OCH$_3$), 5.15 (s, 2H, CH$_2$), 6.10 (t, 1H, NH), 6.70 (s, 1H, Ar), 6.72 (s, 1H, Ar), 8.10 (s, 1H, Ar), 8.20 (s, 1H, Ar); MS: m/e (CI+) 451 (M+1).

EXAMPLE 82

N-[4-Chloro-6-methyl-2-(3-morpholin-4-yl-propylamino)-10,10-dioxo-10,11-dihydro-5-oxa-10lambda*6*-thia-dibenzo[a,d]cycloheptene-8-carbonyl]-guanidine dimesylate The title compound was synthesised from Example 82k as described in the synthesis of Example 50. Yield: 0.074 g, (58%); mp: 223-224° C.; $^1$H NMR (DMSO-d$_6$): δ 1.9 (bs, 2H, CH$_2$), 2.38 (s, 6H, 2CH$_3$), 2.7 (s, 3H, CH$_3$), 3.0-3.3 (bs, 8H, 4CH$_2$), 3.65 (bs, 2H, CH$_2$), 4.0 (bs, 2H, CH$_2$), 5.2 (s, 2H, CH$_2$), 6.35 (s, 1H, NH), 6.7 (s, H, Ar), 6.72 (s, 1H, Ar), 8.11 (s, 1H, Ar), 8.28 (s, 1H, Ar), 8.3-8.6 (bs, 4H, 2NH$_2$), 9.8 (b, 1H, OH); MS: m/e (ES+) (Free base) 523 (M+1); analysis: C$_{25}$H$_{36}$ClN$_5$O$_{11}$S$_3$. calcd.: C, 42.04; H, 5.08; N, 9.81; Cl, 4.96; S, 13.47; found C, 41.39; H, 5.5; N, 10.03; Cl, 4.83; S, 13.55%.

EXAMPLE 82k

4-Chloro-6-methyl-2-(3-morpholin-4-yl-propylamino)-10,10-dioxo-10,11-dihydro-5-oxa-10lambda*6*-thia-dibenzo[a,d]cycloheptene-8-carboxylic acid methyl ester Morpholine (0.058 g, 0.67 mmol) and tetrabutylammonium iodide (0.010 g, 0.027 mmol) were sequentially added with stirring to a solution of Example 153 (0.2 g, 0.45 mmol) in dry methanol (10 mL). The reaction mixture was stirred at 110° C. for 3 h in an atmosphere of nitrogen. It was treated with water and extracted with ethyl acetate. The organic layer was washed with water, brine, dried and purified using flash chromatography (silica gel, methanol/chloroform) to obtain the title compound as a white solid. Yield: 0.110 g; (49.20%); $^1$H NMR (DMSO-d$_6$): δ 1.70 (s, 2H, CH$_2$), 2.30 (m, 8H, 4CH$_2$), 2.65 (s, 3H, CH$_3$), 3.05 (q, 2H, CH$_2$), 3.60 (t, 2H, CH$_2$), 3.90 (s, 3H, OCH$_3$), 5.10 (s, 2H, CH$_2$), 6.25 (t, 1H, NH), 6.69 (s, 1H, Ar), 6.70 (s, 1H, Ar), 8.10 (s, 1H, Ar), 8.15 (s, 1H, Ar); MS: m/e (EI+) 494 (M+1).

EXAMPLE 83

N-{4-Chloro-6-methyl-10,10-dioxo-2-[2-(2-pyridin-2-yl-ethylamino)-ethylamino]-10,11-dihydro-5-oxa-10lambda*6*-thia-dibenzo[a,d]cycloheptene-8-carbonyl}-guanidine trimesylate The title compound was synthesised from Example 83k as described in the synthesis of Example 50. Yield: 0.2 g, (62.11%), mp: 196-198° C., $^1$H NMR (DMSO-d$_6$): δ 2.40 (s, 9H, 3CH$_3$), 2.70 (s, 3H, CH$_3$), 3.15-3.2 (m, 2H, CH$_2$), 3.25-3.3 (m, 2H, CH$_2$), 3.40-3.55 (m, 4H, 2CH$_2$), 5.25 (s, 2H, CH$_2$), 6.80 (s, 1H, Ar), 7.05 (s, 1H, Ar), 7.70 (m, 1H, Ar), 8.20 (s, 1H, Ar), 8.25 (s, 1H, Ar), 8.50-8.55 (m, 1H, Ar), 8.75-8.80 (m, 2H, Ar); MS: m/e (ES+) 543 (M+1).

EXAMPLE 83k

4-Chloro-6-methyl-10,10-dioxo-2-[2-(2-pyridin-2-yl-ethylamino)-ethylamino]-10,11-dihydro-5-oxa-10lambda*6*-thia-dibenzo[a,d]cycloheptene-8-carboxylic acid methyl ester 2-(2-Aminoethyl)pyridine (8.13 mmol) and tetrabutylammonium iodide (0.010 g, 0.027 mmol) were sequentially added with stirring to a solution of the carboxylic acid of Example 56k (0.7 g, 1.62 mmol) in dry methanol (10 mL). The reaction mixture was stirred at 110° C. for 7 h in an atmosphere of nitrogen. It was concentrated and treated with a methanolic HCl solution (10 mL), refluxed overnight, concentrated, treated water and 10% aqueous sodium bicarbonate solution to pH 7. The solid that precipitated was filtered, washed with water, dried and purified using flash chromatography (silica gel, methanol/chloroform) to obtain the title compound as a white solid. Yield: 0.225 g, (26.81%). $^1$H NMR (DMSO-d$_6$): δ 2.70 (s, 3H, CH$_3$), 3.0-3.10 (m, 6H, 3CH$_2$), 3.40-3.55 (m, 2H, CH$_2$), 3.90 (s, 3H, OCH$_3$), 5.20 (s, 2H, CH$_2$), 6.45 (t, 1H, NH), 6.80 (s, 1H, Ar), 6.83 (s, 1H, Ar), 7.30-7.50 (m, 3H, Ar), 7.80 (t, 1H, Ar), 8.20 (s, 1H, Ar), 8.25 (s, 1H, Ar); MS (CI+): m/e 516 (M+1).

EXAMPLE 84

N-(4-Chloro-2-{2-[(furan-2-ylmethyl)-amino]-ethylamino-}-6-methyl-10,10-dioxo-10,11-dihydro-5-oxa-10lambda*6*-thia-dibenzo[a,d]cycloheptene-8-carbonyl)-guanidine trimesylate The title compound was synthesised from Example 84k as described in the synthesis of Example 50. Yield: 0.2 g, (53.33%); mp: 220-221° C., $^1$H NMR (DMSO-$d_6$): δ 2.40 (s, 9H, 3CH$_3$), 2.75 (s, 3H, CH$_3$), 3.10-3.15 (m, 2H, CH$_2$), 3.55-3.6 (m, 2H, CH$_2$), 4.40 (s, 2H, CH$_2$), 5.25 (s, 2H, CH$_2$), 6.65 (s, 1H, Ar), 6.75 (s, 1H, Ar), 6.80 (s, 2H, Ar), 7.90 (s, 1H, Ar), 8.20 (s, 1H, Ar), 8.50 (s, 1H, Ar); MS: m/e (ES+) 518 (M+1); analysis: $C_{25}H_{32}ClN_5O_{11}S_3 \cdot H_2O$ calcd.: C, 41.24; H, 4.71; N, 9.62, Cl; 4.87, S; 13.21; found: C, 40.94; H, 4.23; N, 9.98, Cl; 4.56, S; 13.13%.

EXAMPLE 84k

4-Chloro-2-{2-[(furan-2-ylmethyl)-amino]-ethylamino}-6-methyl-10,10-dioxo-10,11-dihydro-5-oxa-10lambda*6*-thia-dibenzo[a,d]cycloheptene-8-carboxylic acid methyl ester Freshly distilled furfurylamine (0.58 g, 0.60 mmol) and tetrabutylammonium iodide (0.010 g, 0.027 mmol) were sequentially added with stirring to a solution of Example 56k (0.5 g, 1.20 mmol) in dry methanol (10 mL). The reaction mixture was stirred at 110° C. for 5 h in an atmosphere of nitrogen. It was concentrated, treated with methanolic HCl solution (15 mL), refluxed overnight, concentrated, treated with water and extracted with ethyl acetate. The organic layer was washed with water, brine, dried and purified using flash chromatography (silica gel, methanol/chloroform) to obtain the title compound as a white solid. Yield: 0.438 g, (84.88%); $^1$H NMR (DMSO-$d_6$): δ 1.70 (s, 2H, CH$_2$), 2.30 (m, 6H, 3CH$_2$), 2.65 (s, 3H, CH$_3$), 3.05 (q, 2H, CH$_2$), 3.60 (t, 2H, CH$_2$), 3.90 (s, 3H, OCH$_3$), 5.10 (s, 2H, CH$_2$), 6.25 (t, 1H, NH), 6.70 (s, 1H, Ar), 6.70 (s, 1H, Ar), 8.10 (s, 1H, Ar), 8.15 (s, 1H, Ar); MS (CI+): m/e (ES+) 490 (M+1).

EXAMPLE 85

N-(4-Chloro-2-{ethyl-[2-(ethyl-furan-2-ylmethyl-amino)-ethyl]-amino-}-6-methyl-10,10-dioxo-10,11-dihydro-5-oxa-10lambda*6*-thia-dibenzo[a,d]cycloheptene-8-carbonyl)-guanidine trimesylate The title compound was synthesised from Example 85k as described in the synthesis of Example 50. Yield: 0.15 g, (58.73%); mp: 188-189° C., $^1$H NMR (DMSO-$d_6$): δ 1.10 (t, 6H, 2CH$_3$), 2.40 (s, 6H, 2CH$_3$), 2.75 (s, 3H, CH$_3$), 3.15-3.25 (m, 4H, 2CH$_2$), 3.45-3.50 (m, 4H, 2CH$_2$), 4.65 (s, 2H, CH$_2$), 5.30 (s, 2H, CH$_2$), 6.60 (s, 1H, Ar), 6.80 (s, 1H, Ar), 6.85 (s, 1H, Ar), 7.0 (s, 1H, Ar), 7.90 (s, 1H, Ar), 8.25 (s, 1H, Ar), 8.30 (s, 1H, Ar), 8.35-8.55 (m, 4H, guanidinyl); MS: m/e (ES+) 574 (M+1); analysis: $C_{30}H_{44}ClN_5O_{14}S_4$ calcd.: C, 41.78; H, 5.14; N, 8.12; found: C, 41.78; H, 4.70; N, 7.84%.

EXAMPLE 85k

4-Chloro-2-{ethyl-[2-(ethyl-furan-2-ylmethyl-amino)-ethyl]-amino}-6-methyl-10,10-dioxo-10,11-dihydro-5-oxa-10lambda*6*-thia-dibenzo[a,d]cycloheptene-8-carboxylic acid methyl ester Trifluoroacetic acid (0.03 mL, 0.4 mmol) was added to mixture of Example 84k (0.2 g, 0.40 mmol) and acetaldehyde (0.115 mL, 2 mmol) in dry methanol (10 mL) at 0° C. The reaction mixture was stirred at room temperature in an atmosphere of nitrogen for 1.5 h. It was treated with sodium cyanoborohydride (0.064 g, 1 mmol), stirred for 1.5 h, treated with cold water and extracted with ethyl acetate. The organic layer was washed with water, brine, dried and purified using flash chromatography (silica gel, ethyl acetate/pet ether) to obtain the title compound as a white solid. Yield: 0.285 g, (68.69%); $^1$H NMR (DMSO-$d_6$): δ 1.1 (t, 6H, 2CH$_3$), 2.60-2.69 (m, 4H, 2CH$_2$), 2.70 (s, 3H, CH$_3$), 3.30-3.40 (m, 4H, 2CH$_2$), 3.70 (s, 2H, CH$_2$), 3.95 (s, 3H, OCH$_3$), 4.65 (s, 2H, CH$_2$), 6.25-6.85 (m, 3H, Ar), 6.65 (s, 1H, Ar), 7.45 (s, 1H, Ar), 8.10 (s, 1H, Ar), 8.50 (s, 1H, Ar); MS: m/e (CI+) 547 (M+1).

EXAMPLE 86

N-(4-Chloro-6-methyl-10,10-dioxo-2-{2-[(thiophen-2-ylmethyl)-amino]-ethylamino}-10,11-dihydro-5-oxa-10lambda*6*thia-dibenzo[a,d]cycloheptene-8-carbonyl)-guanidine dimesylate The title compound was synthesised from Example 86k as described in the synthesis of Example 50. Yield: 0.12 g, (50%); mp: 243-245° C.; $^1$H NMR (DMSO-$d_6$): δ 2.4 (s, 6H, 2CH$_3$), 2.65 (s, 3H, CH$_3$), 3.11 (bs, 2H, CH$_2$), 4.5 (s, 2H, CH$_2$), 5.21 (s, 2H, CH$_2$), 6.4 (s, 1H, NH), 6.77 (s, 2H, Ar), 7.11 (t, 1H, Ar), 7.3 (d, 1H, Ar), 7.66 (d, 1H, Ar), 8.12 (s, 1H, Ar), 8.25 (s, 1H, Ar), 8.3-8.65 (bs, 4H, 2NH$_2$), 8.95 (bs, 1H, NH), 11.4 (bs, 1H, OH); MS: m/e (ES+) (Free base) 534 (M+1); analysis: $C_{25}H_{32}ClN_5O_{10}S_4$. calcd.: C, 41.35; H, 4.44; N, 9.64; Cl, 4.88; S, 17.66; found C, 40.87; H, 4.52; N, 9.51; C, 14.46; S, 17.13%.

EXAMPLE 86k

4-Chloro-6-methyl-10,10-dioxo-2-{2-[(thiophen-2-ylmethyl)-amino]-ethylamino}-10,11-dihydro-5-oxa-10lambda*6*-thia-dibenzo[a,d]cycloheptene-8-carboxylic acid methyl ester 2-Aminomethyl thiophene (0.38 g, 3.363 mmol) and tetrabutylammonium iodide (0.02 g, 0.054 mmol) were added to a suspension of the carboxylic acid of Example 56k (0.4 g, 0.96 mmol) in methanol (5 mL) under nitrogen in a pressure reactor vessel and heated to 110° C. for 4 h. The reaction mixture was concentrated (oily residue), treated with methanolic HCl (15 mL) and refluxed for 3.5 h. It was concentrated, treated with an aqueous sodium bicarbonate solution to pH 8 and extracted with chloroform. The organic layer was washed with water, brine, dried, concentrated and purified using flash chromatography (silica gel, 0.5% methanol/chloroform) to obtain the title compound. Yield: 0.21 g, (43.5%). $^1$H NMR (CDCl$_3$): δ 2.68 (s, 3H, CH$_3$), 2.98 (t, 2H, CH$_2$), 3.18 (t, 2H, CH$_2$), 3.9 (s, 3H, CH$_3$), 4.6 (s, 2H, CH$_2$), 4.67 (s, 1H, NH), 5.21 (s, 2H, CH$_2$), 6.50 (s, 1H, Ar), 6.55 (s, 1H, Ar), 6.95 (s, 2H, Ar), 7.2 (m, 1H, Ar), 8.05 (s, 1H, Ar), 8.45 (s, 1H, Ar); MS: m/e (ES+) 505 (M+1).

EXAMPLE 87

N-(4-Chloro-2-{ethyl-[2-(ethyl-thiophen-2-ylmethyl-amino)-ethyl]-amino}-6-methyl-10,10-dioxo-10,11-dihydro-5-oxa-10lambda*6*-thia-dibenzo[a,d]cycloheptene-8-carbonyl)-guanidine dimesylate The title compound was synthesised from Example 87k as described in the synthesis of Example 50. Yield: 0.09 g, (65%); mp: 156-158° C.; $^1$H NMR (DMSO-d$_6$): δ 1.1 (q, 6H, 2CH$_3$), 2.4 (s, 6H, 2CH$_3$), 2.7 (s, 3H, CH$_3$), 3.2 (bs, 4H, 2CH$_2$), 3.7 (t, 4H, 2CH$_2$), 4.72 (s, 2H, CH$_2$), 5.2 (s, 2H, CH$_2$), 6.83 (s, 1H, NH), 6.95 (s, 1H, Ar), 7.15 (t, 1H, Ar), 7.42 (d, 1H, Ar), 7.77 (d, 1H, Ar), 8.15 (s, 1H, Ar), 8.3 (s, 1H, Ar), 8.3-8.6 (bs, 4H, 2NH$_2$), 9.7 (bs, 1H, NH), 11.43 (bs, 1H, OH); MS: m/e (ES+) (Free base) 590 (M+1);

EXAMPLE 87k

4-Chloro-2-{ethyl-[2-(ethyl-thiophen-2-ylmethyl-amino)-ethyl]-amino}-6-methyl-10,10-dioxo-10,11-dihydro-5-oxa-10lambda*6*-thia-dibenzo[a,d]cyclo-heptene-8-carboxylic acid methyl ester Trifluoroacetic acid (0.05 mL, 0.67 mmol) was added to a solution of Example 86k (0.17 g, 0.335 mmol) in methanol (10 mL) at 0° C. Acetaldehyde (1 mL, 19.5 mmol) was added and the reaction mixture was stirred at 0-10° C. for 2 h. The reaction mixture was brought to room temperature, treated with sodium cyanoborohydride (0.092 g, 1.34 mmol) and left stirring overnight. It was treated with an aqueous sodium bicarbonate solution, concentrated, treated with water and extracted with ethyl acetate. The organic layer was washed with water, brine, dried, concentrated and purified using flash chromatography (silica gel, 20% ethyl acetate/pet ether) to obtain the title compound. Yield: 0.11 g, (58.3%); $^1$H NMR (CDCl$_3$): δ 1.1 (q, 6H, 2CH$_3$), 2.62 (t, 4H, 2CH$_2$), 2.65 (s, 3H, CH$_3$), 3.32 (m, 4H, 2CH$_2$), 3.83 (s, 2H, CH$_2$), 3.92 (s, 3H, CH$_3$), 5.2 (s, 2H, CH$_2$), 6.32 (s, 1H, CH$_2$), 6.52 (s, 1H, Ar), 7.00 (m, 2H, Ar), 7.32 (s, 1H, Ar), 8.1 (s, 1H, Ar), 8.45 (s, 1H, Ar); MS: m/e (ES+) 563 (M+1).

EXAMPLE 88

N-[2-(2-Benzylamino-ethylamino)-4-chloro-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 88k as described in the synthesis of Example 50. Yield: 0.160 g, (59%); mp: 232-233° C.; $^1$H NMR (DMSO-d$_6$): δ 2.4 (s, 6H, 2CH$_3$), 2.7 (s, 3H, CH$_3$), 3.12 (bs, 2H, CH$_2$), 3.4 (t, 2H, CH$_2$), 4.25 (s, 2H, CH$_2$), 5.2 (s, 2H, CH$_2$), 6.4 (h, 1H, NH), 6.78 (s, 2H, Ar), 7.4-7.6 (m, 5H, Ar), 8.1 (s, 1H, Ar), 8.2 (s, 1H, Ar), 8.3-8.6 (bs, 4H, 2NH$_2$), 8.9 (bs, 2H, NH$_2$), 11.4 (bs, 1H, OH); MS: m/e (ES+) (Free base) 528 (M+1); analysis: C$_{27}$H$_{34}$ClN$_5$O$_{10}$S$_3$, calcd.: C, 45.03; H, 4.76; N, 9.72; Cl, 4.92; S, 13.35; found C, 45.57; H, 4.74; N, 10.02; Cl, 4.69; S, 13.57%.

EXAMPLE 88k 2-(2-Benzylamino-ethylamino)-4-chloro-6-methyl-10,10-dioxo-10,11-dihydro-5-oxa-10lambda*6*-thia-dibenzo[a,d]cycloheptene-8-carboxylic acid methyl ester Benzyl amine (1.08 g, 10.08 mmol) and tetrabutylammonium iodide (0.02 g, 0.054 mmol) were added to a suspension of the carboxylic acid of Example 56k (0.86 g, 2.0677 mmol) in methanol (8 mL) under nitrogen, in a pressure reactor vessel and heated to 110° C. for 4 h. The reaction mixture was concentrated (oily residue), treated with methanolic HCl (25 mL) and refluxed overnight. It was concentrated, treated with an aqueous sodium bicarbonate solution to pH 8 and extracted with chloroform. The organic layer was washed with water, brine, dried, concentrated and purified using flash chromatography (silica gel, 1% methanol/chloroform) to obtain the title compound. Yield: 0.56 g, (54%); $^1$H NMR (CDCl$_3$): δ 2.62 (s, 3H, CH$_3$), 2.95 (t, 2H CH$_2$), 3.2 (m, 2H, CH$_2$), 3.83 (s, 2H, CH$_2$), 3.9 (s, 2H, CH$_2$), 4.95 (s, 1H, NH), 6.5 (s, 1H, Ar), 6.53 (s, 1H, Ar), 7.4 (m, 5H, Ar), 8.1 (s, 1H, Ar), 8.47 (s, 1H, Ar); MS: m/e (ES+) 501 (M+1).

EXAMPLE 89

N-(2-{[2-(Benzyl-ethyl-amino)-ethyl]-ethyl-amino}-4-chloro-6-methyl-10,10-dioxo-10,11-dihydro-5-oxa-10lambda*6*-thia-dibenzo[a,d]cycloheptene-8-carbonyl)-guanidine dimesylate The title compound was synthesised from Example 89k as described in the synthesis of Example 50. Yield: 0.160 g, (61%); mp: 150-152° C.; $^1$H NMR (DMSO-d$_6$): δ 1.03 (t, 3H, CH$_3$), 1.3 (t, 3H, CH$_3$), 2.35 (s, 6H, 2CH$_3$), 2.7 (s, 3H, CH$_3$), 3.2 (h, 4H, 2CH$_2$), 3.6 (t, 4H, 2CH$_2$), 4.43 (bs, 2H, CH$_2$), 5.2 (s, 2H, CH$_2$), 6.8 (s, 1H, Ar), 6.93 (s, 1H, Ar), 7.5-7.7 (m, 5H, Ar), 8.14 (s, 1H, Ar), 8.3 (s, 1H, Ar), 8.3-8.6 (h, 4H, 2NH$_2$), 9.55 (h, 1H, NH), 11.43 (h, 1H, OH); MS: m/e (ES−) 774 (M−1); analysis: C$_{31}$H$_{42}$ClN$_5$O$_{10}$S$_3$, calcd.: C, 47.96; H, 5.45; N, 9.02; found C, 50.89; H, 6.56; N, 9.96%.

EXAMPLE 89k

2-{[2-(Benzyl-ethyl-amino)-ethyl]-ethyl-amino}-4-chloro-6-methyl-10,10-dioxo-10,11-dihydro-5-oxa-10lambda*6*-thia-dibenzo[a,d]cycloheptene-8-carboxylic acid methyl ester Trifluoroacetic acid (0.1 mL, 1.32 mmol) was added to a solution of Example 88k (0.28 g, 0.56 mmol) in methanol (15 mL) at 0° C. Acetaldehyde (2 mL) was added and stirring continued for 2 h. The reaction mixture was brought to room temperature, treated with sodium cyanoborohydride (0.203 g, 2.96 mmol) and allowed to stir overnight. It was then treated with an aqueous sodium bicarbonate solution and cooled to 0° C. The precipitated solid was filtered, washed with methanol, dried and purified using flash chromatography (silica gel, 0.5% methanol/chloroform) to obtain the title compound. Yield: 0.21 g, (67.5%); $^1$H NMR (CDCl$_3$): δ 1.1 (m, 6H, 2CH$_3$), 2.6 (m, 4H, 2CH$_2$), 2.6 (s, 3H, CH$_3$), 3.22 (t, 2H, CH$_2$), 3.25 (t, 2H, CH$_2$), 3.65 (s, 2H, CH$_2$), 3.9 (s, 3H, OCH$_3$), 4.53 (s, 2H, CH$_2$), 6.22 (s, 1H, Ar), 6.52 (s, 1H, Ar), 7.35 (m, 5H, Ar), 8.1 (s, 1H, Ar), 8.45 (s, 1H, Ar); MS: m/e (ES+) 556 (M+1).

EXAMPLE 90

N-{4-Chloro-2-[2-(2-methoxy-benzylamino)-ethylamino]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 90k as described in the synthesis of Example 50. Yield: 0.017 g, (42%); mp: 224-225° C.; $^1$H NMR (DMSO-d$_6$): δ 2.38 (s, 6H, 2CH$_3$), 2.69 (s, 3H, CH$_3$), 3.1 (s, 2H, CH$_2$), 3.85 (s, 3H, OCH$_3$), 4.18 (s, 2H, CH$_2$), 4.18 (s, 2H, CH$_2$), 5.21 (s, 2H, CH$_2$), 6.4 (s, 1H, NH), 6.79 (s, 2H, Ar), 7.03 (t, 1H, Ar), 7.1 (d, 1H, Ar), 7.44 (t, 1H, Ar), 8.16 (s, 1H, Ar), 8.25 (s, 1H, Ar), 8.34 (s, 2H, NH$_2$), 8.56 (s, 1H, Ar), 8.68 (s, 2H, NH$_2$); MS: m/e (ES+) 558 (M+1); analysis: C$_{28}$H$_{36}$ClN$_5$O$_{11}$S$_3$ calcd.: C, 44.83; H, 4.84; N, 9.33; Cl, 4.73; S, 12.82; found: C, 44.01; H, 4.48; N, 8.59; Cl, 4.66; S, 13.31%.

EXAMPLE 90k

Chloro-2-[2-(2-methoxy-benzylamino)-ethylamino]-6-methyl-10,10-dioxo-10,11-dihydro-5-oxa-10lambda*6*-thia-dibenzo[a,d]cycloheptene-8-carboxylic acid methyl ester o-Methoxy benzylamine (0.99 mL, 7.68 mmol) and tetrabutylammonium iodide (10 mg) were added to a suspension of the carboxylic acid of Example 56k (0.8 g, 1.92 mmol) in methanol (5 mL) under argon, in a pressure reactor vessel and heated to 120° C. for 4 h. The reaction mixture was concentrated (oily mass), treated with methanolic HCl (25 mL) and refluxed for 4 h. It was then concentrated, treated with water, aqueous sodium bicarbonate solution to pH 7.5 and extracted with chloroform. The organic layer was washed with water, brine, dried, concentrated and purified using flash chromatography (silica gel, 1.5% methanol/chloroform) to obtain the title compound. Yield: 0.41 g (40%); $^1$H NMR (CDCl$_3$): δ 2.38 (s, 3H, CH$_3$), 2.6 (t, 2H, CH$_2$), 2.92 (q, 2H, CH$_2$), 3.56 (s, 3H, OCH$_3$), 3.6 (s, 3H, CH$_3$), 4.39 (s, 2H, CH$_2$), 5.04 (t, 1H, NH), 5.21 (s, 2H, CH$_2$), 6.22 (d, 1H, Ar), 6.3 (d, 1H, Ar), 6.6 (q, 2H, Ar), 6.94 (t, 2H, Ar), 7.71 (s, 1H, Ar), 8.04 (s, 1H, Ar); MS: m/e (ES+) 530 (M+).

EXAMPLE 91

N-(4-Chloro-2-{2-[ethyl-(2-methoxy-benzyl)-amino]-ethylamino}-6-methyl-10,10-dioxo-10,11-dihydro-5-oxa-10lambda*6*-thia-dibenzo[a,d]cycloheptene-8-carbonyl)-guanidine dimesylate The title compound was synthesised from Example 91k as described in the synthesis of Example 50. Yield: 0.070 g, (10%); $^1$H NMR (DMSO-d$_6$): δ 1.3 (t, 3H, CH$_3$), 2.4 (s, 6H, 2CH$_3$), 2.68 (s, 3H, CH$_3$), 2.77 (s, 2H, CH$_2$), 3.21 (s, 2H, CH$_2$), 3.82 (s, 3H, OCH$_3$), 4.34 (d, 2H, CH$_2$), 5.2 (s, 2H, CH$_2$), 6.78 (d, 2H, Ar), 7.03 (t, 1H, Ar), 7.1 (d, 1H, Ar), 7.46 (m, 2H, Ar), 8.17 (s, 1H, Ar), 8.28 (s, 2H, Ar), 8.36 (s, 2H, NH$_2$), 8.56 (s, 2H, NH$_2$), 8.9 (s, 1H, NH); MS: m/e (ES+) 586 (M+); analysis: C$_{30}$H$_{40}$ClN$_5$O$_{11}$S$_3$: 2H$_2$O calcd.: C, 44.25; H, 5.45; N, 8.60; found: C, 44.01; H, 5.11; N, 8.89%.

EXAMPLE 91k

4-Chloro-2-{2-[ethyl-(2-methoxy-benzyl)-amino]-ethylamino}-6-methyl-10,10-dioxo-10,11-dihydro-5-oxa-10lambda*6*-thia-dibenzo[a,d]cycloheptene-8-carboxylic acid methyl ester Trifluoroacetic acid (0.11 mL, 1.4 mmol) was added to a solution of Example 90k (0.37 g, 0.71 mmol) in methanol (20 mL) at −5° C. Acetaldehyde (2 mL) was added and stirring continued for 4 h. The reaction mixture was brought to room temperature, treated with sodium cyanoborohydride (0.181 g, 2.8 mmol) and allowed to stir for 15 h. It was treated with an aqueous sodium bicarbonate solution, concentrated, treated with water and extracted with ethyl acetate. The organic layer was washed with water, brine, dried, concentrated and purified using flash chromatography (silica gel, 2% methanol/chloroform) to obtain the title compound. Yield: 0.21 g, (52%); $^1$H NMR (CDCl$_3$): δ 1.08 (t, 3H, CH$_3$), 2.62 (s, 2H, CH$_2$), 2.68 (s, 3H, CH$_3$), 2.77 (s, 2H, CH$_2$), 3.1 (s, 2H, CH$_2$), 3.63 (s, 2H, CH$_2$), 3.77 (s, 3H, OCH$_3$), 3.88 (s, 3H, OCH$_3$), 4.6 (s, 2H, CH$_2$), 6.4 (d, 1H, Ar), 6.51 (d, 1H, Ar), 6.9 (m, 2H, Ar), 7.25 (m, H, Ar), 8.05 (d, 1H, Ar), 8.43 (d, 1H, Ar); MS: m/e (ES+) 558 (M+).

EXAMPLE 92

N-[4-Chloro-6-methyl-10,10-dioxo-2-(2-piperidin-1-yl-ethylamino)-10,11-dihydro-5-oxa-10lambda*6*-thia-dibenzo[a,d]cycloheptene-8-carbonyl]-guanidine dimesylate The title compound was synthesised from Example 92k as described in the synthesis of Example 50. Yield: 0.230 g, (65%); mp: 250-251° C.; $^1$H NMR (DMSO-d$_6$): δ 1.40 (m, 2H, CH$_2$), 1.80 (m, 4H, 2CH$_2$), 2.40 (s, 6H, 2CH$_3$), 2.70 (s, 3H, CH$_3$), 3.0 (t, 2H, CH$_2$), 3.20 (t, 2H CH$_2$), 3.40-3.70 (m, 4H, 2CH$_2$), 5.20 (s, 2H, CH$_2$), 6.80 (s, 1H, Ar), 7.10 (s, 1H, Ar), 8.10 (s, 1H, Ar), 8.30 (s, 1H, Ar), 8.50 (m, 4H, guanidinyl); MS: m/e (ES+) 478 (M+1); analysis: C$_{25}$H$_{36}$ClN$_5$O$_{10}$S$_3$.2H$_2$O calcd.: C, 40.90; H, 5.49; N, 9.59; Cl, 4.83; S, 13.10; found: C, 40.35; H, 5.72; N, 10.13; Cl, 4.69; S, 12.73%.

EXAMPLE 92k

4-Chloro-6-methyl-10,10-dioxo-2-(2-piperidin-1-yl-ethylamino)-10,11-dihydro-5-oxa-10lambda*6*-thia-dibenzo[a,d]cycloheptene-8-carboxylic acid methyl ester Piperidine (0.184 g, 2.16 mmol) was added with stirring to a solution of Example 56k. (0.6 g, 1.4 mmol) in DMF (1 mL) in an inert atmosphere and heated at 90° C. for 4 h. The reaction mixture was concentrated, treated with water, and the solid that precipitated was filtered, washed with water and purified using flash chromatography (silica gel, 2% methanol/chloroform) to obtain the title compound. Yield: 0.330 g, (48%); $^1$H NMR (CDCl$_3$): δ 1.18 (bs, 2H, CH$_2$), 1.32 (t, 4H, 2CH$_2$), 2.21 (s, 3H, CH$_3$), 2.3 (t, 2H, CH$_2$), 2.4 (t, 2H, CH$_2$), 2.8 (m, 4H, 2CH$_2$), 3.41 (s, 3H, OCH$_3$), 4.28 (s, 2H, CH$_2$), 5.39 (bs, 1H, NH), 6.15 (s, 2H, Ar), 7.6 (s, 1H, Ar), 7.82 (s, 1H, Ar); MS: m/e (ES+) 478 (M+1).

EXAMPLE 93

N-(4-Chloro-2-[ethyl-(2-piperidin-1-yl-ethyl)-amino]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 93k as described in the synthesis of Example 50. Yield: 0.06 g, (49%), $^1$H NMR (DMSO-d$_6$): δ 1.20 (t, 3H, CH$_3$), 1.40 (t, 2H, CH$_2$), 1.70 (t, 4H, 2CH$_2$), 1.90 (d, 2H, CH$_2$), 2.40 (s, 6H, 2CH$_3$), 2.70 (s, 3H, CH$_3$), 3.0 (q, 2H, CH$_2$), 3.20 (t, 2H, CH$_2$) 3.70 (t, 2H, CH$_2$), 3.80 (t, 2H, CH$_2$), 5.20 (s, 2H, CH$_2$), 6.9 (s, 1H, Ar), 7 (s, 1H, Ar), 8.10 (s, 1H, Ar), 8.12 (s, 1H, Ar), 8.2 (s, 1H, Ar), 8.3-8.7 (m, 4H, guanidinyl); MS: m/e (ES+) 506 (M+1); analysis: C$_{27}$H$_{40}$ClN$_5$O$_{10}$S$_3$. calcd.: C, 44.65; H, 5.55; N, 9.64; Cl, 4.88; S, 13.24; found: C, 45.13; H, 5.44; N, 9.24; Cl, 4.96; S, 13.72%.

EXAMPLE 93k

4-Chloro-2-[ethyl-(2-piperidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Acetaldehyde (0.151 g, 3.4 mmol) was added to a solution of Example 92k (0.330 g, 0.68 mmol) in MeOH (10 mL) at 0°

C. TFA (0.08 g, 0.68 mmol) was then added and stirring continued for 2 h. The reaction mixture was brought to room temperature, treated with sodium cyanoborohydride (0.108 g, 1.7 mmol) and allowed to stir for 4 h. It was concentrated, treated with aqueous sodium bicarbonate solution, water and extracted ethyl acetate. The organic layer was washed with water, brine, dried, concentrated and purified using flash chromatography to obtain the title compound. Yield: 0.80 g, (51%); $^1$H NMR (CDCl$_3$): δ 1.20 (t, 2H, CH$_2$), 1.70 (t, 2H, CH$_2$), 1.80 (t, 4H, 2CH$_2$), 2.70 (s, 3H, CH$_3$), 2.80 (s, 2H, CH$_2$), 2.90 (m, 2H, CH$_2$), 3.40 (q, 2H, CH$_2$), 3.80 (t, 2H, CH$_2$), 3.9 (s, 3H, OCH$_3$), 4.8 (s, 2H, CH$_2$), 6.8 (s, 2H, Ar), 8.10 (s, 1H, Ar), 8.4 (s, 1H, Ar); MS: m/e (ES−) 506 (M−1).

EXAMPLE 94

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-hydroxy-N-(2-piperidin-1-yl-ethyl)-acetamide dimesylate The title compound was synthesised from Example 94k as described in the synthesis of Example 50. Yield: (0.026 g, 12%); mp: 191-193° C.; $^1$H NMR (DMSO-d$_6$): δ 1.61 (s, 2H, CH$_2$), 1.89 (s, 4H, 2CH$_2$), 2.38 (s, 6H, 2CH$_3$), 2.72 (s, 3H, CH$_3$), 3.62 (s, 4H, 2CH$_2$), 4.06 (d, 4H, 2CH$_2$), 4.4 (s, 2H, CH$_2$), 5.42 (s, 2H, Ar), 7.74 (s, 1H, Ar), 7.91 (s, 1H, Ar), 8.23 (s, 1H, Ar), 8.29 (s, 1H, Ar), 8.36 (s, 2H, NH$_2$), 8.57 (s, 2H, NH$_2$), 11.52 (s, 1H, OH); MS: m/e (ES+) 548 (M+) (freebase-OH); analysis: C$_{27}$H$_{38}$ClN$_5$O$_{12}$S$_3$ calcd.: C, 42.88; H, 5.06; N, 9.26; Cl, 4.69; S, 12.72; found: C, 42.93; H, 4.97; N, 9.10; Cl, 5.09; S, 13.22%.

EXAMPLE 94k

4-Chloro-2-[(2-hydroxy-acetyl)-(2-piperidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Chloroacetyl chloride (0.83 mL, 40 mmol) was added to Example 92k (0.5 g, 1.04 mmol) and the reaction mixture was stirred at 90° C. for 1 hr. It was cooled, treated with water and aqueous sodium bicarbonate solution to pH 7.5. The solid that precipitated was washed with water and dried to obtain the title compound. Yield: 0.260 g, (50%); $^1$H NMR (DMSO-d$_6$): δ 1.61 (m, 2H, CH$_2$), 1.89 (m, 4H, 2CH$_2$), 2.70 (s, 3H, CH$_3$), 3.57 (bs, 4H, 2CH$_2$), 3.9 (s, 3H, OCH$_3$), 4.6 (s, 2H, CH$_2$), 4.44 (s, 2H, CH$_2$), 5.36 (s, 2H, CH$_2$), 7.73 (s, 1H, Ar), 7.9 (s, 1H, Ar), 8.19 (d, 2H, Ar).

EXAMPLE 95

Cyclopropanecarboxylic acid (4-chloro-8-guanidinocarbonyl-6-methyl-10,10-dioxo-10,11-dihydro-5-oxa-10lambda*6*-thia-dibenzo[a,d]cycloheptene-2-yl)-(2-piperidin-1-yl-ethyl)-amide trimesylate The title compound was synthesised from Example 95k as described in the synthesis of Example 50. Yield: 0.2 g, (76%); mp: 276° C. $^1$H NMR (DMSO-d$_6$): δ 0.8 (s, 2H, CH$_2$), 1.00 (s, 2H, CH$_2$), 1.40 (m, 2H, CH$_2$), 1.70 (m, 2H, CH$_2$), 1.90 (m, 2H, CH$_2$), 2.4 (s, 9H, 3CH$_3$), 2.8 (s, 3H, CH$_3$), 3.00 (t, 2H, CH$_2$), 3.3 (m, 2H, CH$_2$), 3.60 (s, 2H, CH$_2$), 4.07 (m, 3H, CH$_2$&CH), 5.50 (s, 2H, CH$_2$), 7.75 (s, 1H, Ar), 7.91 (s, 1H, Ar), 8.24 (s, 1H, Ar), 8.30 (s, 1H, Ar), 8.40-8.60 (m, 4H, guanidine-H). MS: m/e (ES+) 574 (M+1). analysis: C$_{30}$H$_{44}$ClN$_5$O$_{14}$S$_4$. calcd.: C, 41.78; H, 5.14; N, 8.12; found: C, 41.94; H, 5.60; N, 8.66%.

EXAMPLE 95k

4-Chloro-2-[cyclopropanecarbonyl-(2-piperidin-1-yl-ethyl)-amino]-6-methyl-10,10-dioxo-10,11-dihydro-5-oxa-10lambda*6*-thia-dibenzo[a,d]cyclohep-tene-8-carboxylic acid methyl ester Cyclopropylacetyl chloride (1 mL) was added to Example 92k (0.4 g, 0.83 mmol) and heated at 70-75° C. for 2 h. It was cooled, treated with methanol, concentrated and extracted with CHCl$_3$. The organic layer was washed with aqueous NaHCO$_3$ solution, water, brine, concentrated and purified using flash chromatography (silica gel, 2-3% MeOH/CHCl$_3$) to obtain the title compound. Yield: 0.230 g, (88%); $^1$H NMR (CDCl$_3$): δ 0.8 (s, 2H, CH$_2$), 1.0 (s, 2H, CH$_2$), 1.5 (m, 6H, 3CH$_2$), 2.4 (m, 6H, 3CH$_2$), 2.8 (s, 3H, CH$_3$), 3.9 (t, 2H, CH$_2$) 4.0 (s, 3H, OCH$_3$), 5.21 (s, 2H, CH$_2$), 7.4 (s, 1H, Ar), 7.7 (s, 1H, Ar), 8.1 (s, 1H, Ar), 8.3 (s, 1H, Ar); MS: m/e (ES+) 549 (M+1).

EXAMPLE 96

N-(4-Chloro-8-guanidinocarbonyl-6-methyl-10,10-dioxo-10,11-dihydro-5-oxa-10lambda*6*-thia-dibenzo[a,d]cyclohepten-2-yl)-2,2-dimethyl-N-(2-piperidin-1-yl-ethyl)-propionamide dimesylate The title compound was synthesised from Example 96k as described in the synthesis of Example 50. Yield: 0.22 g, (62%); $^1$H NMR (DMSO-d$_6$): δ 0.90 (s, 9H, 3CH$_3$), 1.45 (m, 2H, CH$_2$), 1.65 (m, 6H, 3CH$_2$), 2.40 (s, 6H, 2CH$_3$), 2.70 (s, 3H, CH$_3$), 2.90 (m, 2H, CH$_2$), 3.24 (m, 2H, CH$_2$), 5.42 (s, 2H, CH$_2$), 7.0 (s, 2H, 2Ar), 7.40 (s, 1H, Ar), 8.21 (s, 1H, Ar), 8.57 (m, 4H, guanidinyl); MS: m/e (ES+) 591 (M+1).

EXAMPLE 96k

4-Chloro-2-[(2,2-dimethyl-propionyl)-(2-piperidin-1-yl-ethyl)-amino]-6-methyl-10,10-dioxo-10,11-dihydro-5-oxa-10lambda*6*-thia-dibenzo[a,d]cyclo-heptene-8-carboxylic acid methyl ester Pivolyl chloride (0.157 g, 0.941 mmol) was added to Example 92k (0.3 g, 0.627 mmol) and stirred at 70° C. for 1 h. It was treated with MeOH, concentrated and extracted with CHCl$_3$. The organic layer was washed with aqueous NaHCO$_3$ solution, water, brine, concentrated and purified using flash chromatography (silica gel, MeOH/CHCl$_3$) to obtain the title compound. Yield: 0.220 g, (62%); $^1$H NMR (CDCl$_3$): δ 1.0 (s, 9H, 3CH$_3$), 1.5 (m, 2H, CH$_2$), 1.6 (m, 4H, 2CH$_2$), 2.4 (m, 6H, 3CH$_2$), 2.9 (s, 3H, CH$_3$), 4.0 (s, 3H, OCH$_3$), 4.8 (s, 2H, CH$_2$), 7.3 (s, 1H, Ar), 7.5 (s, 1H, Ar), 8.2 (s, 1H, Ar), 8.5 (s, 1H, Ar); MS: m/e (ES+) 566 (M+1).

EXAMPLE 97

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-piperidin-1-yl-ethyl)-acetamide dimesylate The title compound was synthesised from Example 97k as described in the synthesis of Example 1. Yield: 0.070 g, (15%); mp: 160-162° C.; $^1$H NMR (DMSO-d$_6$): δ 1.6 (m, 2H, CH$_2$), 1.78 (m, 4H, 2CH$_2$), 1.81 (m, 3H, CH$_3$), 2.37 (s, 6H, 2CH$_3$), 2.72 (s, 3H, CH$_3$), 2.91 (q, 2H, CH$_2$), 3.22 (s, 2H, CH$_2$), 3.54 (m, 2H, Ar), 3.99 (s, 2H, CH$_2$), 5.38 (s, 2H, CH$_2$), 7.69 (s, 1H, Ar), 7.87 (s, 1H, Ar), 8.22 (s, 1H, Ar), 8.30 (s, 1H, Ar), 8.37 (s, 2H, NH$_2$), 8.55 (s, 2H, NH$_2$), 8.98 (s, 1H, OH), 11.51 (s, 1H, OH); MS: m/e (ES−) 738(M−1); analysis: C$_{27}$H$_{38}$ClN$_5$O$_{13}$S$_3$ calcd.: C, 43.81; H, 5.17; N, 9.46; found: C, 43.90; H, 5.69; N, 8.99%.

EXAMPLE 97k

2-[Acetyl-(2-piperidin-1-yl-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Acetyl chloride (1 mL, excess) was reacted with Example 92k (0.5 g, 1.04 mmol) as described in the synthesis of Example 78k to obtain the title compound. Yield: 0.186 g (85%); $^1$H NMR (CDCl$_3$): δ 1.42 (m, 2H, CH$_2$), 1.55 (m, 4H, 2CH$_2$), 1.89 (s, 3H, CH$_3$), 2.4 (m, 4H, 2CH$_2$), 2.48 (m, 2H, CH$_2$), 2.72 (s, 3H, CH$_3$), 3.81 (t, 2H, CH$_2$), 3.92 (s, 3H, OCH$_3$), 4.72 (s, 2H, CH$_2$), 7.33 (s, 1H, Ar), 7.54 (s, 1H, Ar), 8.12 (s, 1H, Ar), 8.44 (s, 1H, Ar); MS: m/e (ES+) 521 (M+1).

EXAMPLE 98

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-piperidin-1-yl-ethyl)-acetamide dimesylate The title compound was synthesised from Example 98k as described in the synthesis of Example 50. Yield: 0.055 g, (30%); $^1$H NMR (DMSO-d$_6$): δ 1.79 (m, 6H, 3CH$_2$), 2.37 (s, 6H, 2CH$_3$), 2.72 (s, 3H, CH$_3$), 2.96 (s, 2H, CH$_2$), 3.2 (s, 3H, OCH$_3$), 3.62 (m, 4H, 2CH$_2$), 3.83 (s, 2H, CH$_2$), 5.38 (s, 2H, CH$_2$), 7.71 (s, 1H, Ar), 7.78 (s, 1H, Ar), 8.23 (s, 1H, Ar), 8.30 (s, 1H, Ar), 8.35 (s, 2H, NH$_2$), 8.53 (s, 2H, NH$_2$), 9.0 (s, 1H, OH), 11.52 (s, 1H, OH); MS: m/e (ES+) 578 (M+) (freebase); analysis: C$_{28}$H$_{40}$ClN$_5$O$_{12}$S$_3$ calcd.: C, 43.66; H, 5.23; N, 9.09; found: C, 44.09; H, 5.9; N, 8.35%.

EXAMPLE 98k

4-Chloro-2-[(2-methoxy-acetyl)-(2-piperidin-1-yl-ethyl)-amino]-6-methyl-10,10-dioxo-10,11-dihydro-5-oxa-10lambda*6*-thia-dibenzo[a,d]cycloheptene-8-carboxylic acid methyl ester Methoxy-acetyl chloride (1 mL) was reacted with Example 92k (0.2 g) as described in the synthesis of Example 97k to obtain the title compound. Yield: 0.110 g, (50%); $^1$H NMR (CDCl$_3$): δ 1.44 (m, 2H, CH$_2$), 1.57 (m, 4H, 2CH$_2$), 2.4 (m, 4H, 2CH$_2$), 2.44 (m, 2H, CH$_2$), 2.72 (s, 3H, CH$_3$), 3.83 (m, 4H, 2CH$_2$), 3.93 (s, 3H, OCH$_3$), 4.72 (s, 2H, CH$_2$), 7.37 (s, 1H, Ar), 7.58 (s, 1H, Ar), 8.12 (s, 1H, Ar), 8.47 (s, 1H, Ar); MS: m/e (ES+) 551 (M+).

EXAMPLE 99

N-[4-Chloro-2-(2-dimethylamino-ethylamino)-6-methyl-10,10-dioxo-10,11-dihydro-5-oxa-10lambda*6*-thia-dibenzo[a,d]cyclohepten-8-carbonyl]-guanidine dimesylate The title compound was synthesised from Example 99k as described in the synthesis of Example 50. Yield: 0.035 g, (47.29%), $^1$H NMR (DMSO-d$_6$): δ 2.35 (s, 6H, 2CH$_3$), 2.75 (s, 3H, CH$_3$), 2.85 (s, 6H, 2CH$_3$), 3.24 (t, 2H, CH$_2$), 3.41 (t, 2H, CH$_2$), 5.20 (s, 2H, CH$_2$), 6.40 (t, 1H, NH), 6.80 (s, 1H, Ar), 7.0 (s, 1H, Ar), 8.10 (s, 1H, Ar), 8.20 (s, 1H, Ar); MS: m/e (ES+) 465 (M+1); analysis: C$_{22}$H$_{32}$ClN$_5$O$_{10}$S$_3$.2.H$_2$O. calcd.: C, 38.07; H, 5.23; N, 10.00, Cl; 5.11, S; 13.86; found: C, 38.08; H, 4.79; N, 9.13,Cl; 5.09, S; 13.43%.

EXAMPLE 99k

4-Chloro-2-(2-dimethylamino-ethylamino)-6-methyl-10,10-dioxo-10,11-dihydro-5-oxa-10lambda*6*-thia-dibenzo[a,d]cycloheptene-8-carboxylic acid methyl ester, hydrochloric acid salt A methanolic dimethylamine solution (2 mL, 40%) was added to a solution of the carboxylic acid of Example 56k (0.9 g, 2.16 mmol) in methanol in an atmosphere of nitrogen and sealed in a pressure reactor vessel at 110° C. for 4 h. The reaction mixture was cooled, partially concentrated and the solid that precipitated was filtered, washed with methanol, dried, treated with methanolic HCl solution and stirred at 70° C. for 1.5 h. The reaction mixture was cooled and the solid that precipitated was filtered and washed with methanol to obtain the title compound. Yield: 1.56 g, (89%); $^1$H NMR (DMSO-d$_6$): δ 2.66 (d, 3H, CH$_3$), 2.80 (s, 6H, 2CH$_3$), 3.24 (t, 2H, CH$_2$), 3.41 (t, 2H, CH$_2$), 3.90 (s, 3H, OCH$_3$), 5.18 (s, 2H, CH$_2$), 6.6 (bs, 1H, NH), 6.81 (s, 2H, Ar), 8.10 (s, 1H, Ar), 8.17 (s, 1H, Ar), 10.5 (s, 1H, HCl). MS: m/e (ES+) 438 (M+1).

EXAMPLE 100

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-acetamide trimesylate The title compound was synthesised from example 100k as described in the synthesis of Example 50. Yield: 0.206 g, (63%); mp: 128-130° C.; $^1$H NMR (DMSO-d$_6$): δ 1.83 (s, 3H, CH$_3$), 2.40 (s, 9H, 3CH$_3$), 2.73 (s, 3H, CH$_3$), 2.86 (s, 6H, 2CH$_3$), 3.21 (t, 2H, CH$_2$), 3.99 (t, 2H, CH$_2$), 5.38 (s, 2H, CH$_2$), 7.70 (s, 1H, Ar), 7.86 (s, 1H, Ar), 8.22 (s, 1H, Ar), 8.29 (s, 1H, Ar), 8.30-8.70 (m, 4H, guanidinyl); MS: m/e (ES+) 508 (M+1); analysis: C$_{25}$H$_{38}$ClN$_5$O$_{14}$S$_4$.H$_2$O calcd.: C, 36.88; H, 4.95; N, 8.60; found: C, 36.98; H, 5.16; N, 8.49%.

EXAMPLE 100k

2-[Acetyl-(2-dimethylamino-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Example 99k (0.27 g, 0.615 mmol) was treated with acetyl chloride (1.5 mL, 18 mmol) in an atmosphere of nitrogen. The reaction mixture was heated at 65° C. for 1.5 h, then cooled in an ice bath, treated with methanol and extracted with CHCl$_3$. The organic layer was washed with saturated aqueous Na$_2$CO$_3$ solution, water, dried, concentrated and purified using flash chromatography (silica gel, MeOH/CHCl$_3$) to obtain the title compound as a white solid. Yield: 0.240 g, (81%). $^1$H NMR (CDCl$_3$): δ 1.9 (s, 3H, COCH$_3$), 2.23 (s, 6H, 2N—CH$_3$), 2.39 (t, 2H, CH$_2$), 2.72 (s, 3H, CH$_3$), 3.80 (t, 2H, CH$_2$), 3.93 (s, 3H, OCH$_3$), 4.73 (s, 2H, CH$_2$), 7.33 (s, 1H, Ar), 7.44 (s, 1H, Ar), 8.12 (s, 1H, Ar), 8.47 (s, 1H, Ar), MS: m/e (EI+) 480 (M+1).

EXAMPLE 101

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-2,2-dimethyl-propionamide dimesylate The title compound was synthesised from Example 101k as described in the synthesis of Example 50. Yield: 0.161 g, (81%); mp: 171-173° C.; $^1$H NMR (DMSO-$d_6$): δ 0.98 (s, 9H, 3CH$_3$), 2.38 (s, 6H, 2CH$_3$), 2.73 (s, 3H, CH$_3$), 2.85 (s, 6H, 2CH$_3$), 3.25 (s, 2H, CH$_2$), 3.87 (s, 2H, CH$_2$), 5.42 (s, 2H, CH$_2$), 7.71 (s, 1H, Ar), 7.90 (s, 1H, Ar), 8.22 (s, 1H, Ar), 8.29 (s, 1H, Ar), 8.37-8.58 (m, 4H, guanidinyl); MS: m/e (ES+) 550 (M+1); analysis: $C_{27}H_{40}ClN_5O_{11}S_3$. calcd.: C, 43.69; H, 5.43; N, 9.44; Cl, 4.78; S, 12.96; found: C, 42.38; H, 5.52; N, 8.70; Cl, 4.38; S, 12.24%.

EXAMPLE 101k

4-Chloro-2-[(2-dimethylamino-ethyl)-(2,2-dimethyl-propionyl)-amino]-6-methyl-10,10-dioxo-10,11-dihydro-5-oxa-10lambda*6*-thia-dibenzo[a,d]cyclo-heptene-8-carboxylic acid methyl ester Example 99k (0.3 g, 0.68 mmol) was treated with distilled pivaloyl chloride (1.0 mL, 12.2 mmol) in an atmosphere of nitrogen and heated at 100° C. for 10 h. The reaction mixture was cooled in an ice bath, treated with methanol, CHCl$_3$, washed with aqueous saturated Na$_2$CO$_3$ solution, water, concentrated and purified using flash chromatography (silica gel, MeOH/CHCl$_3$) to obtain the title compound as a white solid. Yield: 0.230 g, (64%); $^1$H NMR (CDCl$_3$): δ 0.98 (s, 9H, 3CH$_3$), 2.27 (s, 6H, 2N—CH$_3$), 2.48 (t, 2H, CH$_2$), 2.72 (s, 3H, CH$_3$), 3.74 (t, 2H, CH$_2$), 3.93 (s, 3H, OCH$_3$), 4.72 (s, 2H, CH$_2$), 7.32 (s, 1H, Ar), 7.42 (s, 1H, Ar), 8.12 (s, 1H, Ar), 8.46 (s, 1H, Ar); MS: m/e (ES−) 523 (M+1).

EXAMPLE 102

2-[Bis-(2-chloro-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Sodiumborohydride (1.23 g, 32.51 mmol) was added portionwise with stirring to a solution of chloro-acetic acid (6.23 g, 65.93 mmol) in benzene (120 mL) and dry tetrahydrofuran (10 mL) in an atmosphere of nitrogen at 15° C. The reaction mixture was stirred for 1 h, then treated with the ester of Example 35j (2 g, 5.44 mmol) and refluxed for 3 h. A 10% aqueous sodium bicarbonate solution was added and extraction with ethyl acetate carried out. The organic layer was washed with water, brine, dried, concentrated and crystallized using ethyl acetate/hexane to obtain the title compound as a white solid. Yield: 2.30 g, (86%); mp: 190-191° C.; $^1$H NMR (CDCl$_3$): δ 2.70 (s, 3H, CH$_3$), 3.62 (t, 4H, 2CH$_2$), 3.79 (t, 4H, 2CH$_2$), 3.95 (s, 3H, OCH$_3$), 4.69 (s, 2H, CH$_2$), 6.59 (d, 1H, Ar), 6.70 (d, 1H, Ar), 8.1 (s, 1H, Ar), 8.45 (s, 1H, Ar). MS: m/e (EI+) 493 (M+1).

EXAMPLE 102j

2-[Bis-(2-chloroethyl)amino]-4-chloro-6-methyl-10,10-dioxo-10,11-dihydro-5-oxa-10lambda*6*-thia-dibenzo[a,d]-cycloheptene-8-carboxylic acid Aqueous sodium hydroxide (0.78 g, 19.6 mmol in 45 mL water) was added to a solution of Example 102 (3.21 g, 6.53 mmol) in tetrahydrofuran (45 mL). It was stirred for 3 h, partially concentrated, treated with dil. HCl to pH 7, filtered, washed with water and dried to obtain the title compound as a white solid. Yield: 3.01 g (97%). $^1$H NMR (CDCl$_3$+DMSO-$d_6$): δ 2.40 (s, 3H, CH$_3$), 3.4 (t, 4H, 2CH$_2$), 3.5 (t, 4H, 2CH$_2$), 4.5 (s, 2H, CH$_2$), 6.4 (d, 1H, Ar), 6.5 (d, 1H, Ar), 7.7 (d, 1H, Ar), 8.1 (d, 1H, Ar); MS: m/e (CI+) 478 (M+).

EXAMPLE 103

N[4-Chloro-6-methyl-2-(4-methylpiperazin-1-yl)-10,10-dioxo-10,11-dihydro-5-oxa-10lambda*6*-thia-dibenzo[a,d]cycloheptene-8-carbonyl]-guanidine dimesylate The title compound was synthesised from Example 103k as described in the synthesis of Example 1. Yield: 0.102 g, (72.85%); mp: 214-215° C., $^1$H NMR (DMSO-$d_6$): δ 2.35 (s, 6H, 2CH$_3$), 2.70 (s, 3H, CH$_3$), 2.72-2.75 (m, 4H, 2CH$_2$), 2.90 (s, 3H, CH$_3$), 3.05-3.15 (m, 4H, 2CH$_2$), 5.25 (s, 2H, CH$_2$), 7.25 (s, 2H, Ar), 8.15 (s, 1H, Ar), 8.35 (s, 1H, Ar), MS: m/e (ES+) 478 (M+1). analysis: $C_{23}H_{32}ClN_5O_{11}S_3.H_2O$ calcd.: C, 40.14; H, 4.98; N, 10.18; Cl, 5.15; S, 13.98; found: C, 40.42; H, 5.02; N, 10.18; Cl, 5.74; S; 13.89%.

EXAMPLE 103k

4-Chloro-6-methyl-2-(4-methyl-piperazin-1-yl)-10,10-dioxo-10,11-dihydro-5-oxa-10lambda*6*-thia-dibenzo[a,d]cycloheptene-8-carboxylic acid Methanolic methylamine solution (20% v/v, 6 mL) was added to a solution of Example 102 (0.330 g, 0.69 mmol) in methanol (2 mL) in an atmosphere of nitrogen and sealed in a pressure reactor vessel at 100° C. for 6 h. It was brought to room temperature, flushed with N$_2$ gas, treated with chilled water and dilute HCl to neutral pH. The solid that precipitated was filtered, washed with water, dried and purified using flash chromatography (silica gel, MeOH/CHCl$_3$) to obtain the title compound as an off white solid. Yield: 0.260 g (86.37%). $^1$H NMR (DMSO-$d_6$): δ 2.40 (s, 3H, CH$_3$), 2.70 (s, 3H, CH$_3$), 2.72-2.75 (m, 4H, 2CH$_2$), 3.30-3.35 (m, 4H, 2CH$_2$), 5.10 (s, 2H, CH$_2$), 7.10 (s, 1H, Ar), 7.20 (s, 1H, Ar), 8.10 (s, 1H, Ar) and 8.25 (s, 1H, Ar); MS: m/e (ES+) 436 (M+1).

EXAMPLE 104

N-(4-Chloro-6-methyl-10,10-dioxo-2-piperazin-1-yl-10,11-dihydro-5-oxa-10lambda*6*-thia-dibenzo[a,d] cycloheptene-8-carbonyl)-guanidine trimesylate The title compound was synthesised from Example 104k as described in the synthesis of Example 50. Yield: 0.100 g, (61.72%); mp: 203-205° C.; $^1$H NMR (DMSO-$d_6$): δ 2.35 (s, 9H, 3CH$_3$), 2.70 (s, 3H, CH$_3$), 3.00-3.15 (m, 4H, 2CH$_2$), 3.20-3.30 (m, 4H, 2CH$_2$), 5.20 (s, 2H, CH$_2$), 7.15 (s, 1H, Ar), 7.20 (s, 1H, Ar), 8.70 (s, 1H, Ar), 8.75 (s, 1H, Ar); MS: m/e (ES+) 464 (M+1); analysis: $C_{23}H_{34}ClN_5O_{13}S_4.H_2O$ calcd.: C, 35.87; H, 4.71; N, 9.09; found: C, 35.82; H, 4.82; N, 8.91%.

EXAMPLE 104k

4-Chloro-6-methyl-10,10-dioxo-2-piperazin-1-yl-10,11-dihydro-5-oxa-10lambda*6*-thia-dibenzo[a,d] cycloheptene-8-carboxylic acid methyl ester Aqueous ammonia solution (30%, 4 mL) was added to a solution of Example 102j (0.5 g, 1.04 mmol) in methanol (1 mL), in an atmosphere of nitrogen, sealed in a pressure reactor vessel and heated at 110° C. for 6 h. The reaction mixture was brought to room temperature, concentrated, treated with chilled water and dilute HCl to neutral pH. The solid that precipitated was filtered, washed with water and dried. It was treated with methanolic HCl solution and stirred at 70° C. for 2.5 h. The reaction mixture was cooled and the solid that separated was filtered, washed with methanol, dried and purified using flash chromatography (silica gel, MeOH/CHCl$_3$) to obtain the title compound as an off white solid. Yield: 0.220 g (48.24%); $^1$H NMR (DMSO-d$_6$): δ 2.30 (m, 4H, 2CH$_2$), 2.70 (s, 3H, CH$_3$), 3.10 (m, 4H, 2CH$_2$), 3.95 (s, 3H, OCH$_3$), 5.10 (s, 2H, CH$_2$), 7.10 (s, 1H, Ar), 7.20 (s, 1H, Ar), 8.05 (s, 1H, Ar) 8.20 (s, 1H, Ar): MS: m/e (ES+) 422 (M+1).

EXAMPLE 105

N-[4-Chloro-2-(4-decyl-piperazin-1-yl)-6-methyl-10, 10-dioxo-10,11-dihydro-5-oxa-10lambda*6*-thia-dibenzo[a,d]cycloheptene-8-carbonyl]-guanidine dimesylate The title compound was synthesised from Example 105k as described in the synthesis of Example 50. Yield: 0.060 g, (61%); mp: 184-185° C.; $^1$H NMR (DMSO-d$_6$): δ 0.80 (s, 3H, CH$_3$), 1.30 (s, 16H, 8CH$_2$), 1.70 (s, 2H, CH$_2$), 2.30 (m, 4H, 2CH$_2$), 2.40 (s, 9H, 3CH$_3$), 2.70 (s, 3H, CH$_3$), 3.20 (m, 4H, 2CH$_2$), 3.90 (s, 2H, CH$_2$), 5.30 (s, 2H, CH$_2$), 7.00 (s, 1H, Ar), 7.30 (s, 1H, Ar), 8.10 (s, 1H, Ar), 8.30 (s, 1H, Ar), 8.40 (m, 4H, guanidinyl); MS: m/e (ES+) 604 (M+1).

EXAMPLE 105k

4-Chloro-2-(4-decyl-piperazin-1-yl)-6-methyl-10,10-dioxo-10,11-dihydro-5-oxa-10lambda*6*-thia-dibenzo[a,d]cycloheptene-8-carboxylic acid methyl ester Decanaldehyde (0.071 g, 0.45 mmol) was added with stirring to a solution of Example 104k (0.2 g, 0.45 mmol) in dry methanol (5 mL). Titanium isopropoxide (0.12 g, 0.45 mmol) was added and the reaction mixture was cooled to 10° C. Sodium cyanoborohydride (0.057 g, 0.9 mmol) was added and the reaction mixture was refluxed for 2 h. It was concentrated, treated with water and extracted with n-butanol. The organic layer was washed with water, brine, concentrated and purified using flash chromatography (silica gel, MeOH/CHCl$_3$) to obtain the title compound. Yield.: 0.120 g (46%); $^1$H NMR (CDCl$_3$): δ 0.90 (s, 5H, CH$_3$CH$_2$), 1.20 (m, 12H, 6CH$_2$), 2.28 (s, 4H, 2CH$_2$), 2.30 (t, 2H, CH$_2$), 2.70 (t, 3H, CH$_3$), 3.20 (t, 4H, 2CH$_2$), 3.90 (s, 3H, OCH$_3$), 4.80 (s, 2H, CH$_2$), 6.80 (s, 1H, Ar), 7.00 (s, 1H, Ar), 8.10 (s, 1H, Ar), 8.4 (s 1H, Ar); MS: m/e (EI+) 577 (M+1).

EXAMPLE 106

N-[4-Chloro-6-methyl-10,10-dioxo-2-(4-pentyl-piperazin-1-yl)-10,11-dihydro-5-oxa-10-lambda*6*-thia-dibenzo[a,d]cycloheptene-8-carbonyl]-guanidine dimesylate The title compound was synthesised from Example 106k as described in the synthesis of Example 50. Yield: 0.170 g, (76%); mp: 250-251° C.; $^1$H NMR (DMSO-d$_6$): δ 0.9 (t, 3H, CH$_3$), 1.30 (t, 4H, 2CH$_2$), 1.80 (t, 2H, CH$_2$), 2.40 (s, 6H, 2CH$_3$), 2.80 (s, 3H, CH$_3$), 3.10 (t, 6H, 3CH$_2$), 3.95 (d, 4H, 2CH$_2$), 5.30 (s, 2H, CH$_2$), 7.30 (s, 2H, Ar), 8.10 (s, 1H, Ar), 8.20 (s, 1H, Ar), 8.50 (s, 4H, guanidinyl); MS: m/e (ES+) 534 (M+1); analysis: C$_{27}$H$_{40}$ClN$_5$O$_{10}$S$_3$. calcd.: C, 44.65; H, 5.55; N, 9.64; Cl, 4.88; S, 13.24; found: C, 44.29; H, 5.29; N, 9.63; Cl, 4.52; S, 12.69%.

EXAMPLE 106k

4-Chloro-6-methyl-10,10-dioxo-2-(4-pentyl-piperazin-1-yl)-10,11-dihydro-5-oxa-10lambda*6*-thia-dibenzo[a,d]cycloheptene-8-carboxylic acid methyl ester Pentanaldehyde (0.042 gm, 0.5 mmol) was added with stirring to a solution of Example 104k (0.180 g, 0.4 mmol) in dry methanol (10 mL). Titanium isopropoxide (0.117 g, 0.4 mmol) was added and the reaction mixture was cooled to 10° C. Sodium cyanoborohydride (51 mg, 0.8 mmol) was added and the reaction mixture was heated at 60° C. overnight. It was concentrated, treated with water and extracted with n-butanol. The organic layer was washed with water, brine, concentrated and purified using flash chromatography (silica gel, 1-3% MeOH/CHCl$_3$) to obtain the title compound. Yield: 0.2 g (99%), $^1$H NMR (CDCl$_3$): δ 0.90 (s, 3H, CH$_3$), 1.3 (t, 4H, 2CH$_2$), 1.7 (t, 2H, CH$_2$), 2.40 (t, 2H, CH$_2$), 2.8 (t, 4H, 2CH$_2$), 2.90 (s, 3H, CH$_3$), 3.20 (t, 4H, 2CH$_2$), 3.90 (s, 3H, CH$_3$), 4.8 (s, 2H, CH$_2$), 6.70 (s, 1H, Ar), 6.90 (s, 1H, Ar), 8.1 (s 1H, Ar), 8.4 (s 1H, Ar); MS: m/e (EI+) 507 (M+1).

EXAMPLE 107

N-[4-Chloro-2-(4-cyclopropanecarbonyl-piperazin-1-yl)-6-methyl-10,10-dioxo-10,11-dihydro-5-oxa-10lambda*6*-thia-dibenzo[a,d]cycloheptene-8-carbonyl]-guanidine methane sulphonic acid salt The title compound was synthesised from Example 107k as described in the synthesis of Example 1. Yield: 0.1 g, (32%); mp: 267-268° C.; $^1$H NMR (DMSO-d$_6$): δ 0.7 (s, 4H, 2CH$_2$); 2.1 (m, 1H, CH); 2.4 (s, 3H, CH$_3$); 2.7 (s, 3H, CH$_3$); 3.2-3.9 (4s, 8H, 4CH$_2$); 5.3 (s, 2H, CH$_2$); 7.2 (d, 2H, Ar); 8.1 (s, 1H, Ar); 8.25 (s, 1H, Ar); 8.4-8.5 (d, 4H, 2NH$_2$); MS: m/e (ES+) 628 (M+); analysis: for C$_{25}$H$_{30}$ClN$_5$O$_8$S$_2$ calcd. C, 47.01; H, 4.81; N, 11.15; Cl, 5.64; S, 10.2; found: C, 46.87; H, 4.46; N, 10.81; Cl, 5.48; S, 10.03%.

EXAMPLE 107k

4-Chloro-2-(4-cyclopropanecarbonyl-piperazin-1-yl)-6-methyl-10,10-dioxo-10,11-dihydro-5-oxa-10lambda*6*-thia-dibenzo[a,d]cycloheptene-8-carboxylic acid A solution of cyclopropyl carbonyl chloride (0.22 mL, 2.4 mmol) in dichloromethane (2 mL) was added to a suspension of Example 104k (0.35 g, 0.8 mmol) in pyridine (3 mL)/dichloromethane (1 mL) at 10° C. The reaction mixture was stirred for 45 min, concentrated, treated with chilled water and dilute HCl to pH 6. The precipitated solid was filtered and dried to obtain the title compound. Yield: 0.372 g, (91.5%); $^1$H NMR (DMSO-d$_6$): δ 0.76 (m, 4H, 2CH$_2$); 2.06 (m, 1H, CH); 2.68 (s, 3H, CH$_3$); 3.24 (s, 2H, CH$_2$); 3.32 (s, 2H, CH$_2$); 3.64 (S, 2H, CH$_2$); 3.84 (s, 2H, CH$_2$); 5.15 (s, 2H, CH$_2$); 7.12 (d, 1H, Ar); 7.2 (d, 1H, Ar); 8.1 (s, 1H, Ar); 8.2 (s, 1H, Ar); 8.38 (s, 1H, OH). MS: m/e (ES+) 532 (M+1).

EXAMPLE 108

N-{4-Chloro-2-[4-(4-dimethylamino-benzyl)-piperazin-1-yl]-6-methyl-10,10-dioxo-10,11-dihydro-5-oxa-10lambda*6*-thia-dibenzo[a,d]cycloheptene-8-carbonyl}-guanidine trimesylate The title compound was synthesised from Example 108k as described in the synthesis of Example 50. Yield: 0.255 g, (65.72%); mp: 195-197° C., $^1$H NMR (DMSO-d$_6$): δ 2.40 (s, 9H, 3CH$_3$), 2.70 (s, 3H, CH$_3$), 2.90 (s, 6H, 2CH$_3$), 3.10-3.20 (m, 4H, 2CH$_2$), 3.40-3.45 (m, 2H, CH$_2$), 3.95-4.00 (m, 2H, CH$_2$), 4.35 (s, 2H, CH$_2$), 5.25 (s, 2H, CH$_2$), 6.85-6.90 (m, 1H, Ar), 7.25-7.35 (m, 4H, Ar), 8.20 (s, 1H, Ar), 8.35 (s, 1H, Ar), MS: m/e (ES+) 598 (M+1); analysis: C$_{32}$H$_{45}$ClN$_6$O$_{13}$S$_4$ calcd.: C, 43.41; H, 5.12; N, 9.49; found: C, 43.96; H, 5.76; N, 9.17%.

EXAMPLE 108k

4-Chloro-2-[4-(4-dimethylamino-benzyl)-piperazin-1-yl]-6-methyl-10,10-dioxo-10,11-dihydro-5-oxa-10lambda*6*-thia-dibenzo[a,d]cycloheptene-8-carboxylic acid methyl ester Titanium isopropoxide (0.33 mL, 1.09 mmol) was added to a solution of Example 104k (0.4 g, 0.91 mmol) and dimethylaminobenzaldehyde (0.136 g, 0.91 mmol) in dry methanol (10 mL). The reaction mixture was stirred at 50° C. in an atmosphere of N$_2$ for 1.5 h. It was cooled, treated with sodium cyanoborohydride (0.054 g, 0.86 mmol) and stirred for 1.5 h. It was then treated with cold water and extracted with n-butanol. The organic layer was washed with water, brine, dried, concentrated and purified using flash chromatography (silica gel, MeOH/CHCl$_3$) to obtain the title compound as a white solid. Yield: 0.275 g, (52.78%); $^1$H NMR (DMSO-d$_6$): δ 2.7 (s, 3H, CH$_3$), 3.00 (s, 6H, 2CH$_3$), 3.20-3.25 (m, 4H, 2CH$_2$), 3.55 (s, 4H, 2CH$_2$), 3.95 (s, 3H, OCH$_3$), 4.75 (s, 2H, CH$_2$), 6.7-6.9 (m, 4H, Ar), 7.25 (s, 1H, Ar), 7.3 (s, 1H, Ar), 8.1 (s, 1H, Ar), 8.50 (s, 1H, Ar); MS: m/e (CI+) 570 (M+1).

EXAMPLE 109

N-{4-Chloro-2-[4-(2,4-dichloro-benzyl)-piperazin-1-yl]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 109k as described in the synthesis of Example 50. Yield: 0.180 g, (53.73%), mp: 185-187° C., $^1$H NMR (DMSO-d$_6$): δ 2.40 (s, 6H, 2CH$_3$), 2.70 (s, 3H, CH$_3$), 3.05-3.25 (m, 4H, 2CH$_2$), 3.80-4 (m, 4H, 2CH$_2$), 4.60 (s, 2H, CH$_2$), 5.30 (s, 2H, CH$_2$), 7.30 (s, 2H, Ar), 7.70 (d, 1H, Ar), 7.85 (d, 1H, Ar), 7.90 (s, 1H, Ar), 8.15 (s, 1H, Ar), 8.25 (s, 1H, Ar), MS: m/e (ES+) 623 (M+1); analysis: C$_{29}$H$_{34}$ClN$_5$O$_{10}$S$_3$.H$_2$O calcd.: C, 41.81; H, 4.36; N, 8.41, Cl; 12.77, S; 11.54; found: C, 41.58; H, 4.47; N, 9.05, Cl; 12.61, S; 11.56%.

EXAMPLE 109k

4-Chloro-2-[4-(2,4-dichloro-benzyl)-piperazin-1-yl]-6-methyl-10,10-dioxo-10,11-dihydro-5-oxa-10lambda*6*-thia-dibenzo[a,d]cycloheptene-8-carboxylic acid methyl ester Titanium isopropoxide (0.25 mL, 0.82 mmol) was added to solution of Example 104k (0.3 g, 0.68 mmol) and 2,4-dichlorobenzaldehyde (0.120 g, 0.68 mmol) in dry methanol (10 mL). The reaction mixture was processed as described in the synthesis of Example 108k using sodium cyanoborohydride (0.041 g, 0.65 mmol) to obtain the title compound as a white solid. Yield: 0.285 g, (68.69%); $^1$H NMR (DMSO-d$_6$): δ 2.60-2.80 (m, 7H, 2CH$_2$, CH$_3$), 3.20-3.35 (m, 4H, 2CH$_2$), 3.95 (s, 3H, OCH$_3$), 4.65 (s, 2H, CH$_2$), 6.80 (d, 1H, Ar), 6.90 (d, 1H, Ar), 7.25-7.45 (m, 3H, Ar), 8.10 (s, 1H, Ar), 8.50 (s, 1H, Ar); MS: m/e (ES+) 596 (M+1).

EXAMPLE 110

N-{4-Chloro-6-methyl-10,10-dioxo-2-[4-(1H-pyrrole-2-carbonyl)-piperazin-1-yl]-10,11-dihydro-5-oxa-10lambda*6*-thia-dibenzo[a,d]cycloheptene-8-carbonyl}-guanidine dimesylate The title compound was synthesised from Example 110k as described in the synthesis of Example 50. Yield: 0.280 g, (79.77%); mp: 306-307° C.; $^1$H NMR (DMSO-d$_6$): δ 2.45 (s, 3H, CH$_3$), 2.70 (s, 3H, CH$_3$), 3.40-3.45 (m, 4H, 2CH$_2$), 3.85-3.95 (m, 4H, 2CH$_2$), 5.30 (s, 2H, CH$_2$), 6.10 (s, 1H, Ar), 6.55 (s, 1H, Ar), 6.95 (s, 1H, Ar), 7.15 (s, 1H, Ar), 7.25 (s, 1H, Ar), 8.10 (s, 1H, Ar), 8.35 (s, 1H, Ar), 8.40-8.50 (m, 4H, guanidinyl); MS: m/e (ES+) 557 (M+1); analysis: C$_{26}$H$_{29}$ClN$_6$O$_8$S$_2$.2H$_2$O calcd.: C, 45.31; H, 4.83; N, 12.19; found: C, 44.80; H, 4.56; N, 12.57%.

EXAMPLE 110k

4-Chloro-6-methyl-10,10-dioxo-2-[(4-(1H-pyrrole-2-carbonyl)-piperazin-1-yl]-10,11-dihydro-5-oxa-10lambda*64-thia-dibenzo[a,d]cycloheptene-8-carboxylic acid methyl ester Pyrrole-2-carbonylchloride (0.195 mL, 3.09 mmol) was added to a solution of Example 104k (0.4 g, 1.03 mmol) in dry dichloromethane (10 mL), Pyridine (3 mL, 37.92 mmol) was added and the reaction mixture was stirred at room temperature for 48 h. It was treated with water and extracted with chloroform. The organic layer was washed with water, brine, dried, concentrated and purified using flash chromatography (silica gel, MeOH/CHCl$_3$) to obtain the title compound as a white solid. Yield: 0.487 g, (94.22%); $^1$H NMR (DMSO-d$_6$): δ 2.20 (s, 3H, CH$_3$), 2.75-2.80 (m, 4H, 2CH$_2$), 3.45 (s, 3H, OCH$_3$), 3.45-3.55 (m, 4H, 2CH$_2$), 4.35 (s, 2H, CH$_2$), 5.60 (s, 1H, Ar), 6.00 (s, 1H, Ar), 6.35 (s, 1H, Ar), 6.45 (s, 1H, Ar), 6.50 (s, 1H, Ar), 7.50 (s, 1H, Ar), 7.80 (s, 1H, Ar); MS: m/e (ES+) 529 (M+1).

EXAMPLE 111

N-{4-Chloro-6-methyl-2-[4-(5-methyl-furan-2-ylmethyl)-piperazin-1-yl]-10,10-dioxo-10,11-dihydro-5-oxa-10lambda*6*-thia-dibenzo[a,d]cycloheptene-8-carbonyl}-guanidine dimesylate The title compound was synthesised from Example 111k as described in the synthesis of Example 50. Yield: 0.06 g, (53%); mp: 259° C.; $^1$H NMR (DMSO-d$_6$): δ 2.3 (s, 3H, CH$_3$), 2.35 (s, 6H, 2CH$_3$), 2.8 (s, 3H, CH$_3$), 3.2-3.9 (m, 8H, 4CH$_2$), 4.5 (s, 2H, CH$_2$), 5.3 (s, 2H, CH$_2$), 6.2 (s, 1H, Ar), 6.7 (s, 1H, Ar), 7.2 (d, 2H, Ar), 8.1 (s, 1H, Ar), 8.2 (s, 1H, Ar), 8.3 (s, 2H, NH$_2$), 8.4 (s, 2H, NH$_2$), 10.1 (s 1H, OH), 11.4 (s, 1H, Ar); MS: m/e (ES+) 559 (M+1) (free base); analysis: C$_{29}$H$_{38}$ClN$_5$O$_{10}$S$_3$: H$_2$O calcd.: C, 43.78; H, 4.99; N, 9.12; Cl, 4.61; S, 12.85; found: C, 43.27; H, 4.39; N, 8.38; Cl, 4.39; S, 12.50%.

EXAMPLE 111k

4-Chloro-6-methyl-2-[4-(5-methyl-furan-2-ylmethyl)-piperazin-1-yl]-10,10-dioxo-10,11-dihydro-5-oxa-10lambda*6*-thia-dibenzo[a,d]cycloheptene-8-carboxylic acid methyl ester Titanium isopropoxide (0.085 mL, 0.28 mmol) was added to a solution of Example 104k (0.1 g, 0.22 mmol) and 5-methyl furfuraldehyde (0.115 mL, 1.14 mmol) in dry methanol (10 mL). The reaction mixture was processed as described in the synthesis of Example 108k using sodium cyanoborohydride (0.013 g, 0.21 mmol) to obtain the title compound. Yield: 0.085 g, (70%); $^1$H NMR (CDCl$_3$): δ 2.3 (s, 3H, CH$_3$), 2.6 (t, 4H, 2CH$_2$), 2.7 (s, 3H, CH$_3$), 3.24 (t, 4H, 2CH$_2$), 3.55 (s, 2H, CH$_2$), 3.91 (s, 3H, OCH$_3$), 4.63 (s, 2H, CH$_2$), 5.9 (d, 1H, Ar), 6.1 (d, 1H, Ar), 6.76 (d, 1H, Ar), 6.88 (s, 1H, Ar), 8.06 (s, 1H, Ar), 8.44 (d, 1H, Ar); MS: m/e (EI+) 532 (M+1).

EXAMPLE 112

N-{4-Chloro-6-methyl-2-[4-(2-methyl-benzyl)-piperazin-1-yl]-10,10-dioxo-10,11-dihydro-5-oxa-10lambda*6*-thia-dibenzo[a,d]cycloheptene-8-carbonyl}-guanidine dimesylate The title compound was synthesised from Example 112k as described in the synthesis of Example 50. Yield: 0.040 g, (50%); mp: 267-268° C.; $^1$H NMR (DMSO-d$_6$): δ 2.3 (s, 6H, 2CH$_3$), 2.4 (s, 3H, CH$_3$), 3.2 (d, 4H, 2CH$_2$), 4.0 (d, 4H, 2CH$_2$), 4.4 (s, 2H, CH$_2$), 5.3 (s, 2H, CH$_2$), 7.2 (s, 2H, Ar), 7.3 (m, 3H, Ar), 7.5 (d, 1H, Ar), 8.1 (s, 1H, Ar), 8.3 (s, 1H, Ar), 8.4 (d, 4H, 2NH$_2$); MS: m/e (ES-) 759(M-1); analysis: C$_{30}$H$_{38}$ClN$_5$O$_{10}$S$_3$.2H$_2$O calcd.: C, 45.25; H, 5.32; N, 8.89; Cl, 4.45; S, 12.02; found: C, 45.40; H, 5.01; N, 8.80; Cl, 4.21; S, 12.02%.

EXAMPLE 112k

4-Chloro-6-methyl-2-[4-(2-methyl-benzyl)-piperazin-1-yl]-10,10-dioxo-10,11-dihydro-5-oxa-10lambda*6*-thia-dibenzo[a,d]cycloheptene-8-carboxylic acid methyl ester o-Tolualdehyde (0.041 mL, 0.35 mmol) and titanium isopropoxide (0.136 mL, 0.45 mmol) were added to a suspension of Example 104k (0.16 g, 0.36 mmol) in methanol (7 mL). The reaction mixture was stirred at 70° C. for 1.5 h, cooled to room temperature, treated with sodium cyanoborohydride (0.022 g, 0.34 mmol), then stirred at 70° C. for 1 h and at room temperature overnight. It was treated with water and extracted with n-butanol. The organic layer was washed with water, brine, dried, concentrated and purified using flash chromatography (silica gel, ethyl acetate/pet ether) to obtain the title compound. Yield: 0.060 g, (30%); $^1$H NMR (CDCl$_3$): δ 2.4 (s, 3H, CH$_3$), 2.6 (t, 4H, 2CH$_2$), 2.71 (s, 3H, CH$_3$), 3.21 (t, 4H, 2CH$_2$), 3.53 (s, 2H, CH$_2$), 3.92 (s, 3H, OCH$_3$), 4.67 (s, 2H, CH$_2$), 6.74 (d, 1H, Ar), 6.88 (d, 1H, Ar), 7.13 (t, 1H, Ar), 8.07 (d, 1H, Ar), 8.43 (d, 1H, Ar); MS: m/e (ES+) 542 (M+1).

EXAMPLE 113

N-{4-Chloro-6-methyl-2-[4-(5-methyl-thiophen-2-ylmethyl)-piperazin-1-yl]-10,10-dioxo-10,11-dihydro-5-oxa-10lambda*6*-thia-dibenzo[a,d]cycloheptene-8-carbonyl}-guanidine dimesylate The title compound was synthesised from Example 113k as described in the synthesis of Example 50. Yield: 0.108 g, (55%); mp: 234-235° C.; $^1$H NMR (DMSO-d$_6$): δ 2.4 (s, 3H, CH$_3$), 2.6 (s, 3H, CH$_3$), 2.75 (s, 3H, CH$_3$), 3.1 (m, 4H, 2CH$_2$), 4.0 (m, 4H, 2CH$_2$), 4.6 (s, 2H, CH$_2$), 5.3 (s, 2H, CH$_2$), 6.9 (d, 1H, Ar), 7.2 (d, 1H, Ar), 7.3 (s, 2H, Ar), 8.1 (s 1H, Ar), 8.3 (s, 1H, Ar), 8.4 (s, 2H, NH$_2$), 8.5 (s, 2H, NH$_2$); MS: m/e (ES-) 559(M-1) (free base); analysis: C$_{28}$H$_{36}$ClN$_5$O$_{10}$S$_4$: H$_2$O calcd.: C, 42.88; H, 4.88; N, 8.93; Cl, 4.52; S, 16.35; found: C, 42.35; H, 4.71; N, 9.38;Cl, 4.36; S, 16.69%.

EXAMPLE 113k

4-Chloro-6-methyl-2-[4-(5-methyl-thiophen-2-ylmethyl)-piperazin-1-yl]-10,10-dioxo-10,11-dihydro-5-oxa-10lambda*6*-thia-dibenzo[a,d]cycloheptene-8-carboxylic acid methyl ester 5-Methyl-thiophene-2-carboxyaldehyde (0.50 mL, 0.45 mmol) and titanium isopropoxide (0.17 mL, 0.57 mmol) were added to a suspension of Example 104k (0.2 g, 0.45 mmol) in methanol (30 mL). The reaction mixture was refluxed for 2 h, cooled to room temperature, treated with sodium cyanoborohydride (0.028 g, 0.45 mmol) and stirred for 15 h. It was concentrated, treated with water and extracted with ethyl acetate. The organic layer was washed with water, brine, dried, concentrated and purified using flash chromatography (silica gel, methanol/chloroform) to obtain the title compound. Yield: 0.15 g, (60%); $^1$H NMR (CDCl$_3$): δ 2.46 (s, 3H, CH$_3$), 2.6 (t, 4H, 2CH$_2$), 2.68 (s, 3H, CH$_3$), 3.24 (t, 4H, 2CH$_2$), 3.7 (s, 2H, CH$_2$), 3.9 (s, 3H, OCH$_3$), 4.66 (s, 2H, CH$_2$), 6.6 (d, 1H, Ar), 6.71 (d, 1H, Ar), 6.76 (d, 1H, Ar), 6.89 (d, 1H, Ar), 8.06 (s, 1H, Ar), 8.43 (d, 1H, Ar); MS: m/e (ES+) 548 (M+1).

EXAMPLE 114

N-{4-Chloro-2-[4-(3,4-dimethoxy-benzyl)-piperazin-1-yl]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 114k as described in the synthesis of Example 50. Yield: 0.2 g, (66%); mp: 166-168° C., $^1$H NMR (DMSO-d$_6$): δ 2.4 (s, 6H, 2CH$_3$), 2.67 (s, 3H, CH$_3$), 3.11 (m, 4H, 2CH$_2$), 3.78 (s, 3H, OCH$_3$), 3.80 (s, 3H, OCH$_3$), 3.95 (m, 4H, 2CH$_2$), 4.32 (m, 2H, CH$_2$), 5.22 (s, 2H, CH$_2$), 7.03 (s, 2H, Ar), 7.2 (s, 1H, Ar), 7.25 (s, 3H, Ar), 8.12 (s, 1H, Ar), 8.26 (s, 1H, Ar), 8.3-8.6 (bs, 4H, 2NH$_2$), 9.9 (bs, 1H, NH), 11.42 (s, 1H, OH); MS: m/e (ES+) (Free base) 615 (M+1); analysis: C$_{31}$H$_{40}$ClN$_5$O$_{12}$S$_3$, calcd.: C, 46.18; H, 5.0; N, 8.69; Cl, 4.4; S, 11.98; found C, 43.91; H, 5.73; N, 8.67; Cl, 4.54; S, 11.56%.

EXAMPLE 114k

4-Chloro-2-[4-(3,4-dimethoxy-benzyl)-piperazin-1-yl]-6-methyl-10,10-dioxo-10,11-dihydro-5-oxa-10lambda*6*-thia-dibenzo[a,d]cycloheptene-8-carboxylic acid methyl ester Veratraldehyde (0.114 g, 0.687 mmol) and titanium isopropoxide (0.26 mL, 0.858 mmol) were added to a suspension of Example 104k (0.3 g, 0.687 mmol) in methanol (30 mL). The reaction mixture was refluxed for 1.5 h, cooled to room temperature, treated with sodium cyanoborohydride (0.042 g, 0.66 mmol) and stirred for 3 h. It was concentrated treated with water and extracted with 1-butanol. The organic layer was washed with water, brine, dried, concentrated and purified using flash chromatography (silica gel, 1% methanol/ chloroform) to obtain the title compound. Yield: 0.335 g, (58.3%); $^1$H NMR (DMSO-d$_6$): δ 2.65 (s, 3H, CH$_3$), 3.2 (h, 4H, 2CH$_2$), 3.4 (m, 4H, 2CH$_2$), 3.5 (s, 2H, CH$_2$), 3.75 (s, 6H, 2OCH$_3$), 3.9 (s, 3H, OCH$_3$), 5.2 (s, 2H, CH$_2$), 6.85-7.0 (m, 3H, Ar), 7.1 (s, 1H, Ar), 7.15 (d, 1H, Ar), 8.1 (s, 1H, Ar), 8.24 (s, 1H, Ar); MS: m/e (ES+) 588 (M+1).

EXAMPLE 115

N-{4-Chloro-6-methyl-10,10-dioxo-2-[4-(4-trifluoromethyl-benzyl)-piperazin-1-yl]-10,11-dihydro-5-oxa-10lambda*6*-thia-dibenzo[a,d]cycloheptene-8-carbonyl}-guanidine trimesylate The title compound was synthesised from Example 115k as described in the synthesis of Example 50. Yield: 0.080 g, (48%); mp: 156-160° C.; $^1$H NMR (DMSO-d$_6$): δ 2.4 (s, 9H, 3CH$_3$), 2.7 (s, 3H, CH$_3$), 3.1-3.32 (h, 6H, 3CH$_2$), 3.9 (m, 2H, CH$_2$), 4.5 (m, 2H, CH$_2$), 5.25 (s, 2H, CH$_2$), 7.2 (bs, 2H, Ar), 7.8 (d, 2H, Ar), 8.0 (d, 2H, Ar), 8.15 (s, 1H, Ar), 8.3 (s, 1H, Ar), 8.3-8.5 (h, 4H, 2NH$_2$), 10.04 (h, 1H, NH), 11.4 (b, 1H, OH); MS: m/e (ES+) (Free base) 623 (M+1); analysis: C$_{31}$H$_{39}$ClF$_3$N$_5$O$_{13}$S$_4$, calcd.: C, 40.90; H, 4.32; N, 7.69; Cl, 3.89; S, 14.09; found C, 40.20; H, 3.96; N, 7.04; Cl, 3.88; S, 14.25%.

EXAMPLE 115k

4-Chloro-6-methyl-10,10-dioxo-2-[4-(4-trifluoromethyl-benzyl)-piperazin-1-yl]-10,11-dihydro-5-oxa-10lambda*6*-thia-dibenzo[a,d]cycloheptene-8-carboxylic acid methyl ester p-(Trifluoromethyl)benzaldehyde (0.119 g, 0.687 mmol) and titanium isopropoxide (0.26 mL, 0.858 mmol) were added to a suspension of Example 104k (0.3 g, 0.687 mmol) in methanol (30 mL). The reaction mixture was refluxed for 1.5 h, cooled to room temperature, treated with sodium cyanoborohydride (0.042 g, 0.66 mmol) and stirred for 3 h. It was concentrated, treated with water and extracted with n-butanol. The organic layer was washed with water, brine, dried, concentrated and purified using flash chromatography (silica gel, 20% ethyl acetate/pet ether) to obtain the title compound. Yield: 0.12 g, (28.7%); $^1$H NMR (DMSO-d$_6$): δ 2.6 (h, 4H, 2CH$_2$), 2.7 (s, 3H, CH$_3$), 3.2 (h, 4H, 2CH$_2$), 3.6 (s, 2H, CH$_2$), 3.9 (s, 3H, OCH$_3$), 4.6 (s, 2H, CH$_2$), 6.7 (s, H, Ar), 6.9 (s, 1H, Ar), 7.5 (d, 2H, Ar), 7.6 (d, 2H, Ar), 8.1 (s, 1H, Ar), 8.45 (s, 1H, Ar); MS: m/e (ES+) 596 (M+1).

EXAMPLE 116

N-[4-Chloro-2-(4-ethyl-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 116j as described in the synthesis of Example 50. Yield (0.131 g, 48%); mp: 255-257° C.; $^1$H NMR (DMSO-d$_6$): δ 1.26 (t, 3H, CH$_3$), 2.32 (s, 6H, 2CH$_3$), 2.7 (s, 3H, CH$_3$), 3.07 (h, 4H, 2CH$_2$), 3.21 (h, 2H, CH$_2$), 3.60 (h, 2H, CH$_2$), 3.9 (d, 2H, CH$_2$), 5.21 (s, 2H, CH$_2$), 7.22 (s, 2H, Ar), 8.12 (s, 1H, Ar), 8.28 (s, 1H, Ar), 8.3-8.5 (bs, 4H, 2NH$_2$), 9.47 (h, 1H, NH+), 11.42 (h, 1H, OH); MS: m/e (ES+) (Free base) 492 (M+1); analysis: C$_{24}$H$_{34}$ClN$_5$O$_{10}$S$_3$.H$_2$O, calcd.: C, 41.01; H, 5.13; N, 10.68; Cl, 5.06; S, 13.67; found C, 40.99; H, 5.27; N, 9.56; Cl, 5.31; S, 14.52%.

EXAMPLE 116j

4-Chloro-2-(4-ethyl-piperazin-1-yl)-6-methyl-10,10-dioxo-10,11-dihydro-5-oxa-10lambda*6*-thia-dibenzo[a,d]cycloheptene-8-carboxylic acid Aqueous ethyl amine (3 mL, 70%, 48.8 mmol) was added to Example 102j (0.4 g, 0.83 mmol) in methanol (3 mL), in an atmosphere of nitrogen and it was sealed in a pressure reactor vessel at 120° C. for 8 h. The reaction mixture was cooled, concentrated and purified using flash chromatography (silica gel, 10% methanol chloroform) to obtain the title compound as an off-white solid. Yield: 0.3 g (79.78%). $^1$H NMR (DMSO-d$_6$): δ 1.20 (t, 3H, CH$_3$), 2.65 (s, 3H, CH$_3$), 3.05 (m, 2H, CH$_2$), 3.15 (q, 4H, 2CH$_2$), 3.55 (d, 2H, CH$_2$), 3.85 (d, 2H, CH$_2$), 5.10 (s, 2H, CH$_2$), 7.10 (s, 1H, Ar), 7.13 (d, 2H, Ar), 8.05 (s, 1H, Ar), 8.15 (s, 1H, Ar); MS: m/e (ES+) 451 (M+1).

EXAMPLE 117

N-[4-Chloro-6-methyl-2-morpholin-4-yl-10,10-dioxo-10,11-dihydro-5-oxa-10lambda*6*-thia-dibenzo[a,d]cycloheptene-8-carbonyl]-guanidine dimesylate The title compound was synthesised from Example 117k as described in the synthesis of Example 50. Yield: 0.045 g, (75%); MS: m/e (ES+) 465 (M+1); analysis: C$_{22}$H$_{29}$ClN$_4$O$_{11}$S$_3$.2H$_2$O calcd.: C, 38.12; H, 4.80; N, 8.08; found: C, 38.50; H, 4.60; N, 7.55%.

EXAMPLE 117k

4-Chloro-6-methyl-2-morpholin-4-yl-10,10-dioxo-10,11-dihydro-5-oxa-10lambda*6*-thia-dibenzo[a,d]cycloheptene-8-carboxylic acid methyl ester p-Toluene sulphonic acid (0.090 g, 0.51 mmol) was added to a solution of Example 148 (0.3 g, 0.65 mmol) in toluene (200 mL) and using Dean Stark apparatus, water was azeotropically removed over a period of 6 h. The reaction mixture was concentrated and treated with ethyl acetate and washed with water, brine, dried, concentrated and purified using flash chromatography (silica gel, ethylacetate/pet ether) to obtain the title compound as an off-white solid. Yield: 0.061 g, (21.18%); $^1$H NMR (DMSO-d$_6$): δ 2.80 (s, 3H, CH$_3$), 3.20 (t, 4H, 2CH$_2$), 3.80 (t, 4H, 2CH$_2$), 4.00 (s, 3H, CH$_3$), 5.20 (s, 2H, CH$_2$), 7.10 (s, 1H, Ar), 7.20 (s, 1H, Ar), 8.10 (s, 1H, Ar), 8.20 (s, 1H, Ar); MS: m/e (ES+) 437 (M+1).

EXAMPLE 118

N-[2-(4-Benzyl-piperazin-1-yl)-4-chloro-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 118k as described in the synthesis of Example 50. Yield: 3.10 g, (77.88%), mp: 280-285° C., $^1$H NMR (DMSO-d$_6$): δ 2.40 (s, 6H, 2CH$_3$), 2.70 (s, 3H, CH$_3$), 3.10-3.25 (m, 6H, 3CH$_2$), 3.90-4.00 (m, 2H, CH$_2$), 4.50 (s, 2H, CH$_2$), 5.25 (s, 2H, CH$_2$), 7.25 (s, 2H, Ar), 7.50-7.55 (m, 5H, Ar), 8.15 (s, 1H, Ar), 8.25 (s, 1H, Ar), 8.30-8.50 (m, 4H, guanidinyl); MS: m/e (ES+) 555 (M+1); analysis: C$_{29}$H$_{36}$ClN$_5$O$_{10}$S$_3$.2H$_2$O, calcd.: C, 44.53; H, 5.15; N, 8.95; Cl, 4.53; S, 12.29; found: C, 44.76; H, 5.22; N, 9.89, Cl, 5.19; S, 12.86%.

EXAMPLE 118k 2-(4-Benzyl-piperazin-1-yl)-4-chloro-6-methyl-10,
10-dioxo-10,11-dihydro-5-oxa-10lambda*6*-thia-
dibenzo[a,d]cycloheptene-8-carboxylic acid methyl
ester Benzylamine (25 mL) was added to a mixture of Example 102j (11 g, 22.32 mmol) and tetrabutylammonium iodide (75 mg, 0.20 mmol). The reaction mixture was heated overnight at 110° C. in an atmosphere of nitrogen, cooled, concentrated, treated with methanolic HCl (100 mL) and stirred at 70° C. for 5 h. The reaction mixture was cooled, concentrated, treated with water, aqueous sodium bicarbonate solution to pH 7 and extracted with chloroform. The organic layer was washed with water, brine, dried, concentrated and purified using flash chromatography (silica gel, methanol chloroform) to obtain the title compound as an off-white solid. Yield: 4.70 g, (39%), $^1$H NMR, (DMSO-d$_6$): δ 2.60 (s, 3H, CH$_3$), 3.20-3.25 (m, 6H, 3CH$_2$), 3.40-3.45 (m, 4H, 2CH$_2$), 3.60 (s, 3H, CH$_3$), 5.20 (s, 2H, CH$_2$), 7.05 (s, 1H, Ar), 7.15 (s, 1H, Ar), 7.35 (s, 1H, Ar), 7.40-7.45 (m, 5H, Ar), 8.20 (s, 1H, Ar); MS: m/e (EI+) 527 (M+1).

EXAMPLE 119

N-{4-Chloro-2-[4-(2-dimethylamino-ethyl)-piper-
azin-1-yl]-6-methyl-10,10-dioxo-10,11-dihydro-5-
oxa-10lambda*6*-thia-dibenzo[a,d]cycloheptene-8-
carbonyl}-guanidine trimesylate The title compound was synthesised from Example 119k as described in the synthesis of Example 50. Yield: 0.101 g, (50%); mp: 243-245° C.; $^1$H NMR (DMSO-d$_6$): δ 2.4 (s, 9H, 3CH$_3$), 2.7 (s, 3H, CH$_3$), 2.87 (m, 6H, 3CH$_2$), 3.05-3.32 (m, 4H, 2CH$_2$), 3.40 (d, 2H, CH$_2$), 5.21 (s, 2H, CH$_2$), 7.25 (s, 2H, Ar), 8.12 (s, 1H, Ar), 8.22 (s, 1H, Ar), 8.3-8.7 (bs, 4H, 2NH$_2$); MS: m/e (ES+) (Free base) 535 (M+1); analysis: C$_{27}$H$_{43}$ClN$_6$O$_{13}$S$_4$. calcd. C, 39.39; H, 5.26; N, 10.21; Cl, 4.31; S, 15.58; found C, 38.25; H, 4.49; N, 8.40; Cl, 4.39; S, 15.34%.

EXAMPLE 119k

4-Chloro-2-[4-(2-dimethylamino-ethyl)-piperazin-1-
yl]-6-methyl-10,10-dioxo-10,11-dihydro-5-oxa-
10lambda*6*-thia-dibenzo[a,d]cycloheptene-8-car-
boxylic acid methyl ester N,N-Dimethylamino ethanol (0.35 mL, 3.2 mmol) was added to a solution of 102j (0.4 g, 0.89 mmol) in methanol (5 mL) in an atmosphere of nitrogen and was sealed in a pressure reactor vessel at 110° C. for 5 h. It was brought to room temperature, treated with chilled water and extracted with n-butanol. The organic layer was washed with water, brine, dried, concentrated, treated with methanolic HCl solution, and refluxed at 70° C. for 2 h. The reaction mixture was concentrated, treated with aqueous sodium bicarbonate solution to neutral pH and extracted with n-butanol. The organic layer was washed with water, brine, dried, concentrated and purified using flash chromatography (silica gel, 5% methanol/chloroform) to obtain the title compound. Yield: 0.195 g, (46%); $^1$H NMR (DMSO-d$_6$): δ 2.40 (s, 6H, 2CH$_3$), 2.50 (s, 3H, CH$_3$), 2.75 (s, 4H, 2CH$_2$), 3.20-3.25 (m, 4H, 2CH$_2$), 3.40-3.45 (m, 4H, 2CH$_2$), 3.90 (s, 3H, OCH$_3$), 5.20 (s, 2H, CH$_2$), 7.10 (s, 1H, Ar), 7.15 (s, 1H, Ar), 8.10 (s, 1H, Ar), 8.15 (s, 1H, Ar); MS : m/e (EI+) 508 (M+1).

EXAMPLE 120

N-[4-Chloro-2-(4-isopropyl-piperazin-1-yl)-6-me-
thyl-10,10-dioxo-10,11-dihydro-5-oxa-10lambda*6-
thia-dibenzo[a,d]cycloheptene-8-carbonyl]-guani-
dine dimesylate The title compound was synthesised from Example 120j as described in the synthesis of Example 1. Yield: 0.140 g, (44%); mp: 242-245° C.; $^1$H NMR (DMSO-d$_6$): δ 1.31 (d, 6H, 2CH$_3$), 2.37 (s, 6H, 2CH$_3$), 2.7 (s, 3H, CH$_3$), 3.11 (m, 4H, 2CH$_2$), 3.57 (m, 4H, 2CH$_2$), 4.0 (m, H, CH), 5.22 (s, 2H, CH$_2$), 7.25 (s, 2H, Ar), 8.13 (s, 1H, Ar), 8.27 (s, 1H, Ar), 8.3-8.6 (bs, 4H, 2NH$_2$), 9.42 (h, 1H, NH), 11.4 (h, 1H, OH); MS: m/e (ES+) (Free base) 601 (M−1); analysis: C$_{25}$H$_{36}$ClN$_5$O$_{10}$S$_3$.H$_2$O, calcd. C, 41.92; H, 5.35; N, 9.78; found C, 41.45; H, 4.77; N, 9.44%.

EXAMPLE 120j

4-Chloro-2-(4-isopropyl-piperazin-1-yl)-6-methyl-
10,10-dioxo-10,11-dihydro-5-oxa-10lambda*6*-
thia-dibenzo[a,d]cycloheptene-8-carboxylic acid Isopropyl amine (2 mL, 23.48 mmol) was added to Example 102j (0.5 g, 1.04 mmol) in methanol (5 mL), in an atmosphere of nitrogen, in a pressure reactor vessel and heated at 110° C. for 5 h. The reaction mixture was cooled, concentrated, treated with dil HCl to neutral pH and extracted with n-butanol. The organic layer was washed with water, brine, dried, concentrated and purified by crystallisation (25% ethyl acetate in pet-ether) to obtain the title compound. Yield: 0.225 g, (46%); $^1$H NMR (DMSO-d$_6$): δ 1.05 (s, 6H, 2CH$_3$), 1.20-1.25 (m, 1H, CH), 2.65 (s, 3H, CH$_3$), 2.75-2.80 (m, 4H, 2CH$_2$), 3.20-3.25 (m, 4H, 2CH$_2$), 5.10 (s, 2H, CH$_2$), 7.10 (s, 1H, Ar), 7.15 (s, 1H, Ar), 8.10 (s, 1H, Ar), 8.15 (s, 1H, Ar); MS : m/e (ES+) 465 (M+1).

EXAMPLE 121

N-{4-Chloro-6-methyl-2-[4-(2-morpholin-4-yl-
ethyl)-piperazin-1-yl]-10,10-dioxo-10,11-dihydro-5-
oxa-10lambda*6*-thia-dibenzo[a,d]cycloheptene-8-
carbonyl}-guanidine trimesylate The title compound was synthesised from Example 121k as described in the synthesis of Example 50. Yield: 0.2 g, (42.33%); m.p: 185-187° C.; $^1$H NMR (DMSO-d$_6$+D$_2$O): δ 2.4 (s, 9H, 3CH$_3$), 2.7 (s, 3H, CH$_3$), 2.8 (t, 4H, 2CH$_2$), 3.22 (b, 4H, 2CH$_2$), 3.32 (b, 4H, 2CH$_2$), 3.5 (b, 8H, 4CH$_2$), 5.21 (s, 2H, CH$_2$), 7.2 (b, 2H, Ar), 8.1 (s, 1H, Ar), 8.22 (s, 1H, Ar); MS: m/e (ES+) (Free base) 577 (M+1).

EXAMPLE 121k

4-Chloro-6-methyl-2-[4-(2-morpholin-4-yl-ethyl)-
piperazin-1-yl]-10,10-dioxo-10,11-dihydro-5-oxa-
10lambda*6*-thia-dibenzo[a,d]cycloheptene-8-car-
boxylic acid methyl ester 1-(2-Amino ethyl)-morpholine (0.68 mL, 5.2 mmol) was added to a solution of Example 102j (0.5 g, 1.04 mmol) in methanol (5 mL) followed by the addition of n-tetrabutyl ammonium iodide (0.010 g, 0.02 mmol), in an atmosphere of nitrogen, in a pressure reactor vessel and heated at 110° C. for 5 h. It was brought to room temperature, treated with chilled water and extracted with n-butanol. The organic layer was washed with water, brine, dried, concentrated, treated with methanolic HCl solution, and refluxed at 70° C. for 3 h. The reaction mixture was concentrated, treated with aqueous sodium bicarbonate solution to neutral pH and extracted with n-butanol. The organic layer was washed with water, brine, dried, concentrated and purified using flash chromatography (silica gel, 5% methanol/chloroform) to obtain the title compound. Yield: 0.350 g, (48.3%); $^1$H NMR (DMSO-$d_6$): δ 2.37-2.50 (s, 8H, 4CH$_2$), 2.65 (s, 3H, CH$_3$), 3.20-3.25 (m, 4H, 2CH$_2$), 3.50-3.65 (m, 4H, 2CH$_2$), 3.90 (s, 3H, OCH$_3$), 5.20 (s, 2H, CH$_2$), 7.05 (s, 1H, Ar), 7.10 (s, 1H, Ar), 8.10 (s, 1H, Ar), 8.15 (s, 1H, Ar); MS: m/e (ES+) 551 (M+1).

EXAMPLE 122

N-{4-Chloro-6-methyl-10,10-dioxo-2-[4-(2-pyrrolidin-1-yl-ethyl)-piperazin-1-yl]-10,11-dihydro-5-oxa-10lambda*6*-thia-dibenzo[a,d]cycloheptene-8-carbonyl}-guanidine trimesylate The title compound was synthesised from Example 122k as described in the synthesis of Example 50. Yield: 0.250 g, (60%); mp: 250-252° C.; $^1$H NMR (DMSO-$d_6$): δ 2.0 (bs, 4H, 2CH$_2$), 2.4 (s, 9H, 3CH$_3$), 2.7 (s, 3H, CH$_3$), 3.6 (h, 6H, 3CH$_2$), 4.0 (m, 12H, 6CH$_2$), 5.21 (s, 2H, CH$_2$), 7.25 (s, 2H, Ar), 8.1 (s, 1H, Ar), 8.25 (s, 1H, Ar), 8.3-8.6 (bs, 4H, 2NH$_2$); MS: m/e (ES+) (Free base) 518 (M+1); analysis: $C_{29}H_{45}ClN_6O_{13}S_4$. calcd.: C, 41.01; H, 5.34; N, 9.89; Cl, 4.17; S, 15.10; found C, 40.74; H, 5.70; N, 10.12; Cl, 4.60; S, 15.70%.

EXAMPLE 122k

4-Chloro-6-methyl-10,10-dioxo-2-[4-(2-pyrrolidin-1-yl-ethyl)-piperazin-1-yl]-10,11-dihydro-5-oxa-10lambda*6*-thia-dibenzo[a,d]cycloheptene-8-carboxylic acid methyl ester 1-(2-Aminoethyl)pyrrolidine (1.60 mL, 12.6 mmol) was added to a solution of Example 102j (0.75 g, 1.50 mmol) in methanol (5 mL), in an atmosphere of nitrogen and sealed in a pressure reactor vessel at 110° C. for 5 h. The reaction mixture was brought to room temperature, concentrated, treated with methanolic HCl solution, and refluxed at 70° C. for 2 h. The reaction mixture was concentrated, treated with aqueous sodium bicarbonate solution to neutral pH and extracted with n-butanol. The organic layer was washed with water, brine, dried, concentrated and purified using flash chromatography (silica gel, 5% methanol/chloroform) to obtain the title compound. Yield: 0.320 g, (30.5%); $^1$H NMR (DMSO-$d_6$): δ 1.90-1.95 (m, 4H, 2CH$_2$), 2.62 (s, 6H, 2CH$_3$), 2.70 (s, 3H, CH$_3$), 3.10-3.15 (m, 8H, 4CH$_2$), 3.20-3.25 (m, 4H, 2CH$_2$), 3.90 (s, 3H, OCH$_3$), 5.20 (s, 2H, CH$_2$), 7.10 (s, 1H, Ar), 7.20 (s, 1H, Ar), 8.10 (s, 1H, Ar), 8.15 (s, 1H, Ar); MS : m/e (CI+) 534 (M+).

EXAMPLE 123

N-[4-Chloro-2-(4-cyclopropylmethyl-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 123k as described in the synthesis of Example 1. Yield: 0.023 g, (52%); mp: 282-287° C.; $^1$H NMR (DMSO-$d_6$): δ 0.4 (d, 2H, CH$_2$), 0.65 (d, 2H, CH$_2$), 1.11 (m, 1H, CH), 2.32 (s, 6H, 2CH$_3$), 2.65 (s, 3H, CH$_3$), 3.1-3.13 (h, 6H, 3CH$_2$), 3.65 (h, 2H, CH$_2$), 3.9 (m, 2H, CH$_2$), 5.2 (s, 2H, CH$_2$), 7.25 (s, 2H, Ar), 8.12 (s, 1H, Ar), 8.3 (s, 1H, Ar), 8.35-8.6 (bs, 4H, 2NH$_2$), 9.5 (bs, 1H, NH), 11.35 (h, 1H, OH); MS: m/e (ES+) (Free base) 518 (M+1); analysis: $C_{26}H_{36}ClN_5O_{10}S_3$. calcd.: C, 43.97; H, 5.11; N, 9.86; found C, 43.64; H, 4.99; N, 10.16%.

EXAMPLE 123k

4-Chloro-2-(4-cyclopropylmethyl-piperazin-1-yl)-6-methyl-10,10-dioxo-10,11-dihydro-5-oxa-10lambda*6*-thia-dibenzo[a,d]cycloheptene-8-carboxylic acid Cyclopropylmethyl amine (0.30 mL, 3.34 mmol) was added to a solution of Example 102j (0.2 g, 0.42 mmol) in methanol (5 mL), followed by the addition of n-tetrabutylammonium iodide (0.01 g, 0.020 mmol) in an atmosphere of nitrogen and sealed in a pressure reactor vessel at 110° C. for 10 h. The reaction mixture was brought to room temperature, concentrated, treated with water and extracted with n-butanol. The organic layer was washed with water, brine, dried, concentrated and purified by crystallisation (ethylacetate-pet-ether). Yield: 0.114 g, (53.7%). $^1$H NMR (DMSO-$d_6$): δ 0.1 (d, 2H, CH$_2$), 0.50 (d, 2H, CH$_2$), 0.90 (m, 1H, CH), 2.30 (d, 2H, CH$_2$), 2.70 (s, 3H, CH$_3$), 3.20-3.25 (m, 4H, 2CH$_2$), 5.15 (s, 2H, CH$_2$), 7.10 (s, 1H, Ar), 7.15 (s, 1H, Ar), 8.0 (s, 1H, Ar), 8.20 (s, 1H, Ar).

EXAMPLE 124

N-{4-Chloro-6-methyl-10,10-dioxo-2-[4-(2-piperazin-1-yl-ethyl)-piperazin-1-yl]-10,11-dihydro-5-oxa-10lambda*6*-thia-dibenzo[a,d]cycloheptene-8-carbonyl}-guanidine tetramesylate The title compound was synthesised from Example 124j as described in the synthesis of Example 50. Yield: 0.040 g, (40%), mp: 182-184° C.; $^1$H NMR (DMSO-$d_6$): δ 2.40 (s, 12H, 4CH$_3$), 2.70 (s, 3H, CH$_3$), 2.75-2.90 (m, 4H, 2CH$_2$), 3.25-3.35 (m, 2H, CH$_2$), 3.40-3.80 (m, 14H, 7CH$_2$), 5.25 (s, 2H, CH$_2$), 7.35 (s, 2H, Ar), 8.10 (s, 1H, Ar), 8.25 (s, 1H, Ar); MS: m/e (ES+) 576 (M+1); analysis: $C_{30}H_{50}ClN_7O_{16}S_5$ 2.H$_2$O calcd.: C, 36.16; H, 5.46; N, 9.84; Cl, 3.56, S; 16.09; found: C, 36.05; H, 5.24; N, 9.32, Cl; 4.09, S; 16.47%.

EXAMPLE 124j

4-Chloro-6-methyl-10,10-dioxo-2-[4-(2-piperazin-1-yl-ethyl)-piperazin-1-yl]-10,11-dihydro-5-oxa-10lambda*6*-thia-dibenzo[a,d]cycloheptene-8-carboxylic acid methyl ester N-Aminoethyl piperazine (0.6 mL, 5.2 mmol) was added to a solution of Example 102j (0.5 g, 1.04 mmol) in methanol (5 mL), followed by the addition of n-tetrabutylammonium iodide (0.075 g, 0.20 mmol) in an atmosphere of nitrogen, in a pressure reactor vessel at 120° C. for 5 h. The reaction mixture was brought to room temperature, concentrated and treated with water. The solid that separated was washed with water, dried, treated with methanolic HCl solution, and refluxed at 70° C. for 2 h. The reaction mixture was concentrated, treated with aqueous sodium bicarbonate solution to neutral pH and extracted with n-butanol. The organic layer was washed with water, dried, concentrated and purified using flash chromatography (silica gel, 20% methanol/chloroform) to obtain the title compound. Yield: 0.075 g, (13%); $^1$H NMR (DMSO-$d_6$): δ 2.50-2.60 (m, 4H, 2CH$_2$), 2.70 (s, 3H, CH₃), 3.00-3.40 (m, 14H, 7CH₂), 3.70 (s, 1H, OH), 3.90 (s, 3H, OCH₃), 5.20 (s, 2H, CH₂), 7.10 (s, 1H, Ar), 7.20 (s, 1H, Ar), 8.10 (s, 1H, Ar), 8.20 (s, 1H, Ar); MS: m/e (EI+) 459 (M+1).

EXAMPLE 125

N-[4-Chloro-2-(4-cyclopropyl-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 125k as described in the synthesis of Example 50. Yield: 0.110 g, (58%); mp: 245-248° C.; ¹H NMR (DMSO-d₆): δ 0.93 (m, 2H, CH₂), 1.03 (m, 2H, CH₂), 1.1 (m, 1H, CH), 2.38 (s, 6H, 2CH₃), 2.68 (s, 3H, CH₃), 3.1 (m, 4H, 2CH₂), 3.6 (m, 2H, CH₂), 3.92 (m, 2H, CH₂), 5.22 (s, 2H, CH₂), 7.25 (s, 2H, Ar), 8.1 (s, 1H, Ar), 8.2 (s, 1H, Ar), 8.3-8.6 (bs, 4H, 2NH₂), 9.22 (bs, 1H, NH+); MS: m/e (ES+) (Free base) 504.67 (m+1); analysis: C₂₅H₃₄ClN₅O₁₀S₃.2H₂O. calcd.: C, 41.01; H, 5.23; N, 9.56; Cl, 4.84; S, 13.14; found C, 41.61; H, 5.65; N, 9.45; Cl, 4.52; S, 13.19%.

EXAMPLE 125k

4-Chloro-2-(4-cyclopropyl-piperazin-1-yl)-6-methyl-10,10-dioxo-10,11-dihydro-5-oxa-10lambda*6*-thia-dibenzo[a,d]cycloheptene-8-carboxylic acid methyl ester Cyclopropyl amine (0.819 g, 14.34 mmol) was added to a solution of Example 102j (0.5 g, 1.04 mmol) in methanol (5 mL), followed by addition of n-tetrabutylammonium iodide (0.010 g, 0.027 mmol) in an atmosphere of nitrogen, in a pressure reactor vessel and heated at 110° C. for 10 h. It was brought to room temperature, concentrated, treated with methanolic HCl solution, and refluxed at 70° C. for 2 h. The reaction mixture was concentrated, treated with aqueous sodium bicarbonate solution to neutral pH and extracted with n-butanol. The organic layer was washed with water, brine, dried, concentrated and purified using flash chromatography (silica gel, 5% methanol/chloroform) to obtain the title compound. Yield: 0.220 g, (45%); ¹H NMR (DMSO-d₆): δ 0.4 (m, 4H, 2CH₂), 1.65 (m, 1H, CH), 2.7 (s, 3H, CH₃), 2.80 (d, 4H, 2CH₂), 3.10 (m, 4H, 2CH₂), 3.90 (s, 3H, OCH₃), 5.2 (s, 2H, CH₂), 7.05 (s, 1H, Ar), 7.1 (s, 1H, Ar), 8.1 (s, 1H, Ar), 8.15 (s, 1H, Ar); MS: m/e (EI+) 447 (M+).

EXAMPLE 126k

4-Chloro-6-methyl-2-[4-(3-nitro-benzyl)-piperazin-1-yl]-10,10-dioxo-10,11-dihydro-5-oxa-10lambda*6*-thia-dibenzo[a,d]cycloheptene-8-carboxylic acid methyl ester m-Nitrobenzaldehyde (0.456 g, 3.02 mmol) and titanium isopropoxide (1.23 mL, 4.12 mmol) were added to a solution of Example 125k (1.2 g, 2.75 mmol) in methanol (75 mL) and refluxed for 1.5 h. Sodium cyanoborohydride (0.188 g, 2.75 mmol) was then added to the reaction mixture at 30° C. and refluxed for 3 h. It was cooled, treated with water and filtered. The filtrate was extracted with chloroform. The organic layer was washed with water, brine, dried, concentrated and purified using flash chromatography (silica gel, 5% methanol/chloroform) to obtain the title compound. Yield: 0.74 g (48%); ¹H NMR (CDCl₃): δ 2.6 (t, 4H, 2CH₂), 2.63 (s, 3H, CH₃), 3.22 (t, 4H, 2CH₂), 3.63 (s, 2H, CH₂), 3.9 (s, 3H, OCH₃), 5.2 (s, 2H, CH₂), 6.73 (s, 1H, Ar), 6.9 (s, 1H, Ar), 7.5 (t, 1H, Ar), 7.7 (d, 1H, Ar), 8.1 (s, 1H, Ar), 8.15 (d, 1H, Ar), 8.25 (s, 1H, Ar), 8.45 (s, 1H, Ar); MS: m/e (ES+) 573 (M+1).

EXAMPLE 127

N-{2-[4-(3-Amino-benzyl)-piperazin-1-yl]-4-chloro-6-methyl-10,10-dioxo-10,11-dihydro-5-oxa-10lambda*6*-thia-dibenzo[a,d]cycloheptene-8-carbonyl}-guanidine trimesylate The title compound was synthesised from Example 127k as described in the synthesis of Example 50. Yield: 0.060 g, (38%); mp: 214-215° C.; ¹H NMR (DMSO-d₆): δ 2.32 (s, 9H, 3CH₃), 2.5 (t, 4H, 2CH₂), 2.7 (s, 3H, CH₃), 3.22 (t, 4H, 2CH₂), 4.4 (s, 2H, CH₂), 5.25 (s, 2H, CH₂), 7.08 (d, 1H, Ar), 7.1 (s, 1H, Ar), 7.12 (d, 1H, Ar), 7.2 (bs, 2H, 2Ar), 7.4 (t, 1H, Ar), 8.12 (s, 1H, Ar), 8.22 (s, 1H, Ar), 8.23-8.6 (bd, 4H, 2NH₂); MS: m/e (ES+) 569 (M+1, free base); analysis: C₃₀H₄₁ClN₆O₁₃S₃, calcd.: C, 42.03; H, 4.82; N, 9.8; Cl, 4.14; S, 14.96; found: C, 41.90; H, 5.17; N, 10.34; Cl, 4.67; S, 14.41%.

EXAMPLE 127k

2-[4-(3-Amino-benzyl)-piperazin-1-yl]-4-chloro-6-methyl-10,10-dioxo-10,11-dihydro-5-oxa-10lambda*6*-thia-dibenzo[a,d]cycloheptene-8-carboxylic acid methyl ester Activated Raney-Ni (0.54 g) in DMF (10 mL) was added to a solution of Example 126k (0.73 g, 1.276 mmol) in DMF (25 mL) and the reaction mixture was subjected to hydrogenation at 30 psi for 2 h. It was filtered through celite, concentrated and purified using flash chromatography (silica gel, 1.5% methanol/chloroform) to obtain the title compound. Yield: 0.54 g, (75.5%); ¹H NMR (CDCl₃): δ 2.5 (t, 4H, 2CH₂), 2.7 (s, 3H, CH₃), 3.22 (t, 4H, 2CH₂), 3.5 (s, 2H, CH₂), 3.7 (bs, 2H, NH₂), 3.9 (s, 3H, OCH₃), 4.65 (s, 2H, CH₂), 6.6 (d, 1H, Ar), 6.7 (s, 1H, Ar), 6.72 (d, 1H, Ar), 6.77 (s, 1H, Ar), 6.9 (s, 1H, Ar), 7.1 (t, 1H, Ar), 8.08 (s, 1H, Ar), 8.5 (s, 1H, Ar); MS: m/e (CI+) 542 (M+1).

EXAMPLE 128

N-[4-Chloro-6-methyl-10,10-dioxo-2-(4-pyridin-3-ylmethyl-piperazin-1-yl)-10,11-dihydro-5-oxa-10lambda*6*-thia-dibenzo[a,d]cycloheptene-8-carbonyl]-guanidine trimesylate The title compound was synthesised from Example 128k as described in the synthesis of Example 50. Yield: 0.166 g, (71.24%); mp: 190-192° C.; ¹H NMR (DMSO-d₆): δ 2.40 (s, 9H, 3CH₃), 2.70 (s, 3H, CH₃), 3.10-3.50 (m, 8H, 4CH₂), 4.55 (s, 2H, CH₂), 5.25 (s, 2H, CH₂), 7.25 (s, 2H, Ar), 7.80 (t, 1H, Ar), 8.20 (s, 1H, Ar), 8.30 (s, 1H, Ar), 8.35 (d, 1H, Ar), 8.90 (d, 1H, Ar), 8.95 (s, 1H, Ar); MS: m/e (ES+) 555 (M+1); analysis: C₂₉H₃₉ClN₆O₁₃S₄.2H₂O, calcd.: C, 39.61; H, 4.93; N, 9.56; Cl, 4.03; S, 14.58; found: C, 39.42; H, 4.51; N, 10.05; Cl, 4.07; S, 14.91%.

EXAMPLE 128k

4-Chloro-6-methyl-10,10-dioxo-2-(4-pyridin-3-ylmethyl-piperazin-1-yl)-10,11-dihydro-5-oxa-10lambda*6*-thia-dibenzo[a,d]cycloheptene-8-carboxylic acid methyl ester 3-Aminomethyl-pyridine (0.66 mL, 6.25 mmol) was added to a solution of Example 102j (0.6 g, 1.25 mmol) in methanol (10 mL), followed by addition of n-tetrabutylammonium iodide (0.010 g, 0.027 mmol) in an atmosphere of nitrogen and sealed in a pressure reactor vessel at 110° C. for 6 h. The reaction mixture was brought to room temperature, concentrated, treated with methanolic HCl solution, and refluxed at 70° C. for 6 h. It was concentrated, treated with water, aqueous sodium bicarbonate solution to neutral pH and the solid that separated was washed with water dried, and purified using flash chromatography (silica gel, methanol/chloroform) to obtain the title compound as a white solid. Yield: 0.160 g, (25%); $^1$H NMR (DMSO-$d_6$): δ 2.70 (s, 3H, $CH_3$), 3.20-3.60 (m, 8H, $4CH_2$), 3.65 (s, 2H, $CH_2$), 3.90 (s, 3H, $OCH_3$), 5.10 (s, 2H, $CH_2$), 7.05 (s, 1H, Ar), 7.20 (s, 1H, Ar), 7.40 (t, 1H, Ar), 7.75 (d, 1H, Ar), 8.10 (s, 1H, Ar), 8.20 (s, 1H, Ar), 8.50 (d, 1H, Ar), 8.55 (s, 1H, Ar); MS: m/e (CI+) 528 (M+1).

EXAMPLE 129

N-[4-Chloro-2-(4-cyclobutyl-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 129k as described in the synthesis of Example 50. Yield: 0.390 g, (65.76%), mp: 275-277° C.; $^1$H NMR (DMSO-$d_6$): δ 1.75-1.85 (m, 2H, $CH_2$), 2.20-2.35 (m, 4H, $2CH_2$), 2.40 (s, 6H, $2CH_3$), 2.70 (s, 3H, $CH_3$), 2.95-3.15 (m, 4H, $2CH_2$), 3.40-3.45 (m, 2H, $CH_2$), 3.80 (m, 1H, CH), 3.95-4.00 (m, 2H, $CH_2$), 5.30 (s, 2H, $CH_2$), 7.30 (s, 2H, Ar), 8.20 (s, 1H, Ar), 8.3 (s, 1H, Ar); MS: m/e (ES+) 518 (M+1); analysis: $C_{26}H_{36}ClN_5O_{10}S_3.H_2O$, calcd: C, 42.88; H, 5.26; N, 9.62; Cl, 4.87; S, 13.21; found: C, 42.35; H, 4.82; N, 9.41; Cl, 4.65; S; 13.47%.

EXAMPLE 129k

4-Chloro-2-(4-cyclobutyl-piperazin-1-yl)-6-methyl-10,10-dioxo-10,11-dihydro-5-oxa-10lambda*6*-thia-dibenzo[a,d]cycloheptene-8-carboxylic acid methyl ester Cyclobutylamine (1 mL, excess) was added to a solution of Example 102j (0.6 g, 1.25 mmol) in methanol (10 mL), followed by the addition of n-tetrabutylammonium iodide (0.01 g, 0.027 mmol) in an atmosphere of nitrogen and sealed in a pressure reactor vessel at 110° C. for 6 h. It was brought to room temperature, concentrated, treated with methanolic HCl solution, and refluxed at 70° C. for 6 h. The reaction mixture was concentrated, treated with water, aqueous sodium bicarbonate solution to neutral pH and the solid that separated was washed with water dried, and purified using flash chromatography (silica gel, methanol/chloroform) to obtain the title compound as a white solid. Yield: 0.410 g, (25%); $^1$H NMR (DMSO-$d_6$): δ 1.60-2.10 (m, 6H, $3CH_2$), 2.40-2.50 (m, 4H, $2CH_2$), 2.80 (m, 1H, CH), 3.20-3.30 (m, 4H, $2CH_2$), 3.90 (s, 3H, $OCH_3$), 4.70 (s, 2H, $CH_2$), 6.80 (s, 1H, Ar), 6.90 (s, 1H, Ar), 8.10 (s, 1H, Ar), 8.50 (s, 1H, Ar); MS: m/e (CI+) 491 (M+1).

EXAMPLE 130

N-[4-Chloro-2-(4-cyclohexyl-piperazin-1-yl)-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 130k as described in the synthesis of Example 50. Yield: 0.205 g, (54.23%), mp: 248-250° C.; $^1$H NMR (DMSO-$d_6$): δ 1.3-2.0 (m, 1H, cyclohexyl), 2.68 (s, 3H, $CH_3$), 2.70 (m, 4H, $2CH_2$), 3.25 (m, 4H, $2CH_2$), 3.98 (s, 3H, $OCH_3$), 4.68 (s, 2H, $CH_2S$), 5.25 (s, 2H, $CH_2$), 6.78 (s, 1H, Ar), 6.9 (s, 1H, Ar), 8.1 (s, 1H, Ar), 8.45 (s, 1H, Ar); MS: m/e (ES+) 547 (M+1); analysis: $C_{28}H_{40}ClN_5O_{10}S_3.H_2O$, calcd.: C, 44.47; H, 5.60; N, 9.26; Cl, 4.69; S, 12.72; found: C, 44.79; H, 5.45; N, 9.21, Cl, 4.36; S, 12.74%.

EXAMPLE 130k

4-Chloro-2-(4-cyclohexyl-piperazin-1-yl)-6-methyl-10,10-dioxo-10,11-dihydro-5-oxa-10lambda*6*-thia-dibenzo[a,d]cycloheptene-8-carboxylic acid methyl ester Cyclohexylamine (0.7 mL 6.25 mmol) was added to a solution of Example 102j (0.6 g, 1.25 mmol) in methanol (10 mL), followed by the addition of n-tetrabutylammonium iodide (0.010 g, 0.027 mmol) in an atmosphere of nitrogen and sealed in a pressure reactor vessel at 110° C. for 6 h. It was processed as described in the synthesis of Example 129k to obtain the title compound as a white solid. Yield: 0.290 g, (45.95%); $^1$H NMR (DMSO-$d_6$): δ 1.10-2.00 (m, 1H, cyclohexyl), 2.70 (s, 3H, $CH_3$), 3.20-3.30 (m, 4H, $2CH_2$), 3.75-3.8 (m, 4H, $2CH_2$), 3.95 (s, 3H, $OCH_3$), 4.75 (s, 2H, $CH_2$), 6.70 (s, 1H, Ar), 6.90 (s, 1H, Ar), 8.05 (s, 1H, Ar), 8.45 (s, 1H, Ar); MS: m/e (CI+) 519 (M+1).

EXAMPLE 131

N-[4-Chloro-6-methyl-10,10-dioxo-2-(4-thiophen-2-ylmethyl-piperazin-1-yl)-10,11-dihydro-5-oxa-10lambda*6*-thia-dibenzo[a,d]cycloheptene-8-carbonyl]-guanidine trimesylate The title compound was synthesised from Example 131k as described in the synthesis of Example 50. Yield: 0.180 g, (66.66%); mp: 265-266° C.; $^1$H NMR (DMSO-$d_6$): δ 2.40 (s, 9H, $3CH_3$), 2.70 (s, 3H, $CH_3$), 3.10-3.20 (m, 4H, $2CH_2$), 3.50-3.55 (m, 2H, $CH_2$), 3.95-4.05 (m, 2H, $CH_2$), 4.70 (s, 2H, $CH_2$), 5.25 (s, 2H, $CH_2$), 7.20 (t, 1H, Ar), 7.25 (s, 2H, Ar), 7.40 (s, 1H, Ar), 7.80 (d, 1H, Ar), 8.20 (s, 1H, Ar), 8.30 (s, 1H, Ar); MS: m/e (ES+) 561 (M+1); analysis: $C_{28}H_{38}ClN_5O_{13}S_5$, calcd.: C, 39.64; H, 4.51; N, 8.25; Cl, 4.18; S, 18.89; found: C, 39.98; H, 3.98; N, 8.28; Cl, 4.36; S, 18.58%.

EXAMPLE 131k

4-Chloro-6-methyl-10,10-dioxo-2-(4-thiophen-2-ylmethyl-piperazin-1-yl)-10,11-dihydro-5-oxa-10lambda*6*-thia-dibenzo[a,d]cycloheptene-8-carboxylic acid methyl ester Thiophenemethylamine (0.5 g 4.41 mmol) was added to a solution of Example 102j (0.6 g, 1.25 mmol) in methanol (10 mL), followed by the addition of n-tetrabutylammonium iodide (0.010 g, 0.027 mmol) in an atmosphere of nitrogen and sealed in a pressure reactor vessel at 110° C. for 6 h. It was processed as described in the synthesis of Example 129k to obtain the title compound as a white solid. Yield: 0.370 g, (55.38%); $^1$H NMR (DMSO-d$_6$): δ 2.55-2.60 (m, 4H, 2CH$_2$), 2.70 (s, 3H, CH$_3$), 3.20-3.55 (m, 4H, 2CH$_2$), 3.75 (s, 3H, CH$_3$), 3.95 (s, 3H, OCH$_3$), 4.65 (s, 2H, CH$_2$), 6.75 (s, 1H, Ar), 6.90 (s, 1H, Ar), 6.95-7.05 (m, 2H, Ar), 7.30 (s, 1H, Ar), 8.10 (s, 1H, Ar), 8.40 (s, 1H, Ar); MS: m/e (CI+) 533 (M+1).

EXAMPLE 132

N-{4-Chloro-2-[4-(2-methoxy-benzyl)-piperazin-1-yl]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 132k as described in the synthesis of Example 50. Yield: 0.245 g, (71.63%); mp: 254-255° C.; $^1$H NMR (DMSO-d$_6$): δ 2.40 (s, 6H, 2CH$_3$), 2.75 (s, 3H, CH$_3$), 3.15-3.25 (m, 4H, 2CH$_2$), 3.45-3.55 (m, 4H, 2CH$_2$), 3.95 (s, 3H, OCH$_3$), 4.40 (s, 2H, CH$_2$), 5.30 (s, 2H, CH$_2$), 7.15 (t, 1H, Ar), 7.20 (d, 1H, Ar), 7.25 (s, 2H, Ar), 7.50-7.55 (m, 2H, Ar), 8.25 (s, 1H, Ar), 8.30 (s, 1H, Ar); MS: m/e (ES+) 585 (M+1); analysis: C$_{30}$H$_{38}$ClN$_5$O$_{11}$S$_3$.H$_2$O calcd.: C, 45.36; H, 5.08; N, 8.82; Cl, 4.46; S, 12.11; found: C, 45.85; H, 4.91; N, 8.65; Cl, 4.69; S, 11.93%.

EXAMPLE 132k

4-Chloro-2-[4-(2-methoxy-benzyl)-piperazin-1-yl]-6-methyl-10,10-dioxo-10,11-dihydro-5-oxa-10lambda*6*-thia-dibenzo[a,d]cycloheptene-8-carboxylic acid methyl ester 2-Methoxybenzylamine (1 mL, 2.28 mmol) was added to a solution of Example 102j (0.6 g, 1.25 mmol) in methanol (10 mL), followed by the addition of n-tetrabutylammonium iodide (0.010 g, 0.02 mmol) in an atmosphere of nitrogen and sealed in a pressure reactor vessel at 110° C. for 6 h. It was processed as described in the synthesis of Example 129k to obtain the title compound as a white solid. Yield: 0.250 g, (35.81%); $^1$H NMR (DMSO-d$_6$): δ 2.60-2.70 (m, 4H, 2CH$_2$), 2.72 (s, 3H, CH$_3$), 3.20-3.30 (m, 4H, 2CH$_2$), 3.70 (s, 3H, CH$_3$), 3.90 (s, 3H, OCH$_3$), 3.95 (s, 3H, CH$_3$), 4.70 (s, 2H, CH$_2$), 6.80 (s, 1H, Ar), 6.90 (s, 1H, Ar), 6.95-7.00 (m, 2H, Ar), 7.30 (t, 1H, Ar), 7.40 (d, 1H, Ar), 8.10 (s, 1H, Ar), 8.50 (s, 1H, Ar); MS: m/e (CI+) 557 (M+1).

EXAMPLE 133

4-Chloro-2-(2-chloro-acetylamino)-6-methyl-10,10-dioxo-10,11-dihydro-5-oxa-10lambda*6*-thia-dibenzo[a,d]cycloheptene-8-carboxylic acid methyl ester Chloro-acetyl chloride (3.3 mL, 40.8 mmol) was added with stirring to a solution of the ester of Example 35j (5 g, 13.6 mmol) in CH$_2$Cl$_2$ (100 mL) at 15° C., followed by addition of pyridine (6.6 mL, 81.6 mmol). The reaction mixture was stirred for 2 h, concentrated, treated with water and the solid that precipitated was filtered and purified by refluxing it with stirring in ethyl acetate for 0.5 h. The solid was filtered and dried to obtain the title compound. Yield: 5.5 g, (90.9%); $^1$H NMR (DMSO-d$_6$): δ 2.7 (s, 3H, CH$_3$), 3.9 (s, 3H, OCH$_3$), 4.31 (s, 2H, CH$_2$), 5.4 (s, 2H, CH$_2$), 7.71 (s, 1H, Ar), 7.98 (s, 1H, Ar), 8.12 (s, 1H, Ar), 8.2 (s, 1H, Ar), 10.77 (s, 1H, Ar); MS: m/e (ES−) 442(M−1).

EXAMPLE 134

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-pyperidin-1-yl-acetamide dimesylate The title compound was synthesised from Example 134k as described in the synthesis of Example 50. Yield: 0.225 g, (76.01%); mp: 178-180° C.; $^1$H NMR (DMSO-d$_6$): δ 1.65-1.85 (m, 6H, piperidinyl), 2.45 (s, 6H, N—CH$_2$, piperidinyl), 2.70 (s, 3H, CH$_3$), 5.50 (s, 2H, CH$_2$), 7.00 (s, 1H, NH), 7.70 (s, 1H, Ar), 7.95 (s, 1H, Ar), 8.25 (s, 1H, Ar), 8.30 (s, 1H, Ar), 8.35-8.45 (m, 4H, guanidinyl); MS: m/e (ES+) 520 (M+1); analysis: C$_{25}$H$_{34}$ClN$_5$O$_{11}$S$_3$.H$_2$O, calcd.: C, 41.12; H, 4.97; N, 9.59; found: C, 41.57; H, 5.33; N, 9.43%.

EXAMPLE 134k

4-Chloro-6-methyl-10,10-dioxo-2-(2-piperidin-1-yl-acetylamino)-10,11-dihydro-5-oxa-10lambda*6*-thia-dibenzo[a,d]cycloheptene-8-carboxylic acid methyl ester Piperidine (0.2 mL, 1.80 mmol) was added to a solution of Example 133 (0.4 g, 0.90 mmol) in dry DMF (10 mL). The reaction mixture was stirred at 110° C. for 5 h, concentrated, treated with water and the solid that precipitated was filtered, washed with water and purified using flash chromatography (silica gel, methanol/chloroform) to obtain the title compound as a white solid. Yield: 0.250 g, (56.30%); $^1$H NMR (CDCl$_3$): δ 1.65-1.70 (m, 6H, piperidinyl), 2.45-2.50 (m, 4H, piperidinyl), 2.70 (s, 3H, CH$_3$), 3.10 (s, 2H, CH$_2$), 3.95 (s, 3H, OCH$_3$), 4.70 (s, 2H, CH$_2$), 7.55 (s, 1H, Ar), 7.80 (s, 1H, Ar), 8.10 (s, 1H, Ar), 8.50 (s, 1H, Ar), 9.50 (s, 1H, NH); MS: m/e (ES+) 493 (M+1).

EXAMPLE 135

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-(2,2,2-trifluoro-ethylamino)-acetamide methane sulfonic acid salt The title compound was synthesised from Example 134k as described in the synthesis of Example 50. Yield: 0.240 g, (77.41%); mp: 163-165° C.; $^1$H NMR (DMSO-d$_6$): δ 2.37 (s, 3H, CH$_3$), 2.70 (s, 3H, CH$_3$), 3.40-3.45 (m, 2H, CH$_2$), 4.05 (s, 2H, CH$_2$), 5.36 (s, 2H, CH$_2$), 8.00 (s, 1H, Ar), 8.05 (s, 1H, Ar), 8.28 (s, 2H, Ar), 8.35-8.45 (m, 4H, guanidinyl), 10.17 (s, 1H, NH); MS: (ES+) m/e 533 (M+1); analysis: C$_{21}$H$_{23}$ClF$_3$N$_5$O$_8$S$_2$, calcd.: C, 40.04; H, 3.68; N, 11.12; S, 10.18; found: C, 39.98; H, 3.60; N, 10.74; S, 10.67%.

EXAMPLE 135k

4-Chloro-6-methyl-10,10-dioxo-2-[2-(2,2,2-trifluoro-ethylamino)-acetylamino]-10,11-dihydro-5-oxa-10lambda*6*-thia-dibenzo[a,d]cycloheptene-8-carboxylic acid methyl ester Anhydrous potassium carbonate was added with stirring to a solution of 2,2,2-trifluoroethyl amine hydrochloride (0.256 g, 1.88 mmol) and Example 133 (0.7 g, 1.57 mmol) in dry DMF (10 mL). The reaction mixture was stirred at 50° C. overnight, concentrated, treated with water and the solid that precipitated was filtered, washed with water and purified using flash chromatography (silica gel, methanol/chloroform) to obtain the title compound as a white solid. Yield: 0.280 g, (35%); $^1$H NMR (DMSO-d$_6$): δ 2.67 (s, 3H, CH$_3$), 3.83-3.87 (m, 2H, CH$_2$), 3.88 (s, 3H, OCH$_3$), 4.66 (s, 2H, CH$_2$), 5.38 (s, 2H, CH$_2$), 7.70 (s, 1H, Ar), 7.88 (s, 1H, Ar), 8.15 (s, 1H, Ar), 8.18 (s, 1H, Ar), 8.28 (t, 1H, NH), 10.26 (s, 1H, NH); MS: m/e (ES+) 506 (M+1).

EXAMPLE 136

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-hydroxy-acetamide methane sulfonic acid salt The title compound was synthesised from Example 136k as described in the synthesis of Example 50. Yield: 0.086 g, (67.18%); mp: 180-182° C.; $^1$H NMR (DMSO-d$_6$): δ 2.37 (s, 3H, CH$_3$), 2.68 (s, 3H, CH$_3$), 4.04 (s, 2H, CH$_2$), 5.31 (s, 2H, CH$_2$), 5.77 (s, 1H, OH), 7.95 (s, 1H, Ar), 7.99 (s, 1H, Ar), 8.30 (s, 1H, Ar), 8.34 (s, 1H, Ar); MS: (ES+) m/e 453 (M+1); analysis: C$_{19}$H$_{21}$ClF$_3$N$_4$O$_9$S$_2$, calcd.: C, 41.57; H, 3.86; N, 10.21; S, 11.68; found: C, 41.25; H, 3.90; N, 10.25; S, 12.04%.

EXAMPLE 136k

4-Chloro-2-(2-hydroxy-acetylamino)-6-methyl-10,10-dioxo-10,11-dihydro-5-oxa-10lambda*6*-thia-dibenzo[a,d]cycloheptene-8-carboxylic acid methyl ester The title compound was isolated as a by-product in the synthesis of Example 135k as a white solid. Yield: 0.1 g, (15%); $^1$H NMR (DMSO-d$_6$): δ 2.68 (s, 3H, CH$_3$), 3.88 (s, 3H, OCH$_3$), 4.02 (s, 2H, CH$_2$), 5.33 (s, 2H, CH$_2$), 5.77 (t, 1H, OH), 7.95 (s, 1H, Ar), 7.99 (s, 1H, Ar), 8.15 (s, 1H, Ar), 8.1 (s, 1H, Ar), 10.13 (s, 1H, NH). MS: m/e (EI+) 425 (M+1).

EXAMPLE 137

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-imidazol-1-yl-acetamide dimesylate The title compound was synthesised from Example 137k as described in the synthesis of Example 50. Yield: 0.3 g, (54%); mp: 252-254° C.; $^1$H NMR (DMSO-d$_6$): δ 2.38 (s, 6H, 2CH$_3$), 2.7 (s, 3H, CH$_3$), 5.28 (s, 2H, CH$_2$), 5.42 (s, 2H, CH$_2$), 7.72 (m, 2H, Ar), 7.76 (s, 1H, Ar), 7.91 (s, 1H, Ar), 8.21 (s, 1H, Ar), 8.26 (s, 1H, Ar), 8.26-8.32 (bd, 4H, 2NH$_2$), 9.12 (s, 1H, Ar), 11.0 (s, 1H, OH); MS: m/e (ES+) 503 (M+1, free base); analysis: C$_{23}$H$_{27}$ClN$_6$O$_{11}$S$_3$, calcd. C, 39.74; H, 3.91; N, 12.09; Cl, 5.10; S, 13.84; found: C, 39.30; H, 4.05; N, 12.68; Cl, 5.65; S, 13.21%.

EXAMPLE 137k

4-Chloro-2-(2-imidazol-1-yl-acetylamino)-6-methyl-10,10-dioxo-10,11-dihydro-5-oxa-10lambda*6*-thia-dibenzo[a,d]cycloheptene-8-carboxylic acid methyl ester Imidazole (0.215 g, 3.16 mmol) was added to a solution of Example 133 (0.7 g, 1.58 mmol) in DMF (15 mL) and the reaction mixture was stirred at 120° C. for 2.5 h. It was concentrated, treated with water and the solid that precipitated was filtered, washed with water and purified using flash chromatography (silica gel, 4% methanol/chloroform) to obtain the title compound as a white solid. Yield: 0.4 g, (53.33%); $^1$H NMR (DMSO-d$_6$): δ 2.66 (s, 3H, CH$_3$), 3.9 (s, 3H, OCH$_3$), 4.97 (s, 2H, CH$_2$), 5.4 (s, 2H, CH$_2$), 6.9 (s, 1H, Ar), 7.2 (s, 1H, Ar), 7.64 (s, 1H, Ar), 7.7 (d, 1H, Ar), 7.9 (d, 1H, Ar), 8.12 (s, 1H, Ar), 8.2 (s, 1H, Ar), 10.72 (bs, 1H, NH); MS: m/e (ES+) 476 (M+1).

EXAMPLE 138

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclopropylamino-acetamide dimesylate The title compound was synthesised from Example 138k as described in the synthesis of Example 50. Yield: 0.375 g, (50%); mp: 188-190° C.; $^1$H NMR (DMSO-d$_6$): δ 0.78 (d, 2H, CH$_2$), 0.87 (bs, 2H, CH$_2$), 2.38 (m, 6H, 2CH$_3$), 2.71 (s, 3H, CH$_3$), 2.82 (m, 1H, CH), 4.1 (s, 2H, CH$_2$), 5.45 (s, 2H, CH$_2$), 7.7 (s, 1H, Ar), 7.9 (s, 1H, Ar), 8.12 (s, 1H, Ar), 8.27 (s, 1H, Ar), 8.34-8.57 (b, 4H, 2NH$_2$), 9.1 (b, 1H, NH), 10.98 (s, 1H, NH), 11.47 (bs, 1H, OH); MS: m/e (ES+) 492 (M+1, free base); analysis: C$_{23}$H$_{30}$ClN$_5$O$_{11}$S$_3$, calcd.: C, 40.38; H, 4.42; N, 10.24; Cl, 5.18; S, 14.06; found C, 40.26; H, 5.01; N, 10.76; Cl, 4.91; S, 13.76%.

EXAMPLE 138k

4-Chloro-2-(2-cyclopropylamino-acetylamino)-6-methyl-10,10-dioxo-10,11-dihydro-5-oxa-10lambda*6*-thia-dibenzo[a,d]cycloheptene-8-carboxylic acid methyl ester Cyclopropyl amine (0.285 ml, 4.067 mmol) was added to a solution of Example 133 (0.6 g, 1.35 mmol) in DMF (15 mL) and the reaction mixture was stirred at 80° C. for 2 h. It was concentrated, treated with water and the solid that precipitated was filtered, washed with water and purified using flash chromatography (silica gel, 2% methanol/chloroform) to obtain the title compound as a white solid. Yield: 0.58 g (92%); $^1$H NMR (CDCl$_3$): δ 0.6 (s, 4H, 2CH$_2$), 2.4 (m, 1H, CH), 2.67 (s, 3H, CH$_3$), 3.6 (s, 2H, CH$_2$), 3.9 (s, 3H, OCH$_3$), 4.7 (s, 2H, CH$_2$), 7.6 (s, 1H, Ar), 7.65 (s, 1H, Ar), 8.1 (s, 1H, Ar), 8.45 (s, 1H, Ar), 9.35 (bs, 1H, NH); MS: m/e (ES+) 465 (M+1).

EXAMPLE 139

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclohexylamino-acetamide dimesylate The title compound was synthesised from Example 139k as described in the synthesis of Example 50. Yield: 0.33 g, (68%); mp: 194-196° C.; $^1$H NMR (DMSO-d$_6$): δ 2.44 (m, 1H, CH), 1.31 (m, 4H, 2CH$_2$), 1.6 (d, 2H, CH$_2$), 1.76 (d, 2H, CH$_2$), 2.01 (d, 2H, CH$_2$), 2.38 (s, 6H, 2CH$_3$), 2.71 (s, 3H, CH$_3$), 4.02 (s, 2H, CH$_2$), 5.45 (s, 2H, CH$_2$), 7.7 (s, 1H, Ar), 7.95 (s, 1H, Ar), 8.18 (s, 1H, Ar), 8.27 (s, 1H, Ar), 8.3-8.5 (b, 4H, 2NH$_2$), 10.98 (s, 1H, OH), 11.45 (bs, 1H, NH); MS: m/e (ES+) 534 (M+1, free base); analysis: C$_{26}$H$_{36}$ClN$_5$O$_{11}$S$_3$H$_2$O, calcd.: C, 43.0; H, 5.0; N, 9.64; Cl, 4.88; S, 13.24; found: C, 41.78; H, 5.0; N, 9.40; Cl, 5.21; S, 12.83%.

EXAMPLE 139k

4-Chloro-2-(2-cyclohexylamino-acetylamino)-6-methyl-10,10-dioxo-10,11-dihydro-5-oxa-10lambda*6*-thia-dibenzo[a,d]cycloheptene-8-carboxylic acid methyl ester Cyclohexyl amine (0.3 ml, 2.7 mmol) was added to a solution of Example 133 (0.4 g, 0.9 mmol) in DMF (10 mL). The reaction mixture was stirred at 80° C. for 3 h, concentrated, treated with water and the solid that precipitated was filtered, washed with water and purified using flash chromatography (silica gel, 2% methanol/chloroform) to obtain the title compound. Yield: 0.365 g (80%); $^1$H NMR (CDCl$_3$): δ 1.21 (q, 2H, CH$_2$), 1.25 (q, 2H, CH$_2$), 1.63 (bs, 2H, CH$_2$), 1.73 (bs, 2H, CH$_2$), 1.88 (bs, 2H, CH$_2$), 2.44 (m, 1H, CH), 2.77 (s, 3H, CH$_3$), 3.4 (s, 2H, CH$_2$), 3.9 (s, 3H, OCH$_3$), 4.7 (s, 2H, CH$_2$), 7.57 (d, 1H, Ar), 7.83 (d, 1H, Ar), 8.1 (s, 1H, Ar), 8.4 (s, 1H, Ar), 9.72 (s, 1H, NH); MS m/e (ES+) 507 (M+1).

EXAMPLE 140

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclopentylamino-acetamide dimesylate The title compound was synthesised from Example 140k as described in the synthesis of Example 50. Yield: 0.260 g, (53%); mp: 190-192° C.; $^1$H NMR (DMSO-d$_6$): δ 1.7 (m, 6H, 3CH$_2$), 1.96 (m, 2H, CH$_2$), 2.39 (s, 6H, 2CH$_3$), 2.69 (s, 3H, CH$_3$), 3.46 (m, 1H, CH), 4.0 (s, 2H, CH$_2$), 5.45 (s, 2H, CH$_2$), 7.7 (s, 1H, Ar), 7.95 (s, 1H, Ar), 8.18 (s, 1H, Ar), 8.27 (s, 1H, Ar), 8.35-8.45 (bs, 4H, 2NH$_2$), 10.98 (s, 1H, OH), 11.47 (s, 1H, NH); MS: m/e (ES+) 520 (M+1, free base); analysis: C$_{25}$H$_{34}$ClN$_5$O$_{11}$S$_3$.H$_2$O, calcd.: C, 42.16; H, 4.81; N, 9.83; Cl, 4.98; S, 13.50; found: C, 40.54; H, 5.01; N, 9.55; C, 14.61; S, 12.83%.

EXAMPLE 140k

4-Chloro-2-(2-cyclopentylamino-acetylamino)-6-methyl-10,10-dioxo-10,11-dihydro-5-oxa-10lambda*6*-thia-dibenzo[a,d]cycloheptene-8-carboxylic acid methyl ester Cyclopentyl amine (0.27 ml, 2.7 mmol) was added to a solution of Example 133 (0.4 g, 0.9 mmol) in DMF (10 mL). The reaction mixture was processed as described in the synthesis of Example 139k to obtain the title compound. Yield: 0.37 g, (83%); $^1$H NMR (CDCl$_3$): δ 1.38 (m, 2H, CH$_2$), 1.72 (m, 4H, 2CH$_2$), 1.87 (m, 2H, CH$_2$), 2.7 (s, 3H, CH$_3$), 2.96 (s, 1H, NH), 3.15 (m, 1H, CH), 3.38 (s, 2H, CH$_2$), 3.92 (s, 3H, OCH$_3$), 4.7 (s, 2H, CH$_2$), 7.57 (s, 1H, Ar), 7.83 (s, 1H, Ar), 8.1 (s, 1H, Ar), 8.45 (s, 1H, Ar), 9.64 (s, 1H, NH); MS: m/e (ES+) 493 (M+1).

EXAMPLE 141

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-isopropylamino-acetamide dimesylate The title compound was synthesised from Example 141k as described in the synthesis of Example 50. Yield: 0.160 g, (77%); mp: 192-194° C.; $^1$H NMR (DMSO-d$_6$): δ 1.24 (s, 3H, CH$_3$), 1.27 (s, 3H, CH$_3$), 1.79 (m, 1H, CH), 2.37 (s, 6H, 2CH$_3$); 2.71 (s, 3H, CH$_3$), 4.0 (t, 2H, CH$_2$), 5.45 (s, 2H, CH$_2$), 7.7 (s, 1H, Ar), 7.95 (s, 1H, Ar), 8.17 (s, 1H, Ar), 8.27 (s, 1H, Ar), 8.28-8.5 (b, 2H, NH$_2$), 8.87 (b, 2H, NH$_2$), 10.98 (s, 1H, OH), 11.45 (b, 1H, NH); MS: m/e (ES+) 494 (M+1, free base). analysis: C$_{23}$H$_{32}$ClN$_5$O$_{11}$S$_3$, calcd.: C, 40.26; H, 4.70; N, 10.21; Cl, 5.17; S, 14.02; found: C, 40.97; H, 5.28; N, 10.09; Cl, 5.46; S, 13.62%.

EXAMPLE 141k

4-Chloro-2-(2-isopropylamino-acetylamino)-6-methyl-10,10-dioxo-10,11-dihydro-5-oxa-10lambda*6*-thia-dibenzo[a,d]cycloheptene-8-carboxylic acid methyl ester Isopropyl amine (0.77 ml, 9 mmol) was added to a solution of Example 133 (0.4 g, 0.9 mmol) in DMF (10 mL). The reaction mixture was stirred at 80° C. for 2 h, concentrated, treated with water and the solid that precipitated was filtered, washed with water and purified using flash chromatography (silica gel, 2% methanol/chloroform) to obtain the title compound. Yield: 0.172 g, (40%); $^1$H NMR (CDCl$_3$): δ 1.22 (d, 6H, 2CH$_3$), 2.7 (s, 3H, CH$_3$), 2.87 (septet, 1H, CH), 3.38 (s, 2H, CH$_2$), 3.92 (s, 3H, OCH$_3$), 4.71 (s, 2H, CH$_2$), 7.57 (s, 1H, Ar), 7.82 (s, 1H, Ar), 8.1 (s, 1H, Ar), 8.45 (s, 1H, Ar), 9.68 (s, 1H, NH); MS: m/e (ES+) 467 (M+1).

EXAMPLE 142

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-dimethylamino-acetamide dimesylate The title compound was synthesised from Example 142k as described in the synthesis of Example 50. Yield: 0.140 g, (42%); mp: 190-191° C.; $^1$H NMR (DMSO-d$_6$): δ 2.37 (s, 6H, 2CH$_3$), 2.7 (s, 3H, CH$_3$), 2.97 (s, 6H, 2CH$_3$), 4.19 (s, 2H, CH$_2$), 5.45 (s, 2H, CH$_2$), 7.71 (s, 1H, Ar), 7.94 (s, 1H, Ar), 8.18 (s, 1H, Ar), 8.27 (s, 1H, Ar), 8.3-8.5 (b, 4H, 2NH$_2$), 9.83 (b, 1H, NH), 11.03 (s, 1H, OH), 11.46 (bs, 1H, NH); MS m/e (ES+) 480 (M+1, free base); analysis: C$_{22}$H$_{30}$ClN$_5$O$_{11}$S$_3$.0.5H$_2$O, calcd.: C, 39.31; H, 4.50; N, 10.42; Cl, 5.27; S, 14.31; found: C, 38.73; H, 5.10; N, 10.77; Cl, 5.85; S, 13.59%.

EXAMPLE 142k

4-Chloro-2-(2-dimethylamino-acetylamino)-6-methyl-10,10-dioxo-10,11-dihydro-5-oxa-10lambda*6*-thia-dibenzo[a,d]cycloheptene-8-carboxylic acid methyl ester A mixture of Example 133 (0.4 g, 0.9 mmol), dimethylamine.HCl (0.44 g, 5.4 mmol) and potassium carbonate (0.75 g, 5.0 mmol) in 10 mL of dry DMF was stirred at 80° C.

for 2 h. The reaction mixture was filtered and the solid obtained was washed with water. The filtrate was concentrated, treated with water and extracted with chloroform. The organic layer was washed with water, brine, concentrated and purified using flash chromatography (silica gel, 1% methanol/chloroform) to obtain the title compound. Yield: 0.26 g, (63.73%); $^1$H NMR (DMSO-d$_6$): δ 1.96 (s, 6H, 2CH$_3$), 2.17 (s, 2H, CH$_2$), 2.3 (s, 3H, CH$_3$), 3.51 (s, 3H, OCH$_3$), 4.45 (s, 2H, CH$_2$), 7.29 (s, 1H, Ar), 7.55 (s, 1H, Ar), 7.67 (s, 1H, Ar), 7.95 (s, 1H, Ar), 9.26 (s, 1H, NH); MS: m/e (EI+) 451 (M+1).

EXAMPLE 143

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-cycylobutylamino-acetamide dimesylate The title compound was synthesised from Example 143k as described in the synthesis of Example 50. Yield: 0.0131 g, (72%); mp: 190-192° C.; $^1$H NMR (DMSO-d$_6$): δ 1.80 (m, 6H, 3CH$_2$), 2.20 (m, 1H, CH), 2.40 (s, 6H, 2CH$_3$), 2.70 (s, 3H, CH$_3$), 3.88 (t, 2H, CH$_2$), 3.89 (s, 1H, NH), 5.45 (s, 2H, CH$_2$), 7.69 (s, 1H, Ar), 7.93 (s, 1H, Ar), 8.18 (s, 1H, Ar), 8.27 (s, 1H, Ar), 8.30-8.50 (s, 4H, guanidinyl); MS: m/e (ES+) 506 (M+1); analysis: C$_{24}$H$_{32}$ClN$_5$O$_{11}$S$_3$.2H$_2$O calcd.: C, 39.26; H, 4.94; N, 9.54; Cl, 4.83; S, 13.10; found: C, 38.62; H, 4.38; N, 9.69; Cl, 5.53; S, 13.95%.

EXAMPLE 143k

4-Chloro-2-(2-cyclobutylamino-acetylamino)-6-methyl-10,10-dioxo-10,11-dihydro-5-oxa-10lambda*6*-thia-dibenzo[a,d]cycloheptene-8-carboxylic acid methyl ester Cyclobutylamine (0.192 g, 2.7 mmol) was added to a solution of Example 133 (0.600 g, 1.3 mmol) in DMF (1 mL). The reaction mixture was stirred at 120° C. for 4 h, concentrated, treated with water and the solid that precipitated was filtered, washed with water and purified using flash chromatography (silica gel, 3-4% methanol/chloroform) to obtain the title compound. Yield: 0.450 g, (66.6%); $^1$H NMR (CDCl$_3$-d$_6$): δ 1.80 (m, 6H, 3CH$_2$), 1.94 (t, 3H, CH$_3$), 2.2 (t, 1H, CH), 2.9 (s, 3H, CH$_3$), 3.3 (s, 2H, CH$_2$), 3.9 (s, 3H, CH$_3$), 4.7 (s, 2H, CH$_2$), 7.5 (s, 1H, Ar), 7.8 (s, 1H, Ar), 8.4 (s, 1H, Ar), 9.5 (s, 1H, Ar); MS: m/e (ES+) 423 (M+1).

EXAMPLE 144

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-morpholin-4-yl-acetamide dimesylate The title compound was synthesised from Example 144k as described in the synthesis of Example 50. Yield: 0.06 g, (21%); mp: 188-190° C.; $^1$H NMR (DMSO-d$_6$): δ 2.37 (s, 6H, 2CH$_3$), 2.72 (s, 3H, CH$_3$), 3.7 (t, 4H, 2CH$_2$), 3.9 (d, 4H, 2CH$_2$), 4.28 (s, 2H, CH$_2$), 5.42 (s, 2H, CH$_2$), 7.7 (d, 1H, Ar), 7.91 (d, 1H, Ar), 8.18 (s, 1H, Ar), 8.28 (s, 1H, Ar), 8.35 (s, 2H, NH$_2$), 8.55 (s, 1H, Ar), 11.06 (s, 1H, OH), 11.45 (s, 1H, OH); MS: m/e (ES+) 714 (M+); analysis: C$_{24}$H$_{32}$ClN$_5$O$_{12}$S$_3$ calcd.; C, 40.36; H, 4.52; N, 9.81; Cl, 4.96; S, 13.47; found: C, 39.98; H, 4.79; N, 10.09; Cl, 4.99; S, 13.64%.

EXAMPLE 144k

4-Chloro-6-methyl-2-(2-morpholin-4-yl-acetylamino)-10,10-dioxo-10,11-dihydro-5-oxa-10lambda*6*-thia-dibenzo[a,d]cycloheptene-8-carboxylic acid methyl ester Morpholine (0.235 mL, 2.7 mmol) was added to a solution of Example 133 (0.6 g, 1.3 mmol) in DMF (8 mL). The reaction mixture was stirred at 120° C. for 4 h, concentrated, treated with water and the solid that precipitated was filtered, washed with water and purified using flash chromatography (silica gel, 1% methanol/chloroform) to obtain the title compound. Yield: 0.57 g, (85%); $^1$H NMR (DMSO-d$_6$): δ 2.7 (s, 3H, CH$_3$), 3.2 (s, 2H, CH$_2$), 3.7 (t, 4H, 2CH$_2$), 3.9 (s, 2H, CH$_2$), 4.28 (s, 2H, CH$_2$), 5.35 (s, 2H, CH$_2$), 7.82 (d, 1H, Ar), 8.0 (s, 1H, Ar), 8.12 (s, 1H, Ar), 8.2 (s, 1H, Ar); MS: m/e (CI+) 495 (M+1).

EXAMPLE 145

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-[4-(3-trifluoromethyl-phenyl)-piperazin-1-yl]-acetamide dimesylate The title compound was synthesised from Example 145k as described in the synthesis of Example 50. Yield: 0.225 g, (43%); mp: 222° C.; $^1$H NMR (DMSO-d$_6$): δ 2.6 (s, 6H, 2CH$_3$), 2.7 (s, 3H, CH$_3$), 3.25-3.31 (bs, 4H, 2CH$_2$), 3.61 (s, 2H, CH$_2$), 3.96 (s, 2H, CH$_2$), 4.3 (s, 2H, CH$_2$), 5.45 (s, 2H, CH$_2$), 7.17 (d, 1H, Ar), 7.29 (s, 1H, Ar), 7.32 (s, 1H, Ar), 7.47 (t, 1H, Ar), 7.72 (s, 1H, Ar), 7.96 (s, 1H, Ar), 8.17 (s, 1H, Ar), 8.26 (s, 1H, Ar), 8.25 (s, 2H, NH$_2$), 8.55 (s, 2H, NH$_2$), 10.3 (s, 1H, NH), 11.07 (s, 1H, OH), 11.45 (s, 1H, OH); MS: m/e (ES+) 665 (M+); analysis: C$_{31}$H$_{40}$ClF$_3$N$_6$O$_{11}$S$_3$.H$_2$O calcd.: C, 42.54; H, 4.38; N, 9.60; Cl, 4.05; S, 10.99; found: C, 42.37; H, 3.73; N, 9.75; Cl, 4.31; S, 11.03%.

EXAMPLE 145k

4-Chloro-6-methyl-10,10-dioxo-2-{2-[4-(3-trifluoromethyl-phenyl)-piperazin-1-yl]-acetylamino}-10,11-dihydro-5-oxa-10lambda*6*-thia-dibenzo[a,d] cycloheptene-8-carboxylic acid methyl ester 1-(3-Trifluoromethyl-phenyl)-piperazine (0.518 mL, 2.72 mmol) was reacted with Example 133 (0.4 g, 0.99 mmol) as described in the synthesis of Example 134 to obtain the title compound. Yield: 0.401 g, (70%); $^1$H NMR (DMSO-d$_6$): δ 2.87 (s, 7H, CH$_3$, 2CH$_2$), 3.25-3.31 (bs, 4H, 2CH$_2$), 3.88 (s, 2H, CH$_2$), 5.34 (s, 2H, CH$_2$), 7.08 (d, 1H, Ar), 7.85 (s, 1H, Ar), 7.98 (s, 1H, Ar), 8.18 (s, 1H, Ar), 8.33 (s, 1H, Ar), 10.2 (s, 1H, NH); MS: m/e (ES+) 638 (M+).

EXAMPLE 146

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methylamino-acetamide dimesylate The title compound was synthesised from Example 146k as described in the synthesis of Example 50. Yield: 0.02 g, (32%); mp: 188-190° C.; $^1$H NMR (DMSO-d$_6$): δ 2.33 (s, 6H, 2CH$_3$), 2.58 (s, 3H, CH$_3$), 2.70 (s, 3H, CH$_3$), 3.97 (s, 2H, CH$_2$), 5.39 (s, 2H, CH$_2$), 7.69 (s, 1H, Ar), 7.91 (s, 1H, Ar), 8.15 (s, 1H, Ar), 8.26 (s, 1H, Ar), 8.3 (complex, 4H, 2NH$_2$), 10.91 (s, 1H, OH), 11.38 (s, 1H, OH); MS: m/e (ES+) 466 (M+, free base); analysis: C$_{21}$H$_{32}$ClN$_5$O$_{13}$S$_3$ calcd.: C, 36.34; H, 4.65; N, 10.09; found: C, 36.86; H, 4.07; N, 9.84%.

EXAMPLE 146k

4-Chloro-6-methyl-2-(2-methylamino-acetylamino)-10,10-dioxo-10,11-dihydro-5-oxa-10lambda*6*-thia-dibenzo[a,d]cycloheptene-8-carboxylic acid methyl ester Methyl amine hydrochloride (0.235 g, 3.51 mmol) was reacted with Example 133 (0.26 g, 0.58 mmol) as described in the synthesis of Example 134 to obtain the title compound. Yield: 0.04 g, (20%); $^1$H NMR (CDCl$_3$+DMSO-d$_6$): δ 2.21 (s, 3H, CH$_3$), 2.42 (s, 3H, CH$_3$), 3.12 (s, 2H, CH$_2$), 3.64 (s, 3H, CH$_3$), 4.52 (s, 2H, CH$_2$), 7.38 (d, 1H, Ar), 7.66 (d, 1H, Ar), 7.79 (s, 1H, Ar), 8.10 (s, 1H, Ar); MS: m/e (CI+) 438 (M+).

EXAMPLE 147

N-(4-Chloro-8-guanidinocarbonyl-6-methyl-10,10-dioxo-10,11-dihydro-5-oxa-10lambda*6*-thia-dibenzo[a,d]-cyclohepten-2-yl)-2-pyrrolidine-1-yl-acetamide dimesylate The title compound was synthesised from Example 147k as described in the synthesis of Example 50. Yield: 0.055 g, (81%); mp: 190-192° C.; $^1$H NMR (DMSO-d$_6$): δ 2.00 (m, 4H, 2CH$_2$), 2.40 (s, 6H, 2CH$_3$), 2.70 (s, 3H, CH$_3$), 3.20 (m, 4H, 2CH$_2$), 4.30 (s, 2H, CH$_2$), 5.5 (s, 2H, CH$_2$), 7.70 (s, 1H, Ar), 7.90 (s, 1H, Ar), 8.20 (s, 1H, Ar), 8.30 (s, 1H, Ar), 8.40-8.50 (m, 4H, guanidinyl); MS: m/e (ES+) 506 (M+1); analysis: C$_{24}$H$_{32}$ClN$_5$O$_1$S$_3$.H$_2$O, calcd.: C, 40.23; H, 4.78; N, 9.78; Cl, 4.78; S, 13.43; found: C, 40.13; H, 4.62; N, 9.50; Cl, 5.75; S, 12.82%.

EXAMPLE 147k

4-Chloro-6-methyl-10,10-dioxo-2-(2-pyrrolidin-1-yl-acetylamino)-10,11-dihydro-5-oxa-10lambda*6*-thia-dibenzo[a,d]cycloheptene-8-carboxylic acid methyl ester Example 133 (1 g, 2.25 mmol) in dry DMF (20 mL) was reacted with pyrollidine (0.4 mL, 4.5 mmol) in an atmosphere of nitrogen for 1 h at 90° C. The reaction mixture was concentrated, treated with ice cold water resulting in the precipitation of a brown solid. It was filtered and purified using flash chromatography (silica gel, methanol/chloroform) to obtain the title compound as a white solid. Yield: 0.890 g, (98%); $^1$H NMR (CDCl$_3$): δ 1.93 (t, 4H, 2CH$_2$), 2.69 (s, 3H, CH$_3$), 2.87 (t, 4H, 2CH$_2$), 3.50 (s, 2H, CH$_2$), 3.91 (s, 3H, OCH$_3$), 4.71 (s, 2H, CH$_2$), 7.60 (s, 1H, Ar), 7.84 (s, 1H, Ar), 8.08 (s, 1H, Ar), 8.45 (s, 1H, Ar), 9.69 (bs, 1H, NH); MS: m/e (ES+) 478 (M+1).

EXAMPLE 148

N-{2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carbonyl}-guanidine, methane sulfonic acid salt The title compound was synthesised from Example 148k as described in the synthesis of Example 50. Yield: 0.140 g, (67%); mp: 263-265° C.; $^1$H NMR (DMSO-d$_6$): δ 2.35 (s, 3H, CH$_3$), 2.70 (s, 3H, CH$_3$), 3.40 (t, 4H, 2CH$_2$), 3.60 (t, 4H, 2CH$_2$), 5.20 (s, 2H, CH$_2$), 6.80 (s, 1H, Ar), 6.90 (s, 1H, Ar), 8.15 (s, 1H, Ar), 8.30 (s, 1H, Ar), 8.40-8.60 (m, 4H, guanidinyl); MS: m/e (ES+) 483 (M+1); analysis: C$_{21}$H$_{27}$ClN$_4$O$_9$S$_2$, calcd.: C, 43.53; H, 4.70; N, 9.68; Cl, 6.12; S, 11.07; found: C, 44.26; H, 4.37; N, 7.37; Cl, 6.54; S, 11.30%.

EXAMPLE 148k

2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carboxylic acid methyl ester Ethylene oxide (40 mL) was added to a mixture of the ester of Example 35j (1 g, 2.72 mmol), acetic acid (15 mL) and water (15 mL) at 0-5° C. THF (2 mL) was added and the reaction mixture was stirred at 0-5° C. for 4 h and then left for overnight at room temperature. It was treated with water and aqueous Na$_2$CO$_3$ solution to neutral pH followed by extraction with ethyl acetate. The organic layer was washed with water, brine, dried, concentrated and purified using flash chromatography (silica gel) to obtain the title compound. Yield: 0.9 g, (73%); $^1$H NMR (DMSO-d$_6$): δ 2.8 (s, 3H, CH$_3$), 3.6 (t, 4H, 2CH$_2$), 3.7, (t, 4H, 2CH$_2$), 3.9, (s, 3H, OCH$_3$), 5.2, (s, 2H, CH$_2$) 6.9, (s, 2H, Ar), 8.2 (s, 2H, Ar); MS: m/e (CI+) 455 (M+1).

EXAMPLE 149

N-(2-Amino-4-chloro-6,11,11-trimethyl-10,10-dioxo-10,11-dihydro-5-oxa-10lambda*6*-thia-dibenzo[a,d]cycloheptene-8-carbonyl)-guanidine dimesylate The title compound was synthesised from Example 149k as described in the synthesis of Example 50. Yield: 0.140 g, (45.16%); mp: 205-206° C.; $^1$H NMR (DMSO-d$_6$): δ 1.84 (s, 6H, 2CH$_3$), 2.38 (s, 6H, 2CH$_3$), 2.68 (s, 3H, CH$_3$), 6.73 (s, 2H, Ar), 8.13 (s, 1H, Ar), 8.32 (s, 1H, Ar), 8.45-8.50 (m, 4H, guanidinyl); MS: m/e (ES+) 422 (M+1); analysis: C$_{21}$H$_{23}$ClF$_3$N$_5$O$_8$S$_2$.0.5H$_2$O, calcd.: C, 39.04; H, 4.42; N, 9.11; found: C, 38.26; H, 4.41; N, 9.01%.

EXAMPLE 149k

2-Amino-4-chloro-6,11,11-trimethyl-10,10-dioxo-10,11-dihydro-5-oxa-10lambda*6*-thia-dibenzo[a,d]cycloheptene-8-carboxylic acid methyl ester Sodium hydride was added in small portions to a chilled solution of the ester of Example 28i (0.5 g, 1.41 mmol) in dry DMF (10 mL). The reaction mixture was stirred for 15 min, treated with methyl iodide and stirred for 2.5 h. It was subsequently treated with methanol (1 mL), concentrated, treated with water and the solid that precipitated was filtered, washed with water and dried. This solid was subjected to nitration using con. HNO$_3$ (15 mL) and con. H$_2$SO$_4$ (1.5 mL) as described in the synthesis of Example 32j. A solution of the nitro compound in DMF was subjected to reduction as described in the synthesis of Example 35j. The crude obtained was purified using flash chromatography (silica gel, ethyl acetate/pet ether) to obtain the title compound as a white solid. Yield: 0.228 g, (43.93%); $^1$H NMR (DMSO-d$_6$): δ 1.85 (s, 6H, 2CH$_3$), 2.70 (s, 3H, CH$_3$), 3.90 (s, 3H, OCH$_3$), 5.65 (s, 2H, CH$_2$), 6.70 (s, 2H, Ar), 8.10 (s, 1H, Ar), 8.30 (s, 1H, Ar). MS: m/e (EI+) 395 (M+1).

EXAMPLE 150

N-(4-Chloro-8-guanidinocarbonyl-6-methyl-10,10-dioxo-10,11-dihydro-5-oxa-10-lambda*6*-thia-dibenzo[a,d]cyclohepten-2-yl)-2-cyclopropylamino-N-(2-pyrrolidin-1-yl-ethyl)-acetamide trimesylate The title compound was synthesised from Example 150k as described in the synthesis of Example 50. Yield: 0.055 g, (39.28%); mp: 150-152° C., $^1$H NMR (DMSO-$d_6$): δ 0.67-0.70 (m, 2H, $CH_2$), 0.80-0.82 (m, 2H, $CH_2$), 2.03-2.10 (m, 4H, $2CH_2$), 2.41 (s, 9H, $3CH_3$), 2.63-2.65 (m, 1H, CH), 2.72 (s, 3H, $CH_3$), 3.11-3.18 (m, 2H, $CH_2$), 3.33-3.36 (m, 2H, $CH_2$), 3.70 (m, 2H, $CH_2$), 4.08 (s, 2H, $CH_2$), 5.40 (s, 2H, $CH_2$), 7.02 (s, 1H, NH), 7.86 (s, 1H, Ar), 7.97 (s, 1H, Ar), 8.24 (s, 1H, Ar), 8.30 (s, 1H, Ar), 8.35-8.50 (m, 4H, NH); MS: m/e (ES+) 589 (M+1); analysis: $C_{30}H_{45}ClN_6O_{14}S_4$, calcd.: C, 41.07; H, 5.17; N, 9.58; found: C, 41.21; H, 5.51; N, 9.23%.

EXAMPLE 150k

4-Chloro-2-[(2-cyclopropylamino-acetyl)-(pyrrolidine-1 yl-ethyl)-amino]-6-methyl-10,10-dioxo-10,11-dihydro-5-oxa-10lambda*6*-thia-dibenzo[a,d]-cycloheptene-8-carboxylic acid methylester Cyclopropyl amine (0.38 mL, 5.54 mmol) was added to a solution of Example 162 (0.3 g, 0.55 mmol prepared in situ) and the reaction mixture was stirred at 50° for 1.5 h. It was treated with water and extracted with chloroform. The organic layer was washed with water, brine, dried, concentrated and purified using flash chromatography (silica gel, methanol/chloroform) to obtain the title compound as a white solid. Yield: 0.105 g, (35%); $^1$H NMR (DMSO-$d_6$): δ 0.70 (s, 4H, $2CH_2$), 1.90-2 (m, 4H, $2CH_2$), 2.55 (m, 1H, CH), 2.70 (s, 3H, $CH_3$), 3.20-3.30 (m, 4H, $2CH_2$), 3.70 (s, 2H, $CH_2$), 3.90 (s, 3H, $OCH_3$), 4.08 (s, 2H, $CH_2$), 5.40 (s, 2H, $CH_2$), 7.95 (s, 1H, Ar), 8.25 (s, 1H, Ar), 8.30 (s, 2H, Ar); MS: m/e (ES+) 562 (M+1).

EXAMPLE 151

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-(4-methyl-piperazin-1-yl)-acetamide dimesylate The title compound was synthesised from Example 151k as described in the synthesis of Example 50. Yield: 0.150 g, (60%); $^1$H NMR (DMSO-$d_6$): δ 2.40 (s, 6H, $2CH_3$), 2.70 (s, 3H, $CH_3$), 2.90 (s, 3H, $CH_3$), 3.10 (t, 4H, $2CH_2$), 3.20 (s, 2H, $CH_2$), (3.30 (t, 4H, $2CH_2$), 5.40 (s, 2H, $CH_2$), 7.80 (s, 1H, Ar), 8.0 (s, 1H, Ar), 8.10 (s, 1H, Ar), 8.20 (s, 1H, Ar), 8.30 (s, 1H, Ar), 8.40-8.70 (m, 4H, guanidinyl); MS: m/e (ES+) 535 (M+1); analysis: $C_{25}H_{35}ClN_6O_{11}S_3$, calcd.: C, 40.29; H, 5.00; N, 11.28; Cl, 4.76; S, 12.91; found: C, 39.59; H, 5.06; N, 11.28; Cl, 4.65; S, 13.06%.

EXAMPLE 151k

4-Chloro-6-methyl-2-[2-(4-methyl-piperazin-1-yl)-acetylamino]10,10-dioxo-10,11-dihydro-5-oxa-10lambda*6*-thia-dibenzo[a,d]cycloheptene-8-carboxylic acid methyl ester N-Methyl piperazine (0.140 g, 0.675 mmol) was added to a solution of Example 133 (0.3 g, 1 mmol) in DMF (1 mL) and refluxed for 1.5 h. The reaction mixture was concentrated, treated with water and filtered to obtain the crude title compound, which was purified using flash chromatography (silica gel). Yield: 0.237 g, (70%); $^1$H NMR (DMSO-$d_6$): δ 2.2 (s, 3H, $CH_3$), 2.4 (s, 4H, $2CH_2$), 2.8 (s, 4H, $2CH_2$), 3.2 (s, 2H, $CH_2$), 3.9 (s, 3H, $CH_3$), 5.2 (s, 2H, $CH_2$), 7.8 (s 1H, Ar), 7.9 (s, 1H, Ar), 8.2 (s, 1H, Ar); MS: m/e (ES+) 508 (M+1).

EXAMPLE 152

N-{4-Chloro-6-methyl-10,10-dioxo-2-[4-(tetrahydro-furan-2-ylmethyl)-piperazin-1-yl]-10,11-dihydro-5-oxa-10lambda*6*-thia-dibenzo[a,d]cycloheptene-8-carbonyl}-guanidine dimesylate The title compound was synthesised from Example 152k as described in the synthesis of Example 50. Yield: 0.190 g, (45%); mp: 257-258° C.; $^1$H NMR (DMSO-$D_6$): δ 1.6 (m, 2H, $CH_2$), 1.9 (m, 2H, $CH_2$), 2.1 (m, 1H, CH), 2.35 (s, 6H, $2CH_3$), 2.7 (s, 3H, $CH_3$), 3.2 (m, 6H, $3CH_2$), 3.7 (m, 2H, $CH_2$), 3.9 (m, 2H, $CH_2$), 4.3 (m, 1H, $CH_2$), 5.3 (s 2H, $CH_2$), 7.3 (d, 2H, Ar), 8.15 (s 1H, Ar), 8.25 (s, 1H, Ar), 8.4 (d, 4H, $NH_2$); MS: m/e (ES+) 549 (M+1); analysis: $C_{30}H_{38}ClN_5O_{10}S_3 \cdot H_2O$, calcd.: C, 42.77; H, 5.32; N, 9.24; Cl, 4.68; S, 12.68; found: C, 42.71; H, 5.65; N, 9.57; Cl, 4.36; S, 12.74%.

EXAMPLE 152k

4-Chloro-6-methyl-10,10-dioxo-2-[4-(tetrahydro-furan-2-ylmethyl)-piperazin-1-yl]-10,11-dihydro-5-oxa-10lambda*6*-thia-dibenzo[a,d]cycloheptene-8-carboxylic acid methyl ester Tetrahydrofurfurylamine (0.776 mL, 7.5 mmol) was added to a mixture of Example 102j (0.6 g, 1.25 mmol) and tetrabutylammonium iodide (0.004 g) in methanol (5 mL), under argon, in a pressure reactor vessel heated at 110° C. for 5 h. The reaction mixture was cooled, concentrated, treated with methanolic HCl (15 mL) and refluxed for 4 h. The reaction mixture was cooled, concentrated and extracted with n-butanol. The organic layer was washed with water, brine, dried, concentrated and purified using flash chromatography (silica gel, methanol/chloroform) to obtain the title compound as an off-white solid. Yield: 0.332 g, (51%); $^1$H NMR (DMSO-$d_6$): δ 1.5 (m, 2H, $CH_2$), 1.78 (m, 2H, $CH_2$), 1.92 (m, 2H, $CH_2$), 2.67 (s, 3H, $CH_3$), 3.19 (t, 4H, $2CH_2$), 3.63 (q, 1H, $CH_2$), 3.78 (q, 1H, $CH_2$), 3.9 (s, 3H, $OCH_3$), 3.99 (m, 2H, $CH_2$), 5.17 (s, 2H, $CH_2$), 7.6 (d, 1H, Ar), 7.15 (d, 1H, Ar), 8.11 (s, 1H, Ar), 8.16 (s, 1H, Ar); MS: m/e (ES+) 522 (M+1).

EXAMPLE 153

4-Chloro-2-(3-chloro-propylamino)-6-methyl-10,10-dioxo-10,11-dihydro-5-oxa-10lambda*6*-thia-dibenzo[a,d]cycloheptene-8-carboxylic acid methyl ester Sodiumborohydride (0.31 g, 8.15 mmol) was added in small portions to a solution of chloropropionic acid (1.77 g, 16.3 mmol) in benzene (100 mL)/dry tetrahydrofuran (15 mL) in an atmosphere of nitrogen at 15° C. and stirred for 1 h. It was then treated with the ester of Example 35j (1.0 g, 2.7 mmol) and the reaction mixture was refluxed for 3 h. It was treated with 10% aqueous sodium bicarbonate solution and extracted with ethyl acetate. The organic layer was washed with water, brine, dried, concentrated and crystallizated using ethyl acetate/hexane to obtain the title compound as a white solid. Yield: 0.7 g, (59%); $^1$H NMR (DMSO-d$_6$): δ 2.01 (s, 2H, CH$_2$), 2.65 (s, 3H, CH$_3$), 3.15 (q, 2H, CH$_2$), 3.75 (t, 2H, CH$_2$), 3.92 (s, 3H, OCH$_3$), 5.15 (s, 2H, CH$_2$), 6.3 (t, 1H, NH), 6.65 & 6.79 (s, 2H, Ar), 8.10 (s, 1H, Ar), 8.15 (s, 1H, Ar); MS: m/e (ES+) 445 (M+1).

EXAMPLE 154

N-(2-Amino-4-chloro-6-methyl-10-oxo-10,11-dihydro-5-oxa-10lambda*4*-thia-dibenzo[a,d]cycloheptene-8-carbonyl)-guanidine methane sulfonic acid salt The title compound was synthesised from Example 154d as described in the synthesis of Example 50. Yield: 0.106 g, (32%); mp: 178-179° C.; $^1$H NMR (DMSO-d$_6$): δ 2.3 (s, 3H, CH$_3$), 2.7 (s, 3H, CH$_3$), 4.8 (s, 2H, CH$_2$), 6.8 (d, 2H, Ar), 8.1 (s, 1H, Ar), 8.2 (s, 1H, Ar), 8.35 (s, 2H, NH$_2$), 8.4 (s, 2H, NH$_2$); MS: m/e (ES+) 569(free base); analysis: C$_{17}$H$_{19}$ClN$_4$O$_6$S$_2$.2H$_2$O, calcd.: C, 39.96; H, 4.54; N, 10.96; Cl, 6.94; S, 12.55; found: C, 39.41; H, 4.14; N, 10.61; Cl, 7.17; S, 13.76%.

EXAMPLE 154a

4-Bromo-3-(3-chloro-2-hydroxy-benzylsulfanyl)-5-methyl-benzoic acid methyl ester A solution of tetra-n-butylammonium fluoride (6.12 g, 19 mmol) in tetrahydrofuran (20 mL) was added dropwise to a solution of 4-bromo-3-[2-(tert-butyl-dimethyl-silanyloxy)-3-chloro-benzylsulfanyl]-5-methyl-benzoic acid methyl ester (5 g, 96.9 mmol) in tetrahydrofuran (50 mL) under nitrogen at 5° C. and stirring was continued for 0.5 h. It was concentrated, treated with chilled water and extracted with ethyl acetate. The organic layer was washed with water, brine, dried, concentrated and purified using flash chromatography (silica gel, ethyl acetate/pet ether) to obtain the title compound as a white solid. Yield: 3.0 g, (95%); $^1$H NMR (CDCl$_3$): δ 2.42 (s, 3H, CH$_3$), 3.88 (s, 3H, OCH$_3$), 4.34 (s, 2H, CH$_2$), 6.81 (t, 1H, Ar), 7.29 (t, 2H, Ar), 7.7 (s, 2H, Ar); MS: m/e (EI+) 401 (M+).

EXAMPLE 154b

4-Chloro-6-methyl-1H-5-oxa-10-thia-dibenzo[a,d] cycloheptene-8-carboxylic acid methyl ester Anhydrous potassium carbonate (6.71 g, 48 mmol) was added to a solution of Example 154a (3.9 g, 9.7 mmol) in DMF (200 ml) and the reaction mixture was stirred at 80° C. for 4.5 h. It was concentrated and treated with ethyl acetate, then washed with 10% aqueous HCl, water, brine, dried, concentrated and purified using flash chromatography (silica gel, ethyl acetate/pet ether) to obtain the title compound as a white solid. Yield: 1.2 g (40%); $^1$H NMR (CDCl$_3$): δ 2.64 (s, 3H, CH$_3$), 3.88 (s, 3H, OCH$_3$), 4.2 (s, 2H, CH$_2$), 7.08 (m, 2H, Ar), 7.32 (q, 1H, Ar), 7.6 (s, 1H, Ar), 7.65 (s, 1H, Ar); MS: m/e (EI+) 320 (M+).

EXAMPLE 154c

4-Chloro-6-methyl-2-nitro-10-oxo-10,11-dihydro-5-oxa-10lambda*4*-thia-dibenzo[a,d]cycloheptene-8-carboxylic acid methyl ester Example 154b (0.5 g, 1.5 mmol) was added to a solution of nitric acid (8 ml, 124 mmol) and sulfuric acid (8 mL, 144 mmol) at 0° C. and the reaction mixture was stirred for 1 h. It was slowly poured into ice water and the solid that precipitated was filtered and thoroughly washed with water to obtain the title compound. Yield: 0.59 g (98%); $^1$H NMR (DMSO-d$_6$): δ 2.8 (s, 3H, CH$_3$), 3.9 (s, 3H, OCH$_3$), 4.7 (s, 2H, CH$_2$), 8.10 (s, 1H, Ar), 8.15 (s, 1H, Ar), 8.3 (d, 2H, Ar); MS: m/e (EI+) 381 (M+).

EXAMPLE 154d

2-Amino-4-chloro-6-methyl-10-oxo-10,11-dihydro-5-oxa-10lambda*4*-thia-dibenzo[a,d]cycloheptene-8-carboxylic acid methyl ester A solution of Example 154c (0.59 g, 1.54 mmol) in DMF (60 ml) was subjected to hydrogenation using activated Raney-Ni (0.3 g) at 50 psi for 3 h. It was filtered through a bed of celite, concentrated and purified using flash chromatography (silica gel, methanol/chloroform) to obtain the title compound. Yield: 0.39 g, (71%); $^1$H NMR (DMSO-d$_6$): δ 2.6 (s, 3H, CH$_3$), 3.88 (s, 3H, CH$_3$), 4.65 (q, 2H, CH$_2$), 5.6 (s, 2H, NH$_2$), 6.65 (s, 2H, Ar), 8.0 (s, 1H, Ar), 8.16 (s, 1H, Ar); MS: m/e EI+) 351 (M+).

EXAMPLE 155

N-(6-Methyl-10,10-dioxo-10,11-dihydro-5-oxa-10lambda*6*-thia-11-aza-dibenzo[a,d]cycloheptene-8-carbonyl)-guanidine, methane sulfonic acid salt The title compound was synthesised from Example 155b as described in the synthesis of Example 50. Yield: 0.101 g, (59%); mp: 128-133° C.; $^1$H NMR (DMSO-d$_6$): δ 2.4 (s, 3H, CH$_3$), 2.6 (s, 3H, CH$_3$), 7.1 (m, 1H, Ar), 7.2-7.3 (m, 2H, Ar), 7.5 (m, 1H, Ar), 8.2 (s, 1H, Ar), 8.25 (s, 1H, Ar), 8.3-8.5 (bs, 4H, 2NH$_2$); MS: m/e (ES+) 347 (M+1, free base); analysis: C$_{16}$H$_{18}$N$_4$O$_7$S$_2$.H$_2$O, calcd.: C, 43.43; H, 4.10; N, 12.66; S, 14.49; found: C, 41.32; H, 3.83; N, 11.59; S, 14.06%.

EXAMPLE 155a

4-Bromo-3-(2-hydroxy-phenylsulfamoyl)-5-methyl-benzoic acid methyl ester

A solution of 2-aminophenol (2.5 g, 22.9 mmol) in dry methylene chloride (10 mL) was added to a mixture of 4-bromo-3-chlorosulfonyl-5-methyl-benzoic acid methyl ester (7.18 g, 22.9 mmol) and dry pyridine (10 mL, 124.7 mmol) in methylene chloride (40 mL). The reaction mixture was stirred for 1 h at 10° C. and at room temperature overnight. It was concentrated, treated with 10% HCl (100 mL) and extracted with 1-butanol. The organic layer was washed with water, brine, dried, concentrated, treated with methanolic HCl (60 ml) and refluxed for 3 h. The reaction mixture was concentrated, treated with 10% aqueous sodium bicarbonate solution to alkaline pH and extracted using ethyl acetate. The organic layer was washed with water, brine, dried and purified, using flash chromatography (silica gel, 10% ethyl acetate/pet ether) to obtain the title compound. Yield: 2.2 g, (24%); $^1$H NMR (CDCl$_3$): δ 2.4 (s, 3H, CH$_3$), 3.9 (s, 3H, OCH$_3$), 6.6 (t, 1H, Ar), 6.72 (t, 1H, Ar), 6.74 (d, 1H, Ar), 7.2 (d, 1H, Ar), 7.94 (s, 1H, OH), 7.96 (s, 1H, Ar), 8.5 (s, 1H, Ar); MS: m/e (EI+) 400 (M+1).

EXAMPLE 155b

6-Methyl-10,10-dioxo-10,11-dihydro-5-oxa-10lambda*6*-thia-11-aza-dibenzo[a,d]cycloheptene-8-carboxylic acid methyl ester A mixture of Example 155a (2.0 g, 4.99 mmol) and anhydrous potassium carbonate (1.38 g, 9.99 mmol) in dry DMF (25 mL) was heated at 95° C. for 20 h. The reaction mixture was concentrated treated with water, 10% aqueous HCl solution and extracted with 1-butanol. The organic layer was washed with water, brine, dried, concentrated and purified using flash chromatography (silica gel, 2.5% methanol/chloroform) to obtain the title compound. Yield: 0.9 g, (56.4%) $^1$H NMR (DMSO-$d_6$): δ 2.4 (s, 3H, $CH_3$), 3.9 (s, 3H, $OCH_3$), 7.1 (m, 1H, Ar), 7.2 (m, 2H, Ar), 7.48 (m, 1H, Ar), 8.1 (s, 1H, Ar), 11.1 (s, 1H, NH); MS: m/e (ES+) 320 (M+1).

EXAMPLE 156

N-[4-Chloro-6-methyl-2-(1-methyl-pyrrolidin-2ylideneamino)-10,10-dioxo-10,11-dihydro-5-oxa-10lambda*6*-thia-dibenzo[a,d]cycloheptene-8-carbonyl]-guanidine dimesylate The title compound was synthesised from Example 156k as described in the synthesis of Example 50. Yield: 0.250 g, (65.44%); mp: 210-211° C., $^1$H NMR (DMSO-$d_6$): δ 2.05-2.15 (m, 2H, $CH_2$), 2.40 (s, 6H, $2CH_3$), 2.70 (s, 3H, $CH_3$), 2.90-3.00 (m, 2H, $CH_2$), 3.20 (s, 3H, $CH_3$), 3.35-3.40 (m, 2H, $CH_2$), 5.40 (s, 2H, $CH_2$), 7.55 (s, 1H, Ar), 7.70 (s, 1H, Ar), 8.20 (s, 1H, Ar), 8.30 (s, 1H, Ar) MS: m/e (ES+) 535 (M+1); analysis: $C_{23}H_{30}ClN_5O_{10}S_3.H_2O$, calcd: C, 40.26; H, 4.70; N, 10.20; Cl, 5.17; S, 14.02; found: C, 40.18; H, 4.79; N, 9.81; Cl, 4.76; S, 14.51%.

EXAMPLE 156k

4-Chloro-6-methyl-2-(1-methyl-pyrrolidin-2ylideneamino)-10,10-dioxo-10,11-dihydro-5-oxa-10lambda*6*-thia-dibenzo[a,d]cycloheptene-8-carboxylic acid methyl ester Phosphorous oxychloride (0.205 mL, 13.5 mmol) was added dropwise to a cooled solution of N-methyl pyrrolidone (0.335 mL, 33.5 mmol) in dry acetonitrile (8 mL) and the reaction mixture was stirred for 15 minutes followed by stirring at RT for 1 h. The ester of Example 35j (0.5 g, 1.35 mmol) was added and the reaction mixture was stirred for 2.5 h. Water was added and the pH was adjusted to 8 using an aqueous $NaHCO_3$ solution. The solid that precipitated was filtered washed with water and purified using flash chromatography (silica gel, methanol/chloroform) to obtain the title compound as a white solid. Yield: 0.550 g, (81.96%). $^1$H NMR (DMSO-$d_6$): δ 1.90 (m, 2H, $CH_2$), 2.40 (t, 2H, $CH_2$), 2.70 (s, 3H, $CH_3$), 2.90 (s, 3H, $CH_3$), 3.40 (t, 2H, $CH_2$), 3.90 (s, 3H, $OCH_3$), 5.20 (s, 2H, $CH_2$), 6.95 (s, 2H, Ar), 8.10 (s, 1H, Ar), 8.20 (s, 1H, Ar); MS: m/e (ES+) 449 (M+1).

EXAMPLE 157

2-(4-Benzyl-piperazin-1-yl)-4-chloro-6-methyl-10,10-dioxo-10,11-dihydro-5-oxa-10lambda*6*-thia-dibenzo[a,d]cycloheptene-8-yl-methylene amino guanidine dimesylate Concentrated HCl (0.1 mL) was added to a mixture of Example 157k (0.2 g, 0.4 mmol) and amino guanidine (0.065 g, 0.48 mmol) in dry ethanol (10 mL)/$H_2O$ (0.1 mL), and the reaction mixture was refluxed for 1.2 h. It was concentrated, treated with water and 10% aqueous sodium bicarbonate solution to pH 7.8. The title compound obtained as a solid was filtered, washed with water and dried. Yield: 0.540 g, (57.69%); mp: 198-199° C., $^1$H NMR (DMSO-$d_6$): δ 2.40 (s, 6H, $2CH_3$), 2.75 (s, 3H, $CH_3$), 3.10-3.25 (m, 4H, $2CH_2$), 3.55-3.60 (m, 2H, $CH_2$), 3.90-4.00 (m, 2H, $CH_2$), 4.50 (s, 2H, $CH_2$), 5.20 (s, 2H, $CH_2$), 7.25 (s, 2H, Ar), 7.60-7.65 (m, 5H, Ar), 8.20 (s, 1H, Ar), 8.25 (s, 1H, Ar); MS: m/e (ES+) 553 (M+1); analysis: $C_{29}H_{37}ClN_6O_9S_3.2H_2O$, calcd: C, 44.58; H, 5.29; N, 10.76; Cl, 4.54; S, 12.31; found: C, 44.76; H, 5.38; N, 11.21; Cl, 5.34; S; 12.48%.

EXAMPLE 157k 2-(4-Benzyl-piperazin-1-yl)-4-chloro-6-methyl-10,10-dioxo-10,11-dihydro-5-oxa-10lambda*6*-thia-dibenzo[a,d]cycloheptene-8-carboxaldehyde Borane-THF complex (5.88 mL, 0.9M, 5.11 mmol) was added to a cooled solution of Example 118k (1.75 g, 3.41 mmol) in dry tetrahydrofuran (50 mL) and the reaction mixture was stirred at 0° C. for 3 h in an atmosphere of nitrogen. It was then allowed to stir at 45° C. for 15 h, treated with methanol (10 mL), concentrated, treated with water and extracted with ethyl acetate to obtain the alcohol.

Oxalyl chloride (1.1 eq, 0.9 mL) in $CH_2Cl_2$ was treated with DMSO (0.15 mL, 2.2 eq) and cooled to –60° C. It was treated with the alcohol generated above and allowed to stir for 15 min. TEA (0.64 mL, 5 eq) was added, the reaction mixture was brought to ambient temperature and allowed to stir for 0.5 h. Water was added and extraction carried out using $CHCl_3$. The organic extract was concentrated to obtain the title compound as a white solid. Yield: 0.510 g, (30.17%); $^1$H NMR (DMSO-$d_6$): δ 2.60-2.65 (m, 4H, $2CH_2$), 2.70 (s, 3H, $CH_3$), 3.30-3.35 (m, 4H, $2CH_2$), 3.70 (s, 3H, $OCH_3$), 4.70 (s, 2H, $CH_2$), 6.75 (s, 1H, Ar), 6.90 (s, 1H, Ar), 7.40-7.45 (m, 5H, Ar), 8.00 (s, 1H, Ar), 8.30 (s, 1H, Ar), 9.90 (s, 1H, CHO); MS: m/e (CI+) 497 (M+1).

EXAMPLE 158h 6-methyl-4-nitro-10,10-dioxo-10,11-dihydro-5-oxa-10lambda*6*-thia-dibenzo[a,d]cycloheptene-8-carboxylic acid methylester The title compound was synthesised from 4-bromo-3-mercapto-5-methyl benzoic acid methyl ester (2.8 g, 10.72 mmol) and 2-bromomethyl-6-nitro-phenoxy-tert-butyldimethylsilane (4.08 g, 11.79 mmol) as described in the synthesis of Examples 1f-1i. $^1$H NMR (DMSO-$d_6$): δ 2.35 (s, 3H, $CH_3$), 3.90 (s, 3H, $OCH_3$), 5.5 (s, 2H, $CH_2$), 7.6 (s, 1H, Ar), 7.95 (d, 1H, Ar), 8.10 (d, 1H, Ar), 8.20 (s, 1H, Ar), 8.25 (s, 1H, Ar); MS: m/e (CI+) 363 (M+1).

EXAMPLE 159

N-[4-Amino-6-methyl-10,10-dioxo-10,11-dihydro-5-oxa-10lambda*6*-thia-dibenzo[a,d]cycloheptene-8-carbonyl]-guanidine dimesylate The title compound was synthesised from Example 159k as described in the synthesis of Example 50. Yield: 0.240 g, (89.21%); mp: 255-257° C.; $^1$H NMR (DMSO-$d_6$): δ 2.40 (s, 6H, $2CH_3$), 2.70 (s, 3H, $CH_3$), 5.20 (s, 2H, $CH_2$), 6.95 (d, 1H, Ar), 7.10 (d, 1H, Ar), 7.20 (t, 1H, Ar), 8.20 (s, 1H, Ar), 8.30 (s, 1H, Ar), 8.35-8.55 (m, 4H, guanidinyl); MS: m/e (ES+) 361 (M+1); analysis: $C_{18}H_{24}ClN_4O_{10}S_3$. calcd.: C, 39.12; H, 4.38; N, 10.14; found: C, 38.92; H, 3.82; N, 9.74%.

EXAMPLE 159k

4-Amino-6-methyl-10,10-dioxo-10,11-dihydro-5-oxa-10lambda*6*-thia-dibenzo[a,d]cycloheptene-8-carboxylic acid methylester Raney-Ni (0.5 g) was added to a solution of Example 158 (1.2 g, 3.30 mmol) and subjected to hydrogenation at 35 psi for 1 h. The catalyst was filtered, the filtrate partially concentrated and treated with cold water. The solid that separated was filtered, washed with water and purified using flash chromatography (silica gel, ethyl acetate/pet ether) to obtain the title compound as a white solid. Yield: 0.780 g, (71%); $^1$H NMR (DMSO-$d_6$): δ 2.65 (s, 3H, $CH_3$), 3.90 (s, 3H, $OCH_3$), 5.00 (s, 2H, $CH_2$), 5.20 (s, 2H, $NH_2$), 6.70 (d, 1H, Ar), 6.90 (d, 1H, Ar), 7.10 (t, 1H, Ar), 8.10 (s, 1H, Ar), 8.25 (s, 1H, Ar); MS: m/e (EI+) 333 (M+1).

EXAMPLE 160

4-(2-Chloro-ethylamino)-6-methyl-10,10-dioxo-10,11-dihydro-5-oxa-10lambda*6*-thia-dibenzo[a,d]cycloheptene-8-carboxylic acid methyl ester Sodiumborohydride (0.17 g, 4.49 mmol) was added portionwise to a solution of chloro-acetic acid (0.853 g, 8.99 mmol) in benzene (35 mL) and dry tetrahydrofuran (2 mL) with stirring under nitrogen atmosphere at 15° C. The reaction mixture was stirred for 1 h, treated with Example 159 (0.5 g, 1.49 mmol) and refluxed for 1 h. It was then treated with 10% aqueous sodium bicarbonate solution (15 mL) and extracted with ethyl acetate. The organic layer was washed with water, brine, dried, concentrated and purified using flash chromatography (silica gel, ethyl acetate/hexane) to obtain the title compound as a white solid. Yield: 0.518 g, (95%); $^1$H NMR (DMSO-$d_6$): δ 2.7 (s, 3H, $CH_3$), 3.6 (m, 4H, $2CH_2$), 3.90 (s, 3H, $OCH_3$), 5.15 (s, 2H, $CH_2$), 6.80-6.90 (m, 2H, Ar), 7.26 (t, 1H, Ar), 8.20 (s, 1H, Ar), 8.25 (s, 1H, Ar); MS: m/e (EI+) 395 (M+1).

EXAMPLE 161

N-[6-Methyl-4-(2-morpholin-4-yl-ethylamino)-10,10-dioxo-10,11-dihydro-5-oxa-10lambda*6*-thia-dibenzo[a,d]cycloheptene-8-carbonyl]-guanidine dimesylate The title compound was synthesised from Example 161k as described in the synthesis of Example 50. Yield: (0.190 g, 67.11%); mp: 162-164° C.; $^1$H NMR (DMSO-$d_6$): δ 2.40 (s, 6H, $2CH_3$), 2.60 (t, 2H, $CH_2$), 2.70 (s, 3H, $CH_3$), 3.10-3.20 (m, 4H, $2CH_2$), 3.55-3.65 (m, 4H, $2CH_2$), 4.00-4.10 (m, 2H, $CH_2$), 5.15 (s, 2H, $CH_2$), 6.80 (d, 1H, Ar), 6.95 (d, 1H, Ar), 7.30 (t, 1H, Ar), 8.25 (s, 1H, Ar), 8.30 (s, 1H, Ar), 8.35-8.55 (m, 4H, guanidinyl); MS: m/e (ES+) 553 (M+1); analysis: $C_{29}H_{35}ClN_5O_1S_3 \cdot 2H_2O$. calcd: C, 41.08; H, 5.60; N, 9.98; S, 13.71; found: C, 41.17; H, 5.66; N, 9.74; S, 13.83%.

EXAMPLE 161k

6-Methyl-4-(2-morpholin-4-yl-ethylamino)-10,10-dioxo-10,11-dihydro-5-oxa-10lambda*6*-thia-dibenzo[a,d]cycloheptene-8-carboxylic acid methylester Morpholine (0.2 mL, 2.52 mmol) was added to a solution of Example 160 (0.5 g, 1.26 mmol) in dry dimethylformamide (10 mL) and the reaction mixture was stirred at 110° C. for 3 h. It was concentrated, treated with water and the solid that precipitated was filtered, washed with water, dried and purified using flash chromatography (silica gel, methanol/chloroform) to obtain the title compound as a white solid. Yield: 0.5 g, (88.80%); $^1$H NMR (DMSO-$d_6$): δ 2.35-2.45 (m, 4H, $2CH_2$), 2.60-2.70 (m, 4H, $2CH_2$), 2.80 (s, 3H, $CH_3$), 3.10-3.20 (m, 2H, $CH_2$), 3.55-3.60 (m, 2H, $CH_2$), 3.90 (s, 3H, $OCH_3$), 5.10 (s, 2H, $CH_2$), 6.70-6.85 (m, 2H, Ar), 7.20 (t, 1H, Ar), 8.10 (s, 1H, Ar), 8.25 (s, 1H, Ar); MS: m/e (EI+) 446 (M+1).

EXAMPLE 162

4-Chloro-2-(2-chloroacetyl-2-pyrrolidin-1-yl-ethyl)-amino-6-methyl-10,10-dioxo-10,11-dihydro-5-oxa-10lambda*6*-thia-dibenzo[a,d]cycloheptene-8-carboxylic acid methyl ester Chloro-acetyl chloride (1 mL) was added to Example 72k (0.74 g, 1.59 mmol) and the reaction mixture was stirred for 1 h at 90° C. It was cooled, treated with methanol, chloroform, washed with water, brine, dried, concentrated and purified using flash chromatography (silica gel, methanol/chloroform) to obtain the title compound as a white solid. Yield: 0.7 g, (81%); $^1$H NMR ($CDCl_3$+DMSO-$d_6$): δ 1.90-2.10 (m, 4H, $2CH_2$), 2.70 (s, 3H, $CH_3$), 2.70-2.80 (m, 4H, $2CH_2$), 3.10-3.15 (m, 2H, $CH_2$), 3.75 (s, 3H, $OCH_3$), 3.88 (m, 2H, $CH_2$), 4.69 (s, 2H, $CH_2$), 7.48 (s, 1H, Ar), 7.66 (s, 1H, Ar), 7.91 (s, 1H, Ar), 8.20 (s, 1H, Ar); MS: m/e (EI+) 541 (M+).

EXAMPLE 163

N-{4-Chloro-2-[(3H-imidazol-4-ylmethyl)-amino]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 163k as described in the synthesis of Example 50. Yield: 0.040 g, (34%); mp: 292-294° C.; $^1$H NMR (DMSO-$d_6$): δ 2.4 (s, 6H, $2CH_3$), 2.7 (s, 3H, $CH_3$), 4.7 (d, 2H, $CH_2$), 5.3 (s, 2H, $CH_2$), 6.8 (s, 2H, Ar), 7.1 (t, 1H, Ar), 7.7 (s, 1H, Ar), 8.1 (s, 1H, Ar), 8.3 (s, 1H, Ar), 8.4 (s, 2H, $NH_2$), 8.5 (s, 2H, $NH_2$); MS: m/e (ES−) 570 (M+, monosalt); analysis: $C_{22}H_{27}ClN_6O_{10}S_3 \cdot H_2O$ calcd.: C, 38.57; H, 4.27; N, 12.27; found: C, 38.80; H, 4.17; N, 12.71%.

EXAMPLE 163k

4-Chloro-2-[(3H-imidazol-4-ylmethyl)-amino]-6-methyl-10,10-dioxo-10,11-dihydro -5-oxa-10lambda*6*-thia-dibenzo[a,d]cycloheptene-8-carboxylic acid methyl ester 2-Imidazole carboxyaldehyde (0.07 g, 0.73 mmol) and titanium isopropoxide (0.27 mL, 0.91 mmol) were added to a suspension of Example 35j (0.27 g, 0.73 mmol) in methanol (30 mL) and refluxed for 2 h. The reaction mixture was cooled to 25° C., treated with sodium cyanoborohydride (0.092 g, 1.46 mmol) and stirred for 15 h. It was concentrated, treated water, basified with sodium bicarbonate solution to pH 7.5 and extracted with n-butanol. The organic layer was concentrated and purified using flash chromatography (silica gel, methanol/chloroform) to obtain the title compound. Yield: 0.087 g, (26%); $^1$H NMR (DMSO-d$_6$): δ 2.63 (s, 3H, CH$_3$), 3.89 (s, 3H, OCH$_3$), 4.26 (d, 2H, CH$_2$), 5.12 (s, 2H, CH$_2$), 6.73 (t, 1H, Ar), 6.8 (d, 2H, Ar), 8.09 (s, 1H, Ar), 8.16 (d, 2H, Ar); MS: m/e (ES+) 449 (M+1).

EXAMPLE 164

N-{4-Chloro-6-methyl-2-[(5-methyl-thiophen-2-ylmethyl)-amino]-10,10-dioxo-10,11-dihydro-5-oxa-10lambda*6*-thia-dibenzo[a,d]cycloheptene-8-carbonyl}-guanidine trimesylate The title compound was synthesised from Example 164k as described in the synthesis of Example 50. Yield: 0.018 g, 30%); mp: 230-232° C.; $^1$H NMR (DMSO-d$_6$): δ 2.3 (s, 3H, CH$_3$), 2.35 (s, 3H, CH$_3$), 2.7 (s, 3H, CH$_3$), 4.4 (s, 2H, CH$_2$), 5.2 (s, 2H, CH$_2$), 6.6 (s, 1H, Ar), 6.7 (s, 1H, Ar), 6.8 (d, 1H, Ar), 6.9 (d, 1H, Ar), 8.1 (s, 1H, Ar), 8.3 (s, 1H, Ar), 8.45 (d, 4H, 2NH$_2$); MS: m/e (ES−) 503 (M−1, freebase); analysis: C$_{24}$H$_{29}$ClN$_4$O$_{10}$S$_4$, calcd.: C, 41.35; H, 4.35; N, 8.04; Cl, 5.09; S, 18.29; found: C, 41.87; H, 3.80; N, 8.449; Cl, 5.34; S, 17.84%.

EXAMPLE 164k

4-Chloro-6-methyl-2-[(5-methyl-thiophen-2-ylmethyl)-amino]-10,10-dioxo-10,11-dihydro-5-oxa-10lambda*6*-thia-dibenzo[a,d]cycloheptene-8-carboxylic acid methyl ester 5-Methyl-2-thiophene carboxyaldehyde (0.18 g, 0.6 mmol) and titanium isopropoxide (0.3 mL, 0.16 mmol) were added to a suspension of Example 35j (0.3 g, 0.81 mmol) in methanol (30 mL) and refluxed for 3 h. The reaction mixture was cooled to 25° C., treated with sodium cyanoborohydride (0.06 g, 0.81 mmol) and refluxed for 3 h. It was concentrated, treated with water, aqueous sodium bicarbonate solution and extracted with ethyl acetate. The organic layer was washed with water and brine, dried, concentrated and purified using flash chromatography (silica gel, methanol/chloroform) to obtain the title compound. Yield: 0.03 g, (8%); $^1$H NMR (DMSO-d$_6$): δ 2.40 (s, 3H, CH$_3$), 3.91 (s, 3H, OCH$_3$), 3.94 (d, 2H, CH$_2$), 5.21 (s, 2H, CH$_2$), 6.6 (d, 1H, Ar), 6.71 (d, 1H, Ar), 6.82 (m, 2H, Ar), 8.06 (s, 1H, Ar), 8.20 (s, 1H, Ar); MS: m/e (ES+) 478 (M+1).

EXAMPLE 165

N-{4-Chloro-6-methyl-10,10-dioxo-2-[(pyridin-3-ylmethyl)-amino]-10,11-dihydro-5-oxa-10lambda*6*-thia-dibenzo[a,d]cycloheptene-8-carbonyl}-guanidine dimesylate The title compound was synthesised from Example 165k as described in the synthesis of Example 50. Yield: 0.125 g, (41%); mp: 238° C.; $^1$H NMR (DMSO-d$_6$): δ 2.35 (s, 6H, 2CH$_3$), 2.65 (s, 3H, CH$_3$), 4.5 (s, 2H, CH$_2$), 5.2 (s, 2H, CH$_2$), 6.8 (d, 2H, Ar), 8.0 (t, 1H, Ar), 8.1 (s, 1H, Ar), 8.25 (s, 1H, Ar), 8.3 (s, 2H, NH$_2$), 8.4 (d, 1H, Ar), 8.5 (s, 2H, NH$_2$), 8.8 (d, 1H, Ar), 8.9 (s, 1H, Ar); MS: m/e (ES−) 486.61 (M+1, freebase); analysis: C$_{24}$H$_{28}$ClN$_5$O$_{10}$S$_3$ calcd.: C, 42.51; H, 4.16; N, 10.33; found: C, 42.28; H, 4.53; N, 10.96%.

EXAMPLE 165k

4-Chloro-6-methyl-10,10-dioxo-2-[(pyridin-3-ylmethyl)-amino]-10,11-dihydro-5-oxa-10lambda*6*-thia-dibenzo[a,d]cycloheptene-8-carboxylic acid methyl ester Pyridine-3-carboxyaldehyde (0.1 mL, 1.08 mmol) and p-toluene sulfonic acid (in catalytic amount) were added to a suspension of Example 35j (0.4 g, 1.08 mmol) in benzene (40 mL). The reaction mixture was refluxed using Dean-Stark apparatus for 4 h. It was concentrated, treated with methanol, refluxed for 4 h, and stirred at 25° C. overnight. Sodium cyanoborohydride (0.076 g, 1.2 mmol) was added and the reaction mixture was stirred for 3 h. It was treated with aqueous sodium bicarbonate solution and extracted with ethyl acetate. The organic layer was washed with water, brine, dried, concentrated and purified using flash chromatography (silica gel, methanol/chloroform) to obtain the title compound. Yield: 0.127 g, (25%); $^1$H NMR (DMSO-d$_6$): δ 2.62 (s, 3H, CH$_3$), 3.9 (s, 3H, CH$_3$), 4.33 (d, 2H, CH$_2$), 5.18 (s, 2H, CH$_2$), 6.69 (d, 1H, Ar), 6.8 (d, 1H, Ar), 6.9 (t, 1H, NH), 7.38 (q, 1H, Ar), 7.75 (d, 1H, Ar), 8.1 (s, 1H, Ar), 8.17 (s, 1H, Ar), 8.48 (d, 1H, Ar), 8.6 (s, 1H, Ar).

EXAMPLE 166

N-(10,10-Dioxo-10,11-dihydro-5H-10lambda*6*-thia-5-aza-dibenzo[a,d]cycloheptene-8-carbonyl)-guanidine, methane sulfonic acid salt The title compound was synthesised from Example 166f as described in the synthesis of Example 1. Yield: (50%); mp: 308-310° C.; $^1$H NMR (DMSO-d$_6$): δ 2.35 (s, 3H, CH$_3$SO$_3$H), 4.90 (s, 2H, CH$_2$), 7.15 (t, 1H, Ar), 7.30-7.50 (m, 4H, Ar), 8.00 (d, 1H, Ar), 8.30 (NH$_2$ exchangeable with D$_2$O), 8.50 (s, 1H, Ar), 10.0 (s, NH exchangeable with D$_2$O); MS: m/e (ES−) 329 (M+); IR cm$^{-1}$: 3350-3300, 1700, 1630-1580, 1500, 1360, 1310-1280, 1230, 1130, 1050, 760.

EXAMPLE 166a

1-Bromomethyl-2-nitro-benzene

1-Methyl-2-nitro-benzene was reacted with N-bromosuccinamide as described in the synthesis of Example 1e to obtain the title compound.

EXAMPLE 166b

4-Bromo-3-(2-nitro-benzylsulfanyl)-benzoic acid methyl ester

4-Bromo-3-mercapto-benzoic acid methyl ester was reacted with 1-bromomethyl-2-nitro-benzene as described in the synthesis of Example 1f to obtain the title compound. Yield: (64%); $^1$H NMR (CDCl$_3$): δ 3.90 (s, 3H, OCH$_3$), 4.55

(s, 2H, CH$_2$), 7.40-7.55 (m, 3H, Ar), 7.60 (d, 1H, Ar), 7.70 (d, 1H, Ar), 7.90 (d, 1H, Ar), 8.10 (d, 1H, Ar).

EXAMPLE 166c

4-Bromo-3-(2-nitro-phenylmethanesulfonyl)-benzoic acid methyl ester

The title compound was obtained by treating Example 166b with m-chloroperbenzoic acid as described in the synthesis of Example 1g. $^1$H NMR (CDCl$_3$): δ 3.95 (s, 3H, OCH$_3$), 5.30 (s, 2H, CH$_2$), 7.60 (m, 2H, Ar), 7.90 (d, 1H, Ar), 8.00-8.10 (m, 3H, Ar), 8.50 (s, 1H, Ar).

EXAMPLE 166d 3-(2-Amino-benzylsulfanyl)-4-bromo-benzoic acid methyl ester

Example 166c (0.650 g, 1.7 mmol) was subjected to catalytic reduction as described in the synthesis of Example 35 to obtain the title compound which was purified using flash chromatography (silica gel, EtOAc-PE60-80° C.). Yield: 73.33%; $^1$H NMR (CDCl$_3$): δ 3.90 (s, 3H, OCH$_3$), 4.70 (s, 2H, CH$_2$), 6.65 (t, 1H, Ar), 6.70 (d, 1H, Ar), 6.85 (d, 1H, Ar), 7.10 (t, 1H, Ar) 7.80 (d, 1H, Ar), 8.10 (d, 1H, Ar), 8.60 (s, 1H, Ar).

EXAMPLE 166e 10,10-Dioxo-10,11-dihydro-5H-10lambda*6*-thia-5-aza-dibenzo[a.d]cycloheptene-8-carboxylic acid methyl ester NaH (0.599 g, 24.95 mmol, 50% dispersion in oil) was added in an atmosphere of N$_2$ to a solution of Example 166d (0.320 g, 0.83 mmol) in DMF (10 mL) at 0° C. and the reaction mixture was stirred for 45 min. It was treated with crushed ice to obtain the title compound as a solid, which was filtered, washed with water and dried. Yield: 48%; $^1$H NMR (DMSO-d$_6$): δ 3.90 (s, 3H, OCH$_3$), 4.80 (s, 2H, CH$_2$), 7.10 (t, 1H, Ar), 7.35 (m, 4H, Ar), 8.00 (d, 1H, Ar), 8.40 (s, 1H, Ar), 9.90 (s, 1H, NH).

EXAMPLE 166f 10,10-Dioxo-10,11-dihydro-5H-10lambda*6*-thia-5-aza-dibenzo[a.d]cycloheptene-8-carboxylic acid Example 166d was hydrolysed using NaOH (3 eq) as described in the synthesis of Example 1i. Yield: 93%; $^1$H NMR (DMSO-d$_6$): δ 4.80 (s, 2H, CH$_2$), 7.10 (t, 1H, Ar), 7.30 (d, 1H, Ar), 7.35 (m, 4H, Ar), 7.40 (d, 1H, Ar), 7.90 (d, 1H, Ar), 8.35 (s, 1H, Ar), 9.80 (s, 1H, NH); MS: m/e (EI+) 289 (M+).

EXAMPLE 167

N-(2-Chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 167f as described in the synthesis of Example 1. Yield: (66%); mp: 264-266° C.; $^1$H NMR (DMSO-d$_6$): δ 2.35 (s, 3H, CH$_3$SO$_3$H), 4.95 (s, 2H, CH$_2$), 7.30 (d, 2H, Ar), 7.40 (m, 2H, Ar), 7.60 (s, 1H, Ar), 8.00 (d, 1H, Ar), 8.30-8.40 (NH$_2$ exchangeable with D$_2$O), 8.50 (s, 1H, Ar), 10.10 (s, NH exchangeable with D$_2$O); MS: m/e (ES−) 363 (M+); IR cm$^{-1}$: 3350-3300, 1700, 1600, 1520, 1480, 1310, 1250-1150, 1050, 820.

EXAMPLE 167f

2-Chloro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 2-bromomethyl-4-chloro-1-nitro-benzene as described in the synthesis of Examples 166a-166f. Yield: 58.23%; $^1$H NMR (DMSO-d$_6$): δ 4.90 (s, 2H, CH$_2$), 7.25 (d, 1H, Ar), 7.40 (d, 2H, Ar), 7.60 (s, 1H, Ar), 7.95 (d, 1H, Ar), 8.40 (s, 1H, Ar), 10.0 (s, 1H, NH), 13.0 (s, 1H, COOH); MS: m/e (EI+) 323 (M+).

2-Bromomethyl-4-chloro-1-nitro-benzene was synthesized from 4-chloro-2-methyl-1-nitro-benzene as described in the synthesis of example 166a.

EXAMPLE 168

N-(4-Chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 168f as described in the synthesis of Example 1. Yield: 55%; mp: 266-268° C.; $^1$H NMR (DMSO-d$_6$): δ 2.40 (s, 3H, CH$_3$SO$_3$H), 4.90 (s, 2H, CH$_2$), 7.25 (t, 1H, Ar), 7.40 (d, 1H, Ar), 7.55 (d, 1H, Ar), 7.65 (d, 1H, Ar), 8.10 (d, 1H, Ar), 8.25-8.40 (NH$_2$ exchangeable with D$_2$O), 8.50 (s, 1H, Ar), 9.20 (s, NH exchangeable with D$_2$O); MS: m/e (ES+) 365 (M+); IR cm$^{-1}$: 3350-3300, 3200-3100, 1700, 1600, 1460, 1300, 1250-1150, 1050, 920, 830, 750.

EXAMPLE 168f

4-Chloro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 1-bromomethyl-3-chloro-2-nitro-benzene as described in the synthesis of Examples 166a-166f. Yield: 16.10%; $^1$H NMR (DMSO-d$_6$): δ 4.90 (s, 2H, CH$_2$), 7.25 (t, 1H, Ar), 7.50 (d, 1H, Ar), 7.55 (d, 1H, Ar), 7.70 (d, 1H, Ar), 7.90 (d, 1H, Ar), 8.40 (s, 1H, Ar), 9.0 (s, 1H, NH); MS: m/e (ES−) 323 (M+).

1-Bromomethyl-3-chloro-2-nitro-benzene was synthesized from 1-chloro-3-methyl-2-nitro-benzene as described in the synthesis of Example 166a.

EXAMPLE 169

N-(3-Chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 169f as described in the synthesis of Example 1. Yield: 57.82%; mp: 286-288° C.; $^1$H NMR (DMSO-d$_6$): δ 2.35 (s, 3H, CH$_3$SO$_3$H), 4.90 (s, 2H, CH$_2$), 7.20 (d, 1H, Ar), 7.35 (s, 1H, Ar), 7.50 (m, 2H, Ar), 8.05 (d, 1H, Ar), 8.20-8.40 (NH$_2$ exchangeable with D$_2$O), 8.50 (s, 1H, Ar), 10.10 (s, NH

EXAMPLE 169f

3-Chloro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 1-bromomethyl-4-chloro-2-nitro-benzene as described in the synthesis of Examples 166a-166f. Yield: 8.97%; $^1$H NMR (DMSO-d$_6$): δ 4.90 (s, 2H, CH$_2$), 7.15 (d, 1H, Ar), 7.40 (m, 3H, Ar), 8.00 (d, 1H, Ar), 8.40 (s, 1H, Ar), 9.55 (s, 1H, Ar), 12.80 (s, 1H, COOH); MS: m/e (EI+) 323 (M+).

1-Bromomethyl-4-chloro-2-nitro-benzene was synthesized from 4-chloro-1-methyl-2-nitro-benzene as described in the synthesis of Example 166a.

EXAMPLE 170

N-(1-Chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 170f as described in the synthesis of Example 1. Yield: 61.16%; mp: 328-330° C.; $^1$H NMR (DMSO-d$_6$): δ 2.35 (s, 3H, CH$_3$SO$_3$H), 5.00 (s, 2H, CH$_2$), 7.35 (m, 3H, Ar), 7.55 (d, 1H, Ar), 8.05 (d, 1H, Ar), 8.20-8.40 (NH$_2$ exchangeable with D$_2$O), 8.50 (s, 1H, Ar), 10.20 (s, NH exchangeable with D$_2$O); MS: m/e (ES+) 364 (M+); IR cm$^{-1}$: 3300, 3100-3050, 1720, 1610, 1590, 1470, 1370, 1280, 1250-1150, 1050, 960, 800, 780.

EXAMPLE 170f

1-Chloro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 2-bromomethyl-1-chloro-3-nitro-benzene as described in the synthesis of Examples 166a-166f. Yield: 11.73%; $^1$H NMR (DMSO-d$_6$): δ 4.90 (s, 2H, CH$_2$), 7.40 (m, 3H, Ar), 7.45 (d, 1H, Ar), 8.00 (d, 1H, Ar—H), 8.40 (s1H, Ar—), 10.00 (s, 1H, Ar), 13.0 (s, 1H, COOH); MS: m/e (EI+) 323 (M+).

2-Bromomethyl-1-chloro-3-nitro-benzene was synthesized from 1-chloro-2-methyl-3-nitro-benzene as described in the synthesis of Example 166a.

EXAMPLE 171

N-(3-Fluoro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 171f as described in the synthesis of Example 1. Yield: 58.33%; mp: 300° C.; $^1$H NMR (DMSO-d$_6$): δ 2.35 (s, 3H, CH$_3$SO$_3$H), 4.90 (s, 2H, CH$_2$), 7.00 (t, 1H, Ar), 7.10 (d, 1H, Ar), 7.40-7.50 (m, 2H, Ar), 8.05 (d, 1H, Ar), 8.30-8.45 (NH$_2$ exchangeable with D$_2$O), 8.50 (s, 1H, Ar); MS: m/e (ES−) 348 (M+); IR cm$^{-1}$: 3350, 3400, 1710, 1600, 1500, 1250, 1050, 750.

EXAMPLE 171f

3-Fluoro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 1-bromomethyl-4-fluoro-2-nitro-benzene as described in the synthesis of Examples 166a-166f. Yield: 6.99%; $^1$H NMR (DMSO-d$_6$): δ 4.90 (s, 2H, CH$_2$), 6.90 (m, 1H, Ar), 7.08 (m, 1H, Ar), 7.38 (d, 1H, Ar), 7.48 (t, 1H, Ar), 8.00 (d, 1H, Ar), 8.40 (s, 1H, Ar), 9.90 (s, 1H, NH), 13.00 (s, 1H, COOH); MS: m/e (EI+) 307 (M+).

1-Bromomethyl-4-fluoro-2-nitro-benzene was synthesized from 4-fluoro-1-methyl-2-nitro-benzene as described in the synthesis of Example 166a.

EXAMPLE 172

N-(2-Fluoro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 172f as described in the synthesis of Example 1. Yield: (23.14%); mp: 174-175° C.; $^1$H NMR (DMSO-d$_6$): δ 2.40 (s, 3H, CH$_3$SO$_3$H), 4.90 (s, 2H, CH$_2$), 6.80-7.10 (m, 3H, Ar), 8.10 (d, 1H, Ar), 8.25 (d, 1H, Ar), 8.30-8.35 (NH$_2$ exchangeable with D$_2$O), 8.45 (s, 1H, Ar); MS: m/e (ES+) 348 (M+); IR cm$^{-1}$: 3350, 3200, 1700, 1595, 1500, 1500, 1200, 1050, 775.

EXAMPLE 172f

2-Fluoro-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 2-bromomethyl-4-fluoro-1-nitro-benzene as described in the synthesis of Examples 166a-166f. Yield: 19.39%; $^1$H NMR (DMSO-d$_6$): δ 4.70 (s, 2H, CH$_2$), 6.70 (m, 2H, Ar), 7.40 (m, 1H, Ar), 8.10 (s, 2H, Ar), 8.40 (s, 1H, Ar); MS: m/e (EI+) 307 (M+).

2-Bromomethyl-4-fluoro-1-nitro-benzene was synthesized from 4-fluoro-2-methyl-1-nitro-benzene as described in the synthesis of Example 166a.

EXAMPLE 173

N-(2-Ethanesulfonyl-4-methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 173f as described in the synthesis of Example 1. Yield: 82%; mp: 240-241° C.; $^1$H NMR (DMSO-d$_6$): δ 1.10 (t, 3H, CH$_3$), 2.35 (s, 3H, CH$_3$SO$_3$H), 2.55 (s, 3H, CH$_3$), 3.3 (q, 2H, CH$_2$), 5.10 (s, 2H, CH$_2$), 7.80 (d, 1H, Ar), 7.95 (s, 1H, Ar), 8.10 (d, 1H, Ar), 8.25 (s, 1H, Ar), 8.50 (s, 1H, Ar), 8.55 (NH$_2$ exchangeable with D$_2$O); MS: m/e (ES+) 434 (M+); IR cm$^{-1}$: 3375, 3150, 1750, 1600, 1550, 1275, 1150, 825, 750.

EXAMPLE 173f

2-Ethanesulfonyl-4-methyl-10,10-dioxo-10,11-dihydro-5H-10lambda*6*-thia-5-aza-dibenzo[a.d]cycloheptene-8-carboxylic acid The title compound was synthesised from 4-bromo-3-mercapto-benzoic acid methyl ester and 1-bromomethyl-5-ethanesulfonyl-3-methyl-2-nitro-benzene as described in the synthesis of Examples 166a-166f. Yield: 12.75%; $^1$H NMR (DMSO-$d_6$): δ 1.15 (t, 3H, $CH_3$), 3.30 (q, 2H, $CH_2$), 5.10 (s, 2H, $SO_2CH_2$), 7.70 (d, 1H, Ar), 7.80 (s, 1H, Ar), 7.90 (s, 1H, Ar), 8.05 (d, 1H, Ar), 8.40 (s, 1H, Ar), 8.90 (s, 1H, NH); MS: m/e (EI+) 393 (M+). 1-Bromomethyl-5-ethanesulfonyl-3-methyl-2-nitro-benzene was synthesized from 5-ethanesulfonyl-1,3-dimethyl-2-nitro-benzene as described in the synthesis of Example 166a.

EXAMPLE 174

N-(7-Chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 174f as described in the synthesis of Example 1. Yield: 66%; mp: 212-213° C.; $^1$H NMR (DMSO-$d_6$): δ 2.35 (s, 3H, $CH_3SO_3H$), 4.90 (s, 2H, $CH_2$), 7.15 (t, 1H, Ar), 7.25 (d, 1H, Ar), 7.40-7.50 (m, 2H, Ar), 7.55 (s, 1H, Ar), 8.20 (s, 1H, Ar), 8.40-8.50 ($NH_2$ exchangeable with $D_2O$), 9.15 (NH, exchangeable with $D_2O$); MS: m/e (ES+) 364 (M+); IR $cm^{-1}$: 3350, 3150, 1650, 1575, 1475, 1250-1150, 1050, 990, 750.

EXAMPLE 174f

7-Chloro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 1-bromomethyl-2-nitro-benzene as described in the synthesis of Examples 166a-166f. Yield: 25.9%; $^1$H NMR (DMSO-$d_6$): δ 4.90 (s, 2H, $CH_2$), 7.10 (t, 1H, Ar), 7.25 (s, 1H, Ar), 7.30-7.40 (m, 2H, Ar), 7.55 (s, 1H, Ar), 8.20 (s, 1H, Ar), 9.90 (s, 1H, NH); MS: m/e (EI+) 323 (M+).

EXAMPLE 175

N-(4,7-Dichloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 175f as described in the synthesis of Example 1. Yield: 57.24%; mp: 205-206° C.; $^1$H NMR (DMSO-$d_6$): δ 2.35 (s, 3H, $CH_3SO_3H$), 5.00 (s, 2H, $CH_2$), 7.30 (t, 1H, Ar), 7.50 (d, 1H, Ar), 7.60 (d, 1H, Ar), 7.90 (s, 1H, Ar), 8.25 (s, 1H, Ar), 8.40-8.50 ($NH_2$ exchangeable with $D_2O$), 9.15 (NH, exchangeable with $D_2O$); MS: m/e (EI+) 398 (M+); IR $cm^{-1}$: 3350, 3150, 1725, 1605, 1525, 1475, 1275, 1175, 1050, 790.

EXAMPLE 175f 4,7-Dichloro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 1-bromomethyl-3-chloro-2-nitro-benzene as described in the synthesis of Examples 166a-166f. Yield: (24.31%); $^1$H NMR (DMSO-$d_6$): δ 5.00 (s, 2H, $CH_2$), 7.25 (t, 1H, Ar), 7.46 (d, 1H, Ar), 7.55 (d, 1H, Ar), 7.85 (s, 1H, Ar), 8.35 (s, 1H, Ar—H), 9.10 (s, 1H, NH); MS: m/e (EI+) 357 (M+).

EXAMPLE 176

N-(4-tert-Butyl-7-chloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 176f as described in the synthesis of Example 1. Yield: 48.29%; mp: 258-260° C.; $^1$H NMR (DMSO-$d_6$): δ 1.30 (s, 9H, $3CH_3$), 2.40 (s, 3H, $CH_3SO_3H$), 4.80 (s, 2H, $CH_2$), 7.55 (d, 1H, Ar), 7.65 (t, 1H, Ar), 7.80 (d, 1H, Ar), 8.10 (s, 1H, Ar), 8.25 (s, 1H, Ar), 8.45-8.5 ($NH_2$ exchangeable with $D_2O$); MS: m/e (ES−) 419 (M+); IR $cm^{-1}$: 3400, 1725, 1350, 1250-1150, 1050, 850.

EXAMPLE 176f 4-tert-Butyl-7-chloro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 1-bromomethyl-3-tert-butyl-2-nitro-benzene as described in the synthesis of Examples 166a-166f; Yield: 6.91%; $^1$H NMR (DMSO-$d_6$): δ 1.30 (s, 9H, $3CH_3$), 4.70 (s, 2H, $CH_2$), 7.50 (d, 1H, Ar), 7.60 (d, 1H, Ar), 7.25 (d, 1H, Ar), 7.90 (s, 1H, Ar), 8.05 (s, 1H, Ar); MS: m/e (EI+) 379 (M+).

1-Bromomethyl-3-tert-butyl-2-nitro-benzene was synthesized from 1-methyl-3-tert-butyl-2-nitro-benzene as described in the synthesis of Example 50a.

EXAMPLE 177

N-(7-Chloro-4-methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 177f as described in the synthesis of Example 1. Yield: 57.14%; mp: 284-285° C.; $^1$H NMR (DMSO-$d_6$): δ 2.35 (s, 3H, $CH_3SO_3H$), 2.40 (s, 3H, $CH_3$), 4.90 (s, 2H, $CH_2$), 7.15 (t, 1H, Ar), 7.25-7.35 (m, 2H, Ar), 7.80 (s, 1H, Ar), 8.80 (s, 1H, Ar), 8.30-8.40 ($NH_2$ exchangeable with $D_2O$), 10.20 (NH exchangeable with $D_2O$); MS: m/e (ES+) 378 (M+); IR $cm^{-1}$: 3350, 3200, 1725, 1600, 1310, 1200, 1050, 800.

EXAMPLE 177f

7-Chloro-4-methyl-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 1-bromomethyl-3-methyl-2-nitro-benzene as described in the synthesis of Examples 166a-166f. Yield: 9.96%; $^1$H NMR (DMSO-$d_6$): δ 2.30 (s, 3H, $CH_3$), 4.90 (s, 2H, $CH_2$), 7.10 (t, 1H, Ar), 7.30 (m, 2H, Ar), 7.75 (s, 1H, Ar), 8.35 (s, 1H, Ar), 8.70 (s, 1H, NH); MS: m/e (EI+) 337 (M+).

1-Bromomethyl-3-methyl-2-nitro-benzene was synthesized from 1,3-dimethyl-2-nitro-benzene as described in the synthesis of Example 166a.

EXAMPLE 178

N-(7-Chloro-1-fluoro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 178f as described in the synthesis of Example 1. Yield: 64.2%; mp: 218-219° C.; $^1$H NMR (DMSO-$d_6$): δ 2.35 (s, 3H, $CH_3SO_3H$), 4.85 (s, 2H, $CH_2$), 7.00-7.15 (m, 2H, Ar), 7.40 (m, 1H, Ar), 7.50 (s, 1H, Ar), 8.20 (s, 1H, Ar), 8.30-8.40 ($NH_2$ exchangeable with $D_2O$), 10.20 (NH exchangeable with $D_2O$); MS: m/e (ES+) 382 (M+); IR $cm^{-1}$: 3350, 3200, 1725, 1625, 1500, 1200, 1050, 850.

EXAMPLE 178f

7-Chloro-1-fluoro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 2-bromomethyl-1-fluoro-3-nitro-benzene as described in the synthesis of Examples 166a-166f. Yield: 31%; $^1$H NMR (DMSO-$d_6$): δ 4.80 (s, 2H, $CH_2$), 7.00-7.10 (m, 2H, Ar), 7.40 (q, 1H, Ar), 7.50 (s, 1H, Ar), 8.35 (s, 1H, Ar); MS: m/e (EI+) 341 (M+).

2-bromomethyl-1-fluoro-3-nitro-benzene was synthesized from 2-methyl-1-fluoro-3-nitro-benzene as described in the synthesis of Example 166a.

EXAMPLE 179

N-(2,7-Dichloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 179f as described in the synthesis of Example 1. Yield: 62%; mp: 288-289° C.; $^1$H NMR (DMSO-$d_6$): δ 2.35 (s, 3H, $CH_3SO_3H$), 4.95 (s, 2H, $CH_2$), 7.30 (d, 1H, Ar), 7.45 (d, 1H, Ar), 7.55 (s, 1H, Ar), 7.60 (s, 1H, Ar), 8.20 (s, 1H, Ar), 8.40-8.50 ($NH_2$ exchangeable with $D_2O$), 9.15 (NH exchangeable with $D_2O$); MS: m/e (ES+) 399 (M+). IR $cm^{-1}$: 3350, 3150, 1725, 1600, 1500, 1325, 1250-1150, 1050, 750.

EXAMPLE 179f 2,7-Dichloro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 2-bromomethyl-4-chloro-1-nitro-benzene as described in the synthesis of Examples 166a-166f. Yield: 9.9%; $^1$H NMR (DMSO-$d_6$): δ 4.80 (s, 2H, $CH_2$), 7.25 (d, 1H, Ar), 7.50 (m, 3H, Ar), 8.30 (s, 1H, Ar), 9.50 (s, 1H, NH); MS: m/e (EI+) 358 (M+).

2-Bromomethyl-4-chloro-1-nitro-benzene was synthesized from 2-methyl-4-chloro-1-nitro-benzene as described in the synthesis of Example 166a.

EXAMPLE 180

N-(7-Chloro-2-fluoro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 180f as described in the synthesis of Example 1. Yield: 56.55%; mp: 278-279° C.; $^1$H NMR (DMSO-$d_6$): δ 2.35 (s, 3H, $CH_3SO_3H$), 4.90 (s, 2H, $CH_2$), 7.25-7.30 (m, 2H, Ar), 7.35 (d, 1H, Ar), 7.50 (s, 1H, Ar), 8.20 (s, 1H, Ar), 8.40-8.50 ($NH_2$ exchangeable with $D_2O$); MS: m/e (EI+) 383 (M+); IR $cm^{-1}$: 3350, 3200, 1700, 1600, 1300, 1250-1150, 1050.

EXAMPLE 180f

7-Chloro-2-fluoro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 2-bromomethyl-4-fluoro-1-nitro-benzene as described in the synthesis of Examples 166a-166f. Yield: 59.27%; $^1$H NMR (DMSO-$d_6$): δ 4.10 (s, 2H, $CH_2$), 7.25 (d, 2H, Ar), 7.35 (d, 1H, Ar), 7.45 (s, 1H, Ar), 8.40 (s, 1H, Ar), 9.90 (s, 1H, NH); MS: m/e (EI+) 342 (M+).

EXAMPLE 181

N-(7-Chloro-2-ethanesulfonyl-4-methyl-10,10-dioxo-10,11-dihydro-5H-10lambda *6*-thia-5-aza-dibenzo[a.d]cycloheptene-8-carbonyl)-guanidine, methane sulfonic acid salt The title compound was synthesised from Example 181f as described in the synthesis of Example 1. Yield: 60.12%; mp: 302-303° C.; $^1$H NMR (DMSO-$d_6$): δ 1.10 (t, 3H, $CH_3$), 2.35 (s, 3H, $CH_3SO_3H$), 3.30 (q, 2H, $CH_2$), 5.10 (s, 2H, $CH_2$), 7.80 (s, 1H, Ar), 7.95 (s, 1H, Ar), 8.25 (s, 1H, Ar), 8.40-8.50 ($NH_2$ exchangeable with $D_2O$), 9.00 (s, 1H, Ar); MS: m/e (ES+) 471 (M+); IR $cm^{-1}$: 3375, 3155, 1750, 1600, 1550, 1275, 1150, 1050, 825, 750.

EXAMPLE 181f

7-Chloro-2-ethanesulfonyl-4-methyl-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 1-bromomethyl-5-ethanesulfonyl-3-methyl-2-nitro-benzene as described in the synthesis of Examples 166a-166f. Yield: 9.74%; $^1$H NMR (DMSO-$d_6$): δ 1.10 (t, 3H, $CH_3$), 3.30 (q, 2H, $CH_2$), 5.10 (s, 2H, $SO_2CH_2$), 7.80 (s, 1H, Ar), 7.85 (s, 1H, Ar), 7.90 (s, 1H, Ar), 8.40 (s, 1H, Ar), 8.90 (s, 1H, NH), 12.8 (s, 1H, COOH); MS: m/e (EI+) 429 (M+).

1-Bromomethyl-5-ethanesulfonyl-3-methyl-2-nitro-benzene was synthesized from 5-ethylsulfonyl-1,3-dimethyl-2-nitro-benzene as described in the synthesis of Example 166a.

EXAMPLE 182

N-(1,7-Dichloro-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 182f as described in the synthesis of Example 1. Yield: 42%; mp: 261-262° C.; $^1$H NMR (DMSO-$d_6$): δ 2.35 (s, 3H, $CH_3SO_3H$), 5.00 (s, 2H, $CH_2$), 7.30 (d, 1H, Ar), 7.35-7.45 (m, 2H, Ar), 7.60 (s, 1H, Ar), 8.25 (s, 1H, Ar), 8.40-8.50 ($NH_2$ exchangeable with $D_2O$); MS: m/e (EI+) 399 (M+, free base); IR $cm^{-1}$: 3300, 3150, 3100, 1725, 1600, 1525, 1450, 1200, 1050, 800.

EXAMPLE 182f 1,7-Dichloro-10,10-dioxo-10,11-dihydro-5H-10lambda*6*-thia-5-aza-dibenzo[a.d]cycloheptene-8-carboxylic acid The title compound was synthesised from 2,4-dichloro-5-mercapto-benzoic acid methyl ester and 2-bromomethyl-1-chloro-3-nitro-benzene as described in the synthesis of Examples 166a-166f. Yield: 6.66%; $^1$H NMR (DMSO-$d_6$): δ 4.90 (s, 2H, $CH_2$), 7.30 (d, 1H, Ar), 7.40 (m, 2H, Ar), 7.50 (s, 1H, Ar), 8.40 (s, 1H, Ar), 10.10 (s, 1H, NH); MS: m/e (EI+) 358 (M+).

EXAMPLE 183

N-(7-Methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 183f as described in the synthesis of Example 1. Yield: 42.13%; mp: 292-294° C.; $^1$H NMR (DMSO-$d_6$): δ 2.35 (s, 3H, $CH_3SO_3H$), 2.40 (s, 3H, $CH_3$), 4.80 (s, 2H, $CH_2$), 7.10 (t, 1H, Ar), 7.25 (m, 2H, Ar), 7.40 (dd, 2H, Ar), 8.10 (s, 1H, Ar), 8.30-8.50 ($NH_2$ exchangeable with $D_2O$); MS: m/e (ES+) 345 (M+, free base); IR $cm^{-1}$: 3300, 3200-3100, 3000, 1720, 1600, 1530, 1500, 1320, 1260, 1210-1150, 1050, 880, 750.

EXAMPLE 183f

7-Methyl-10,10-dioxo-10,11-dihydro-5H-10lambda*6*-thia-5-aza-dibenzo[a.d]cycloheptene-8-carboxylic acid The title compound was synthesised from 4-chloro-5-mercapto-2-methyl-benzoic acid methyl ester and 1-bromomethyl-2-nitro-benzene as described in the synthesis of Examples 166a-166f. Yield: 5%; $^1$H NMR (DMSO-$d_6$): δ 2.60 (s, 3H, $CH_3$), 4.80 (s, 2H, $CH_2$), 7.10 (t, 1H, Ar), 7.20 (s, 1H, Ar), 7.25-7.40 (m, 3H, Ar), 8.40 (s, 1H, Ar), 9.45 (s, 1H, NH); MS: m/e (EI+) 303 (M+).

EXAMPLE 184

N-(4,7-Dimethyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 184f as described in the synthesis of Example 1. Yield: 71.12%; mp: 284-286° C.; $^1$H NMR (DMSO-$d_6$): δ 2.35 (s, 3H, $CH_3SO_3H$), 2.40 (s, 3H, $CH_3$), 2.50 (s, 3H, $CH_3$), 4.80 (s, 2H, $CH_2$), 7.10 (t, 1H, Ar), 7.30 (m, 2H, Ar), 7.45 (s, 1H, Ar), 8.10 (s, NH, exchangeable with $D_2O$), 8.60 (s, 1H, Ar); MS: m/e (ES+) 359 (M+, free base); IR $cm^{-1}$: 3350, 3150, 1710, 1600, 1530, 1480, 1260, 1200, 1150, 950, 890, 780.

EXAMPLE 184f 4,7-Dimethyl-10,10-dioxo-10,11-dihydro-5H-10lambda*6*-thia-5-aza-dibenzo[a.d]cycloheptene-8-carboxylic acid The title compound was synthesised from 4-bromo-5-mercapto-2-methyl-benzoic acid methyl ester and 1-bromomethyl-3-methyl-2-nitro-benzene as described in the synthesis of Examples 166a-166f. Yield: 23.07%; $^1$H NMR (DMSO-$d_6$): δ 2.55 (s, 3H, $CH_3$), 4.80 (s, 2H, $CH_2$), 7.10 (t, 1H, Ar), 7.34 (m, 2H, Ar), 7.40 (s, 1H, Ar), 8.35 (s, 1H, Ar), 8.45 (s, 1H, NH), 12.70 (s, 1H, OH); MS: m/e (EI+) 317 (M+).

EXAMPLE 185

N-(4-Chloro-7-methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 185f as described in the synthesis of Example 1. Yield: 58.54%; mp: 278-280° C.; $^1$H NMR (DMSO-$d_6$): δ 2.35 (s, 3H, $CH_3SO_3H$), 2.50 (s, 3H, $CH_3$), 4.95 (s, 2H, $CH_2$), 7.25 (t, 1H, Ar), 7.45 (d, 1H, Ar), 7.50 (s, NH, exchangeable with $D_2O$), 7.60 (d, 1H, Ar), 8.10 (s, 1H, Ar), 8.25-8.50 ($NH_2$ exchangeable with $D_2O$), 8.90 (s, 1H, Ar); MS: m/e (EI+) 378 (M+, free base); IR $cm^{-1}$: 3400-3350, 3150, 1700, 1610, 1520, 1480, 1330, 1260, 1210-1180, 1050, 800.

EXAMPLE 185f

4-Chloro-7-methyl-10,10-dioxo-10,11-dihydro-5H-10lambda*6*-thia-5-aza-dibenzo[a.d]cycloheptene-8-carboxylic acid The title compound was synthesised from 4-bromo-5-mercapto-2-methyl-benzoic acid methyl ester and 1-bromomethyl-3-chloro-2-nitro-benzene as described in the synthesis of Examples 166a-166f. Yield: 27.98%; $^1$H NMR (DMSO-d$_6$): δ 2.45 (s, 3H, CH$_3$), 4.90 (s, 2H, CH$_2$), 7.20 (t, 1H, Ar), 7.40 (s, 2H, Ar), 7.60 (d, 1H, Ar), 8.35 (s, 1H, Ar—H); MS: m/e (EI+) 337 (M+).

EXAMPLE 186

N-(4,6-Dimethyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 186f as described in the synthesis of Example 1. Yield: 77%; mp: 268-269° C.; $^1$H NMR (DMSO-d$_6$): δ 2.30 (s, 3H, CH$_3$SO$_3$H), 2.45 (s, 3H, CH$_3$), 2.60 (s, 3H, CH$_3$), 4.90 (s, 2H, CH$_2$), 7.20 (t, 1H, Ar), 7.30 (m, 2H, Ar), 7.60 (s, 1H, Ar), 7.90 (s, 1H, Ar), 8.30 (NH$_2$, NH exchangeable with D$_2$O); MS: m/e (ES+) 359 (M+, free base); IR cm$^{-1}$: 3480, 3400-3300, 3100-3000, 1700, 1650-1600, 1480, 1310-1280, 1250, 1200-1180, 1070, 920, 800, 750.

EXAMPLE 186f 4,6-Dimethyl-10,10-dioxo-10,11-dihydro-5H-10lambda*6*-thia-5-aza-dibenzo[a.d]cycloheptene-8-carboxylic acid The title compound was synthesised from 4-bromo-3-mercapto-5-methyl-benzoic acid methyl ester and 1-bromomethyl-3-methyl-2-nitro-benzene as described in the synthesis of Examples 166a-166f. Yield: 25.16%; $^1$H NMR (DMSO-d$_6$): δ 2.40 (s, 3H, CH$_3$), 2.60 (s, 3H, CH$_3$), 4.80 (s, 2H, CH$_2$), 7.25 (t, 1H, Ar), 7.30 (d, 1H, Ar), 7.40 (s, 2H, Ar, NH), 7.90 (s, 1H, Ar), 8.30 (s, 1H, Ar); MS: m/e (EI+) 317 (M+).

EXAMPLE 187

N-(1-Fluoro-6-methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 187f as described in the synthesis of Example 1. Yield: 79%; MS: m/e (ES−) 361 (M+);

EXAMPLE 187f

1-Fluoro-6-methyl-10,10-dioxo-10,11-dihydro-5H-10lambda*6*-thia-5-aza-dibenzo[a.d]cycloheptene-8-carboxylic acid The title compound was synthesised from 4-bromo-3-mercapto-5-methyl-benzoic acid methyl ester and 2-bromomethyl-1-fluoro-2-nitro-benzene as described in the synthesis of Examples 166a-166f. Yield: 43.80%; $^1$H NMR (DMSO-d$_6$): δ 2.60 (s, 3H, CH$_3$), 3.90 (s, 3H, OCH$_3$), 4.80 (s, 2H, CH$_2$), 7.10 (t, 1H, Ar), 7.35 (m, 2H, Ar), 8.00 (s, 1H, NH), 8.20 (s, 1H, Ar), 8.30 (s, 1H, Ar).

EXAMPLE 188

N-(4-Chloro-6-methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 188f as described in the synthesis of Example 1. Yield: 62%; mp: 271-272° C.; $^1$H NMR (DMSO-d$_6$): δ 2.35 (s, 3H, CH$_3$SO$_3$H), 2.70 (s, 3H, CH$_3$), 5.10 (s, 2H, CH$_2$), 7.40 (t, 1H, Ar), 7.50 (d, 1H, Ar), 7.60 (d, 1H, Ar), 8.00 (d, 1H, Ar), 7.80 (s, NH exchangeable with D$_2$O) 8.30 (NH$_2$, exchangeable with D$_2$O), 8.40 (s, 1H, Ar); MS: m/e (ES+) 379 (M+, free base); IR cm$^{-1}$: 3400-3300, 1700, 1600, 1520, 1470, 1280, 1220, 1160, 1050, 930, 800, 750.

EXAMPLE 188f

4-Chloro-6-methyl-10,10-dioxo-10,11-dihydro-5H-10lambda*6*-thia-5-aza-dibenzo[a.d]cycloheptene-8-carboxylic acid The title compound was synthesised from 4-bromo-3-mercapto-5-methyl-benzoic acid methyl ester and 1-bromomethyl-3-chloro-2-nitro-benzene as described in the synthesis of Examples 166a-166f. Yield: 22.45%; $^1$H NMR (DMSO-d$_6$): δ 2.60 (s, 3H, CH$_3$), 5.00 (s, 2H, CH$_2$), 7.25 (t, 1H, Ar), 7.50 (d, 1H, Ar—H), 7.60 (d, 1H, Ar), 7.70 (s, 1H, NH), 8.00 (s, 1H, Ar), 8.30 (s, 1H, Ar); MS: m/e (EI+) 337 (M+).

EXAMPLE 189

N-(6-Methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 189f as described in the synthesis of Example 1. Yield: 72%; $^1$H NMR (DMSO-d$_6$): δ 2.35 (s, 3H, CH$_3$SO$_3$H), 2.60 (s, 3H, CH$_3$), 5.40 (s, 2H, CH$_2$), 7.20 (t, 1H, Ar), 7.40-7.50 (m, 2H, Ar), 7.90 (s, 1H, Ar), 8.20 (s, 1H, Ar), 8.30 (NH, exchangeable with D$_2$O) 8.40 (s, 1H, Ar—H); MS: m/e (ES+) 345 (M+, free base); IR cm$^{-1}$: 3400-3300, 2900, 1710, 1620-1580, 1500, 1280, 1200, 1180, 1050, 910, 780.

EXAMPLE 189f

6-Methyl-10,10-dioxo-10,11-dihydro-5H-10lambda*6*-thia-5-aza-dibenzo[a.d]cycloheptene-8-carboxylic acid The title compound was synthesised from 4-bromo-3-mercapto-5-methyl-benzoic acid methyl ester and 1-bromomethyl-2-nitro-benzene as described in the synthesis of Examples 166a-166f. Yield: 19.46%; $^1$H NMR (DMSO-d$_6$): δ 2.40 (s, 3H, CH$_3$), 4.90 (s, 2H CH$_2$), 7.20 (t, 1H, Ar), 7.30-7.45 (m, 3H, Ar), 7.95 (d, 1H, Ar), 8.30 (s, 1H, Ar), 9.50 (s, 1H, NH).

EXAMPLE 190

N-(10,10-dioxo-7-pyrrol-1-yl-10,11-dihydro-5H-10lambda*6*-thia-5-aza-dibenzo[a.d]cycloheptene-8-carbonyl)-guanidine, methane sulfonic acid salt The title compound was synthesised from Example 190f as described in the synthesis of Example 1. Yield: 47.1%; mp: 204-206° C.; $^1$H NMR (DMSO-d$_6$): δ 2.35 (s, 3H, CH$_3$SO$_3$H), 4.90 (s, 2H, CH$_2$), 6.30 (s, 2H, pyrrolyl), 7.00 (s, 2H, pyrrolyl-H), 7.10-7.45 (m, 4H, Ar), 7.45 (s, 1H, Ar—H), 8.2 (s, 1H, Ar), 8.40-8.50 (NH$_2$ exchangeable with D$_2$O); MS: m/e (ES+) 395 (M+, free base); IR cm$^{-1}$: 3350, 3250-3100, 1700, 1595, 1300, 1250, 1095, 775.

EXAMPLE 190f 10,10-Dioxo-7-pyrrol-1-yl-10,11-dihydro-5H-10lambda*6*-thia-5-aza-dibenzo[a.d]cycloheptene-8-carboxylic acid The title compound was synthesised from Example 174f as described in the synthesis of Example 18i. Yield: 9%; $^1$H NMR (DMSO-d$_6$): δ 4.90 (s, 2H, CH$_2$), 6.25 (s, 2H, pyrrolyl), 6.95 (s, 2H, pyrrolyl), 7.10 (t, 1H, Ar), 8.30 (s, 1H, Ar), 8.30 (s, 1H, Ar), 9.20 (s, 1H, NH); MS: m/e (ES+) 353 (M+, free base)

EXAMPLE 191

N-(7-Benzylamino-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 191f as described in the synthesis of Example 1. Yield: 31%; mp: 203-205° C.; $^1$H NMR (DMSO-d$_6$): δ 2.30 (s, 3H, CH$_3$SO$_3$H), 4.50 (s, 2H, CH$_2$), 4.80 (s, 2H, CH$_2$), 6.60 (s, 1H, Ar), 7.10 (t, 1H, Ar), 7.20 (d, 1H, Ar), 7.30-7.40 (m, 2H, Ar), 7.42 (m, 5H, Ar), 8.25 (s, 1H, Ar), 9.65 (s, 1H, Ar), 11.00 (NH$_2$ exchangeable with D$_2$O); MS: m/e (ES+) 435 (M+, free base); IR cm$^{-1}$: 3350, 3150, 1700, 1650, 1590, 1490, 1275, 1200, 1050, 750.

EXAMPLE 191f

7-Benzylamino-10,10-dioxo-10,11-dihydro-5H-10lambda*6*-thia-5-aza-dibenzo[a.d]cycloheptene-8-carboxylic acid The title compound was synthesised from Example 174f as described in the synthesis of Example 18x. Yield: 18.66%; $^1$H NMR (DMSO-d$_6$): δ 4.40 (d, 2H, N—CH$_2$), 4.70 (s, 1H, Ar), 7.00 (t, 1H, Ar), 7.20 (d, 1H, Ar), 7.30-7.50 (m, 7H, Ar), 8.35 (s, 1H, Ar), 9.20 (s, 1H, NH), 9.30 (s, 1H, NH); MS: m/e (ES+) 394 (M+, free base).

EXAMPLE 192

N-(5-Methyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 192f as described in the synthesis of Example 1. Yield: 34%; mp: 250-251° C.; $^1$H NMR (DMSO-d$_6$): δ 2.35 (s, 3H, CH$_3$SO$_3$H), 3.50 (s, 3H, CH$_3$), 5.00 (s, 2H, CH$_2$), 7.35 (t, 1H, Ar), 7.45 (t, 1H, Ar), 7.55 (m, 3H, Ar), 8.10 (d, 1H, Ar), 8.30 (NH$_2$, exchangeable with D$_2$O), 8.40 (s, 1H, Ar), 11.00 (NH, exchangeable with D$_2$O); MS: m/e (ES+) 345 (M+, free base); IR cm$^{-1}$: 3300, 3100, 1700, 1600-1580, 1480, 1270, 1210-1140, 1040, 910, 760.

EXAMPLE 192f

5-Methyl-10,10-dioxo-10,11-dihydro-5H-10lambda*6*-thia-5-aza-dibenzo[a.d]cycloheptene-8-carboxylic acid Methyl iodide (0.03 ml, 0.49 mmol), tetrabutylammonium hydrogen sulphate (0.112 g, 0.33 mmol) and 50% aqueous sodium hydroxide (0.5 mL) were added to a solution of Example 166e (0.1 g, 0.33 mmol) in benzene (2 mL). The reaction mixture was stirred for 7 h at room temperature, treated with water and extracted with ethyl acetate. The organic extract was washed with water, 10% aqueous HCl, dried, concentrated and subjected to hydrolysis as described in Example 1i to obtain the title compound. (Synthesis 124, (1976)). Yield: 8.80%; $^1$H NMR (DMSO-d$_6$): δ 3.50 (s, 3H, CH$_3$), 5.00 (s, 2H, CH$_2$), 7.30-7.60 (m, 5H, Ar), 8.01 (d, 1H, Ar), 8.20 (s, 1H, Ar); MS: m/e (ES+) 304 (M+).

EXAMPLE 193

N-(5-Allyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 193f as described in the synthesis of Example 1. Yield: 71.42%; $^1$H NMR (DMSO-d$_6$): δ 2.40 (s, 3H, CH$_3$SO$_3$H), 4.60 (d, 2H, N—CH$_2$), 5.10 (s, 2H, CH$_2$), 5.35 (d, 2H, CH$_2$), 5.80 (m, 1H, CH), 7.40-7.50 (m, 3H, Ar), 7.60 (m, 2H, Ar), 8.10 (d, 1H, Ar), 8.30 (s, 1H, Ar), 8.50 & 11.10 (NH, exchangeable with D$_2$O); MS: m/e (ES+) 370 (M+, free base); IR cm$^{-1}$: 3350, 2950, 1730, 1610, 1500, 1310, 1250, 1200, 1140, 1050, 920, 790.

EXAMPLE 193f

5-Allyl-10,10-dioxo-10,11-dihydro-5H-10lambda*6*-thia-5-aza-dibenzo[a.d]cycloheptene-8-carboxylic acid Allyl bromide (0.042 mL, 0.49 mmol), tetrabutylammonium hydrogen sulphate (0.033 g, 0.099 mmol) and 25% aqueous sodium hydroxide (0.5 mL) were added to a solution of Example 166e (0.1 g, 0.33 mmol) in benzene (2 mL). The reaction mixture was stirred for 7 h at room temperature, treated with water and extracted with ethyl acetate. The organic extract was washed with water, 10% aqueous HCl, dried, concentrated and subjected to hydrolysis as described in Example 1i to obtain the title compound. Yield: 13.41%; $^1$H NMR (DMSO-d$_6$): δ 4.50 (d, 2H, CH$_2$), 5.00 (s, 2H, CH$_2$), 5.30 (d, 2H, CH$_2$), 5.80 (m, 1H, CH), 7.30-7.60 (m, 5H, Ar), 8.10 (d, 1H, Ar), 8.20 (s, 1H, Ar); MS: m/e (ES+) 330 (M+).

EXAMPLE 194

N-(4-Chloro-5,6,11-trimethyl-10,10-dioxo-10,11-dihydro-5H-10lambda*6*-thia-5-aza-dibenzo[a.d]cycloheptene-8-carbonyl)-guanidine, methane sulfonic acid salt The title compound was synthesised from Example 194f as described in the synthesis of the synthesis of Example 1. Yield: 61%; $^1$H NMR (DMSO-d$_6$): δ 1.75 (d, 3H, CH$_3$), 2.35 (s, 3H, CH$_3$SO$_3$H), 2.75 (s, 3H, CH$_3$), 3.40 (s, 3H, N—CH$_3$), 5.40 (q, 1H, CH), 7.55 (m, 3H, Ar), 8.10 (s, 1H, Ar), 8.15 (s, 1H, Ar) 8.20-8.30 (NH exchangeable with D$_2$O); MS: m/e (ES+) 406 (M+, free base); IR cm$^{-1}$: 3400-3300, 2930, 1700, 1610, 1450, 1300, 1210-1180, 1110, 1050, 800, 780.

EXAMPLE 194f

4-Chloro-5,6,11-trimethyl-10,10-dioxo-10,11-dihydro-5H-10lambda*6*-thia-5-aza-dibenzo[a.d]cycloheptene-8-carboxylic acid Example 166e (0.2 g, 0.56 mmols) was treated with excess methyl iodide (0.1 ml, 1.68 mmol) as described in the synthesis of Example 192f to obtain the title compound. Yield: 15%; $^1$H NMR (DMSO-d$_6$): δ 1.80 (d, 6H, 2CH$_3$), 2.60 (s, 3H, CH$_3$), 5.40 (q, 1H, CH), 7.50-7.20 (m, 3H, Ar), 8.00 (s, 1H, Ar), 8.10 (s, 1H, Ar); MS: m/e (ES+) 406 (M+).

EXAMPLE 195

N-(10,10-Dioxo-10,11-dihydro-5H-10lambda*6*-thia-5-aza-dibenzo[a.d]cycloheptene-2-carbonyl)-guanidine, methane sulfonic acid salt A mixture of Example 195f (0.2 g, 0.4 mmol) and aminoguanidine (0.065 g, 0.48 mmol) in dry ethanol (10 mL), water (0.1 mL) and concentrated HCl (0.1 mL) was refluxed for 1.2 h. The reaction mixture was concentrated, treated with water and 10% aqueous NaHCO$_3$ to pH 7.8 to obtain the title compound as a solid which was filtered, washed with water and dried. Yield: 50%; mp: 260-261° C.; $^1$H NMR (DMSO-d$_6$): δ 2.35 (s, 3H, CH$_3$SO$_3$H), 4.90 (s, 2H, CH$_2$), 7.10 (t, 1H, Ar), 7.40 (d, 1H, Ar), 7.45 (d, 1H, Ar), 7.60 (t, 1H, Ar), 7.90 (d, 2H, Ar), 8.00 (s, 1H, Ar), 8.40 & 9.90 (NH, exchangeable with D$_2$O); MS: m/e (ES+) 330 (M+, free base); IR cm$^{-1}$: 3400-3300, 1730, 1710, 1640-1600, 1550, 1500, 1380, 1280, 1200, 1050, 780.

EXAMPLE 195f 10,10-Dioxo-10,11-dihydro-5H-10lambda*6*-thia-5-aza-dibenzo[a.d]cycloheptene-2-carboxylic acid The title compound was synthesised from 2-bromo-benzenethiol and 3-bromomethyl-4-nitro-benzoic acid methyl ester as described in the synthesis of examples 166a-166f. Yield: 6.86%. $^1$H NMR (DMSO-d$_6$): δ 4.90 (s, 2H, CH$_2$), 7.00 (t, 1H, Ar), 7.30 (d, 1H, Ar), 7.40 (d, 1H, Ar), 7.45 (d, 1H, Ar), 7.50 (t, 1H, Ar) 7.8 (d, 2H, Ar), 9.8 (s, 1H, NH); MS: m/e (ES+) 390 (M+).

EXAMPLE 196

N-(10,10-Dioxo-10,11-dihydro-5H-10lambda*6*-thia-5-aza-dibenzo[a.d]cycloheptene-1-carbonyl)-guanidine, methane sulfonic acid salt The title compound was synthesised from Example 196f as described in the synthesis of Example 1. Yield: 73%; mp: 265-266° C.; $^1$H NMR (DMSO-d$_6$): δ 2.35 (s, 3H, CH$_3$SO$_3$H), 5.10 (s, 2H, CH$_2$), 6.90 (t, 1H, Ar), 7.40 (m, 3H, Ar), 7.50 (m, 2H, Ar), 7.30 (d, 1H, Ar), 8.10 & 9.40 (NH, exchangeable with D$_2$O); MS: m/e (ES+) 330 (M+, free base); IR cm$^{-1}$: 3400, 3340, 1740, 1610, 1500-1470, 1300, 1200, 1140, 1050, 910, 790.

EXAMPLE 196f 10,10-Dioxo-10,11-dihydro-5H-10lambda*6*-thia-5-aza-dibenzo[a.d]cycloheptene-1-carboxylic acid The title compound was synthesised from 2-bromo-benzenethiol and 2-bromomethyl-3-nitro-benzoic acid methyl ester as described in the synthesis of Examples 166a-166f. Yield: 24%; $^1$H NMR (DMSO-d$_6$): δ 5.20 (s, 2H, CH$_2$), 6.90 (t, 1H, Ar), 7.40 (m, 4H, Ar), 7.70 (d, 1H, Ar), 7.80 (d, 1H, Ar), 9.80 (s, 1H, NH); MS: m/e (ES+) 289 (M+).

EXAMPLE 197

N-{4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carbonyl}-guanidine dimesylate The title compound was synthesised from Example 197k as described in the synthesis of Example 50. Yield: 0.146 g, (53.09%); mp: 185-187° C.; $^1$H NMR (DMSO-d$_6$): δ 2.35 (s, 6H, 2CH$_3$), 2.70 (s, 3H, CH$_3$), 3.15-3.25 (m, 8H, 4CH$_2$), 3.60-3.70 (m, 2H, CH$_2$), 3.75-3.80 (m, 2H, CH$_2$), 5.25 (s, 2H, CH$_2$), 7.35 (s, 2H, Ar), 8.10 (s, 1H, Ar), 8.30 (s, 1H, Ar); MS: m/e (ES+) 508 (M+1); analysis: C$_{24}$H$_{34}$ClN$_5$O$_{11}$S$_3$.H$_2$O, calcd.: C, 40.62; H, 5.54; N, 10.24; Cl, 5.25, S, 13.06 found: C, 40.14; H, 5.05; N, 9.75; Cl, 4.94, S, 13.39%.

EXAMPLE 197k

4-Chloro-2-[4-(2-hydroxy-ethyl)-piperazine-1-yl]-6-methyl-10,10-dioxo-10,11-dihydro-5-oxa-10lambda*6*-thia-dibenzo[a,d]cycloheptene-8-carboxylic acid methyl ester Ethanol amine (0.25 mL, 4.17 mmol) was added to a solution of Example 102j (0.5 g, 1.04 mmol) in methanol (5 mL) in an atmosphere of nitrogen and sealed in a pressure reactor vessel at 120° C. for 4 h. It was brought to room temperature, treated with, chilled water, dilute HCl to neutral pH and extracted with n-butanol. The organic layer was washed with water, brine, dried, concentrated, treated with methanolic HCl solution, and refluxed at 70° C. for 3 h. The reaction mixture was concentrated, treated with aqueous sodium bicarbonate solution to neutral pH and extracted with ethyl acetate. The organic layer was washed with water, brine, dried, concentrated and purified using flash chromatography (silica gel, 5% methanol/chloroform) to obtain the title compound. Yield: 0.337 g, (67.13%); $^1$H NMR (DMSO-d$_6$): δ 2.70 (s, 3H, CH$_3$), 3.05-3.15 (m, 4H, 2CH$_2$), 3.40-3.45 (m, 8H, 4CH$_2$), 3.70 (s, 1H, OH), 3.90 (s, 3H, OCH$_3$), 5.20 (s, 2H, CH$_2$), 7.10 (s, 1H, Ar), 7.20 (s, 1H, Ar), 8.15 (s, 1H, Ar), 8.20 (s, 1H, Ar); MS: m/e (EI+) 481 (M+1).

EXAMPLE 198

N-(2-Aminomethyl-4-chloro-6-methyl-10,10-dioxo-10,11-dihydro-5-oxa-10lambda*6*-thia-dibenzo[a.d]cycloheptene-8-carbonyl)-guanidine trimesylate The title compound was synthesised from Example 198k as described in the synthesis of Example 50. Yield: 0.072 g, (44.72%); mp: 242-44° C.; $^1$H NMR (DMSO-d$_6$): δ 2.50 (s, 6H, 2CH$_3$), 2.70 (s, 3H, CH$_3$), 4.09 (s, 2H, CH$_2$), 5.38 (s, 2H, CH$_2$), 7.62 (s, 1H, Ar), 7.80 (s, 1H, Ar), 8.19 (s, 1H, Ar), 8.27 (s, 1H, Ar), 8.27-8.40 (m, 4H, guanidinyl); MS: m/e (ES+) 408 (M+1, free base); analysis: C$_{20}$H$_{29}$ClN$_4$O$_{13}$S$_4$.H$_2$O calcd., C, 33.59; H, 4.37; N, 7.83; found: C, 33.72; H, 4.19; N; 8.19%.

EXAMPLE 198k

2-Aminomethyl-4-chloro-6-methyl-10,10-dioxo-10,11-dihydro-5-oxa-10lambda *6*-thia-dibenzo[a,d]cycloheptene-8-carboxylic acid methyl ester An aqueous sodium nitrite solution (0.440 g, 5.98 mmol, 5 mL) was added dropwise with stirring to a mixture of the ester of 35j (2 g, 5.44 mmol), concentrated HCl (20 mL), water (40 mL) and DMF (1 mL) at 0° C. and the reaction mixture was stirred for 20 minutes at 0° C. It was neutralized with a 20% aqueous sodium carbonate solution at the same temperature. The reaction mixture was then added slowly with stirring to a solution of potassium cyanide (0.420 g, 5.44 mmol) and cuprous cyanide (0.580 g, 6.53 mmol) in water (25 mL) at 0° C. The reaction mixture was stirred for 1 h and subsequently heated at 60° C. for 1 h. It was cooled, the solid obtained was filtered, washed with water, dried and purified using flash chromatography (silica gel, 5% hexane/chloroform). The compound obtained was subjected to reduction using platinum oxide (0.1 g) in ethanol (170 mL) and acetic acid (1.5 mL) to obtain the title compound as a white solid. Yield: 0.810 g, (35.68%); $^1$H NMR (DMSO-d$_6$): δ 2.69 (s, 3H, CH$_3$), 3.90 (s, 3H, OCH$_3$), 4.10 (t, 2H, CH$_2$), 5.40 (s, 2H, CH$_2$), 7.70 (s, 1H, Ar), 8.00 (s, 1H, Ar), 8.20 (s, 1H, Ar), 8.22 (s, 1H, Ar), 8.60 (bs, 2H, NH$_2$); MS: m/e (ES+) 381 (M+1).

EXAMPLE 199

N-(4-chloro-2-diethylaminomethyl-6-methyl-10,10-dioxo-10,11-dihydro-5-oxa-10lambda*6*-thia-dibenzo[a,d]cycloheptene-8-carbonyl)-guanidine, dimesylate The title compound was synthesised from Example 199i as described in the synthesis of Example 50. Yield: 0.130 g, (60.68%); mp: 230-232° C.; $^1$H NMR (DMSO-d$_6$): δ 1.24 (t, 6H, 2CH$_3$), 2.38 (s, 6H, 2CH$_3$), 2.71 (s, 3H, CH$_3$), 3.11 (q, 4H, 2CH$_2$), 4.39 (s, 2H, CH$_2$), 5.40 (s, 2H, CH$_2$), 7.74 (s, 1H, Ar), 7.90 (s, 1H, Ar), 8.20 (s, 1H, Ar), 8.28 (s, 1H, Ar), 8.35-8.56 (m, 4H, guanidinyl); MS: m/e (ES+) 464 (M+1, free base); analysis: C$_{23}$H$_{33}$ClN$_4$O$_{10}$S$_3$, calcd.: C, 42.04; H, 5.06; N, 8.53; found: C, 41.51; H, 5.15; N; 8.16%.

EXAMPLE 199i

4-Chloro-2-diethylaminomethyl-6-methyl-10,10-dioxo-10,11-dihydro-5-oxa-10lambda*6*-thia-dibenzo[a,d]cycloheptene-8-carboxylic acid methyl ester Acetaldehyde (0.1 ml, 2.35 mmol) was added to a cooled solution of Example 198k (0.2 g, 0.47 mmol) in dry methanol (15 mL). Subsequently TFA (0.036 ml, 0.47 mmol) was added and the reaction mixture was stirred for 2 h. at 0° C. NaBH$_3$CN (0.075 g, 1.17 mmol) was added and the reaction mixture was stirred for 15 h at room temperature. It was treated with a 10% aqueous sodium bicarbonate solution (1 mL) and the solid that precipitated was filtered, washed with water, dried and purified using flash chromatography (silica gel, methanol/chloroform) to obtain the title compound as a white solid. Yield: 0.150 g, (76.53%); $^1$H NMR (DMSO-d$_6$): δ 1.05 (t, 6H, 2CH$_3$), 2.55 (q, 4H, 2CH$_2$), 2.70 (s, 3H, CH$_3$), 3.55 (s, 2H, CH$_2$), 4.00 (s, 3H, OCH$_3$), 4.70 (s, 2H, CH$_2$), 7.39 (s, 1H, Ar), 7.50 (s, 1H, Ar), 8.10 (s, 1H, Ar), 8.50 (s, 1H, Ar); MS: m/e (ES+) 438 (M+1).

EXAMPLE 200

N-(4-Chloro-6-methyl-10,10-dioxo-2-pyrrol-1-ylm-ethyl-10,11-dihydro-5-oxa-10lambda*6*-thia-dibenzo[a,d]cycloheptene-8-carbonyl)-guanidine, methane sulfonic acid salt The title compound was synthesised from Example 200i as described in the synthesis of Example 50. Yield: 0.066 g, (61.45%); mp: 215-216° C.; $^1$H NMR (DMSO-d$_6$): δ 2.39 (s, 3H, CH$_3$), 2.72 (s, 3H, CH$_3$), 3.18 (s, 2H, CH$_2$), 5.34 (s, 2H, CH$_2$), 6.07 (s, 1H, Ar), 6.85 (s, 2H, Ar), 7.38 (s, 1H, Ar), 7.45 (s, 1H, Ar), 8.16 (s, 1H, Ar), 8.27 (s, 1H, Ar), 8.30-8.55 (m, 4H, guanidinyl); MS: m/e (ES+) 432 (M+1, free base); analysis: C$_{22}$H$_{23}$ClN$_4$O$_7$S$_2$.2H$_2$O. calcd.: C, 44.71; H, 4.60; N; 9.48; found: C, 45.15; H, 4.07; N; 9.68%.

EXAMPLE 200i

4-Chloro-6-methyl-10,10-dioxo-2-pyrrol-1-ylm-ethyl-10,11-dihydro-5-oxa-10lambda*6*-thia-dibenzo[a,d]cycloheptene-8-carboxylic acid methyl ester 2,5-Dimethoxytetrahydrofuran (0.090 mL, 0.655 mmol) was added with stirring to a solution of Example 198k (0.2 g, 0.52 mmol) in dry dioxane (10 mL) followed by the addition of 4-chloropyridine hydrochloride (0.008 g, 0.05 mmol). The reaction mixture was allowed to stir at 110° C. for 2 h under nitrogen atmosphere. It was concentrated, treated with cold water and the solid that precipitated was filtered, washed with water, dried and purified using flash chromatography (silica gel, chloroform/pet ether) to obtain the title compound as a white solid. Yield: 0.086 g, (41.54%); $^1$H NMR (DMSO-d$_6$): δ 2.69 (s, 3H, CH$_3$), 3.92 (s, 3H, OCH$_3$), 4.67 (s, 2H, CH$_2$), 5.02 (s, 2H, CH$_2$), 6.22 (s, 2H, Ar), 6.68 (s, 2H, Ar), 7.04 (s, 1H, Ar), 7.38 (s, 1H, Ar), 8.09 (s, 1H, Ar), 8.46 (s, 1H, Ar); MS: m/e (ES+) 432 (M+1).

EXAMPLE 201

N-[2-(Benzylamino-methyl)-4-chloro-6-methyl-10,10-dioxo-10,11-dihydro-5-oxa-10lambda*6*-thia-dibenzo[a,d]cycloheptene-8-carbonyl]-guanidine, dimesylate The title compound was synthesised from Example 201i as described in the synthesis of Example 50. Yield: 0.090 g, (76.92%); mp: 248-250° C.; $^1$H NMR (DMSO-d$_6$): δ 2.38 (s, 6H, 2CH$_3$), 2.71 (s, 3H, CH$_3$), 4.25 (bs, 2H, CH$_2$), 5.20 (s, 2H, CH$_2$), 5.41 (s, 2H, CH$_2$), 7.45-7.47 (m, 5H, Ar), 7.67 (s, 1H, Ar), 7.86 (s, 1H, Ar), 8.21 (s, 1H, Ar); 8.28 (s, 1H, Ar), 8.35-8.57 (m, 4H, guanidinyl); MS: m/e (ES+) 498 (M+1, free base); analysis: $C_{26}H_{31}ClN_4O_{10}S_3$, calcd.: C, 45.18; H, 4.52; N, 8.11; found: C, 44.78; H, 4.48; N; 8.40%.

EXAMPLE 201i 2-(Benzylamino-methyl)-4-chloro-6-methyl-10,10-dioxo-10,11-dihydro-5-oxa-10lambda*6*-thia-dibenzo[a,d]cycloheptene-8-carboxylic acid methyl ester Sodium acetate (0.107 g, 1.30 mmol) was added to a solution of Example 198k (0.2 g, 0.52 mmol) in dry methanol (15 mL). Subsequently benzaldehyde (0.083 mL, 0.78 mmol) was added and the reaction mixture was stirred for 2.5 h. It was then chilled and treated with sodium borohydride (0.19 g, 0.52 mmol). The reaction mixture was stirred overnight at room temperature, then treated with an aqueous 10% sodium bicarbonate solution (2 mL), diluted with water and extracted with ethyl acetate. The organic layer was washed with water, brine, dried, concentrated and purified using flash chromatography (silica gel, methanol/chloroform) to obtain the title compound as a white solid. Yield: 0.095 g, (38.46%); $^1$H NMR (DMSO-d$_6$): δ 2.70 (s, 3H, CH$_3$), 3.81 (s, 4H, 2CH$_2$), 3.91 (s, 3H, OCH$_3$), 4.71 (s, 2H, CH$_2$), 7.26-7.34 (m, 5H, Ar), 7.51 (s, 1H, Ar), 8.09 (s, 2H, Ar), 8.46 (s, 1H, Ar); MS: m/e (EI+) 472 (M+1).

EXAMPLE 202

5-10,10-Trioxo-10,11-dihydro-5H-10-lambda*6*-thia-dibenzo[a,d]cycloheptene-8-carboxylic acid methyl ester m-Chloroperbenzoic acid (1.96 g, 11.4 mmol) was added to a solution of compound of Example 202a (0.65 g, 2.28 mmol) in dichloromethane (20 mL) in a two portions at 0° C. and stirred the reaction mixture at 25° C. for 2 h. The reaction mixture was concentrated, treated with sodium bicarbonate solution (50 mL), extracted with ethyl acetate. The combined organic layer was washed with water, brine, dried, concentrated and purified using flash chromatography (silica gel, 1% MeOH in CHCl$_3$) to obtain the title compound. Yield: 0.6 g (83%); $^1$H NMR (CDCl$_3$): δ 4.0 (s, 3H, CH$_3$), 4.82 (s, 2H, CH$_2$), 7.29 (t, 1H, Ar), 7.59 (m, 2H, Ar), 7.85 (d, 1H, Ar), 8.02 (d, 1H, Ar), 8.10 (d, 1H, Ar), 8.35 (d, 1H, Ar); MS: m/e (EI+) 316 (M+1).

EXAMPLE 202a 5-oxo-5,11-dihydro-10-thia-dibenzo[a,d]cycloheptene-8-carboxylic acid methyl ester The title compound was obtained using the reported procedure (J. Med. Chem., 21, 10, 1035, (1978)). Yield: 55%; $^1$H NMR (CDCl$_3$): δ 3.93 (s, 3H, OCH$_3$), 4.08 (s, 2H, CH$_2$), 7.27 (d, 1H, Ar—H), 7.36 (t, 1H, Ar—H), 7.49 (t, 1H, Ar—H), 7.6 (d, 1H, Ar), 7.85 (d, 1H, Ar—H), 8.0 (s, 1H, Ar—H), 8.23 (s, 1H, Ar—H); MS: m/e (EI+) 284 (M+1).

EXAMPLE 203

5-Hydroxy-10,10-dioxo-10,11-dihydro-5H-10lambda*6*-thia-dibenzo[a,d]cycloheptene-8-carboxylic acid methyl ester Platinum oxide (0.015 g, 10% w/w) was added to a solution of compound of example 202 (0.15 g, 0.47 mmol) in ethanol (50 mL) and acetic acid (20 ml). The reaction mixture was subjected to hydrogenation at 100 psi of hydrogen at 65° C. for 11 h. It was cooled to 30° C. and filtered through high flow bed. The mixture was concentrated, diluted with water and extracted it with ethyl acetate. The combined organic layer was washed with 10% sodium bicarbonate solution (15 ml), water, brine, concentrated and crystallized with ethyl acetate/pet ether to obtain the title compound. Yield: 125 mg (82%); $^1$H NMR (DMSO-d$_6$): δ 3.87 (s, 3H, CH$_3$), 5.23 (d, 1H, CH$_a$), 5.53 (d, 1H, CH$_{a'}$), 6.49 (d, 1H, CH$_b$), 6.49 (d, 1H, CH$_{b'}$), 7.33 (m, 2H, Ar), 7.48 (d, 1H, Ar), 7.57 (d, 1H, Ar), 8.0 (d, 1H, Ar), 8.17 (d, 1H, Ar); MS: m/e (CI+) 319 (M+1).

EXAMPLE 204

10,10-Dioxo-10,11-dihydro-5H-10lambda*6*-thia-dibenzo[a,d]cycloheptene-8-carboxylic acid methyl ester Pd/C (0.015 g, 10% w/w) and catalytic amount of perchloric acid was added to a solution compound of Example 203 (0.11 g, 0.3 mmol) in acetic acid (60 ml). The reaction mixture was subjected to hydrogenation at 100 psi of hydrogen at 65° C. for 6.5 h. The reaction mixture was cooled to 25° C. and filtered through high flow bed. The filtrate was concentrated, diluted with water and extracted with ethyl acetate. The combined organic layer was washed with water, brine, concentrated and purified using flash chromatography (silica gel, ethyl acetate and pet ether) to obtain the title compound. Yield: 0.05 g (47%); $^1$H NMR (CDCl$_3$): δ 3.8 (s, 2H, CH$_2$), 3.9 (s, 3H, CH$_3$), 4.32 (s, 2H, CH$_2$), 7.38 (m, 5H, Ar), 8.09 (d, 1H, Ar), 8.61 (s, 1H, Ar); MS: m/e (CI+) 303 (M+1).

The efficacy of the present compounds in inhibiting the activity of NHE can be determined by a number of pharmacological assays well known in the art and described below. The exemplified pharmacological assays which follow have been carried out with the compounds of the present invention and their salts.

In Vitro Studies:

Primary Screening Assay in Human Platelets

Experiments on inhibition of NHE in human platelets are based on those published in (Cardiovasc. Res. 29: 260-268, (1995), J. Med. Chem. 41, 3736-3747, (1998)) Blood (150 mL) collected in a siliconized glass bottle from healthy volunteers was treated with aqueous acid citrate dextrose (ACD) solution (25 mL) [composition: citric acid (38 mM/L), glucose (136 mM/L) and trisodium citrate (75 mM/L)] and immediately centrifuged at 200 g for 20 min. The platelet rich plasma (PRP) was separated and a platelet count carried out using a Beckman Coulter A$^c$ T® cell counter. The cell count was adjusted to 3×10$^8$ platelets/mL using platelet free plasma.

Activation of Na⁺/H⁺ exchanger by intracellular acidification: 150 μL of PRP was added to 750 μL of propionate buffer [composition: KCl (5 mM/L), CaCl$_2$ (1 mM/L), MgCl$_2$ (1 mM/L), glucose (10 mM/L), HEPES (20 mM/L), sodium propionate (140 mM/L)] of pH 6.6, in a cuvette. Optical density was recorded at 630 nm using a Shimadzu spectrophotometer (UV 1601). The micromolar concentrations of a few representative compounds required to inhibit 50% of NHE-1 activity (IC$_{50}$), in isolated human platelets (acidified human platelet swelling assay) is shown in Table 2. IC$_{50}$ values are the mean of three experimental readings using PRP isolated from the blood of three different donors.

TABLE 2

| Example No | Structure | IC$_{50}$ (μM) |
|---|---|---|
| 27 | 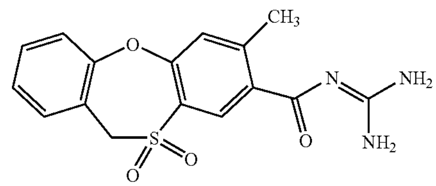 | 0.1 |
| 31 | 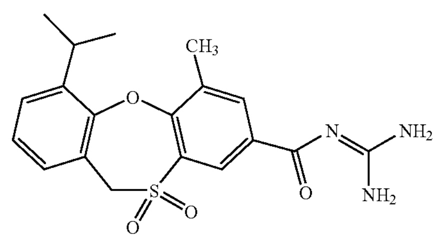 | 0.2 |
| 35 | 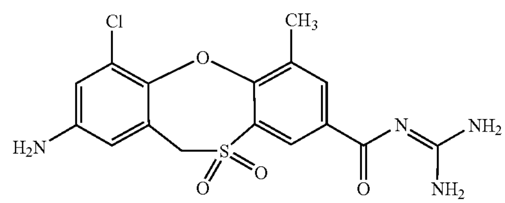 | 0.02 |
| 45 | 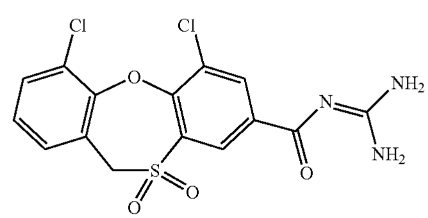 | 0.07 |
| 48 | 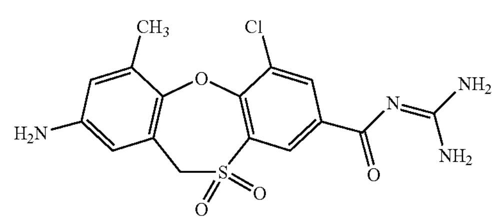 | 0.04 |
| 52 | 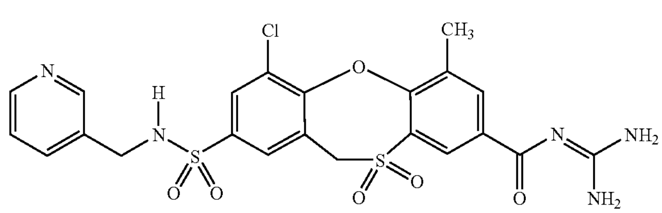 | 0.08 |

TABLE 2-continued

| Example No | Structure | IC$_{50}$ (μM) |
|---|---|---|
| 58 | 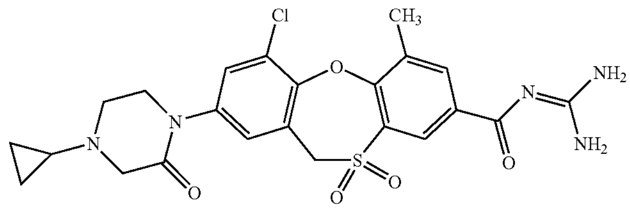 | 0.087 |
| 64 | 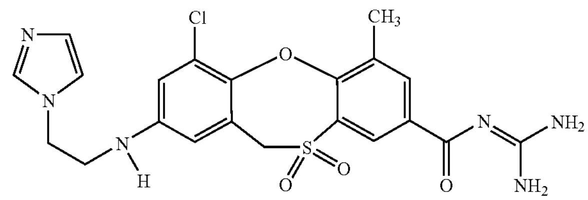 | 0.028 |
| 73 | 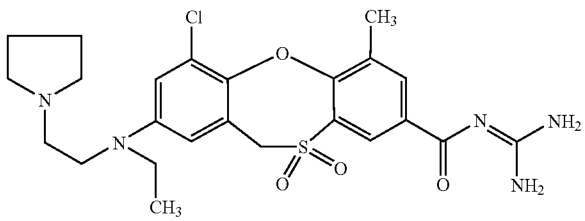 | 0.032 |
| 118 | 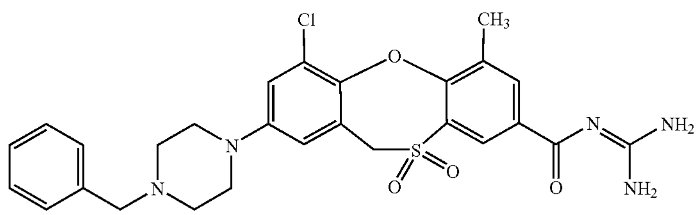 | 0.1 |
| 183 | 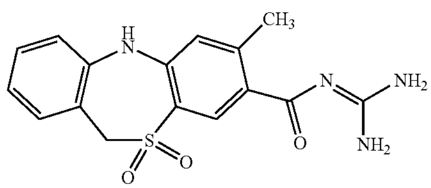 | 0.1 |
| 194 | 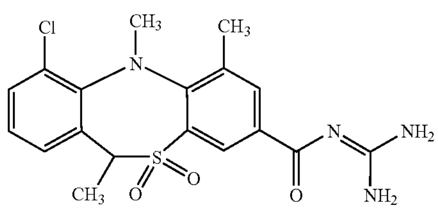 | 0.2 |
| 198 | 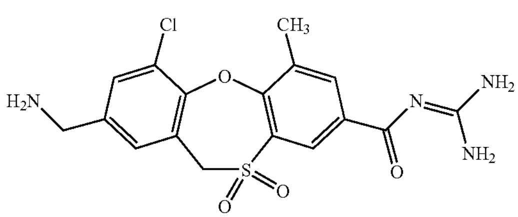 | 0.03 |

The results in Table 2 indicate that the compounds of the present invention have significant inhibitory effects against NHE-1 isoform which is predominantly present in human platelets.

In Vivo Studies:

a. Ischemia and Reperfusion-Induced Arrhythmias and Myocardial Infarction Experiments in Anaesthetized Rats is Described Below.

The protocol used for these experiments closely follows that described by Ohara et al (Jpn. J. Pharmacol. 80, 295-302, (1999)).

Wistar rats (preferably male, 250-300 g) were anaesthetized with sodium pentobarbitone (60 mg/kg) intraperitoneally. Tracheotomy was performed through a ventral midline cervical incision and the rats were ventilated using a respiratory pump (Rhema respiratory pump: 1-1.5 mL of air/100 g body weight, 60 strokes/min). The left carotid artery and left jugular vein were isolated and cannulated with fluid filled catheters for monitoring blood pressure and administering the test compound respectively. Blood pressure was recorded using a P23 Db Statham pressure transducer attached to a Nihon Kohden recorder or Hellige polygraph. After thoracotomy between the 4th and 5th intercostal space, the heart was exposed, and a loose ligature was placed around the left anterior descending coronary artery (LAD) 2-3 mm from its origin using a fine cotton thread and Lane's cleft palate 9 mm half circle fine suture needle (Needle Industries (India) Pvt. Ltd., Nilgiris, Tamilnadu). The epicardial ECG was monitored on a cardioscope (BPL), the heart rate was monitored on a heart rate meter (PFM 2 Mino pulse rate meter, Hugo Sachs Electronik) and the body temperature was maintained at 37-38° C. with the help of a 100W bulb and monitored with a rectal probe connected to a telethermometer. (Yellow Springs Inc., USA).

An equilibration period of 20 min was allowed during which an animal showing spontaneous arrhythmias or a mean blood pressure of <70 mm Hg was excluded from the study.

The test compounds were dissolved in saline or 5% dextrose or distilled water. After recording the control or initial heart rate and blood pressure, the test compound infusion (in doses of 0.1, 0.3, 1.0, 3.0 mg/kg/h, and if needed in doses of 7.5 or 10 mg/kg/h)/vehicle (@3 mL/h) was begun 15 min before the induction of the regional ischemia and continued through the ischemia and reperfusion phases till the end of the experiment, the total time for infusion being 2 h 15 min.

LAD was ligated to a tygon tube to create regional ischemia. After 1 h of ischemia, LAD was deligated and reperfusion allowed for 1 h. Associated changes in the ECG pattern and blood pressure were continuously monitored. Cardiac Index (CI) or Rate Pressure Product (RPP)=MBP× HR) was calculated at various intervals of time to obtain the cardiac oxygen consumption. Arrhythmias were evaluated according to the Lambeth convention (Cardiovasc. Res. 22, 447-455, (1988)).

At the end of the reperfusion period, LAD was then religated and heparinized saline (0.5 ml of 100 iu/mL) was given intravenously through the carotid artery catheter. 1% Evans blue dye (2 mL) was then injected slowly intravenously. The whole heart, except the area at risk (non-perfused or ischemic area), was stained blue. The heart was isolated and the dye sticking externally was washed off using saline. The heart was wrapped in a piece of foodwrap film and stored overnight at −20° C. The frozen heart was sliced into 5 transverse sections. The right ventricle was removed from these heart sections. After washing the slices with saline they were incubated with 1% triphenyltetrazolium chloride dye (in phosphate buffer, pH 7.4) at 37° C. for 10-15 min to delineate non-infarcted viable tissue (stained brick red) from the infarcted or necrotic (nonstained or pale pink) tissue within the area at risk. The stained slices were kept in 10% formalin saline for 48 h. The extent of staining of various areas was measured by computerized planimetry (Image Pro Plus, Media Cybernetics, USA). The infarct size expressed as a percentage of area-at-risk was compared with that of the control. Inhibition of infarction by treatment was calculated by comparing the mean percentage infarction in the test group with that of the mean percentage infarction in the control group in an experiment. Each set of observations involved a minimum of 4-6 experiments using different Wistar rats in the control or test group.

The statistical significance was calculated by using Student's t-test.

The compounds exhibited potent anti-arrhythmic and anti-infarction activity against ischemia and reperfusion induced cardiac injury in Coronary artery ligated (CAL) rats.

b. Myocardial Infarction in Anaesthetized Rabbit:

The protocol for this experiment closely follows that adapted by Knight Delvin R. et.al. (J. Pharmacol. Exp. Ther 297: 254-259, (2001))

Male or female New Zealand albino rabbits (2-3 kg) were intramuscularly anaesthetized with 1 mL/kg of a freshly prepared mixture in the ratio of 1:0.5, of ketamine hydrochloride (50 mg/mL) and xylazine hydrochloride (20 mg/mL). After deep anaesthesia was achieved, tracheotomy was carried out, followed by artificial ventilation (7-8 mL/kg and 35-40 strokes/min), using a mixture of pure oxygen and compressed air, provided with the help of a Rhema respiratory pump. The left jugular vein, left carotid artery, right femoral vein and artery were cannulated for anaesthesia (using a 1:7 dilution of xylazine of the original 20 mg/mL and @10 mL/h), recording of blood pressure, administration of test compounds vehicle (saline or 5% dextrose, at doses of 2 mg/kg/h, 4 mg/kg/h, 8 mg/kg/h) and withdrawal of blood samples, respectively. The body temperature was maintained at 37-38° C. with the help of a heat lamp and monitored using a rectal probe connected to a telethermometer.

The heart was exposed through the $3^{rd}/4^{th}$ intercostal spaces and was suspended in a pericardial cradle. A ligature was placed around a small branch of left anterior descending coronary artery (LAD) near its origin. The arterial blood pressure was recorded using a polygraph recorder (Nihon Kohden), and the heart rate was monitored using a heart rate meter (Hugo Sachs electronics). The control values for MBP and HR were recorded 40-min after dissection. The cardiac Index (CI) or Rate Pressure Product (RPP)=(MBP×HR) was calculated at various intervals of time. After recording the control heart rate and blood pressure, the test compound infusion/vehicle (@6 ml/h) in different rabbits, was begun 30 min before the induction of regional ischemia and continued through the ischemia and reperfusion phases till the end of the experiment over a period of 2.5 h. The LAD branch was ligated to a small plastic tube to cause regional ischemia. After 30 min of ischemia, LAD was deligated and reperfusion was allowed for 2 h. The LAD was then religated and 1% Evans blue dye (10 ml, prepared in phosphate buffer, pH 7.4) was injected through the carotid cannula. The whole heart, except the ischemic area or the area at risk, was stained blue. It was isolated and the dye sticking to it externally was washed off using saline. The heart was wrapped in a piece of foodwrap film and was stored at −20° C. overnight. The next day it was cut into 5 slices and the non-stained area at risk for each slice was traced on an acetate sheet. Assessment of infarction was done using triphenyltetrazolium chloride dye (1%, prepared in phosphate buffer, pH 7.4) which stained the viable tissue brick red while the infarcted or necrotic tissue remained unstained. Outlines of the slices and of the areas at risk and infarction were traced on a glass/acetate sheet and a reduced paper copy of this tracing was used for area measurements determined by computerized planimetry (Image Pro Plus, Media Cybernetics, USA). The infarct size, expressed as a percentage of area at risk, was compared with that of the control. The statistical significance was calculated using Student's 't' test.

Compounds described above had a significant cardioprotective effect in CAL rabbits. They exhibited potent anti arrhythmic and anti infarction activity against ischemia and reperfusion-induced cardiac injury.

We claim:
1. A compound of formula 1

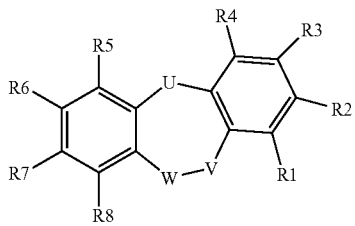

wherein,
R1, R2, R3, R4, R5, R6, R7 and R8 are independently from each other selected from: hydrogen, halogen, hydroxy, hydroxyalkyl, formyl, alkoxy, $(C_3$-$C_6)$cycloalkoxy, aryloxy, alkylthio, alkylcarbonyl, carboxy, alkylcarboxylate, alkyl, alkenyl, $(C_3$-$C_6)$cycloalkyl, aryl, aryloxycarbonyl, alkylaminoalkyl, aminocarbonyl, cyano, nitro, amidino, sulfonyl chloride, sulfonyl hydrazide, alkylsulfonyl, heterocyclylsulfonyl, heteroarylsulfonyl, sulfonamide, alkyl-NH—$SO_2$—, cycloalkyl-NH—$SO_2$—, heterocyclyl-NH—$SO_2$—, heteroaryl-NH—$SO_2$—, heteroaryl-alkyl-NH—$SO_2$—, arylalkyl, heterocyclyl, heteroaryl, guanidino carbonyl, guanidino, —NR'R''and N=R''';
R' and R'' are independently from each other selected from: hydrogen, alkyl, $(C_3$-$C_6)$cycloalkyl, aryl, arylalkyl, haloalkyl, thioalkyl, hydroxyalkyl, alkoxyalkyl, aryloxyalkyl, carboxyalkyl, aminoalkyl, mono- or di-alkyl-substituted aminoalkyl, $(C_3$-$C_6)$cycloalkylaminoalkyl, arylalkylaminoalkyl, alkoxyarylalkyl aminoalkyl, heterocyclylalkyl, heterocyclylaminoalkyl, heterocyclylalkylaminoalkyl, heterocyclylalkyl-N[(alkyl)]-alkyl, heteroarylalkyl, heteroarylalkylaminoalkyl, alkoxyarylalkyl-N[(alkyl)]-alkyl, arylalkyl-N[(alkyl)]-alkyl, alkoxycarbonyl, $(C_3$-$C_6)$cycloalkylcarbonyl, $(C_3$-$C_6)$cycloalkylaminocarbonyl, arylcarbonyl, aryloxycarbonyl, aralkoxycarbonyl, heterocyclylcarbonyl, CHO and alkyl carbonyl (where said alkyl is unsubstituted or substituted by one, two or three of the same or different substituents selected from: halo, hydroxy, alkoxy, alkylamino, $(C_3$-$C_6)$cycloalkyl amino, aryl and heterocyclyl);
R''' is selected from: heterocyclyl, $(C_3$-$C_6)$cycloalkyl and alkyl;
where aryl is $(C_6$-$C_{10})$aryl which is unsubstituted or substituted by one or two of the same or different groups selected from: nitro, alkyl, alkoxy, halogen, haloalkyl, amino, mono- or dialkylamino, and heterocyclylalkylaminoalkyl; heteroaryl is a 5 or 6 membered ring system containing one, two or three ring atoms selected from N, O and S, which is unsubstituted or substituted by one or two of the same or different groups selected from: halogen, nitro, amino, alkylamino, alkyl, alkoxy and alkylcarbonyl; heterocyclyl is a 5 or 6 membered ring system containing one, two or three ring atoms selected from N, O and S, which is unsubstituted or substituted by one or two of the same or different groups selected from: alkyl, $(C_3$-$C_6)$cycloalkyl, hydroxyalkyl, alkylaminoalkyl, $(C_3$-$C_6)$cycloalkylalkyl, $(C_3$-$C_6)$cycloalkyl carbonyl, heterocyclylalkyl, heteroarylalkyl, heteroarylcarbonyl, arylalkyl, and oxo; guanidino and guanidinocarbonyl are unsubstituted or substituted by one, two or three of the same or different groups selected from: alkyl and alkylcarbonyl;
with the proviso that at least one of R1, R2, R3, R4, R5, R6, R7 or R8 is guanidino or guanidino carbonyl;
U is C(O), $CR^aR^b$, O, $NR^a$, or $S(O)_m$;
V is $CR^aR^b$ or $NR^a$;
W is $S(O)_m$;
wherein,
$R^a$ is H, alkyl, $(C_3$-$C_6)$cycloalkyl, alkenyl or arylalkyl;
$R^b$ is H, alkyl, OH, $OR^a$ or $OCOR^a$; and
m is the integer 0, 1 or 2;
in all its stereoisomeric and tautomeric forms and mixtures thereof in all ratios, and pharmaceutically acceptable salts thereof.

2. A compound of the formula I as defined in claim 1, wherein R1, R2, R3, R4, R5, R6, R7 and R8 are independently from each other selected from: hydrogen, halogen, hydroxy, cyano, nitro, formyl, carboxy, guanidino, guanidino carbonyl, $(C_1$-$C_4)$alkyl, $(C_3$-$C_6)$cycloalkyl, $(C_1$-$C_4)$alkoxy, $(C_3$-$C_6)$cycloalkoxy, $(C_1$-$C_4)$alkylthio, $(C_1$-$C_4)$alkoxycarbonyl, $(C_6$-$C_{10})$aryloxycarbonyl, $(C_6$-$C_{10})$aryl, $(C_6$-$C_{10})$aryloxy, pyrrolyl, pyrrolidinyl, piperidinyl, piperazinyl, morpholinyl, amino, $(C_1$-$C_4)$alkylamino, thio-$(C_1$-$C_4)$alkylamino, $(C_1$-$C_4)$alkoxy-substituted$(C_1$-$C_4)$alkylamino, di-$(C_1$-$C_4$-alkyl)amino, chloro$(C_1$-$C_4)$alkylamino, di-[chloro-$(C_1$-$C_4)$alkyl]amino, hydroxy$(C_1$-$C_4)$alkylamino, dihydroxy-$(C_1$-$C_4)$alkyl]amino, mono- or di-$(C_1$-$C_4$-alkyl) substituted-amino-$(C_1$-$C_4)$alkylamino, $(C_6$-$C_{10})$aryloxy$(C_1$-$C_4)$alkylamino, $(C_6$-$C_{10})$aryl$(C_1$-$C_4)$alkoxy$(C_1$-$C_4)$alkylamino, benzylamino, morpholinyl-$(C_1$-$C_4)$alkylamino, $(C_1$-$C_4)$alkylsubstituted-thiophenyl-$(C_1$-$C_4)$alkylamino, pyrrolidinyl$(C_1$-$C_4)$alkylamino, pyridyl$(C_1$-$C_4)$alkylamino, piperidinyl$(C_1$-$C_4)$alkylamino, 3H-imidazolyl$(C_1$-$C_4)$alkylamino, piperazinyl$(C_1$-$C_4)$alkylamino, morpholinyl$(C_1$-$C_4)$alkylamino$(C_1$-$C_4$-alkyl), pyrrolidinyl $(C_1$-$C_4)$alkylamino $(C_1$-$C_4$-alkyl), piperidinyl$(C_1$-$C_4)$alkylamino$(C_1$-$C_4$-alkyl), furanyl$(C_1$-$C_4)$alkylamino, benzylamino$(C_1$-$C_4)$alkylamino, morpholinylamino$(C_1$-$C_4)$alkylamino, $(C_3$-$C_6)$cycloalkylamino$(C_1$-$C_4)$alkylamino, furanyl$(C_1$-$C_4)$alkyl-N[$(C_1$-$C_4)$alkyl]$CH_2CH_2$—N[$(C_1$-$C_4)$alkyl]-, thiophenyl$(C_1$-$C_4)$alkyl-N[$(C_1$-$C_4)$alkyl]-$CH_2CH_2$—N[$(C_1$-$C_4)$alkyl]-, benzyl-NR$C_1$-$C_4)$alkyl]-$CH_2CH_2$—N[$(C_1$-$C_4)$alkyl]-, $(C_1$-$C_4)$alkylcarbonylamino, $(C_1$-$C_4)$alkoxycarbonylamino, $(C_6$-$C_{10})$aryloxycarbonylamino, $(C_6$-$C_{10})$aryl$(C_1$-$C_4)$alkoxycarbonylamino, morpholinylacetamido, morpholinyl $(C_1$-$C_4)$alkyl-N[C(O)$CH_3$]-, morpholinyl$(C_1$-$C_4)$alkyl-N(C(O)$CH_2CH_3$)—, morpholinyl$(C_1$-$C_4)$alkyl-N[C(O)$CH_2OCH_3$]-, morpholinyl$(C_1$-$C_4)$alkyl-N[C(O)-isobutoxy]-, morpholinyl$(C_1$-$C_4)$alkyl-N[C(O)cyclopropyl]-, pyrrolidinyl$(C_1$-$C_4)$alkyl-N[C(O)$CH_3$]—, pyrrolidinyl-$(C_1$-$C_4)$alkyl-N[C(O)$CH_2CH_3$]—, pyrrolidinyl$(C_1$-$C_4)$alkyl-N[C(O) isobutoxy]-, pyrrolidinyl$(C_1$-$C_4)$alkyl-N[C(O)cyclopropyl]-, pyrrolidinyl$(C_1$-$C_4)$alkyl-N[C(O)$CH_2CH_3$]—, piperidinyl$(C_1$-$C_4)$alkyl-N[C(O)—$CH_3$], piperidinyl$(C_1$-$C_4)$alkyl-N[C(O)—$CH_2OCH_3$]-, piperidinyl$(C_1$-$C_4)$alkyl-N[C(O)—$CH_2OH$]—, piperidinyl$(C_1$-$C_4)$alkyl-N[C(O)C$(CH_3)_3$]—, piperidinyl$(C_1$-$C_4)$alkyl-N[C(O)-isobutoxy]-, piperidinyl$(C_1$-$C_4)$alkyl-N[C(O)-cyclopropyl]-, $(C_1$-$C_4)$alkylamino ($C_1$-$C_4$)alkyl-N[C(O)—$CH_3$], ($C_1$-$C_4$)alkylamino($C_1$-$C_4$) alkyl-N[C(O)C($CH_3$)$_3$], halo($C_1$-$C_4$)alkyl-N[C(O)—$CH_2$Cl]—, ($C_3$-$C_6$)cycloalkyl-NH-acetamido, ($C_1$-$C_4$)alkyl-NH-acetamido, ($C_1$-$C_4$)alkylamino($C_1$-$C_4$)alkylacetamido, pyrrolidinyl acetamido, piperidinyl acetamido, piperazinyl acetamido, phenyl piperazinyl acetamido, imidazolyl acetamido, 1-carboxyalkyl pyrrolidinium-($C_1$-$C_4$)alkylamino, 1-carboxy, 4-($C_1$-$C_4$-alkyl)piperazinium-($C_1$-$C_4$)alkylamino, sulfonylchloride, ($C_1$-$C_4$)alkylsulfonyl, heterocyclylsulfonyl, heteroarylsulfonyl, sulfonylhydrazide, sulfonamide, ($C_1$-$C_4$)alkyl-NH—$SO_2$—, ($C_3$-$C_6$)cycloalkyl-NH—$SO_2$—, heterocyclyl-NH—$SO_2$—, heteroaryl-NH—$SO_2$— and heterocyclyl=N—;

where pyrrolyl, pyrrolidinyl, piperidinyl, piperazinyl, morpholinyl, furanyl, benzyl and imidazolyl are each unsubstituted or substituted by one or two of the same or different groups selected from: ($C_1$-$C_4$)alkyl, hydroxy($C_1$-$C_4$)alkyl, ($C_1$-$C_4$)alkoxy, oxo, ($C_1$-$C_4$)alkylamino($C_1$-$C_4$)alkyl, ($C_3$-$C_6$)cycloalkyl, ($C_3$-$C_6$)cycloalkyl($C_1$-$C_4$)alkyl, ($C_1$-$C_4$)alkylcarbonyl, ($C_3$-$C_6$)cycloalkylcarbonyl, heterocyclylcarbonyl, heterocyclyl($C_1$-$C_4$)alkyl, benzyl (where the benzyl is unsubstituted or substituted by one or two of the same or different groups selected from: ($C_1$-$C_4$)alkyl, ($C_1$-$C_4$)alkoxy, amino, mono- or di-substituted amino [where the substituents on the amino group may be independently selected from ($C_1$-$C_4$) alkyl, halo($C_1$-$C_4$)alkyl, hydroxy($C_1$-$C_4$)alkyl, ($C_1$-$C_4$) alkoxy($C_1$-$C_4$)alkyl, ($C_1$-$C_4$)acyl, halo($C_1$-$C_4$)acyl, heterocyclyl($C_1$-$C_4$)alkyl, heteroaryl($C_1$-$C_4$)alkyl, amino($C_1$-$C_4$) alkyl and ($C_1$-$C_4$)alkoxy($C_6$-$C_{10}$)aryl($C_1$-$C_4$)alkyl], nitro, halo, halo($C_1$-$C_4$)alkyl, and heterocyclyl($C_1$-$C_4$)alkylamino ($C_1$-$C_4$)alkyl;

where alkyl is unsubstituted or substituted by one or two of the same or different groups selected from: halo, hydroxy, mono- or di-substituted amino [where the substituents on the amino group may be independently selected from ($C_1$-$C_4$) alkyl, halo($C_1$-$C_4$)alkyl, hydroxy($C_1$-$C_4$)alkyl, ($C_1$-$C_4$) alkoxy($C_1$-$C_4$)alkyl, ($C_1$-$C_4$)acyl, halo($C_1$-$C_4$)acyl, heterocyclyl($C_1$-$C_4$)alkyl, heteroaryl($C_1$-$C_4$)alkyl, amino($C_1$-$C_4$) alkyl and ($C_1$-$C_4$)alkoxy($C_6$-$C_{10}$)aryl($C_1$-$C_4$)alkyl], benzyl amino, pyridyl, piperidinyl, pyrrole, furanyl, morpholinyl, thiophenyl, phenyl, ($C_3$-$C_6$)cycloalkyl, heterocyclyl and heteroaryl; and where ($C_6$-$C_{10}$)aryl, or each of heteroaryl and heterocyclyl, which is a 5 or 6 membered ring system containing one, two or three ring atoms selected from N, O and S, are independently from each other unsubstituted or substituted by one or two of the same or different groups selected from: ($C_1$-$C_4$) alkyl, ($C_1$-$C_4$)alkoxy and halo($C_1$-$C_4$)alkyl;

with the proviso that at least one of R1, R2, R3, R4, R5, R6, R7 or R8 is guanidino or guanidino carbonyl;

in all its stereoisomeric and tautomeric forms and mixtures thereof in all ratios, and its pharmaceutically acceptable salts thereof.

3. A compound of formula 1 as defined in claim 1, which has the structure of formula 1a

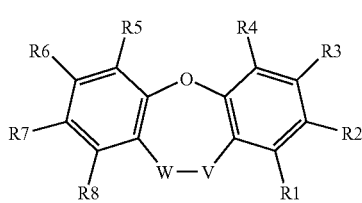

1a wherein
R1, R2, R3, R4, R5, R6, R7, R8 and W are as defined in claim 1, with the proviso that at least one of R1, R2, R3, R4, R5, R6, R7 or R8 is guanidino or guanidino carbonyl; and
V is $CH_2$, $CHCH_3$, $C(CH_3)_2$, NH or $NCH_3$;
in all its stereoisomeric and tautomeric forms and mixtures thereof in all ratios, and its pharmaceutically acceptable salts thereof.

4. A compound of formula 1 as defined in claim 1, which has the structure of formula 1b

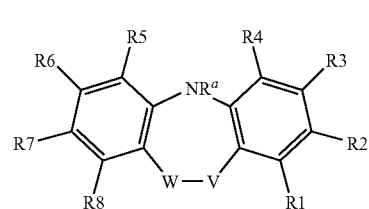

Ib wherein
R1, R2, R3, R4, R5, R6, R7, R8 and W are as defined in claim 1, with the proviso that at least one of R1, R2, R3, R4, R5, R6, R7 or R8 is guanidino or guanidino carbonyl;
$R^a$ is H, ($C_1$-$C_4$)alkyl, ($C_3$-$C_6$)cycloalkyl or ($C_2$-$C_4$)alkenyl; and
V is $CH_2$, $CHCH_3$, $C(CH_3)_2$, NH or $NCH_3$;
in all its stereoisomeric and tautomeric forms and mixtures thereof in all ratios, and pharmaceutically acceptable salts thereof.

5. A compound of formula I as defined in claim 1, wherein U is C(O), CHOH or $CH_2$, V is $CH_2$, R7 is guanidino carbonyl.

6. The compound of formula 1 as defined in claim 1, wherein R7 is guanidino or guanidino carbonyl.

7. The compound of formula 1 as defined in claim 1, wherein W is $SO_2$.

8. A compound of formula 1 as defined in claim 1, wherein R1, R3, R4, R5, R6 and R8 are independently from each other selected from: hydrogen, hydroxyl, halogen, nitro, cyano, amino, ($C_1$-$C_4$)alkyl, ($C_3$-$C_6$)cycloalkyl, ($C_1$-$C_4$)alkoxy, ($C_1$-$C_4$)alkylcarbonyl, ($C_1$-$C_4$)carboxy, phenyl, 5- or 6-membered heterocyclyl, 5- or 6-membered heteroaryl, 5- or 6-membered heterocyclyl($C_1$-$C_4$)alkyleneamino, 5- or 6-membered heteroarylamino, and phenyl($C_1$-$C_4$)alkylene amino.

9. A compound of formula 1a as defined in claim 3, selected from:
N-(10,10-Dioxo-10,11-dihydro-5-oxa-10lambda*6*-thia-dibenzo[a.d]cycloheptene-8-carbonyl)-guanidine;
N-(2,4-Dichloro-10,10-dioxo-10,11-dihydro-5-oxa-10lambda*6*-thia-dibenzo[a,d]cycloheptene-8-carbonyl)-guanidine;
N-(2-Chloro-10,10-dioxo-10,11-dihydro-5-oxa-10lambda*6*-thia-dibenzo[a,d]cycloheptene-8-carbonyl)-guanidine;
N-(4-Chloro-10,10-dioxo-10,11-dihydro-5-oxa-10lambda*6*-thia-dibenzo[a,d]cycloheptene-8-carbonyl)-guanidine;
N-(3-Fluoro-10,10-dioxo-10,11-dihydro-5-oxa-10lambda*6*-thia-dibenzo[a,d]cycloheptene-8-carbonyl)-guanidine;

N-(1-Fluoro-10,10-dioxo-10,11-dihydro-5-oxa-10lambda*6*-thia-dibenzo[a,d]cycloheptene-8-carbonyl)-guanidine;
N-(2-Fluoro-10,10-dioxo-10,11-dihydro-5-oxa-10lambda*6*-thia-dibenzo[a,d]cycloheptene-8-carbonyl)-guanidine;
N-(4-Isopropyl-10,10-dioxo-10,11-dihydro-5-oxa-10lambda*6*-thia-dibenzo[a,d]cycloheptene-8-carbonyl)-guanidine;
N-(4-Methyl-10,10-dioxo-10,11-dihydro-5-oxa-10lambda*6*-thia-dibenzo[a,d]cycloheptene-8-carbonyl)-guanidine;
N-(4-Amino-10,10-dioxo-10,11-dihydro-5-oxa-10lambda*6*-thia-dibenzo[a,d]cycloheptene-8-carbonyl)-guanidine;
N-(10,10-dioxo-4-pyrrol-1-yl-10,11-dihydro-5-oxa-10lambda*6*-thia-dibenzo[a,d]cycloheptene-8-carbonyl)-guanidine;
N-(2-Methanesulfonyl-10,10-dioxo-10,11-dihydro-5-oxa-10lambda*6*-thia-dibenzo[a,d]cycloheptene-8-carbonyl)-guanidine;
N-(7-Chloro-10,10-dioxo-10,11-dihydro-5-oxa-10lambda*6*-thia-dibenzo[a,d]cycloheptene-8-carbonyl)-guanidine;
N-(10,10-dioxo-7-piperidin-1-yl-10,11-dihydro-5-oxa-10lambda*6*-thia-dibenzo[a,d]cycloheptene-8-carbonyl)-guanidine;
N-(10,10-dioxo-7-pyrrolidin-1-yl-10,11-dihydro-5-oxa-10lambda*6*-thia-dibenzo[a,d]cycloheptene-8-carbonyl)-guanidine;
N-(7-Chloro-1-fluoro-10,10-dioxo-10,11-dihydro-5-oxa-10lambda*6*-thia-dibenzo[a,d]cycloheptene-8-carbonyl)-guanidine;
N-(7-Chloro-2-fluoro-10,10-dioxo-10,11-dihydro-5-oxa-10lambda*6*-thia-dibenzo[a,d]cycloheptene-8-carbonyl)-guanidine;
N-(10,10-Dioxo-7-pyrrol-1-yl-10,11-dihydro-5-oxa-10lambda*6*-thia-dibenzo[a,d]cycloheptene-8-carbonyl)-guanidine;
N-(7-Chloro-4-methyl-10,10-dioxo-10,11-dihydro-5-oxa-10lambda*6*-thia-dibenzo[a,d]cycloheptene-8-carbonyl)-guanidine;
N-(4-Methyl-10,10-dioxo-7-pyrrol-1-yl-10,11-dihydro-5-oxa-10lambda*6*-thia-dibenzo[a,d]cycloheptene-8-carbonyl)-guanidine;
N-(7-Chloro-2-methanesulfonyl-4-methyl-10,10-dioxo-10,11-dihydro-5-oxa-10lambda*6*-thia-dibenzo[a,d]cycloheptene-8-carbonyl)-guanidine;
N-(7-Chloro-4-isopropyl-10,10-dioxo-10,11-dihydro-5-oxa-10lambda*6*-thia-dibenzo[a,d]cycloheptene-8-carbonyl)-guanidine;
N-(2,7-Dichloro-10,10-dioxo-10,11-dihydro-5-oxa-1°lambda*6*-thia-dibenzo[a,d]cycloheptene-8-carbonyl)-guanidine;
N-(7-Benzylamino-4-methyl-10,10-dioxo-10,11-dihydro-5-oxa-10lambda*6*-thia-dibenzo[a,d]cycloheptene-8-carbonyl)-guanidine;
N-(4-Chloro-7-methyl-10,10-dioxo-10,11-dihydro-5-oxa-10lambda*6*-thia-dibenzo[a,d]cycloheptene-8-carbonyl)-guanidine;
N-(4,7-Dimethyl-10,10-dioxo-10,11-dihydro-5-oxa-10lambda*6*-thia-dibenzo[a,d]cycloheptene-8-carbonyl)-guanidine;
N-(7-Methyl-10,10-dioxo-10,11-dihydro-5-oxa-10lambda*6*-thia-dibenzo[a,d]cycloheptene-8-carbonyl)-guanidine;
N-(4-Chloro-6-methyl-10,10-dioxo-10,11-dihydro-5-oxa-10lambda*6*-thia-dibenzo[a,d]cycloheptene-8-carbonyl)-guanidine;
N-(2-Chloro-6-methyl-10,10-dioxo-10,11-dihydro-5-oxa-10lambda*6*-thia-dibenzo[a,d]cycloheptene-8-carbonyl)-guanidine;
N-(4-Chloro-2-methanesulfonyl-6-methyl-10,10-dioxo-10,11-dihydro-5-oxa-10lambda*6*-thia-dibenzo[a,d]cycloheptene-8-carbonyl)-guanidine;
N-(4-Isopropyl-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-2-nitro-10,10-dioxo-10,11-dihydro-5-oxa-10lambda*6*-thia-dibenzo[a,d]cycloheptene-8-carbonyl)-guanidine;
N-(4,6-Dimethyl-10,10-dioxo-10,11-dihydro-5-oxa-10lambda*6*-thia-dibenzo[a,d]cycloheptene-8-carbonyl)-guanidine;
N-(4-Isopropyl-6-methyl-2-nitro-10,10-dioxo-10,11-dihydro-5-oxa-10lambda*6*-thia-dibenzo[a,d]cycloheptene-8-carbonyl)-guanidine;
N-(2-Amino-4-chloro-6-methyl-10,10-dioxo-10,11-dihydro-5-oxa-10lambda*6*-thia-dibenzo[a,d]cycloheptene-8-carbonyl)-guanidine;
N-(2-Amino-4,6-dimethyl-10,10-dioxo-10,11-dihydro-5-oxa-10lambda*6*-thia-dibenzo[a,d]cycloheptene-8-carbonyl)-guanidine;
N-(4-Chloro-2-iodo-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-10,10-dioxo-2-pyrrol-1-yl-10,11-dihydro-5-oxa-10lambda*6*-thia-dibenzo[a,d]cycloheptene-8-carbonyl)-guanidine;
N-[2-(2,5-Dimethyl-pyrrol-1-yl)-4,6-dimethyl-10,10-dioxo-10,11-dihydro-5-oxa-10lambda*6*-thia-dibenzo[a,d]cycloheptene-8-carbonyl]-guanidine;
N-(2-Dimethylamino-4,6-dimethyl-10,10-dioxo-10,11-dihydro-5-oxa-10lambda*6*-thia-dibenzo[a,d]cycloheptene-8-carbonyl)-guanidine;
N-(4-Chloro-2-dimethylamino-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-2-methylamino-10,10-dioxo-10,11-dihydro-5-oxa-10lambda*6*-thia-dibenzo[a,d]cycloheptene-8-carbonyl)-guanidine;
N-(2-[N-Benzyloxycarbonyl-guanidino]-4-Chloro-6-methyl-10,10-dioxo-10,11-dihydro-5-oxa-10lambda*6*-thia-dibenzo[a,d]cycloheptene-8-carbonyl)-guanidine;
N-(4-Chloro-2-isobutylamino-6-methyl-10,10-dioxo-10,11-dihydro-5-oxa-10lambda*6*-thia-dibenzo[a,d]cycloheptene-8-carbonyl)-guanidine;
N-(4,6-Dichloro-10,10-dioxo-10,11-dihydro-5-oxa-10lambda*6*-thia-dibenzo[a,d]cycloheptene-8-carbonyl)-guanidine,
N-(2-Amino-4,6-dichloro-10,10-dioxo-10,11-dihydro-5-oxa-10lambda*6*-thia-dibenzo[a,d]cycloheptene-8-carbonyl)-guanidine;
N-(6-Chloro-4-methyl-10,10-dioxo-10,11-dihydro-5-oxa-10lambda*6*-thia-dibenzo[a,d]cycloheptene-8-carbonyl)-guanidine;
N-(2-Amino-6-chloro-4-methyl-10,10-dioxo-10,11-dihydro-5-oxa-10lambda*6*-thia-dibenzo[a,d]cycloheptene-8-carbonyl)-guanidine;
4-Chloro-8-guanidinocarbonyl-6-methyl-10,10-dioxo-10,11-dihydro-5-oxa-10lambda*6*-thia-dibenzo[a,d]cycloheptene-2-sulfonic acid amide;

N-(6-chloro-4-methyl-10,10-dioxo-10,11-dihydro-5-oxa-10lamda*6*-thia-dibenzo [a,d]cyclopentene-8-carbonyl)-guanidine;
4-Chloro-8-guanidinocarbonyl-6-methyl-10,10-dioxo-10, 11-dihydro-5-oxa-10lambda*6*-thia-dibenzo[a,d]cycloheptene-2-sulfonic acid (5-cyclopropyl-[1,3,4]thiadiazol-2-yl)-amide;
4-Chloro-8-guanidinocarbonyl-6-methyl-10,10-dioxo-10, 11-dihydro-5-oxa-10lambda*6*-thia-dibenzo[a,d]cycloheptene-2-sulfonic acid (pyridin-3-ylmethyl)-amide;
N-[4-Chloro-6-methyl-10,10-dioxo-2-(piperazine-1-sulfonyl)-10,11-dihydro-5-oxa-10lambda*6*-thia-dibenzo[a,d]cycloheptene-8-carbonyl]guanidine;
N-[4-Chloro-6-methyl-2-(4-methyl-piperazine-1-sulfonyl)-10,10-dioxo-10,11-dihydro-5-oxa-10lambda*6*-thia-dibenzo[a,d]cyclohepten-8-carbonyl]-guanidine;
N-[4-Chloro-6-methyl-2-(morpholine-4-sulfonyl)-10,10-dioxo-10,11-dihydro-5-oxa-10lambda*6*-thia-dibenzo[a,d]cycloheptene-8-carbonyl]guanidine;
N-[4-Chloro-2-(4-cyclopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[4-Chloro-2-(4-cyclopentyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[4-Chloro-2-(4-isopropyl-2-oxo-piperazin-1-yl)-6-methyl-10,10-dioxo-10,11-dihydro-5-oxa-10lambda*6*-thia-dibenzo[a,d]cycloheptene-8-carbonyl]-guanidine;
N-[2-(4-Benzyl-2-oxo-piperazin-1-yl)-4-chloro-6-methyl-10,10-dioxo-10,11-dihydro-5-oxa-10lambda*6*-thia-dibenzo[a,d]cycloheptene-8-carbony]-guanidine;
N-{4-Chloro-6-methyl-242-(4-methylpiperazin-1-yl)-ethylamino]-10,10-dioxo-10,11-dihydro-5-oxa-10lambda*6*-thia-dibenzo[a,d]cycloheptene-8-carbonyl}-guanidine;
1-Carboxymethyl-1-[2-(4-chloro-8-guanidinocarbonyl-6-methyl-10,10-dioxo-10,11-dihydro-5-oxa-10lambda*6*-thia-dibenzo[a,d]cyclohepten-2-ylamino)-ethyl]-4-methyl piperazin-1-ium;
N-[4-Chloro-2-(2-imidazol-1-yl-ethylamino)-6-methyl-10,10-dioxo-10,11-dihydro-5-oxa-10lambda*6*-thia-dibenzo[a,d]cycloheptene-8-carbonyl]-guanidine;
N-[2-(2-Amino-ethylamino)-4-chloro-6-methyl-10,10-dioxo-10,11-dihydro-5-oxa-10lambda*6*-thia-dibenzo[a,d]cycloheptene-8-carbonyl]-guanidine;
N-[4-Chloro-6-methyl-2-(2-morpholin-4-yl-ethylamino)-10,10-dioxo-10,11-dihydro-5-oxa-10lambda*6*-thia-dibenzo[a,d]cycloheptene-8-carbonyl]-guanidine;
N-{4-Chloro-2-[ethyl-(2-morpholin-4-yl-ethyl)-amino]-6-methyl-10,10-dioxo-10,11-dihydro-5-oxa-10lambda*6*-thia-dibenzo[a,d]cycloheptene-8-carbonyl}-guanidine;
N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-morpholin-4-yl-ethyl)-acetamide;
N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-morpholin-4-yl-ethyl)-acetamide;
N-(4-Chloro-2-{2-[4-(2-hydroxy-ethyl)-piperazin-1-yl]-ethylamino}-6-methyl-10,10-dioxo-10,11-dihydro-5-oxa-10lambda*6*-thia-dibenzo[a,d]cycloheptene-8-carbonyl)-guanidine;

N-{4-Chloro-6-methyl-2-(2-methylamino-ethylamino)-10,10-dioxo-10,11-dihydro-5-oxa-10lambda*6*-thia-dibenzo[a,d]cycloheptene-8-carbonyl}-guanidine;
N-[4-Chloro-6-methyl-10,10-dioxo-2-(2-pyrrolidin-1-yl-ethyl amino)-10,10-dioxo-10,11-dihydro-5-oxa-10lambda*6*-thia-dibenzo[a,d]cycloheptene-8-carbonyl]-guanidine;
N-{4-Chloro-2-[ethyl-(2-pyrrolidin-1-yl-ethyl)-amino]-6-methyl-10,10-dioxo-10,11-dihydro-5-oxa-10lambda*6*-thia-dibenzo[a,d]cycloheptene-8-carbonyl}-guanidine;
(4-Chloro-8-guanidinocarbonyl-6-methyl-10,10-dioxo-10,11-dihydro-5-oxa-10lambda*6*-thia-dibenzo[a,d]cycloheptene-2-yl)-(2-pyrrolidin-1-yl-ethyl)-carbamic acid isobutylester;
1-Carboxymethyl-1-[2-(4-chloro-8-guanidinocarbonyl-6-methyl-10,10-dioxo-10,11-dihydro-5-oxa-10-lambda*6*-thia-dibenzo[a,d]cycloheptene-2-ylamino)-ethyl]-pyrrolidinium;
Cyclopropanecarboxylic acid (4-chloro-8-guanidinocarbonyl-6-methyl-10,10-dioxo-10,11-dihydro-5-oxa-10lambda*6*-thia-dibenzo[a,d]cyclohepten-2-yl)-(2-pyrrolidin-1-yl-ethyl)-amide;
N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-pyrrolidin-1-yl-ethyl)-acetamide;
N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-pyrrolidin-1-yl-ethyl)-acetamide;
N-{4-Chloro-6-methyl-2-[2-(2-morpholin-4-yl-ethylamino)-ethylamino]-10,10-dioxo-10,11-dihydro-5-oxa-10lambda*6*-thia-dibenzo[a,d]cycloheptene-8-carbonyl}-guanidine;
N-{4-Chloro-6-methyl-2-[2-(2-morpholin-4-ylamino)-ethylamino]-10,10-dioxo-10,11-dihydro-5-oxa-10lambda*6*-thia-dibenzo[a,d]cycloheptene-8-carbonyl}-guanidine;
N-[4-Chloro-2-(2-cyclopropylamino-ethylamino)-6-methyl-10,10-dioxo-10,11-dihydro-5-oxa-10lambda*6*-thia-dibenzo[a,d]cycloheptene-8-carbonyl]-guanidine;
N-[4-Chloro-6-methyl-2-(3-morpholin-4-yl-propylamino)-10,10-dioxo-10,11-dihydro-5-oxa-10lambda*6*-thia-dibenzo[a,d]cycloheptene-8-carbonyl]-guanidine;
N-{4-Chloro-6-methyl-10,10-dioxo-2-[2-(2-pyridin-2-yl-ethylamino)-ethylamino]-10,11-dihydro-5-oxa-10lambda*6*-thia-dibenzo[a,d]cycloheptene-8-carbonyl}-guanidine;
N-(4-Chloro-2-{2-[(furan-2-ylmethyl)-amino]-ethylamino-}-6-methyl-10,10-dioxo-10,11-dihydro-5-oxa-10lambda*6*-thia-dibenzo[a,d]cycloheptene-8-carbonyl)-guanidine;
N-(4-Chloro-2-{ethyl-[2-(ethyl-furan-2-ylmethyl-amino)-ethyl]-amino-}-6-methyl-10,10-dioxo-10,11-dihydro-5-oxa-10lambda*6*-thia-dibenzo[a,d]cycloheptene-8-carbonyl)-guanidine;
N-(4-Chloro-6-methyl-10,10-dioxo-2-{2-[(thiophen-2-ylmethyl)-amino]-ethylamino}-10,11-dihydro-5-oxa-10lambda*6*thia-dibenzo[a,d]cycloheptene-8-carbonyl)-guanidine;
N-(4-Chloro-2-{ethyl-[2-(ethyl-thiophen-2-ylmethyl-amino)-ethyl]-amino}-6-methyl-10,10-dioxo-10,11-dihydro-5-oxa-10lambda*6*-thia-dibenzo[a,d]cycloheptene-8-carbonyl)-guanidine;

N-[2-(2-Benzylamino-ethylamino)-4-chloro-6-methyl-10,10-dioxo-10,11-dihydro-5-oxa-10lambda*6*-thia-dibenzo[a,d]cycloheptene-8-carbonyl]-guanidine;

N-(2-{[2-(Benzyl-ethyl-amino)-ethyl]-ethyl-amino}-4-chloro-6-methyl-10,10-dioxo-10,11-dihydro-5-oxa-10lambda*6*-thia-dibenzo[a,d]cycloheptene-8-carbonyl)-guanidine;

N-{4-Chloro-2-[2-(2-methoxy-benzylamino)-ethylamino]-6-methyl-10,10-dioxo-10,11-dihydro-5-oxa-10lambda*6*-thia-dibenzo[a,d]cycloheptene-8-carbonyl}-guanidine;

N-(4-Chloro-2-{2-[ethyl-(2-methoxy-benzyl)-amino]-ethylamino}-6-methyl-10,10-dioxo-10,11-dihydro-5-oxa-10lambda*6*-thia-dibenzo[a,d]cycloheptene-8-carbonyl)-guanidine;

N-[4-Chloro-6-methyl-10,10-dioxo-2-(2-piperidin-1-yl-ethylamino)-10,11-dihydro-5-oxa-10lambda*6*-thia-dibenzo[a,d]cycloheptene-8-carbonyl]-guanidine;

N-(4-Chloro-2-[ethyl-(2-piperidin-1-yl-ethyl)-amino]-6-methyl-10,10-dioxo-10,11-dihydro-5-oxa-10-lambda*6*-thia-dibenzo[a,d]cycloheptene-8-carbonyl}-guanidine;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-hydroxy-N-(2-piperidin-1-yl-ethyl)-acetamide;

Cyclopropanecarboxylic acid (4-chloro-8-guanidinocarbonyl-6-methyl-10,10-dioxo-10,11-dihydro-5-oxa-10lambda*6*-thia-dibenzo[a,d]cycloheptene-2-yl)-(2-piperidin-1-yl-ethyl)-amide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2,2-dimethyl-N-(2-piperidin-1-yl-ethyl)-propionamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-piperidin-1-yl-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methoxy-N-(2-piperidin-1-yl-ethyl)-acetamide;

N-[4-Chloro-2-(2-dimethylamino-ethylamino)-6-methyl-10,10-dioxo-10,11-dihydro-5-oxa-10lambda*6*-thia-dibenzo[a,d]cyclohepten-8-carbonyl]-guanidine;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-N-(2-dimethylamino-ethyl)-2,2-dimethyl-propionamide;

N-[4-Chloro-6-methyl-2-(4-methylpiperazin-1-yl)-10,10-dioxo-10,11-dihydro-5-oxa-10lambda*6*-thia-dibenzo[a,d]cycloheptene-8-carbonyl]-guanidine;

N-(4-Chloro-6-methyl-10,10-dioxo-2-piperazin-1-yl-10,11-dihydro-5-oxa-10lambda*6*-thia-dibenzo[a,d]cycloheptene-8-carbonyl)-guanidine;

N-[4-Chloro-2-(4-decyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-10,10-dioxo-2-(4-pentyl-piperazin-1-yl)-10,11-dihydro-5-oxa-10-lambda*6*-thia-dibenzo[a,d]cycloheptene-8-carbonyl]-guanidine;

N-[4-Chloro-2-(4-cyclopropanecarbonyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{4-Chloro-2-[4-(4-dimethylamino-benzyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-[4-Chloro-2-[4-(2,4-dichloro-benzyl)-piperazin-1-yl]-6-methyl-10,10-dioxo-10,11-dihydro-5-oxa-10lambda*6*-thia-dibenzo[a,d]cycloheptene-8-carbonyl]-guanidine;

N-{4-Chloro-6-methyl-10,10-dioxo-2-[4-(1H-pyrrole-2-carbonyl)-piperazin-1-yl]-10,11-dihydro-5-oxa-10lambda*6*-thia-dibenzo[a,d]cycloheptene-8-carbonyl}-guanidine;

N-{4-Chloro-6-methyl-2-[4-(5-methyl-furan-2-ylmethyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-2-[4-(2-methyl-benzyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-2-[4-(5-methyl-thiophen-2-ylmethyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-2-[4-(3,4-dimethoxy-benzyl)-piperazin-1-yl]-6-methyl-10,10-dioxo-10,11-dihydro-5-oxa-10lambda*6*-thia-dibenzo[a,d]cycloheptene-8-carbony}-guanidine;

N-{4-Chloro-6-methyl-10,10-dioxo-2-[4-(4-trifluoromethyl-benzyl)-piperazin-1-yl]-10,11-dihydro-5-oxa-10lambda*6*-thia-dibenzo[a,d]cycloheptene-8-carbonyl}-guanidine;

N-{4-Chloro-2-(4-ethyl-piperazin-1-yl)-6-methyl-10,10-dioxo-10,11-dihydro-5-oxa-10lambda*6*-thia-dibenzo[a,d]cycloheptene-8-carbonyl}guanidine;

N-{4-Chloro-6-methyl-2-morpholin-4-yl-10,10-dioxo-10,11-dihydro-5-oxa-10lambda*6*-thia-dibenzo[a,d]cycloheptene-8-carbonyl}-guanidine;

N-[2-(4-Benzyl-piperazin-1-yl)-4-chloro-6-methyl-10,10-dioxo-10,11-dihydro-5-oxa-10lambda*6*-thia-dibenzo[a,d]cycloheptene-8-carbonyl]-guanidine;

N-{4-Chloro-2-[4-(2-dimethylamino-ethyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-[4-Chloro-2-(4-isopropyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{4-Chloro-6-methyl-2-[4-(2-morpholin-4-yl-ethyl)-piperazin-1-yl]-10,10-dioxo-10,11-dihydro-5-oxa-10lambda*6*-thia-dibenzo[a,d]cycloheptene-8-carbonyl}-guanidine;

N-{4-Chloro-6-methyl-10,10-dioxo-2-[4-(2-pyrrolidin-1-yl-ethyl)-piperazin-1-yl]-10,11-dihydro-5-oxa-10lambda*6*-thia-dibenzo[a,d]cycloheptene-8-carbonyl}-guanidine;

N-[4-Chloro-2-(4-cyclopropylmethyl-piperazin-1-yl)-6-methyl-10,10-dioxo-10,11-dihydro-5-oxa-10lambda*6*-thia-dibenzo[a,d]cycloheptene-8-carbonyl]guanidine;

N-{4-Chloro-6-methyl-10,10-dioxo-2-[4-(2-piperazin-1-yl-ethyl)-piperazin-1-yl]-10,11-dihydro-5-oxa-10lambda*6*-thia-dibenzo[a,d]cycloheptene-8-carbonyl}-guanidine;

N-[4-Chloro-2-(4-cyclopropyl-piperazin-1-yl)-6-methyl-10,10-dioxo-10,11-dihydro-5-oxa-10lambda*6*-thia-dibenzo[a,d]cycloheptene-8-carbonyl]-guanidine;

N-{2-[4-(3-Amino-benzyl-piperazin-1-yl]-4-chloro-6-methyl-10,10-dioxo-10,11-dihydro-5-oxa-10lambda*6*-thia-dibenzo[a,d]cycloheptene-8-carbonyl}-guanidine;

N-[4-Chloro-6-methyl-10,10-dioxo-2-(4-pyridin-3-ylmethyl-piperazin-1-yl)-10,11-dihydro-5-oxa-10lambda*6*-thia-dibenzo[a,d]cycloheptene-8-carbonyl]-guanidine;

N-[4-Chloro-2-(4-cyclobutyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-2-(4-cyclohexyl-piperazin-1-yl)-6-methyl-10,10-dioxo-10,11-dihydro-5-oxa-10lambda*6*-thia-dibenzo[a,d]cycloheptene-8-carbonyl]-guanidine;

N-[4-Chloro-6-methyl-10,10-dioxo-2-(4-thiophen-2-ylmethyl-piperazin-1-yl)-10,11-dihydro-5-oxa-10lambda*6*-thia-dibenzo[a,d]cycloheptene-8-carbonyl]-guanidine;

N-{4-Chloro-2-[4-(2-methoxy-benzyl-piperazin-1-yl]-6-methyl-10,10-dioxo-10,11-dihydro-5-oxa-10lambda*6*-thia-dibenzo[a,d]cycloheptene-8-carbonyl}-guanidine;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-pyperidin-1-yl-acetamide;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-(2,2,2-trifluoro-ethylamino)-acetamide;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-hydroxy-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-imidazol-1-yl-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclopropylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-cyclohexylamino-acetamide;

N-(4-Chloro-8-guanidinocarbonyl-6-methyl-10,10-dioxo-10,11-dihydro-5-oxa10lambda*6*-thia-dibenzo[a,d]cyclohepten-2-yl)-2-cyclopentylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-isopropylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-dimethylamino-acetamide;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-cycylobutylamino-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-morpholin-4-yl-acetamide;

N-(4-Chloro-8-guanidinocarbonyl-6-methyl-10,10-dioxo-10,11-dihydro-5-oxa-10lambda*6*-thia-dibenzo[a,d]cyclohepten-2-yl)-2-[4-(3-trifluoromethyl-phenyl)-piperazin-1-yl]-acetamide, N-(4-Chloro-8-guanidinocarbonyl-6-methyl-10,10-dioxo-10,11-dihydro-5-oxa-10lambda*6*-thia-dibenzo[a,d]cyclohepten-2-yl)-2-methylamino-acetamide dimesylate;

N-(4-Chloro-8-guanidinocarbonyl-6-methyl-10,10-dioxo-10,11-dihydro-5-oxa-10lambda*6*-thia-dibenzo[a,d]-cyclohepten-2-yl)-2-pyrrolidine-1-yl-acetamide;

N-{2-[Bis-(2-hydroxy-ethyl)-amino]-4-chloro-6-methyl-10,10-dioxo-10,11-dihydro-5-oxa-10lambda*6*-thia-dibenzo[a,d]cycloheptene-8-carbonyl}-guanidine;

N-(2-Amino-4-chloro-6,11,11-trimethyl-10,10-dioxo-10,11-dihydro-5-oxa-10lambda*6*-thia-dibenzo[a,d]cycloheptene-8-carbonyl)-guanidine;

N-(4-Chloro-8-guanidinocarbonyl-6-methyl-10,10-dioxo-10,11-dihydro-5-oxa-10lambda*6*-thia-dibenzo[a,d]cycloheptene-2-yl)-2-cyclopropylamino-N-(2-pyrrolidin-1-yl-ethyl)-acetamide;

N-(4-Chloro-8-guanidinocarbonyl-6-methyl-10,10-dioxo-10,11-dihydro-5-oxa-10lamda*6*-thia-dibenzo[a,d]cyclopenten-2-yl)-2-(4-methyl-piperazin-1-yl)-acetamide;

N-{4-Chloro-6-methyl-10,10-dioxo-2-[4-(tetrahydro-furan-2-ylmethyl)-piperazin-1-yl]-10,11-dihydro-5-oxa-10lambda*6*-thia-dibenzo[a,d]cycloheptene-8-carbonyl}-guanidine;

N-(2-Amino-4-chloro-6-methyl-10-oxo-10,11-dihydro-5-oxa-10lambda*4*-thia-dibenzo[a,d]cycloheptene-8-carbonyl)-guanidine;

N-(6-Methyl-10,10-dioxo-10,11-dihydro-5-oxa-10lambda*6*-thia-11-aza-dibenzo[a,d]cycloheptene-8-carbonyl)-guanidine;

N-[4-Chloro-6-methyl-2-(1-methyl-pyrrolidin-2-ylidineamino)-10,10-dioxo-10,11-dihydro-5-oxa-10lambda*6*-thia-dibenzo[a,d]cycloheptene-8-carbonyl]-guanidine;

2-(4-Benzyl-piperazin-1-yl)-4-chloro-6-methyl-10,10-dioxo-10,11-dihydro-5-oxa-10lambda*6*-thia-dibenzo[a,d]cycloheptene-8-yl-methylene amino guanidine;

N-[4-Amino-6-methyl-10,10-dioxo-10,11-dihydro-5-oxa-10lambda*6*-thia-dibenzo[a,d]cycloheptene-8-carbonyl]-guanidine;

N-[6-Methyl-4-(2-morpholin-4-yl-ethylamino)-10,10-dioxo-10,11-dihydro-5-oxa-10lambda*6*-thia-dibenzo[a,d]cycloheptene-8-carbonyl]-guanidine;

N-[4-Chloro-2-[(3H-imidazol-4-ylmethyl)-amino]-6-methyl-10,10-dioxo-10,11-dihydro-5-oxa-10lambda*6*-thia-dibenzo[a,d]cycloheptene-8-carbonyl]-guanidine;

N-{4-Chloro-6-methyl-2-[(5-methyl-thiophen-2-ylmethyl)-amino]-10,10-dioxo-10,11-dihydro-5-oxa-10lambda*6*-thia-dibenzo[a,d]cycloheptene-8-carbonyl}-guanidine;

N-{4-Chloro-6-methyl-10,10-dioxo-2-[(pyridin-3-ylmethyl)-amino]-10,11-dihydro-5-oxa-10lambda*6*-thia-dibenzo[a,d]cycloheptene-8-carbonyl}-guanidine;

N-{4-Chloro-2-[4-(2-hydroxy-ethyl)-piperazin-1-yl]-6-methyl-10,10-dioxo-10,11-dihydro-5-oxa-10lambda*6*-thia-dibenzo[a,d]cycloheptene-8-carbonyl}-guanidine;

N-(2-Aminomethyl-4-chloro-6-methyl-10,10-dioxo-10,11-dihydro-5-oxa-10lambda*6*-thia-dibenzo[a.d]cycloheptene-8-carbonyl)-guanidine;

N-(4-Chloro-2-diethylaminomethyl-6-methyl-10,10-di-
oxo-10,11-dihydro-5-oxa-10lambda*6*-thia-dibenzo
[a,d]cycloheptene-8-carbonyl)-guanidine, N-(4-Chloro-6-methyl-10,10-dioxo-2-pyrrol-1-ylmethyl-
10,11-dihydro-5-oxa-10lambda*6*-thia-dibenzo[a,d]
cycloheptene-8-carbonyl)-guanidine; and N-[2-(Benzylamino-methyl)-4-chloro-6-methyl-10,10-
dioxo-10,11-dihydro-5-oxa-10lambda*6*-thia-
dibenzo[a,d]cycloheptene-8-carbonyl]-guanidine;

and -their pharmaceutically acceptable salts.

10. A compound of formula 1b as defined in claim 4, selected from:

N-(10,10-Dioxo-10,11-dihydro-5H-10lambda*6*-thia-5-aza-dibenzo[a.d]cycloheptene-8-carbonyl)-guanidine;

N-(2-Chloro-10,10-dioxo-10,11-dihydro-5H-10lambda*6*-thia-5-aza-dibenzo[a.d]cycloheptene-8-carbonyl)-guanidine;

N-(4-Chloro-10,10-dioxo-10,11-dihydro-5H-10lambda*6*-thia-5-aza-dibenzo[a.d]cycloheptene-8-carbonyl)-guanidine;

N-(3-Chloro-10,10-dioxo-10,11-dihydro-5H-10lambda*6*-thia-5-aza-dibenzo[a.d]cycloheptene-8-carbonyl)-guanidine;

N-(1-Chloro-10,10-dioxo-10,11-dihydro-5H-10lambda*6*-thia-5-aza-dibenzo[a.d]cycloheptene-8-carbonyl)-guanidine;

N-(3-Fluoro-10,10-dioxo-10,11-dihydro-5H-10lambda*6*-thia-5-aza-dibenzo[a.d]cycloheptene-8-carbonyl)-guanidine;

N-(2-Fluoro-10,10-dioxo-10,11-dihydro-5H-10lambda*6*-thia-5-aza-dibenzo[a.d]cycloheptene-8-carbonyl)-guanidine;

N-(2-Ethanesulfonyl-4-methyl-10,10-dioxo-10,11-dihydro-5H-10lambda*6*-thia-5-aza-dibenzo[a.d]cycloheptene-8-carbonyl)-guanidine;

N-(7-Chloro-10,10-dioxo-10,11-dihydro-5H-10lambda*6*-thia-5-aza-dibenzo[a.d]cycloheptene-8-carbonyl)-guanidine;

N-(4,7-Dichloro-10,10-dioxo-10,11-dihydro-5H-10lambda*6*-thia-5-aza-dibenzo[a.d]cycloheptene-8-carbonyl)-guanidine;

N-(4-tert-Butyl-7-chloro-10,10-dioxo-10,11-dihydro-5H-10lambda*6*-thia-5-aza-dibenzo[a.d]cycloheptene-8-carbonyl)-guanidine;

N-(7-Chloro-4-methyl-10,10-dioxo-10,11-dihydro-5H-10lambda*6*-thia-5-aza-dibenzo[a.d]cycloheptene-8-carbonyl)-guanidine;

N-(7-Chloro-1-fluoro-10,10-dioxo-10,11-dihydro-5H-10lambda*6*-thia-5-aza-dibenzo[a.d]cycloheptene-8-carbonyl)-guanidine;

N-(2,7-Dichloro-10,10-dioxo-10,11-dihydro-5H-10lambda*6*-thia-5-aza-dibenzo[a.d]cycloheptene-8-carbonyl)-guanidine;

N-(7-Chloro-2-fluoro-10,10-dioxo-10,11-dihydro-5H-10lambda*6*-thia-5-aza-dibenzo[a.d]cycloheptene-8-carbonyl)-guanidine;

N-(7-Chloro-2-ethanesulfonyl-4-methyl-10,10-dioxo-10,11-dihydro-5H-10lambda*6*-thia-5-aza-dibenzo[a.d]cycloheptene-8-carbonyl)-guanidine;

N-(1,7-Dichloro-10,10-dioxo-10,11-dihydro-5H-10lambda*6*-thia-5-aza-dibenzo[a.d]cycloheptene-8-carbonyl)-guanidine;

N-(7-Methyl-10,10-dioxo-10,11-dihydro-5H-10lambda*6*-thia-5-aza-dibenzo[a.d]cycloheptene-8-carbonyl)-guanidine;

N-(4,7-Dimethyl-10,10-dioxo-10,11-dihydro-5H-10lambda*6*-thia-5-aza-dibenzo[a.d]cycloheptene-8-carbonyl)-guanidine, N-(4-Chloro-7-methyl-10,10-dioxo-10,11-dihydro-5H-10lambda*6*-thia-5-aza-dibenzo[a.d]cycloheptene-8-carbonyl)-guanidine;

N-(4,6-Dimethyl-10,10-dioxo-10,11-dihydro-5H-10lambda*6*-thia-5-aza-dibenzo[a.d]cycloheptene-8-carbonyl)-guanidine;

N-(1-Fluoro-6-methyl-10,10-dioxo-10,11-dihydro-5H-10lambda*6*-thia-5-aza-dibenzo[a.d]cycloheptene-8-carbonyl)-guanidine;

N-(4-Chloro-6-methyl-10,10-dioxo-10,11-dihydro-5H-10lambda*6*-thia-5-aza-dibenzo[a.d]cycloheptene-8-carbonyl)-guanidine;

N-(6-Methyl-10,10-dioxo-10,11-dihydro-5H-10lambda*6*-thia-5-aza-dibenzo[a.d]cycloheptene-8-carbonyl)-guanidine;

N-(10,10-Dioxo-7-pyrrol-1-yl-10,11-dihydro-5H-10lambda*6*-thia-5-aza-dibenzo[a.d]cycloheptene-8-carbonyl)-guanidine;

N-(7-Benzylamino-10,10-dioxo-10,11-dihydro-5H-10lambda*6*-thia-5-aza-dibenzo[a.d]cycloheptene-8-carbonyl)-guanidine;

N-(5-Methyl-10,10-dioxo-10,11-dihydro-5H-10lambda*6*-thia-5-aza-dibenzo[a.d]cycloheptene-8-carbonyl)-guanidine;

N-(5-Allyl-10,10-dioxo-10,11-dihydro-5H-10lambda*6*-thia-5-aza-dibenzo[a.d]cycloheptene-8-carbonyl)-guanidine;

N-(4-Chloro-5,6,11-trimethyl-10,10-dioxo-10,11-dihydro-5H-10lambda*6 *-thia-5-aza-dibenzo[a.d]cycloheptene-8-carbonyl)-guanidine;

N-(10,10-Dioxo-10,11-dihydro-5H-10lambda*6*-thia-5-aza-dibenzo[a.d]cycloheptene-2-carbonyl)-guanidine; and N-(10,10-Dioxo-10,11-dihydro-5H-10lambda*6*-thia-5-aza-dibenzo[a.d]cycloheptene-1-carbonyl)-guanidine;

and -their pharmaceutically acceptable salts.

11. A process for the preparation of a compound of the formula 1 as defined in claim 1,

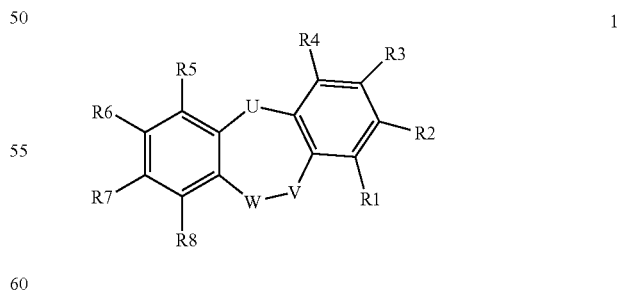

wherein at least one of R1, R2, R3, R4, R5, R6, R7 and R8 is C(O) N═C(NH$_2$)$_2$ and the remaining groups R1 to R8 and U, V and W are as defined in claim 1, which comprises reacting a compound of the formula 3

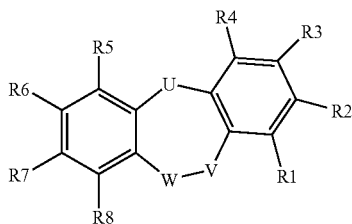

wherein
at least one of R1, R2, R3, R4, R5, R6, R7 and R8 is —C(O)Y, wherein Y is a leaving group, and the remaining groups R1 to R8 and U, V and W are as defined in claim 1, with guanidine, and optionally treating with an acid or base as appropriate to convert the compound of formula 1 into a pharmaceutically acceptable salt.

12. A pharmaceutical composition, comprising a therapeutically effective amount of a compound of formula 1 as defined in claim 1, or a tautomer, stereoisomer, pharmaceutically acceptable salt thereof, and a pharmaceutically acceptable carrier or diluent.

13. The compound of claim 3, wherein R7 is guanidino or guanidino carbonyl.

14. The compound of claim 4, wherein R7 is guanidino or guanidino carbonyl.

15. The compound of claim 3, wherein W is $SO_2$.

16. The compound of claim 4, wherein W is $SO_2$.

* * * * *